(12) United States Patent
Perret et al.

(10) Patent No.: US 12,570,712 B2
(45) Date of Patent: Mar. 10, 2026

(54) CYCLIN A1 SPECIFIC T CELL RECEPTORS AND USES THEREOF

(71) Applicant: FRED HUTCHINSON CANCER CENTER, Seattle, WA (US)

(72) Inventors: Rachel Perret, Seattle, WA (US); Philip D. Greenberg, Mercer Island, WA (US)

(73) Assignee: FRED HUTCHINSON CANCER CENTER, Seattle, WA (US)

( * ) Notice: Subject to any disclaimer, the term of this patent is extended or adjusted under 35 U.S.C. 154(b) by 1165 days.

(21) Appl. No.: 16/968,547

(22) PCT Filed: Feb. 12, 2019

(86) PCT No.: PCT/US2019/017708

§ 371 (c)(1),
(2) Date: Aug. 7, 2020

(87) PCT Pub. No.: WO2019/157524

PCT Pub. Date: Aug. 15, 2019

(65) Prior Publication Data

US 2020/0405762 A1 Dec. 31, 2020

Related U.S. Application Data

(60) Provisional application No. 62/667,207, filed on May 4, 2018, provisional application No. 62/630,198, filed on Feb. 13, 2018, provisional application No. 62/629,648, filed on Feb. 12, 2018.

(51) Int. Cl.
| | |
|---|---|
| *C07K 14/725* | (2006.01) |
| *A61K 35/17* | (2025.01) |
| *A61K 38/20* | (2006.01) |
| *A61K 39/00* | (2006.01) |
| *A61K 40/11* | (2025.01) |
| *A61K 40/32* | (2025.01) |
| *A61K 40/42* | (2025.01) |
| *A61P 35/00* | (2006.01) |
| *C07K 14/705* | (2006.01) |
| *C07K 14/73* | (2006.01) |
| *C07K 16/28* | (2006.01) |
| *C07K 16/32* | (2006.01) |
| *C12N 5/0783* | (2010.01) |
| *C12N 15/86* | (2006.01) |

(52) U.S. Cl.
CPC .......... *C07K 14/7051* (2013.01); *A61K 35/17* (2013.01); *A61K 38/2013* (2013.01); *A61K 39/00* (2013.01); *A61K 40/11* (2025.01); *A61K 40/32* (2025.01); *A61K 40/4239* (2025.01); *A61P 35/00* (2018.01); *C07K 14/70514* (2013.01); *C07K 14/70517* (2013.01); *C07K 16/2833* (2013.01); *C07K 16/32* (2013.01); *C12N 5/0636* (2013.01); *C12N 15/86* (2013.01)

(58) Field of Classification Search
CPC ..................................................... A61K 35/17
See application file for complete search history.

(56) References Cited

U.S. PATENT DOCUMENTS

| | | | |
|---|---|---|---|
| 6,410,319 | B1 | 6/2002 | Raubitschek et al. |
| 6,461,813 | B2 | 10/2002 | Lorens |
| 7,342,092 | B2 | 3/2008 | Sugiyama |
| 7,608,685 | B1 | 10/2009 | Sugiyama et al. |
| 7,622,119 | B2 | 11/2009 | Sugiyama |
| 9,062,127 | B2 | 6/2015 | Voss et al. |
| 10,208,086 | B2 | 2/2019 | Greenberg et al. |
| 10,227,388 | B2 | 3/2019 | Mahr et al. |
| 10,317,402 | B2 | 6/2019 | Parenteau et al. |
| 2002/0053092 | A1 | 5/2002 | Readhead et al. |
| 2004/0087025 | A1 | 5/2004 | June et al. |
| 2010/0047239 | A1 | 2/2010 | Wu et al. |
| 2010/0310534 | A1 | 12/2010 | Oved et al. |
| 2011/0052530 | A1 | 3/2011 | Dudley et al. |
| 2011/0189141 | A1 | 8/2011 | Kieback et al. |
| 2011/0236375 | A1 | 9/2011 | Lazar et al. |
| 2011/0243972 | A1 | 10/2011 | Jaffee |
| 2019/0119326 | A1 | 4/2019 | Greenberg et al. |

FOREIGN PATENT DOCUMENTS

| | | |
|---|---|---|
| JP | 2014533950 A | 12/2014 |
| WO | 2013/071154 A1 | 5/2013 |
| WO | 2014/031687 A1 | 2/2014 |
| WO | 2016/090177 A1 | 6/2016 |
| WO | 2016/161273 A1 | 10/2016 |
| WO | 2017/046198 A1 | 3/2017 |
| WO | WO 2017158116 A1 | 9/2017 |

OTHER PUBLICATIONS

Alli et al. (PLoS One. Mar. 23, 2011; 6 (3): e18027; pp. 1-10).*
Sharma et al. (J. Biol. Chem. Feb. 2, 2018; 293 (5): 1820-34).*
Smith et al. (Nat. Commun. Nov. 7, 2014; 5: 5223; pp. 1-13).*
Dimitri et al. (Mol. Cancer. Mar. 18, 2022; 21 (1): 78; pp. 1-13).*
Birnbaum et al. (Proc. Natl. Acad. Sci. USA. Dec. 9, 2014; 111 (49): 17576-81).*
Waschbisch et al. (Clin. Exp. Immunol. Aug. 2014; 177 (2): 404-11).*
Robbins et al. (J. Immunol. May 1, 2008; 180 (9): 6116-31; author manuscript; pp. 1-31).*
Cohen et al. (Cancer Res. Apr. 15, 2007; 67 (8): 3898-903).*
Li et al. (Immunology. Aug. 1996; 88 (4): 524-30).*

(Continued)

*Primary Examiner* — Peter J Reddig
(74) *Attorney, Agent, or Firm* — Seed Intellectual Property Law Group LLP

(57) ABSTRACT

The present disclosure provides binding proteins, including TCRs, that specifically bind human cyclin A1 (CCNA1), host cells expressing such antigen specific binding proteins, nucleic acids encoding the same, and compositions for use in treating diseases or disorders in which cells overexpress CCNA1, such as in cancer.

21 Claims, 10 Drawing Sheets

Specification includes a Sequence Listing.

(56)                References Cited

OTHER PUBLICATIONS

Brentjens et al., "Genetically Targeted T Cells Eradicate Systemic Acute Lymphoblastic Leukemia Xenografts," *Clin Cancer Res* 13(18):5426-5435, Sep. 15, 2007.

Dossett et al., "Adoptive Immunotherapy of Disseminated Leukemia With TCR-transduced, CD8+ T Cells Expressing a Known Endogenous TCR," *Molecular Therapy* 17(4):742-749, Apr. 2009.

Kalos et al., "T Cells with Chimeric Antigen Receptors Have Potent Antitumor Effects and Can Establish Memory in Patients with Advanced Leukemia," *Science Translational Medicine* 3(95):95ra73, Aug. 10, 2011 (11 pages).

Kim et al., "Analysis of the Paired TCR α- and β-chains of Single Human T Cells," *PLoS ONE* 7(5):e37338, May 2012 (12 pages).

Kuball et al., "Facilitating matched pairing and expression of TCR chains introduced into human T cells," *Blood* 109(6):2331-2338, Mar. 15, 2007.

Leen et al., "Improving T Cell Therapy for Cancer," *Annu. Rev. Immunol.* 25:243-265, 2007.

Munson et al., "Identification of shared TCR sequences from T cells in human breast cancer using emulsion RT-PCR," *Proceedings of the National Academy of Sciences* 113(29):8272-8277, Jul. 19, 2016.

Narayan et al., "Acute myeloid leukemia immunopeptidome reveals HLA presentation of mutated nucleophosmin," *PLOS ONE* 14(7):e0219547, Jul. 10, 2019 (18 pages).

Porter et al., "Chimeric Antigen Receptor-Modified T Cells in Chronic Lymphoid Leukemia," *N Engl J Med* 365(8):725-733, Aug. 25, 2011.

Redmond et al., "Single-cell TCRseq: paired recovery of entire T-cell alpha and beta chain transcripts in T-cell receptors from single-cell RNAseq," *Genome Medicine* 8:80, 2016 (13 pages).

Schmitt et al., "T Cell Receptor Gene Therapy for Cancer," *Human Gene Therapy* 20:1240-1248, Nov. 2009.

Stromnes et al., "Re-adapting T cells for cancer therapy: from mouse models to clinical trials," *Immunol Rev.* 257(1):145-164, Jan. 2014 (NIH Public Access Author Manuscript, available in PMC Jan. 1, 2015) (34 pages).

Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008.

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007 (16 pages).

Akatsuka et al., "Efficient cloning and expression of HLA class I cDNA in human B-lymphoblastoid cell lines," *Tissue Antigens* 59:502-511, 2002.

Blair et al., "Most Acute Myeloid Leukemia Progenitor Cells With Long-Term Proliferative Ability In Vitro and In Vivo Have the Phenotype CD34+/CD71-/HLA-DR-," *Blood* 92(11):4325-4335, 1998.

Bonnet et al., "CD8+ minor histocompatibility antigen-specific cytotoxic T lymphocyte clones eliminate human acute myeloid leukemia stem cells," *Proc. Natl. Acad. Sci. USA* 96:8639-8644, 1999.

Bonnet et al., "Human acute myeloid leukemia is organized as a hierarchy that originates from a primitive hematopoietic cell," *Nature Medicine* 3(7):730-737, 1997.

Brait et al., "Aberrant Promoter Methylation of Multiple Genes during Pathogenesis of Bladder Cancer," *Cancer Epidemiol Biomarkers Prev* 17(10):2786-2794, 2008.

Breems et al., "Prognostic Index for Adult Patients With Acute Myeloid Leukemia in First Relapse," *J Clin Oncol* 23:1969-1978, 2005.

Chaise et al., "DNA vaccination induces WT1-specific T-cell responses with potential clinical relevance," *Blood* 112(7):2956-2964, 2008.

Chan et al., "NGF inhibits human leukemia proliferation by downregulating cyclin A1 expression through promoting acinus/CtBP2 association," *Oncogene* 28:3825-3836, 2009.

Cheever et al., "The Prioritization of Cancer Antigens: A National Cancer Institute Pilot Project for the Acceleration of Translational Research," *Clin Cancer Res* 15(17):5323-5337, 2009.

Cho et al., "Induction of cell apoptosis in non-small cell lung cancer cells by cyclin A1 small interfering RNA," *Cancer Sci* 97(10):1082-1092, 2006.

Coletta et al., "Six1 Overexpression in Mammary Cells Induces Genomic Instability and Is Sufficient for Malignant Transformation," *Cancer Res* 68(7):2204-2213, 2008.

Cornelissen et al., "Results of a HOVON/SAKK donor versus no-donor analysis of myeloablative HLA-identical sibling stem cell transplantation in first remission acute myeloid leukemia in young and middle-aged adults: benefits for whom?" *Blood* 109(9):3658-3666, 2007.

Dossett et al., "Adoptive Immunotherapy of Disseminated Leukemia With TCR-transduced, CD8+ T Cells Expressing a Known Endogenous TCR," *Molecular Therapy* 17(4):742-749, 2009.

Doubrovina et al., "In vitro Stimulation with WT1 Peptide-Loaded Epstein-Barr Virus-Positive B Cells Elicits High Frequencies of WT1 Peptide-Specific T Cells with In vitro and In vivo Tumoricidal Activity," *Clinical Cancer Research* 10:7207-7219, 2004.

Egloff et al., "Cyclin B1 and Other Cyclins as Tumor Antigens in Immunosurveillance and Immunotherapy of Cancer," *Cancer Res* 66(1):6-9, 2006.

Ekberg et al., "Post-translational modification of cyclin A1 is associated with staurosporine and TNFα induced apoptosis in leukemic cells," *Mol Cell Biochem* 320:115-124, 2009.

Farhadieh et al., "Mutant p53 and cyclin A1 protein expression in primary laryngeal squamous cell carcinomas do not correlate to second primary tumours of the head and neck," *Anz J Surg* 79:48-54, 2009.

Fijak et al., "The testis in immune privilege," *Immunological Reviews* 213:66-81, 2006.

GenBank Database Accession No. NM_001111047.1, May 18, 2014, 4 pages.

GenBank Database Accession No. NP_001104517.1, May 18, 2014, 3 pages.

Ho et al., "Adoptive immunotherapy: Engineering T cell responses as biologic weapons for tumor mass destruction," *Cancer Cell* 3:431-437, 2003.

Ho et al., "In vitro methods for generating CD8+ T-cell clones for immunotherapy from the naïve repertoire," *Journal of Immunological Methods* 310:40-52, 2006.

Holm et al., "Cyclin A1 expression and associations with disease characteristics in childhood acute lymphoblastic leukemia," *Leukemia Research* 30:254-261, 2006.

Jang et al., "Serine/Arginine Protein-Specific Kinase 2 Promotes Leukemia Cell Proliferation by Phosphorylating Acinus and Regulating Cyclin A1," *Cancer Res* 68(12):4559-4570, 2008.

Ji et al., "DNA damage response involves modulation of Ku70 and Rb functions by cyclin A1 in leukemia cells," *Int. J. Cancer* 121:706-713, 2007.

Keilholz et al., "A clinical and immunologic phase 2 trial of Wilms tumor gene product 1 (WT1) peptide vaccination in patients with AML and MDS," *Blood* 113(26):6541-6548, 2009.

Kondo et al., "Using CD40-activated B Cells to Efficiently Identify Epitopes of Tumor Antigens," *J Immunother* 32(2):157-160, 2009.

Krug et al., "Cyclin A1 regulates WT1 expression in acute myeloid leukemia cells," *International Journal of Oncology* 34:129-136, 2009.

Lapidot et al., "A cell initiating human acute myeloid leukaemia after transplantation into SCID mice," *Nature* 367:645-648, 1994.

Lele et al., "Distinct Regions of the Mouse Cyclin A1 Gene, Ccnal, Confer Male Germ-Cell Specific Expression and Enhancer Function," *Biology of Reproduction* 71:1340-1347, 2004.

Levine et al., "Prospective Trial of Chemotherapy and Donor Leukocyte Infusions for Relapse of Advanced Myeloid Malignancies After Allogeneic Stem-Cell Transplantation," *J Clin Oncol* 20:405-412, 2002.

Li et al., "Model-based analysis of oligonucleotide arrays: Expression index computation and outlier detection," *PNAS* 98(1):31-36, 2001.

(56) References Cited

OTHER PUBLICATIONS

Liao et al., "Altered myelopoiesis and the development of acute myeloid leukemia in transgenic mice overexpressing cyclin A1," *PNAS* 98(12):6853-6858, 2001.

Lundegaard et al., "NetMHC-3.0: accurate web accessible predictions of human, mouse and monkey MHC class 1 affinities for peptides of length 8-11," *Nucleic Acids Research* 36:W509-W512, 2008.

Majeti et al., "Dysregulated gene expression networks in human acute myelogenous leukemia stem cells," *PNAS* 106(9):3396-3401, 2009.

Nickerson et al., "Cyclin A1-deficient mice lack histone H3 serine 10 phosphorylation and exhibit altered aurora B dynamics in late prophase of male meiosis," *Developmental Biology* 306:725-735, 2007.

Park et al., "Cancer Stem Cell-Directed Therapies: Recent Data From the Laboratory and Clinic," *Molecular Therapy* 17(2):219-230, 2009.

Rammensee et al., "SYFPEITHI: database for MHC ligands and peptide motifs," *Immunogenetics* 50:213-219, 1999.

Rezvani et al., "Leukemia-associated antigen-specific T-cell responses following combined PR1 and WT1 peptide vaccination in patients with myeloid malignancies," *Blood* 111(1):236-242, 2008.

Riddell et al., "Class I MHC-restricted cytotoxic T lymphocyte recognition of cells infected with human cytomegalovirus does not require endogenous viral gene expression," *The Journal of Immunology* 146(8):2795-2804, 1991.

Riddell et al., "The use of anti-CD3 and anti-CD28 monoclonal antibodies to clone and expand human antigen-specific T cells," *Journal of Immunological Methods* 128:189-201, 1990.

Robins et al., "Comprehensive assessment of T-cell receptor β-chain diversity in αβ cells," *Blood* 114(19):4099-4107, 2009.

Robins et al., "Overlap and Effective Size of the Human CD8+ T Cell Receptor Repertoire," *Sci Transl Med* 2, 10 pages, 2010.

Robins et al., "Ultra-sensitive detection of rare T cell clones," *Journal of Immunological Methods* 375:14-19 (2012).

Rosinski et al., "DDX3Y encodes a class I MHC-restricted H-Y antigen that is expressed in leukemic stem cells," *Blood* 111(9):4817-4826, 2008.

Schmitt et al., "T Cell Receptor Gene Therapy for Cancer," *Human Gene Therapy* 20:1240-1248, 2009.

Simpson et al., "Cancer/Testis Antigens, Gametogenesis and Cancer," *Nature Reviews* 5:615-625, 2005.

Spisak et al., "Applicability of antibody and mRNA expression microarrays for identifying diagnostic and progression markers of early and late stage colorectal cancer," *Disease Markers* 28:1-14, 2010.

Stirewalt et al., "Identification of Genes with Abnormal Expression Changes in Acute Myeloid Leukemia," *Genes, Chromosomes & Cancer* 47:8-20, 2008.

Till et al., "Adoptive immunotherapy for indolent non-Hodgkin lymphoma and mantle cell lymphoma using genetically modified autologous CD20-specific T cells," *Blood* 112(6):2261-2271 (2008).

Van Driessche et al., "Antigen-specific cellular immunotherapy of leukemia," *Leukemia* 19:1863-1871, 2005.

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, 2007.

Warren et al., "Exhaustive T-cell repertoire sequencing of human peripheral blood samples reveals signatures of antigen selection and a directly measured repertoire size of at least 1 million clonotypes," *Genome Research* 21:790-797 2011.

Wegiel et al., "Multiple Cellular Mechanisms Related to Cyclin A1 in Prostate Cancer Invasion and Metastasis," *J Natl Cancer Inst* 100:1022-1036, 2008.

Wilde et al., "Dendritic cells pulsed with RNA encoding allogeneic MHC and antigen induce T cells with superior antitumor activity and higher TCR functional avidity," *Blood* 114(10):2131-2139, 2008.

Wolgemuth et al., "The A-type cyclins and the meiotic cell cycle in mammalian male germ cells," *International Journal of Andrology* 27:192-199, 2004.

Xue et al., "Elimination of human leukemia cells in NOD/SCID mice by WT1-TCR gene-transduced human T Cells," *Blood* 106(9):3062-3067, 2005.

Yanada et al., "Efficacy of Allogeneic Hematopoietic Stem Cell Transplantation Depends on Cytogenetic Risk for Acute Myeloid Leukemia in First Disease Remission," *Cancer* 103(8) 1652-1658, 2005.

Yang et al., "Characterization of a Second Human Cyclin A That Is Highly Expressed in Testis and in Several Leukemic Cell Lines," *Cancer Research* 57:913-920, 1997.

Yang et al., "Gene promoter methylation patterns throughout the process of cervical carcinogenesis," *Cellular Oncology* 32:131-143, 2010.

International Search Report & Written Opinion, for International Patent Application No. PCT/US2019/017708, mailed Jun. 7, 2019. (10 pages).

Ochsenreither et al., "Cyclin-A1 represents a new immunogenic targetable antigen expressed in acute myeloid leukemia stem cells with characteristics of a cancer-testis antigen," *Blood* 119(23):5492-5501, 2012.

Perret et al., "Creating a TCR gene-therapy toolbox for acute myeloid leukemia," *Keystone Symposia—Emerging Cellular Therapies: T Cells and Beyond*, Keystone, CO, USA, Feb. 13, 2018.

Perret et al., "Expanding the scope of WT1- and cyclin A1-specific TCR gene therapy for AML and other cancers," *J. Immunol.* 196(1Supplement), 2016.

Schmitt et al., "Generation of TCRs of higher affinity by antigen-driven differentiation of progenitor T cells in vitro," *Nat. Biotechnol.* 35(12):1188-1195, 2017.

Haga-Friedman et al., "Incorporation of Transmembrane Hydrophobic Mutations in the TCR Enhance Its Surface Expression and T Cell Functional Avidity," *The Journal of Immunology* 188(11):5538-5546, Jun. 1, 2012. (10 pages).

Lefranc et al., "IMGT unique numbering for immunoglobulin and T cell receptor variable domains and Ig superfamily V-like domains," *Developmental and Comparative Immunology* 27:55-77, Jan. 2003. (23 pages).

Voss et al., "Molecular Design of the Cαβ Interface Favors Specific Pairing of Introduced TCRαβ in Human T Cells," *The Journal of Immunology* 180(1):391-401, Jan. 1, 2008. (12 pages).

* cited by examiner

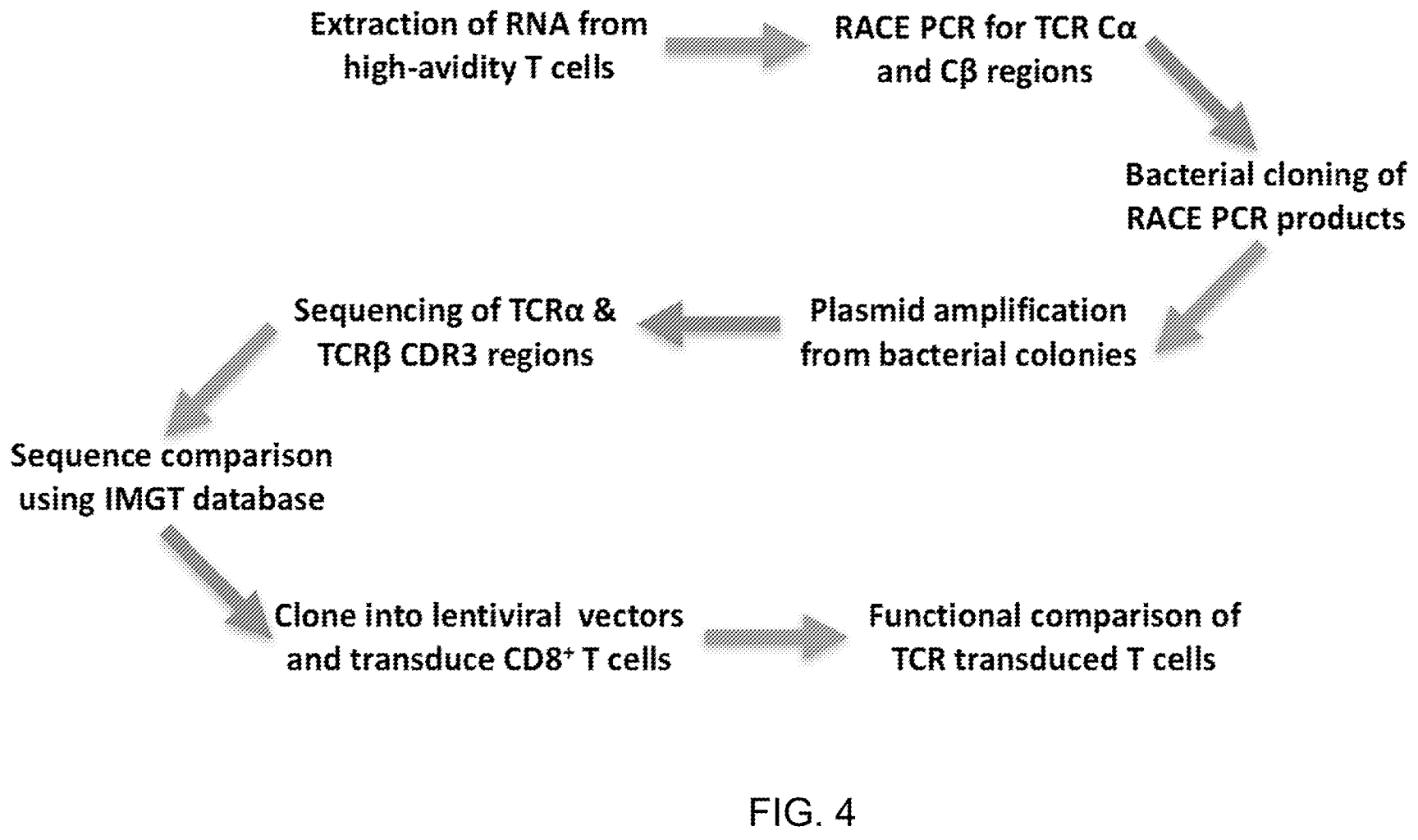

Extraction of RNA from high-avidity T cells

RACE PCR for TCR Cα and Cβ regions

Bacterial cloning of RACE PCR products

Plasmid amplification from bacterial colonies

Sequencing of TCRα & TCRβ CDR3 regions

Sequence comparison using IMGT database

Clone into lentiviral vectors and transduce CD8+ T cells

Functional comparison of TCR transduced T cells

FIG. 4

MHC binding & proteasome cleavage prediction

| Algorithm | Peptide | | |
|---|---|---|---|
| Score: High -> Low | 227-235 | 341-351 | 370-379 |
| SYFPEITHI: Binding score | 20 | 24 | 29 |
| NetMHCpan 4.0: $IC_{50}$ (nM) | 32.5 | 74.7 | 13.1 |
| IEDB: ANN $IC_{50}$ (nM) | 27.03 | 113.39 | 12.05 |
| BiMAS: Dissociation half-time | 79.89 | NA | 5.459 |
| MAPPP: Cleavage probability | 0.9560 | 0 | 0 |

* $IC_{50}$ values <50 nM are considered high affinity, <500 nM intermediate affinity and <5000 nM low affinity.

FIG. 5C

CYCLIN A1 SPECIFIC T CELL RECEPTORS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056-460USPC-SL-V2.txt. The text file is 301,522 bytes, was created on Jun. 24, 2025, and is being submitted electronically.

BACKGROUND

Adoptive immunotherapy involving ex vivo expansion and infusion of tumor-reactive T-cells is an emerging treatment modality, especially in patients for whom conventional therapy fails (Stromnes et al., *Immunol. Rev.* 257:145-64, 2014). In some cases, tumor-reactive T cells comprise an endogenous, exogenous, and/or engineered receptor specific for an antigen specific to or overexpressed on a tumor.

Cancer-testes antigen cyclin A1 (CCNA1) is an alternative A-type cyclin and is an attractive target for treatment of various cancers due its overexpression in acute myeloid leukemia (AML) and a number of epithelial cancers including testicular, endometrial, and ovarian cancer. Cyclin A1 is thought to promote cell proliferation and survival, has been shown to be leukemogenic in mice, and is detected in leukemic stem cells of more than 50% of AML patients.

Provided herein are methods for identifying tumor-reactive T cells reactive to cyclin A1, methods for identifying T-cell receptors (TCRs) specific for cyclin A1, as well as specific TCRs identified using the methods described herein.

BRIEF DESCRIPTION OF THE DRAWINGS

FIG. 4 shows a schematic for isolation, identification, and expression of high-affinity TCRs selected from high-avidity clones.

FIGS. 5A-5D show that HLA-A2:01/cyclin A1 TCRs recognized peptide pulsed targets and killed HLA-matched cyclin A1+leukemia cell lines and primary AML cells.

DETAILED DESCRIPTION

Figure 1:
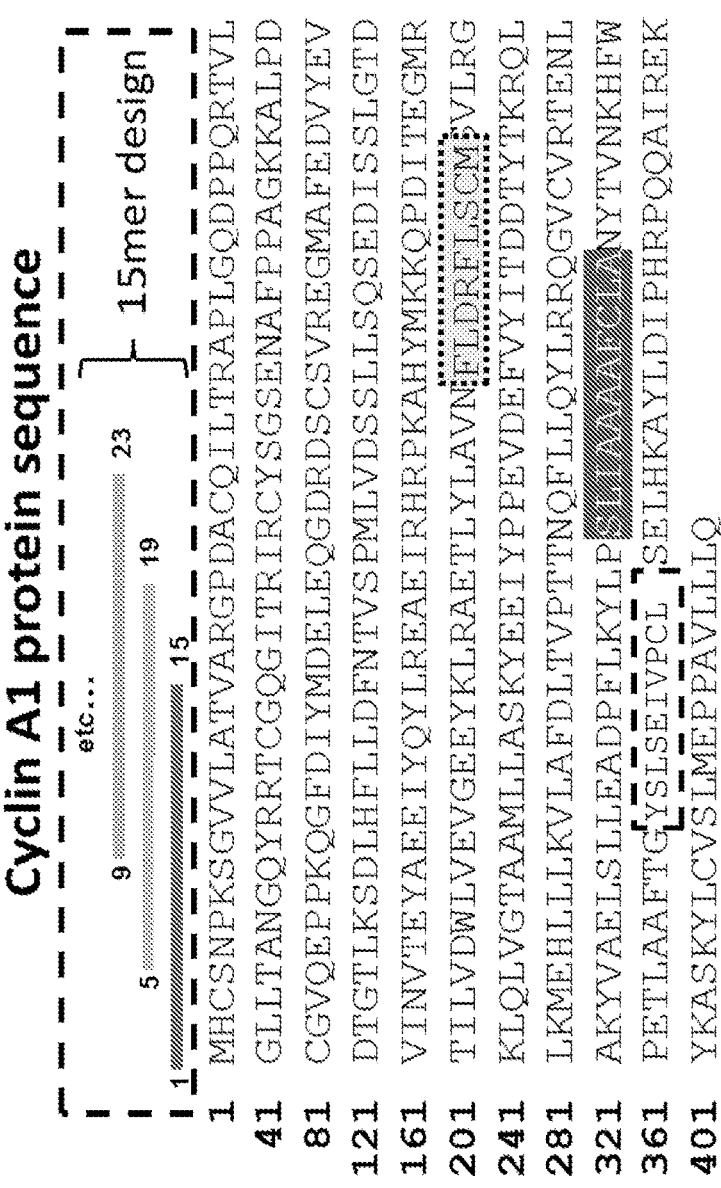
FIG. 1 depicts the Cyclin A1 TCR discovery scheme, targeting HLA-A2 restricted epitopes. Positions of lead HLA-A2 peptides 227-235 (SEQ ID NO:1), 341-351 (SEQ ID NO:2), and 370-379 (SEQ ID NO:3) on cyclin A1 protein sequence (SEQ ID NO:4) are shown.
Figure 1:

In certain aspects, the present disclosure provides binding proteins (e.g., T cell receptors (TCRs)) specific for cyclin A1 associated with a major histocompatibility complex (MHC) (e.g., human leukocyte antigen (HLA)), for use in, for example, adoptive immunotherapy to treat cancer.

The compositions and methods described herein will in certain embodiments have therapeutic utility for the treatment of diseases and conditions associated with CCNA1 overexpression (e.g., detectable CCNA1 expression at a level that is greater in magnitude, in a statistically significant manner, than the level of CCNA-1 expression that is detectable in a normal or disease-free cell). Such diseases include various forms of hyperproliferative disorders, such as acute myeloid leukemia. Non-limiting examples of these and related uses are described herein and include in vitro, ex vivo and in vivo stimulation of CCNA1 antigen-specific T cell responses, such as by the use of recombinant T cells expressing a TCR specific for a CCNA1 peptide (e.g., FLDRFLSCM (SEQ ID NO: 1), SLIAAAAFCLA (SEQ ID NO:2), or YSLSEIVPCL (SEQ ID NO:3)).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 14%, 13%, 12%, 11%, 10%, 9%, 8%, 7%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4– CD8– double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

As used herein, a "hematopoietic progenitor stem cell" refers to undifferentiated hematopoietic cells that are capable of self-renewal either in vivo, essentially unlimited propagation in vitro, and capable of differentiation to other cell types including cells of the T cell lineage. Hematopoietic stem cells may be isolated, for example, but not limited to, from fetal liver, bone marrow, cord blood.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ Lin⁻ $CD117^{+}$ phenotype or those found in the thymus (referred to as progenitor thymocytes).

As used herein, the term "host" refers to a cell (e.g., T cell) or microorganism targeted for genetic modification with a heterologous or exogenous nucleic acid molecule to produce a polypeptide of interest (e.g., high or enhanced affinity anti-CCNA-1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased costimulatory factor expression). In certain embodiments, a host cell is a human hematopoietic progenitor cell transduced with a heterologous or exogenous nucleic acid molecule encoding a TCRβ, TCRα chain or both, specific for a CCNA-1 antigen peptide. In certain embodiments, a host cells are autologous, allogeneic or syngeneic to subject to receive the host cells containing a polynucleotide encoding a binding protein of this disclosure.

A "T cell" or "T lymphocyte" is an immune system cell that matures in the thymus and produces T cell receptors (TCRs), which can be obtained (enriched or isolated) from, for example, peripheral blood mononuclear cells (PBMCs) and are referred to herein as "bulk" T cells. After isolation of T cells, both cytotoxic (CD8+) and helper (CD4+) T cells can be sorted into naïve, memory, and effector T cell subpopulations, either before or after expansion. T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells (TEM, decreased expression of CD62L, CCR7, CD28, CD45RA, and increased expression of CD127 as compared to naïve T cells or $T_{CM}$). Effector T cells ($T_E$) refers to antigen-experienced CD8+cytotoxic T lymphocytes that has decreased expression of CD62L, CCR7, CD28, and are positive for granzyme and perforin as compared to $T_{CM}$.

Helper T cells ($T_H$) are CD4+ cells that influence the activity of other immune cells by releasing cytokines. CD4+ T cells can activate and suppress an adaptive immune response, and which action is induced will depend on presence of other cells and signals. T cells can be collected in accordance with known techniques, and the various subpopulations or combinations thereof can be enriched or depleted by known techniques, such as by affinity binding to antibodies, flow cytometry, or immunomagnetic selection. Other exemplary T cells include regulatory T cells, such as CD4+ CD25+ (Foxb3+) regulatory T cells and Treg17 cells, as well as Tr1, Th3, CD8+ CD28+, and Qa-1 restricted T cells.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, $3^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like immunoglobulins, the extracellular portion of TCR chains (e.g., α-chain, β-chain) contain two immunoglobulin domains, a variable domain (e.g., α-chain variable domain or $V_α$, β-chain variable domain or $V_β$; typically amino acids 1 to 116 based on Kabat numbering, Kabat et al., "Sequences of Proteins of Immunological Interest, US Dept. Health and Human Services, Public Health Service National Institutes of Health, 1991, $5^{th}$ ed.) at the N-terminus, and one constant domain (e.g., α-chain constant domain or $C_α$, typically amino acids 117 to 259 based on Kabat, β-chain constant domain or $C_β$, typically amino acids 117 to 295 based on Kabat) adjacent to the cell membrane. Also like immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammals.

The term "variable region" or "variable domain" refers to the domain of a TCR α-chain or β-chain (or γ chain and δ chain for γδ TCRs) that is involved in binding of the TCR to antigen. The variable domains of the α-chain and β-chain ($V_α$ and $V_β$, respectively) of a native TCR generally have similar structures, with each domain comprising four conserved framework regions (FRs) and three CDRs. The $V_α$ domain is encoded by two separate DNA segments, the variable gene segment and the joining gene segment (V-J); the $V_β$ domain is encoded by three separate DNA segments, the variable gene segment, the diversity gene segment, and the joining gene segment (V-D-J). A single $V_α$ or $V_β$ domain may be sufficient to confer antigen-binding specificity. Furthermore, TCRs that bind a particular antigen may be isolated using a $V_α$ or $V_β$ domain from a TCR that binds the antigen to screen a library of complementary $V_β$ or Vα domains, respectively.

The terms "complementarity determining region," and "CDR," which are synonymous with "hypervariable region" or "HVR," are known in the art to refer to non-contiguous sequences of amino acids within TCR variable regions, which confer antigen specificity and/or binding affinity. In general, there are three CDRs in each α-chain variable region (αCDR1, αCDR2, αCDR3) and three CDRs in each β-chain variable region (βCDR1, βCDR2, βCDR3). CDR3 is thought to be the main CDR responsible for recognizing processed antigen. CDR1 and CDR2 mainly interact with the MHC. However, the CDR1 loops of the alpha chain and beta chain have also been shown to interact with the N-terminal and C-terminal ends of the antigenic peptide, respectively, and may contribute to both peptide specificity and MHC binding.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antigen" or "Ag" as used herein refers to an immunogenic molecule that provokes an immune response. This immune response may involve antibody production, activation of specific immunologically-competent cells (e.g., T cells), or both. An antigen (immunogenic molecule) may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen. Exemplary antigens include CCNA-1.

The term "epitope" or "antigenic epitope" includes any molecule, structure, amino acid sequence or protein determinant that is recognized and specifically bound by a cognate binding molecule, such as an immunoglobulin, T cell receptor (TCR), chimeric antigen receptor, or other binding molecule, domain or protein. Epitopic determinants generally contain chemically active surface groupings of molecules, such as amino acids or sugar side chains, and can have specific three dimensional structural characteristics, as well as specific charge characteristics. For example, a CCNA-1 protein or fragment thereof may be an antigen that contains one or more antigenic epitopes.

"Major histocompatibility complex" (MHC) refers to glycoproteins that deliver peptide antigens to a cell surface. MHC class I molecules are heterodimers having a membrane spanning α chain (with three a domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by CD8+ T cells. MHC class II molecules deliver peptides originating in the vesicular system to the cell surface, where they are recognized by CD4+ T cells. Human MHC is referred to as human leukocyte antigen (HLA).

A "binding domain" (also referred to as a "binding region" or "binding moiety"), as used herein, refers to a molecule or portion thereof (e.g., peptide, oligopeptide, polypeptide, protein) that possesses the ability to specifically and non-covalently associate, unite, or combine with a target (e.g., CCNA-1, CCNA-1 peptide:MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for their specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule (e.g., CCNA-1 peptide:HLA or a tetramer such an HLA complex) with an affinity or $K_a$ (i.e., an equilibrium association constant of a particular binding interaction with units of 1/M) equal to or greater than $10^5$ $M^{-1}$ (which equals the ratio of the on-rate $[k_{on}]$ to the off-rate $[k_{off}]$ for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant $(K_d)$ of a particular binding interaction with units of M (e.g., $10^{-5}$ M to $10^{-13}$ M).

In certain embodiments, a receptor or binding domain may have "enhanced affinity," which refers to selected or engineered receptors or binding domains with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate $(k_{off})$ for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

A variety of assays are known for identifying binding domains of the present disclosure that specifically bind a particular target, as well as determining binding domain or binding protein affinities, such as Western blot, ELISA, analytical ultracentrifugation, spectroscopy, surface plasmon resonance (Biacore®) analysis, MHC tetramer assay (see, e.g., Scatchard et al., *Ann. N.Y. Acad. Sci.* 51:660, 1949; Wilson, Science 295:2103, 2002; Wolff et al., *Cancer Res.* 53:2560, 1993; Altman et al., Science 274:94-96, 1996; and U.S. Pat. Nos. 5,283,173, 5,468,614, or the equivalent).

The term "CCNA-1-specific binding protein" refers to a protein or polypeptide that specifically binds to CCNA-1 or a peptide or fragment thereof. In some embodiments, a protein or polypeptide binds to CCNA-1 or a peptide thereof, such as a CCNA-1 peptide in complexed with an MHC or HLA molecule, e.g., on a cell surface, with at or at least about a particular affinity. In certain embodiments, a CCNA-1-specific binding protein binds a CCNA-1-derived peptide:HLA complex (or CCNA-1-derived peptide:MHC complex) with a $K_d$ of less than about $10^8$ M, less than about $10^{-9}$ M, less than about $10^{-10}$ M, less than about $10^{-11}$ M, less than about $10^{-12}$ M, or less than about $10^{-13}$ M, or with an affinity that is about the same as, at least about the same as, or is greater than at or about the affinity exhibited by an exemplary CCNA-1 specific binding protein provided herein, such as any of the CCNA-1-specific TCRs provided herein, for example, as measured by the same assay. In certain embodiments, a CCNA-1-specific binding protein comprises a CCNA-1-specific immunoglobulin superfamily binding protein or binding portion thereof.

Assays for assessing affinity or apparent affinity or relative affinity are known. In certain examples, apparent affinity for a TCR is measured by assessing binding to various concentrations of tetramers, for example, by flow cytometry using labeled tetramers. In some examples, apparent $K_D$ of a TCR is measured using 2-fold dilutions of labeled tetramers at a range of concentrations, followed by determination of binding curves by non-linear regression, apparent $K_D$ being determined as the concentration of ligand that yielded half-maximal binding.

The term "CCNA-1 binding domain" or "CCNA-1 binding fragment" refers to a domain or portion of a CCNA-1-specific binding protein responsible for the specific CCNA-1 binding. A CCNA-1-specific binding domain alone (i.e., without any other portion of a CCNA-1-specific binding protein) can be soluble and can bind to CCNA-1 with a $K_d$ of less than about $10^{-8}$ M, less than about $10^9$ M, less than about $10^{-10}$ M, less than about $10^{-11}$ M, less than about $10^{-12}$ M, or less than about $10^{-13}$ M. Exemplary CCNA-1-specific binding domains include CCNA-1-specific scTCR (e.g., single chain αβTCR proteins such as Vα-L-Vβ, Vβ-L-Vα, Vα-Cα-L-Vβ, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-CCNA-1 TCR or antibody.

Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8th Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules.

"Cyclin-A1" or "CCNA-1" refers to a protein belonging to the cyclin family that is involved in cell cycle control of the male germline meiotic cell cycle. Cyclin A1 is minimally expressed in normal tissues, except the testis, and overexpressed in many cancers including acute myeloid leukemia (AML) and a number of epithelial cancers, including tes-ticular, endometrial, and ovarian cancer. In certain embodiments, CCNA1 refers to isoform 3 of the protein, which differs from isoform 1 in that amino acids 1-44 are missing. In a particular embodiment, CCNA1 comprises an amino acid sequence set forth in SEQ ID NO:4.

"CCNA-1 antigen" or "CCNA-1 peptide antigen" refers to a naturally or synthetically produced portion of a CCNA-1 protein ranging in length from about 7 amino acids to about 15 amino acids, which can form a complex with a MHC (e.g., HLA) molecule and such a complex can bind with a TCR specific for a CCNA-1 peptide:MHC (e.g., HLA) complex. CCNA-1 antigen peptides are presented in the context of class I MHC. In particular embodiments, a CCNA-1 peptide is FLDRFLSCM (SEQ ID NO:1), SLIAAAAFCLA (SEQ ID NO:2), or YSLSEIVPCL (SEQ ID NO:3), which associate with human class I HLA and, more specifically, associates with allele HLA-A*02:01.

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

"Junction amino acids" or "junction amino acid residues" refer to one or more (e.g., about 2-10) amino acid residues between two adjacent motifs, regions or domains of a polypeptide, such as between a binding domain and an adjacent constant domain or between a TCR chain and an adjacent self-cleaving peptide. Junction amino acids may result from the construct design of a binding protein (e.g., amino acid residues resulting from the use of a restriction enzyme site during the construction of a nucleic acid molecule encoding a binding protein).

An "altered domain" or "altered protein" refers to a motif, region, domain, peptide, polypeptide, or protein with a non-identical sequence identity to a wild type motif, region, domain, peptide, polypeptide, or protein (e.g., a wild type TCRα chain, TCRβ chain, TCRα constant domain, TCRβ constant domain) of at least 85% (e.g., 86%, 87%, 88%, 89%0, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 100%) identity.

As used herein, "nucleic acid" or "nucleic acid molecule" refers to any of deoxyribonucleic acid (DNA), ribonucleic acid (RNA), oligonucleotides, polynucleotides, fragments thereof generated, for example, by the polymerase chain reaction (PCR) or by in vitro transcription, and also to fragments generated by any of ligation, scission, endonuclease action, or exonuclease action. In certain embodiments, the nucleic acids of the present disclosure are produced by PCR. Nucleic acids can be composed of monomers that are naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Nucleic acid molecules can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region ("leader and trailer") as well as intervening sequences (introns) between individual coding segments (exons).

The term "construct" refers to any polynucleotide that contains a recombinant nucleic acid molecule. A construct may be present in a vector (e.g., a bacterial vector, a viral vector) or may be integrated into a genome.

A "vector" is a nucleic acid molecule that is capable of transporting another nucleic acid. Vectors may be, for example, plasmids, cosmids, viruses, phage, a RNA vector, or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

The term "expression", as used herein, refers to the process by which a polypeptide is produced based on the encoding sequence of a nucleic acid molecule, such as a gene. The process can include transcription, post-transcriptional control, post-transcriptional modification, translation, post-translational control, post translational modification, or any combination thereof.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "introduced" in the context of inserting a nucleic acid molecule into a cell, means "transfection", or "transformation", or "transduction" and includes reference to the incorporation of a nucleic acid molecule into a eukaryotic or prokaryotic cell wherein the nucleic acid molecule can be incorporated into the genome of a cell (e.g., a chromosome, a plasmid, a plastid, or a mitochondrial DNA), converted into an autonomous replicon, or transiently expressed (e.g., transfected mRNA).

As used herein, "heterologous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous nucleic acid molecule, construct or sequence can be from a different genus or species. In certain embodiments, a heterologous nucleic acid molecule is added (i.e., not endogenous or native) to a host cell or host genome by, for example, conjugation, transformation, transfection, transduction, electroporation, or the like, wherein the added molecule can integrate into the host genome or exist as extra-chromosomal genetic material (e.g., as a plasmid or other form of self-replicating vector), and can be present in multiple copies. In addition, "heterologous" refers to a non-native enzyme, protein or other activity encoded by a non-endogenous nucleic acid molecule introduced into the host cell, even if the host cell encodes a homologous protein or activity.

The term "homologous" or "homolog" refers to a molecule or activity found in or derived from a host cell, species or strain. For example, a heterologous molecule or gene encoding the molecule may be homologous to a native host or host cell molecule or gene that encodes the molecule, respectively, and may optionally have an altered structure, sequence, expression level or combinations thereof.

As used herein, the term "endogenous" or "native" refers to a gene, protein, compound, molecule or activity that is normally present in a host or host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., a promoter, translational attenuation sequences) can be used to alter or regulate expression of a second native gene or nucleic acid molecule, wherein the expression or regulation of the second native gene or nucleic acid molecule differs from normal expression or regulation in a parent cell.

As used herein, the term "engineered," "recombinant," "modified" or "non-natural" refers to an organism, micro-organism, cell, nucleic acid molecule, or vector that has been modified by introduction of a heterologous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins, binding proteins, or enzymes, or other nucleic acid molecule additions, deletions, substitutions, or other functional disruption of or addition to a cell's genetic material. Exemplary modifications include those in coding regions or functional fragments thereof heterologous or homologous polypeptides from a reference or parent molecule. Additional exemplary modifications include, for example, modifications in non-coding regulatory regions in which the modifications alter expression of a gene or operon.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-77, 1975; Lewin, Genes IV, Oxford University Press, NY and Cell Press, Cambridge, MA, p. 8, 1990).

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST 2.0 software as defined by Altschul et al. (1997), *Nucl. Acids Res.* 25:3389-3402, with the parameters set to default values.

As used herein, "hyperproliferative disorder" refers to excessive growth or proliferation as compared to a normal or undiseased cell. Exemplary hyperproliferative disorders include tumors, cancers, hematological malignancies, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like). In certain embodiments, a hyperproliferative disorder is acute myelogenous leukemia.

"Adoptive cellular immunotherapy" or "adoptive immunotherapy" refers to the administration of naturally occurring or genetically engineered, disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

"Treat" or "treatment" or "ameliorate" refers to medical management of a disease, disorder, or condition of a subject (e.g., a human or non-human mammal, such as a primate, horse, dog, mouse, rat). In general, an appropriate dose or treatment regimen comprising a host cell expressing a CCNA1-specific binding protein of the present disclosure is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a binding protein or cell expressing a binding protein of this disclosure refers to that amount of compound or cells sufficient to result in amelioration of one or more symptoms of the disease being treated in a statistically significant manner. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously. Another combination may be a cell expressing more than one active ingredient, such as two different binding proteins, or other relevant therapeutic.

CCNA-1 Specific Binding Proteins

Cyclin A1 refers to a protein encoded by the CCNA1 gene. CCNA1 is a member of the cyclin family, whose expression is normally limited to the testes, where it is involved in regulating spermatogenesis. CCNA1 is highly expressed in leukemic cells and other malignancies and may promote cell proliferation and survival. Several peptides of the CCNA1 protein are known to be tumor-associated antigen peptides that are HLA A*02:01-restricted antigens. Due to these characteristics, the CCNA1 protein is an attractive target for clinical development.

In certain aspects, the present disclosure provides binding proteins (e.g., an immunoglobulin superfamily binding protein or portion thereof) that specifically bind CCNA1 peptide FLDRFLSCM (SEQ ID NO:1), CCNA1 peptide SLIAAAAFCLA (SEQ ID NO:2), or CCNA1 peptide YSL-SEIVPCL (SEQ ID NO:3).

In one aspect, the present disclosure provides a binding protein (e.g., an immunoglobulin superfamily binding protein or portion thereof), comprising: (a) a T cell receptor (TCR) α chain variable ($V_\alpha$) domain comprising a complementary determining region 3 (CDR3) amino acid sequence set forth in any one of SEQ ID NOS:5, 7, 9, 11, 13, 15, 17, and 19, or a CDR3 amino acid sequence set forth in any one of SEQ ID NOS: 5, 7, 9, 11, 13, 15, 17, and 19 with up to five amino acid substitutions, insertions and/or deletions, and a TCR β chain variable (Vβ) domain; (b) TCR $V_\alpha$ domain, and a TCR $V_\beta$ domain comprising a CDR3 amino acid sequence set forth in any one of SEQ ID NOS:6, 8, 10, 12, 14, 16, 18, 20, and 189, or a CDR3 amino acid sequence set forth in any one of SEQ ID NOS: 6, 8, 10, 12, 14, 16, 18, 20, and 189 with up to five amino acid substitutions, insertions and/or deletions; or (c) a $V_\alpha$ domain of (a) and a $V_\beta$ of (b), wherein the binding protein is capable of specifically binding to a human cyclin A1 (CCNA1) peptide 227-235 FLDRFLSCM (SEQ ID NO:1):human leukocyte antigen (HLA) complex.

In certain embodiments, (a) the $V_\alpha$ domain comprises the CDR3 amino acid sequence of SEQ ID NO:5 and the Vβ domain comprises the CDR3 amino acid sequence of SEQ ID NO:6; (b) the Vα domain comprises the CDR3 amino acid sequence of SEQ ID NO:7 and the Vβ domain comprises the CDR3 amino acid sequence of SEQ ID NO:8; (c) the Vα domain comprises the CDR3 amino acid sequence of SEQ ID NO:9 and the Vβ domain comprises the CDR3 amino acid sequence of SEQ ID NO:10; (d) the Vα domain comprises the CDR3 amino acid sequence of SEQ ID NO:11 and the Vβ domain comprises the CDR3 amino acid sequence of SEQ ID NO:12; (e) the Vα domain comprises the CDR3 amino acid sequence of SEQ ID NO:13 and the Vβ domain comprises the CDR3 amino acid sequence of SEQ ID NO:14; (f) the Vα domain comprises the CDR3 amino acid sequence of SEQ ID NO: 15 and the Vβ domain comprises the CDR3 amino acid sequence of SEQ ID NO: 16; (g) the Vα domain comprises the CDR3 amino acid sequence of SEQ ID NO: 17 and the Vβ domain comprises the CDR3 amino acid sequence of SEQ ID NO:18; (h) the Vα domain comprises the CDR3 amino acid sequence of SEQ ID NO:19 and the Vβ domain comprises the CDR3 amino acid sequence of SEQ ID NO:20; or (i) the Vα domain comprises the CDR3 amino acid sequence of SEQ ID NO:7 and the Vβ domain comprises the CDR3 amino acid sequence of SEQ ID NO:189.

In one aspect, the present disclosure provides a binding protein (e.g., an immunoglobulin superfamily binding protein or portion thereof), comprising: (a) a T cell receptor (TCR) α chain variable ($V_\alpha$) domain comprising a complementary determining region 3 (CDR3) amino acid sequence set forth in any one of SEQ ID NOS: 89 (IMGT), 97 (IMGT), 105, 113 (IMGT), 119 (IMGT), 127 (IMGT), 133 (IMGT), and 137 (IMGT), or a CDR3 amino acid sequence set forth in any one of SEQ ID NOS: 89 (IMGT), 97 (IMGT), 105, 113 (IMGT), 119 (IMGT), 127 (IMGT), 133 (IMGT), and 137 (IMGT) with up to five amino acid substitutions, insertions and/or deletions, and a TCR β chain variable (Vβ) domain; (b) TCR Vα domain, and a TCR $V_\beta$ domain comprising a CDR3 amino acid sequence set forth in any one of SEQ ID NOS:93 (IMGT), 101 (IMGT), 109 (IMGT), 117 (IMGT), 123 (IMGT), 129 (IMGT), 140 (IMGT), and 190 (IMGT), or a CDR3 amino acid sequence set forth in any one of SEQ ID NOS: 93 (IMGT), 101 (IMGT), 109 (IMGT), 117 (IMGT), 123 (IMGT), 129 (IMGT), 140 (IMGT), and 190 (IMGT) with up to five amino acid substitutions, insertions and/or deletions; or (c) a Vα domain of (a) and a Vβ of (b), wherein the binding protein is capable of specifically binding to a human cyclin A1 (CCNA1) peptide 227-235 FLDRFLSCM (SEQ ID NO:1):human leukocyte antigen (HLA) complex.

In certain embodiments, (a) the Vα domain comprises the CDR3 amino acid sequence of SEQ ID NO:89 (IMGT) and the Vβ domain comprises the CDR3 amino acid sequence of SEQ ID NO:93 (IMGT); (b) the Vα domain comprises the CDR3 amino acid sequence of SEQ ID NO:97 (IMGT) and the Vβ domain comprises the CDR3 amino acid sequence of SEQ ID NO:101 (IMGT); (c) the Vα domain comprises the CDR3 amino acid sequence of SEQ ID NO:105 and the Vβ domain comprises the CDR3 amino acid sequence of SEQ ID NO:109 (IMGT); (d) the Vα domain comprises the CDR3 amino acid sequence of SEQ ID NO:113 (IMGT) and the Vβ domain comprises the CDR3 amino acid sequence of SEQ ID NO:117 (IMGT); (e) the Vα domain comprises the CDR3 amino acid sequence of SEQ ID NO:119 (IMGT) and the Vβ domain comprises the CDR3 amino acid sequence of SEQ ID NO:123 (IMGT); (f) the Vα domain comprises the CDR3 amino acid sequence of SEQ ID NO:127 (IMGT) and the Vβ domain comprises the CDR3 amino acid sequence of SEQ ID NO:129 (IMGT); (g) the Vα domain comprises the CDR3 amino acid sequence of SEQ ID NO:133 (IMGT) and the Vβ domain comprises the CDR3 amino acid sequence of SEQ ID NO:129 (IMGT); (h) the Vα domain comprises the CDR3 amino acid sequence of SEQ ID NO:137 (IMGT) and the Vβ domain comprises the CDR3 amino acid sequence of SEQ ID NO:140 (IMGT); or (i) the Vα domain comprises the CDR3 amino acid sequence of SEQ ID NO:97 (IMGT) and the Vβ domain comprises the CDR3 amino acid sequence of SEQ ID NO:190 (IMGT).

Peptide-MHC complexes, such as CCNA1 peptide:MHC complexes, are recognized by and bound through the TCR Vα and TCR Vβ domains. During lymphocyte development, Vα exons are assembled from different variable and joining gene segments (V-J), and Vβ exons are assembled from different variable, diversity, and joining gene segments (V-D-J). The TCRα chromosomal locus has 70-80 variable gene segments and 61 joining gene segments. The TCRβ chromosomal locus has 52 variable gene segments, and two separate clusters of each containing a single diversity gene segment, together with six or seven joining gene segments. Functional Vα and Vβ gene exons are generated by the recombination of a variable gene segment with a joining gene segment for Vα, and a variable gene segment with a diversity gene segment and a joining gene segment for Vβ.

The Vα and Vβ domains each comprise three hypervariable loops, also referred to as complementary determining regions (CDRs) that contact the peptide-MHC complex. CDR1 and CDR2 are encoded within the variable gene segment, whereas CDR3 is encoded by the region spanning the variable and joining segments for Vα, or the region spanning variable, diversity, and joining segments for Vβ. Thus, if the identity of the variable gene segment of a Vα or Vβ is known, the sequences of their corresponding CDR1 and CDR2 can be deduced. Compared with CDR1 and CDR2, CDR3 is significantly more diverse because of the addition and loss of nucleotides during the recombination process.

TCR variable domain sequences can be aligned to a numbering scheme (International Immunogenetics Information System (IMGT) and Aho), allowing equivalent residue positions to be annotated and for different molecules to be compared using Antigen receptor Numbering And Receptor Classification (ANARCI) software tool (2016, Bioinformatics 15:298-300). A numbering scheme provides a standardized delineation of framework regions and CDRs in the TCR variable domains.

Table 1 provides the identities of the variable gene segment and joining gene segment for a TCR Vα comprising a CDR3 comprising an amino acid sequence of any one of SEQ ID NOS:5, 7, 9, 11, 13, 15, 17, 19, 21, and 23, and the identities of the variable gene segment and joining gene segment for a TCR Vβ comprising a CDR3 comprising an amino acid sequence of any one of SEQ ID NOS:6, 8, 10, 12, 14, 16, 18, 20, 22, 24, and 189. Accordingly, the CDR1 and CDR2 sequences of the Vα and Vβ domains may be deduced from the corresponding variable gene segments.

In some embodiments, (a) the Vβ domain comprises the CDR1 amino acid sequence encoded by a TRBV9*01 gene; and the Vα domain comprises the CDR1 amino acid sequence encoded by a TRAV30*01 gene; (b) the Vβ domain comprises the CDR1 amino acid sequence encoded by a TRBV2*01 gene; and the Vα domain comprises the CDR1 amino acid sequence encoded by a TRAV10*01 gene; (c) the Vβ domain comprises the CDR1 amino acid sequence encoded by a TRBV6-6*01 gene; and the Vα domain comprises the CDR1 amino acid sequence encoded by a TRAV24*01 gene; (d) the Vβ domain comprises the CDR1 amino acid sequence encoded by a TRBV5-6*01 gene; and the Vα domain comprises the CDR1 amino acid sequence encoded by a TRAV21*01 gene; (e) the Vβ domain comprises the CDR1 amino acid sequence encoded by a TRBV7-3*01 gene; and the Vα domain comprises the CDR1 amino acid sequence encoded by a TRAV21*02 gene; (f) the Vβ domain comprises the CDR1 amino acid sequence encoded by a TRBV7-3*01 gene; and the Vα domain comprises the CDR1 amino acid sequence encoded by a TRAV12-2*02 gene; (g) the Vβ domain comprises the CDR1 amino acid sequence encoded by a TRBV7-3*01 gene; and the Vα domain comprises the CDR1 amino acid sequence encoded by a TRAV17*01 gene; (h) the Vβ domain comprises the CDR1 amino acid sequence encoded by a TRBV7-2*01 gene; and the Vα domain comprises the CDR1 amino acid sequence encoded by a TRAV17*01 gene; or (i) the Vβ domain comprises the CDR1 amino acid sequence encoded by a TRBV10-2*01 gene; and the Vα domain comprises the CDR1 amino acid sequence encoded by a TRAV10*01 gene.

In some embodiments, (a) the Vβ domain comprises the CDR1 amino acid sequence of SEQ ID NO:91 and the Vα domain comprises the CDR1 amino acid sequence of SEQ ID NO:87; (b) the Vβ domain comprises the CDR1 amino acid sequence of SEQ ID NO:99 and the Vα domain comprises the CDR1 amino acid sequence of SEQ ID NO:95; (c) the Vβ domain comprises the CDR1 amino acid sequence of SEQ ID NO:107 and the Vα domain comprises the CDR1 amino acid sequence of SEQ ID NO:103; (d) the Vβ domain comprises the CDR1 amino acid sequence of SEQ ID NO:115 and the Vα domain comprises the CDR1 amino acid sequence of SEQ ID NO:111; (e) the Vβ domain comprises the CDR1 amino acid sequence of SEQ ID NO:121 and the Vα domain comprises the CDR1 amino acid sequence of SEQ ID NO:111; (f) the Vβ domain comprises the CDR1 amino acid sequence of SEQ ID NO: 121 and the Vα domain comprises the CDR1 amino acid sequence of SEQ ID NO:125; (g) the Vβ domain comprises the CDR1 amino acid sequence of SEQ ID NO:121 and the Vα domain comprises the CDR1 amino acid sequence of SEQ ID NO:131; or (h) the Vβ domain comprises the CDR1 amino acid sequence of SEQ ID NO:167 and the Vα domain comprises the CDR1 amino acid sequence of SEQ ID NO:95.

In some embodiments, (a) the Vβ domain comprises the CDR2 amino acid sequence encoded by a TRBV9*01 gene; and the Vα domain comprises the CDR2 amino acid sequence encoded by a TRAV30*01 gene; (b) the Vβ domain comprises the CDR2 amino acid sequence encoded by a TRBV2*01 gene; and the Vα domain comprises the CDR2 amino acid sequence encoded by a TRAV10*01 gene; (c) the Vβ domain comprises the CDR2 amino acid sequence encoded by a TRBV6-6*01 gene; and the Vα domain comprises the CDR2 amino acid sequence encoded by a TRAV24*01 gene; (d) the Vβ domain comprises the CDR2 amino acid sequence encoded by a TRBV5-6*01 gene; and the Vα domain comprises the CDR2 amino acid sequence encoded by a TRAV21*01 gene; (e) the Vβ domain comprises the CDR2 amino acid sequence encoded by a TRBV7-3*01 gene; and the Vα domain comprises the CDR2 amino acid sequence encoded by a TRAV21*02 gene; (f) the Vβ domain comprises the CDR2 amino acid sequence encoded by a TRBV7-3*01 gene; and the Vα domain comprises the CDR2 amino acid sequence encoded by a TRAV12-2*02 gene; (g) the Vβ domain comprises the CDR2 amino acid sequence encoded by a TRBV7-3*01 gene; and the Vα domain comprises the CDR2 amino acid sequence encoded by a TRAV17*01 gene; (h) the Vβ domain comprises the CDR2 amino acid sequence encoded by a TRBV7-2*01 gene; and the Vα domain comprises the CDR2 amino acid sequence encoded by a TRAV17*01 gene; or (i) the Vβ domain comprises the CDR2 amino acid sequence encoded by a TRBV10-2*01 gene; and the Vα domain comprises the CDR2 amino acid sequence encoded by a TRAV10*01 gene.

In some embodiments, (a) the Vβ domain comprises the CDR2 amino acid sequence of SEQ ID NO:92 and the Vα domain comprises the CDR2 amino acid sequence of SEQ ID NO:88; (b) the Vβ domain comprises the CDR2 amino acid sequence of SEQ ID NO:100 and the Vα domain comprises the CDR2 amino acid sequence of SEQ ID NO:96; (c) the Vβ domain comprises the CDR2 amino acid sequence of SEQ ID NO: 108 and the Vα domain comprises the CDR2 amino acid sequence of SEQ ID NO:104; (d) the Vβ domain comprises the CDR2 amino acid sequence of SEQ ID NO:116 and the Vα domain comprises the CDR2 amino acid sequence of SEQ ID NO:112; (e) the Vβ domain comprises the CDR2 amino acid sequence of SEQ ID NO:122 and the Vα domain comprises the CDR2 amino acid sequence of SEQ ID NO:112; (f) the Vβ domain comprises the CDR2 amino acid sequence of SEQ ID NO:122 and the Vα domain comprises the CDR2 amino acid sequence of SEQ ID NO:126; (g) the Vβ domain comprises the CDR2 amino acid sequence of SEQ ID NO:122 and the Vα domain comprises the CDR2 amino acid sequence of SEQ ID NO:132; (h) the Vβ domain comprises the CDR2 amino acid sequence of SEQ ID NO:129 and the Vα domain comprises the CDR2 amino acid sequence of SEQ ID NO:132; or (i) the Vβ domain comprises the CDR2 amino acid sequence of SEQ ID NO:168 and the Vα domain comprises the CDR2 amino acid sequence of SEQ ID NO:96.

Thus, in certain embodiments, (a) the Vβ domain comprises the CDR3 amino acid sequence of SEQ ID NO:6 or 93 (IMGT) and a CDR1 amino acid sequence and a CDR2 amino acid sequence encoded by a TRBV9*01 gene; and the Vα domain comprises the CDR3 amino acid sequence of SEQ ID NO:5 or 89 (IMGT) and a CDR1 amino acid sequence and a CDR2 amino acid sequence encoded by a TRAV30*01 gene; (b) the Vβ domain comprises the CDR3 amino acid sequence of SEQ ID NO:8 or 190 (IMGT) and a CDR1 amino acid sequence and a CDR2 amino acid sequence encoded by a TRBV2*01 gene; and the Vα domain comprises the CDR3 amino acid sequence of SEQ ID NO:7 or 97 (IMGT) and a CDR1 amino acid sequence and a CDR2 amino acid sequence encoded by a TRAV10*01 gene; (c) the Vβ domain comprises the CDR3 amino acid sequence of SEQ ID NO:10 or 109 (IMGT) and a CDR1 amino acid sequence and a CDR2 amino acid sequence encoded by a TRBV6-6*01 gene; and the Vα domain comprises the CDR3 amino acid sequence of SEQ ID NO:9 or 105 and a CDR1 amino acid sequence and a CDR2 amino acid sequence encoded by a TRAV24*01 gene; (d) the Vβ domain comprises the CDR3 amino acid sequence of SEQ ID NO:12 or 117 (IMGT) and a CDR1 amino acid sequence and a CDR2 amino acid sequence encoded by a TRBV5-6*01 gene; and the Vα domain comprises the CDR3 amino acid sequence of SEQ ID NO:11 or 113 (IMGT) and a CDR1 amino acid sequence and a CDR2 amino acid sequence encoded by a TRAV21*01 gene; (e) the Vβ domain comprises the CDR3 amino acid sequence of SEQ ID NO:14 or 123 (IMGT) and a CDR1 amino acid sequence and a CDR2 amino acid sequence encoded by a TRBV7-3*01 gene; and the Vα domain comprises the CDR3 amino acid sequence of SEQ ID NO:13 or 119 (IMGT) and a CDR1 amino acid sequence and a CDR2 amino acid sequence encoded by a TRAV21*02 gene; (f) the Vβ domain comprises the CDR3 amino acid sequence of SEQ ID NO:16 or 129 (IMGT) and a CDR1 amino acid sequence and a CDR2 amino acid sequence encoded by a TRBV7-3*01 gene; and the Vα domain comprises the CDR3 amino acid sequence of SEQ ID NO:15 or 127 (IMGT) and a CDR1 amino acid sequence and a CDR2 amino acid sequence encoded by a TRAV12-2*02 gene; (g) the Vβ domain comprises the CDR3 amino acid sequence of SEQ ID NO:18 or 129 (IMGT) and a CDR1 amino acid sequence and a CDR2 amino acid sequence encoded by a TRBV7-3*01 gene; and the Vα domain comprises the CDR3 amino acid sequence of SEQ ID NO:17 or 133 (IMGT) and a CDR1 amino acid sequence and a CDR2 amino acid sequence encoded by a TRAV17*01 gene; (h) the Vβ domain comprises the CDR3 amino acid sequence of SEQ ID NO:20 or 140 (IMGT) and a CDR1 amino acid sequence and a CDR2 amino acid sequence encoded by a TRBV7-2*01 gene; and the Vα domain comprises the CDR3 amino acid sequence of SEQ ID NO:19 or 137 (IMGT) and a CDR1 amino acid sequence and a CDR2 amino acid sequence encoded by a TRAV17*01 gene; or (i) the Vβ domain comprises the CDR3 amino acid sequence of SEQ ID NO:189 or 101 (IMGT) and a CDR1 amino acid sequence and a CDR2 amino acid sequence encoded by a TRBV10-2*01 gene; and the Vα domain comprises the CDR3 amino acid sequence of SEQ ID NO:7 or 97 (IMGT) and a CDR1 amino acid sequence and a CDR2 amino acid sequence encoded by a TRAV10*01 gene.

In certain embodiments, (a) the Vβ domain comprises the CDR1 amino acid sequence of SEQ ID NO: 91, the CDR2 amino acid sequence of SEQ ID NO:92, and the CDR3 amino acid sequence of SEQ ID NO:6 or 93 (IMGT); and the Vα domain comprises the CDR1 amino acid sequence of SEQ ID NO:87, the CDR2 amino acid sequence of SEQ ID NO:88, and the CDR3 amino acid sequence of SEQ ID NO:5 or 89 (IMGT); (b) the Vβ domain comprises the CDR1 amino acid sequence of SEQ ID NO:99, the CDR2 amino acid sequence of SEQ ID NO:100, and the CDR3 amino acid sequence of SEQ ID NO:189 or 101 (IMGT); and the Vα domain comprises the CDR1 amino acid sequence of SEQ ID NO:95, the CDR2 amino acid sequence of SEQ ID NO:96, and the CDR3 amino acid sequence of SEQ ID NO:7 or 97 (IMGT); (c) the Vβ domain comprises the CDR1 amino acid sequence of SEQ ID NO:107, the CDR2 amino acid sequence of SEQ ID NO:108, and the CDR3 amino acid sequence of SEQ ID NO:10 or 109 (IMGT); and the Vα domain comprises the CDR1 amino acid sequence of SEQ ID NO: 103, the CDR2 amino acid sequence of SEQ ID NO:104, and the CDR3 amino acid sequence of SEQ ID NO:9 or 105; (d) the Vβ domain comprises the CDR1 amino acid sequence of SEQ ID NO:115, the CDR2 amino acid sequence of SEQ ID NO:116, and the CDR3 amino acid sequence of SEQ ID NO:12 or 117 (IMGT); and the Vα domain comprises the CDR1 amino acid sequence of SEQ ID NO:111, the CDR2 amino acid sequence of SEQ ID NO:112, and the CDR3 amino acid sequence of SEQ ID NO:11 or 113 (IMGT); (e) the Vβ domain comprises the CDR1 amino acid sequence of SEQ ID NO:121, the CDR2 amino acid sequence of SEQ ID NO:122, and the CDR3 amino acid sequence of SEQ ID NO:14 or 123 (IMGT); and the Vα domain comprises the CDR1 amino acid sequence of SEQ ID NO:111, the CDR2 amino acid sequence of SEQ ID NO:112, and the CDR3 amino acid sequence of SEQ ID NO:13 or 119 (IMGT); (f) the Vβ domain comprises the CDR1 amino acid sequence of SEQ ID NO:121, the CDR2 amino acid sequence of SEQ ID NO:122, and the CDR3 amino acid sequence of SEQ ID NO:16 or 129 (IMGT); and the Vα domain comprises the CDR1 amino acid sequence of SEQ ID NO:125, the CDR2 amino acid sequence of SEQ ID NO:126, and the CDR3 amino acid sequence of SEQ ID NO:15 or 127 (IMGT); (g) the Vβ domain comprises the CDR1 amino acid sequence of SEQ ID NO:121, the CDR2 amino acid sequence of SEQ ID NO:122, and the CDR3 amino acid sequence of SEQ ID NO:18 or 129 (IMGT); and the Vα domain comprises the CDR1 amino acid sequence of SEQ ID NO:131, the CDR2 amino acid sequence of SEQ ID NO:132, and the CDR3 amino acid sequence of SEQ ID NO:17 or 133 (IMGT); (h) the Vβ domain comprises the CDR1 amino acid sequence of SEQ ID NO:121, the CDR2 amino acid sequence of SEQ ID NO:139, and the CDR3 amino acid sequence of SEQ ID NO:20 or 140 (IMGT); and the Vα domain comprises the CDR1 amino acid sequence of SEQ ID NO:131, the CDR2 amino acid sequence of SEQ ID NO:132, and the CDR3 amino acid sequence of SEQ ID NO:19 or 137 (IMGT); or (i) the Vβ domain comprises the CDR1 amino acid sequence of SEQ ID NO:167, the CDR2 amino acid sequence of SEQ ID NO:168, and the CDR3 amino acid sequence of SEQ ID NO:8 or 190 (IMGT); and the Vα domain comprises the CDR1 amino acid sequence of SEQ ID NO:95, the CDR2 amino acid sequence of SEQ ID NO:96, and the CDR3 amino acid sequence of SEQ ID NO:7 or 97(IMGT).

In certain embodiments, the binding protein comprises: (a) a Vα domain that is at least about 75%, 80%, 85%, 90%, 91%, 92%, 93%, 94%, 95%, 96%, 97%, 98%, 99%, or 100% identical to the Vα amino acid sequence contained in any one of SEQ ID NOS:36, 38, 40, 42, 44, 86, 49, 51, 53, 57, 59, 63, 65, 67, 81, and 83; (b) a Vβ domain that is at least about 75%, 80%, 85%, 90%, 91%, 92%, 93%, 94%, 95%, 96%, 97%, 98%, 99%, or 100% identical to the Vβ amino acid sequence contained in any one of SEQ ID NOS:36, 38, 40, 42, 46, 86, 49, 51, 55, 57, 61, 63, 67, 81, and 83; or (c) a Vα domain of (a) and a Vβ of (b); wherein at least three or four of the CDRs have no mutations and the CDRs that do have mutations have three or less amino acid substitutions, insertions, and/or deletions. Such variant Vα and Vβ may be used in binding proteins described herein provided that the binding proteins retain or substantially retain the ability to specifically bind to CCNA1 peptide (SEQ ID NO:1):HLA complex.

In further embodiments, the binding protein comprises: (a) a Vα domain comprising or consisting of the Vα amino acid sequence contained in any one of SEQ ID NOS: 36, 38, 40, 42, 44, 86, 49, 51, 53, 57, 59, 63, 65, 67, 81, 83, 162, 165, 170, 172, 174, 176, 178, 180, and 186; (b) a Vβ domain comprising or consisting of the Vβ amino acid sequence contained in any one of SEQ ID NOS:36, 38, 40, 42, 46, 86, 49, 51, 55, 57, 61, 63, 67, 81, 83, 162, 165, 170, 172, 174, 176, 178, 180, and 186; or (c) a Vα domain of (a) and a Vβ of (b).

In some embodiments, the binding protein comprises: (a) a Vα domain that is at least about 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID NOS:90, 98, 106, 114, 120, 128, 134, and 138; (b) a Vβ domain that is at least about 75%, 80%, 85%, 86%, 87%, 88%, 89%, 90%, 91%, 92%, 93%, 94%, 95%, 96%, 97%, 98%, 99%, or 100% identical to the amino acid sequence of any one of SEQ ID NOS:94, 102, 110, 118, 124, 130, 136, 141, and 166; or (c) a Vα domain of (a) and a Vβ of (b), wherein at least three or four of the CDRs have no mutations and the CDRs that do have mutations have three or less amino acid substitutions, insertions, and/or deletions. Such variant Vα and Vβ may be used in binding proteins described herein provided that the binding proteins retain or substantially retain the ability to specifically bind to CCNA1 peptide (SEQ ID NO:1):HLA complex.

In some embodiments, the binding protein comprises: (a) a Vα domain comprising or consisting of the amino acid sequence of any one of SEQ ID NOS:90, 98, 106, 114, 120, 128, 134, and 138; (b) a Vβ domain comprising or consisting of the Vβ amino acid sequence of any one of SEQ ID NOS:94, 102, 110, 118, 124, 130, 136, 141, and 166; or (c) a Vα domain of (a) and a Vβ of (b).

An exemplary binding protein comprises: (a) the Vα domain comprising the Vα amino acid sequence contained in SEQ ID NO:36 and the Vβ domain comprising the Vβ amino acid sequence contained in SEQ ID NO:36; (b) the Vα domain comprising the Vα amino acid sequence contained in SEQ ID NO:38 and the Vβ domain comprising the Vβ amino acid sequence contained in SEQ ID NO:38; (c) the Vα domain comprising the Vα amino acid sequence contained in SEQ ID NO:40 and the Vβ domain comprising the Vβ amino acid sequence contained in SEQ ID NO:40; (d) the Vα domain comprising the Vα amino acid sequence contained in SEQ ID NO:42 and the Vβ domain comprising the Vβ amino acid sequence contained in SEQ ID NO:42; (e) the Vα domain comprising the Vα amino acid sequence contained in SEQ ID NO:44 and the Vβ domain comprising the Vβ amino acid sequence contained in SEQ ID NO:46; (f) the Vα domain comprising the Vα amino acid sequence contained in SEQ ID NO:86 and the Vβ domain comprising the Vβ amino acid sequence contained in SEQ ID NO:86; (g) the Vα domain comprising the Vα amino acid sequence contained in SEQ ID NO:49 and the Vβ domain comprising the Vβ amino acid sequence contained in SEQ ID NO:49; (h) the Vα domain comprising the Vα amino acid sequence contained in SEQ ID NO: 51 and the Vβ domain comprising the Vβ amino acid sequence contained in SEQ ID NO:51; (i) the Vα domain comprising the Vα amino acid sequence contained in SEQ ID NO:53 and the Vβ domain comprising the Vβ amino acid sequence contained in SEQ ID NO:55; (j) the Vα domain comprising the Vα amino acid sequence contained in SEQ ID NO: 57 and the Vβ domain comprising the Vβ amino acid sequence contained in SEQ ID NO:57; (k) the Vα domain comprising the Vα amino acid sequence contained in SEQ ID NO:59 and the Vβ domain comprising the Vβ amino acid sequence contained in SEQ ID NO:61; (1) the Vα domain comprising the Vα amino acid sequence contained in SEQ ID NO:63 and the Vβ domain comprising the Vβ amino acid sequence contained in SEQ ID NO:63; (m) the Vα domain comprising the Vα amino acid sequence contained in SEQ ID NO:65 and the Vβ domain comprising the Vβ amino acid sequence contained in SEQ ID NO:67; (n) the Vα domain comprising the Vα amino acid sequence contained in SEQ ID NO:67 and the Vβ domain comprising the Vβ amino acid sequence contained in SEQ ID NO:67; (o) the Vα domain comprising the Vα amino acid sequence contained in SEQ ID NO:81 and the Vβ domain comprising the Vβ amino acid sequence contained in SEQ ID NO:81; (p) the Vα domain comprising the Vα amino acid sequence contained in SEQ ID NO:83 and the Vβ domain comprising the Vβ amino acid sequence contained in SEQ ID NO:83; (q) the Vα domain comprising the Vα amino acid sequence contained in SEQ ID NO:162 and the Vβ domain comprising the Vβ amino acid sequence contained in SEQ ID NO:162; (r) the Vα domain comprising the Vα amino acid sequence contained in SEQ ID NO:165 and the Vβ domain comprising the Vβ amino acid sequence contained in SEQ ID NO:165; (s) the Vα domain comprising the Vα amino acid sequence contained in SEQ ID NO:170 and the Vβ domain comprising the Vβ amino acid sequence contained in SEQ ID NO:170; (t) the Vα domain comprising the Vα amino acid sequence contained in SEQ ID NO:172 and the Vβ domain comprising the Vβ amino acid sequence contained in SEQ ID NO:172; (u) the Vα domain comprising the Vα amino acid sequence contained in SEQ ID NO:174 and the Vβ domain comprising the Vβ amino acid sequence contained in SEQ ID NO:174; (v) the Vα domain comprising the Vα amino acid sequence contained in SEQ ID NO:176 and the Vβ domain comprising the Vβ amino acid sequence contained in SEQ ID NO:176; (w) the Vα domain comprising the Vα amino acid sequence contained in SEQ ID NO:178 and the Vβ domain comprising the Vβ amino acid sequence contained in SEQ ID NO:178; (x) the Vα domain comprising the Vα amino acid sequence contained in SEQ ID NO:180 and the Vβ domain comprising the Vβ amino acid sequence contained in SEQ ID NO:180; or (y) the Vα domain comprising the Vα amino acid sequence contained in SEQ ID NO:186 and the Vβ domain comprising the Vβ amino acid sequence contained in SEQ ID NO:186.

An exemplary binding protein comprises: (a) the Vα domain comprising the amino acid sequence of SEQ ID NO:90 and the Vβ domain comprising the amino acid sequence of SEQ ID NO:94; (b) the Vα domain comprising the amino acid sequence of SEQ ID NO:98 and the Vβ domain comprising the amino acid sequence of SEQ ID NO:102; (c) the Vα domain comprising the amino acid sequence of SEQ ID NO:106 and the Vβ domain comprising the amino acid sequence of SEQ ID NO:110; (d) the Vα domain comprising the amino acid sequence of SEQ ID NO:114 and the Vβ domain comprising the amino acid sequence of SEQ ID NO:118; (e) the Vα domain comprising the amino acid sequence of SEQ ID NO:120 and the Vβ domain comprising the amino acid sequence of SEQ ID NO:124; (f) the Vα domain comprising the amino acid sequence of SEQ ID NO:128 and the Vβ domain comprising the amino acid sequence of SEQ ID NO:130; (g) the Vα domain comprising the amino acid sequence of SEQ ID NO:134 and the Vβ domain comprising the amino acid sequence of SEQ ID NO:136; (h) the Vα domain comprising the amino acid sequence of SEQ ID NO:138 and the Vβ domain comprising the amino acid sequence of SEQ ID NO:141; or (i) the Vα domain comprising the amino acid sequence of SEQ ID NO:98 and the Vβ domain comprising the amino acid sequence of SEQ ID NO: 166.

In another aspect, the present disclosure provides a binding protein (e.g., an immunoglobulin superfamily binding protein or portion thereof), comprising: (a) a T cell receptor (TCR) α chain variable (Vα) domain comprising a complementary determining region 3 (CDR3) amino acid sequence set forth in SEQ ID NO:21 or 143 (IMGT), or a CDR3 amino acid sequence set forth in SEQ ID NO:21 or 143 (IMGT) with up to five amino acid substitutions, insertions and/or deletions, and a TCR β chain variable (Vβ) domain; (b) a TCR Vα domain, and a TCR Vβ domain comprising a CDR3 amino acid sequence set forth in SEQ ID NO:22 or 147 (IMGT), or a CDR3 amino acid sequence set forth in SEQ ID NO:22 or 147 (IMGT) with up to five amino acid substitutions, insertions and/or deletions; or (c) a Vα domain of (a) and a Vβ of (b), wherein the binding protein is capable of specifically binding to a human cyclin A1 (CCNA1) peptide 341-351 SLIAAAAFCLA (SEQ ID NO:2):human leukocyte antigen (HLA) complex. In specific embodiments, the Vα domain comprises the CDR3 amino acid sequence of SEQ ID NO:21 or 143 (IMGT) and the Vβ domain comprises the CDR3 amino acid sequence of SEQ ID NO:22 or 147 (IMGT).

In some embodiments, (a) the Vβ domain comprises the CDR1 amino acid sequence encoded by a TRBV19*01 gene; and the Vα domain comprises the CDR1 amino acid sequence encoded by a TRAV24*01 gene. In some embodiments, (a) the Vβ domain comprises the CDR1 amino acid sequence of SEQ ID NO:145 and the Vα domain comprises the CDR1 amino acid sequence of SEQ ID NO:103.

In some embodiments, (a) the Vβ domain comprises the CDR2 amino acid sequence encoded by a TRBV19*01 gene; and the Vα domain comprises the CDR2 amino acid sequence encoded by a TRAV24*01 gene. In some embodiments, (a) the Vβ domain comprises the CDR2 amino acid sequence of SEQ ID NO:146 and the Vα domain comprises the CDR2 amino acid sequence of SEQ ID NO:142.

In certain embodiments, the Vβ domain comprises: (a) the CDR3 amino acid sequence of SEQ ID NO:22 or 147 (IMGT) and a CDR1 amino acid sequence and a CDR2 amino acid sequence encoded by a TRBV19*01 gene; (b) the Vα domain comprises the CDR3 amino acid sequence of SEQ ID NO:21 or 143 (IMGT) and a CDR1 amino acid sequence and a CDR2 amino acid sequence encoded by a TRAV24*01 gene; or both (a) and (b).

In certain embodiments, (a) the Vβ domain comprises the CDR1 amino acid sequence of SEQ ID NO: 145, the CDR2 amino acid sequence of SEQ ID NO:146, and the CDR3 amino acid sequence of SEQ ID NO:147 (IMGT); and the Vα domain comprises the CDR1 amino acid sequence of SEQ ID NO:103, the CDR2 amino acid sequence of SEQ ID NO:142, and the CDR3 amino acid sequence of SEQ ID NO:143 (IMGT).

In certain embodiments, the binding protein comprises (a) a Vα domain that is at least about 75%, 80%, 85%, 90%, 91%, 92%, 93%, 94%, 95%, 96%, 97%, 98%, 99%, or 100% identical to the Vα amino acid sequence of SEQ ID NO:69 or contained in SEQ ID NO:73 or 182; (b) a Vβ domain that is at least about 75%, 80%, 85%, 90%, 91%, 92%, 93%, 94%, 95%, 96%, 97%, 98%, 99%, or 100% identical to the Vβ amino acid sequence of SEQ ID NO:71 or contained in SEQ ID NO:73 or 182; or (c) a Vα domain of (a) and a Vβ of (b); wherein at least three or four of the CDRs have no mutations and the CDRs that do have mutations have three or less amino acid substitutions, insertions, and/or deletions. Such variant Vα and Vβ domains may be used in binding proteins described herein provided that the binding proteins retain or substantially retain the ability to specifically bind to CCNA1 peptide (SEQ ID NO:2):HLA complex.

In some embodiments, the binding protein comprises: (a) a Vα domain that is at least about 75%, 85%, 86%, 87%, 88%, 89%, 90%, 91%, 92%, 93%, 94%, 95%, 96%, 97%, 98%, 99%, or 100% identical to the amino acid sequence of SEQ ID NO:144; (b) a Vβ domain that is at least about 75%, 85%, 86%, 87%, 88%, 89%, 90%, 91%, 92%, 93%, 94%, 95%, 96%, 97%, 98%, 99%, or 100% identical to the amino acid sequence of SEQ ID NO:148; or (c) a Vα domain of (a) and a Vβ of (b).

In some embodiments, the binding protein comprises: (a) a Vα domain comprising or consisting of the amino acid sequence of SEQ ID NO:144; (b) a Vβ comprising or consisting of the amino acid sequence of SEQ ID NO:148; or (c) a Vα domain of (a) and a Vβ of (b). In some aspects, the exemplary binding protein comprises the Vα domain comprising the amino acid sequence of SEQ ID NO:144 and the Vβ domain comprising the amino acid sequence of SEQ ID NO:148.

In certain embodiments, the binding protein comprises: (a) a Vα domain comprising or consisting of the Vα amino acid sequence of SEQ ID NO:69 or contained in SEQ ID NO:73; (b) a Vβ domain comprising or consisting of the Vβ amino acid sequence of SEQ ID NO:71 or contained in SEQ ID NO:73; or (c) a Vα domain of (a) and a Vβ of (b). In specific embodiments, the binding protein comprises: (a) the Vα domain comprising the Vα amino acid sequence of SEQ ID NO:69 and the Vβ domain comprising the Vβ amino acid sequence of SEQ ID NO:71; or (b) the Vα domain comprising the Vα amino acid sequence contained in SEQ ID NO:73 and the Vβ domain comprising the Vβ amino acid sequence contained in SEQ ID NO:73.

In another aspect, the present disclosure provides a binding protein (e.g., an immunoglobulin superfamily binding protein or portion thereof), comprising: (a) a T cell receptor (TCR) α chain variable (Vα) domain comprising a complementary determining region 3 (CDR3) amino acid sequence set forth in SEQ ID NO:23 or 151 (IMGT), or a CDR3 amino acid sequence set forth in SEQ ID NO:23 or 151 (IMGT) with up to five amino acid substitutions, insertions and/or deletions, and a TCR β chain variable (Vβ) domain; (b) a TCR Vα domain, and a TCR Vβ domain comprising a CDR3 amino acid sequence set forth in SEQ ID NO:24 or 153 (IMGT), or a CDR3 amino acid sequence set forth in SEQ ID NO:24 or 153 (IMGT) with up to five amino acid substitutions, insertions and/or deletions; or (c) a Vα domain of (a) and a Vβ of (b), wherein the binding protein is capable of specifically binding to a human cyclin A1 (CCNA1) peptide 370-379 YSLSEIVPCL (SEQ ID NO:3):human leukocyte antigen (HLA) complex.

In certain embodiments, the Vα domain comprises the CDR3 amino acid sequence of SEQ ID NO:23 or 151 (IMGT) and the Vβ domain comprises the CDR3 amino acid sequence of SEQ ID NO:24 or 153 (IMGT).

In some embodiments, (a) the Vβ domain comprises the CDR1 amino acid sequence encoded by a TRBV5-6*01 gene; and the Vα domain comprises the CDR1 amino acid sequence encoded by a TRAV19*01 gene. In some embodiments, (a) the Vβ domain comprises the CDR1 amino acid sequence of SEQ ID NO:115 and the Vα domain comprises the CDR1 amino acid sequence of SEQ ID NO:149.

In some embodiments, (a) the Vβ domain comprises the CDR2 amino acid sequence encoded by a TRBV5-6*01 gene; and the Vα domain comprises the CDR2 amino acid sequence encoded by a TRAV19*01 gene. In some embodiments, (a) the Vβ domain comprises the CDR2 amino acid sequence of SEQ ID NO:116 and the Vα domain comprises the CDR2 amino acid sequence of SEQ ID NO:150.

In certain embodiments, (a) the Vβ domain comprises the CDR3 amino acid sequence of SEQ ID NO:24 or 153

(IMGT) and a CDR1 amino acid sequence and a CDR2 amino acid sequence encoded by a TRBV5-6*01 gene; (b) the Vα domain comprises the CDR3 amino acid sequence of SEQ ID NO:23 or 151 (IMGT) and a CDR1 amino acid sequence and a CDR2 amino acid sequence encoded by a TRAV19*01 gene; or both (a) and (b).

In certain embodiments, (a) the Vβ domain comprises the CDR1 amino acid sequence of SEQ ID NO: 115, the CDR2 amino acid sequence of SEQ ID NO:116, and the CDR3 amino acid sequence of SEQ ID NO:153 (IMGT); and the Vα domain comprises the CDR1 amino acid sequence of SEQ ID NO:149, the CDR2 amino acid sequence of SEQ ID NO:150, and the CDR3 amino acid sequence of SEQ ID NO:151 (IMGT).

In certain embodiments, the binding protein comprises: (a) a Vα domain that is at least about 75%, 80%, 85%, 90%, 91%, 92%, 93%, 94%, 95%, 96%, 97%, 98%, 99%, or 100% identical to the Vα amino acid sequence contained in SEQ ID NO:75, 79, or 184; (b) a Vβ domain that is at least about 75%, 80%, 85%, 90%, 91%, 92%, 93%, 94%, 95%, 96%, 97%, 98%, 99%, or 100% identical to the Vβ amino acid sequence contained in SEQ ID NO:77, 79, or 184; or (c) a Vα domain of (a) and a Vβ of (b); wherein at least three or four of the CDRs have no mutations and the CDRs that do have mutations have three or less amino acid substitutions, insertions, and/or deletions. Such variant Vα and Vβ domains may be used in binding proteins described herein provided that the binding proteins retain or substantially retain the ability to specifically bind to CCNA1 peptide (SEQ ID NO:3):HLA complex.

In some embodiments, the binding protein comprises: (a) a Vα domain that is at least about 75%, 85%, 86%, 87%, 88%, 89%, 90%, 91%, 92%, 93%, 94%, 95%, 96%, 97%, 98%, 99%, or 100% identical to the amino acid sequence of SEQ ID NO: 152; (b) a Vβ domain that is at least about 75%, 85%, 86%, 87%, 88%, 89%, 90%, 91%, 92%, 93%, 94%, 95%, 96%, 97%, 98%, 99% or 100% identical to the amino acid sequence of SEQ ID NO:154; or (c) a Vα domain of (a) and a Vβ of (b). In some embodiments, the binding protein comprises: (a) a Vα domain comprising or consisting of the amino acid sequence of SEQ ID NO:152; (b) a Vβ domain comprising or consisting of the amino acid sequence of SEQ ID NO:154; or (c) a Vα domain of (a) and a Vβ of (b). In some aspects, the exemplary binding protein comprises the Vα domain comprising the amino acid sequence of SEQ ID NO:152 and the Vβ domain comprising the amino acid sequence of SEQ ID NO: 154.

In certain embodiments, the binding protein comprises: (a) a Vα domain comprising or consisting of the Vα amino acid sequence contained in SEQ ID NO:75, 79, or 184; (b) a Vβ domain comprising or consisting of the Vβ amino acid sequence contained in SEQ ID NO:77, 79, or 184; or (c) a Vα domain of (a) and a Vβ of (b). In specific embodiments, the binding protein comprises: (a) the Vα domain comprising the Vα amino acid sequence contained in SEQ ID NO:75 and the Vβ domain comprising the Vβ amino acid sequence contained in SEQ ID NO:77; (b) the Vα domain comprising the Vα amino acid sequence contained in SEQ ID NO:79 and the Vβ domain comprising the Vβ amino acid sequence contained in SEQ ID NO:79; or (c)) the Vα domain comprising the Vα amino acid sequence contained in SEQ ID NO:184 and the Vβ domain comprising the Vβ amino acid sequence contained in SEQ ID NO:184.

In another aspect, the present disclosure provides binding proteins that are capable of specifically binding to a CCNA1 peptide YSLSEIVPCL (SEQ ID NO:3). In certain embodiments, the binding protein is capable of binding to CCNA1 peptide YSLSEIVPCL (SEQ ID NO:3):HLA complex.

Methods of identifying binding pairs of TCR Vα and Vβ domains are known in the art and include, for example, PCT Patent Publication No. WO 2016/161273; Redmond et al., 2016, Genome Med. 8: 80; Munson et al., 2016, Proc. Natl. Acad. Sci. 113:8272-7; Kim et al., 2012, PLoS ONE 7:e37338 (each of the methods from which are incorporated by reference in its entirety). Accordingly, a Vα domain for the CCNA1-specific Vβ domains described herein (e.g., a Vβ domain comprising CDR3 as set forth in any one of SEQ ID NOS: 6, 8, 10, 12, 14, 16, 18, 20, 22, 24, 93 (IMGT), 101 (IMGT), 109 (IMGT), 117 (IMGT), 123 (IMGT), 129 (IMGT), 140 (IMGT), 147 (IMGT), 153 (IMGT), 189, or 190 (IMGT)), or vice versa (e.g., a Vα domain comprising CDR3 as set forth in any one of SEQ ID NOS: 5, 7, 9, 11, 13, 15, 17, 19, 21, 23, 89 (IMGT), 97 (IMGT), 105, 113 (IMGT), 119 (IMGT), 127 (IMGT), 133 (IMGT), 137 (IMGT), 143 (IMGT), or 151 (IMGT)), may be identified using methods known in the art.

Conservative substitutions of amino acids are well known and may occur naturally or may be introduced when the binding protein or TCR is recombinantly produced. Amino acid substitutions, deletions, and additions may be introduced into a protein using mutagenesis methods known in the art (see, e.g., Sambrook et al., *Molecular Cloning: A Laboratory Manual,* 3d ed., Cold Spring Harbor Laboratory Press, NY, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art, "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, the CCNA1-specific binding proteins provided in the present disclosure are capable of specifically binding a CCNA1 peptide in an HLA*02:01 restricted manner.

Exemplary binding proteins of the present disclosure include TCRs, antigen binding fragments of a TCR, and chimeric antigen receptors. Exemplary TCRs include αβ TCR, γδ TCR, single chain TCR (scTCR), soluble TCR, and single domain TCR. Binding proteins of the present disclosure may be chimeric, humanized, or human.

Another exemplary binding protein is a TCR-CAR. A TCR-CAR is a heterodimeric fusion protein generally comprising a soluble TCR (a VαCα polypeptide chain and a VβCβ polypeptide chain) wherein the VβCβ polypeptide chain is linked to a transmembrane domain and an intracellular signaling component (e.g., comprising an ITAM-containing T cell activating domain and optionally a costimulatory signaling domain) (see, e.g., Walseng et al., 2017 Scientific Reports 7:10713, incorporated by reference in its entirety).

In any of the embodiments described herein, binding proteins of the present disclosure, e.g., TCRs, may further comprise a TCR constant domain, e.g., joined to the C-terminus of a $V_\alpha$ domain, a $V_\beta$ domain, or both. A TCR β-chain constant domain may be encoded by a TRBC1 gene or TRBC2 gene. An exemplary TCR β-chain constant domain (Cβ) is a TRBC1 constant domain comprising at least about 75%, 80%, 85%, 90%, 91%, 92%, 93%, 94%, 95%, 96%, 97%, 98%, 99%, or 100% identity to the amino acid sequence of SEQ ID NO:34 or a TRBC2 constant domain comprising at least about 75%, 80%, 85%, 90%, 91%, 92%, 93%, 94%, 95%, 96%, 97%, 98%, 99%, or 100% identity to the amino acid sequence of SEQ ID NO:84. A TCR α-chain constant domain (Cα) may be encoded by a TRAC gene. An exemplary TCR α-chain constant domain is a TRAC constant domain comprising at least about 75%, 80%, 85%, 90%, 91%, 92%, 93%, 94%, 95%, 96%, 97%, 98%, 99%, or 100% identity to the amino acid sequence to SEQ ID NO:33, 156, or 157.

In certain embodiments, a TCR Cα domain, a Cβ domain, or both comprises a cysteine substitution to create an inter-chain disulfide bond between the constant domain cysteine residues which is not present in native TCRs. In particular embodiments, a binding protein comprises: (a) a Cα domain comprising a cysteine substitution at a position corresponding to position 49 of SEQ ID NO:33, at a position corresponding to position 48 of SEQ ID NO: 156, at a position corresponding to position 47 of SEQ ID NO: 157 (Thr→Cys), (b) a Cβ domain comprising a cysteine substitution at a position corresponding to position 57 of SEQ ID NO:34 or position 56 of SEQ ID NO:84 (Ser→Cys), or (c) both (a) and (b).

In any of the embodiments described herein, binding proteins of the present disclosure, e.g., TCRs, may further comprise a TCR constant domain, e.g., joined to the C-terminus of a Vα domain, a $V_\beta$ domain, or both. An exemplary TCR β-chain constant domain (Cβ) is a TRBC1 constant domain comprising at least about 75%, 80%, 85%, 90%, 91%, 92%, 93%, 94%, 95%, 96%, 97%, 98%, 99%, or 100% identity to the amino acid sequence of SEQ ID NO:155 or a TRBC2 constant domain comprising at least about 75%, 80%, 85%, 90%, 91%, 92%, 93%, 94%, 95%, 96%, 97%, 98%, 99%, or 100% identity to the amino acid sequence of SEQ ID NO:135. A TCR α-chain constant domain (Cα) may be encoded by a TRAC gene. An exemplary TCR α-chain constant domain is a TRAC constant domain comprising at least about 75%, 80%, 85%, 90%, 91%, 92%, 93%, 94%, 95%, 96%, 97%, 98%, 99%, or 100% identity to the amino acid sequence to SEQ ID NO:158, 159, or 160.

In certain embodiments, a TCR Cα domain is a truncated TCR Cα domain. In a particular embodiment, the truncated TCR α-chain constant domain is truncated at its C-terminus. In some embodiments, a truncated TCR α-chain constant domain can have truncations of 1, 2, 3, 4, or more amino acids at its C-terminus corresponding to the amino acid sequence of SEQ ID NO:33. In a particular embodiment, the truncated TCR α-chain constant domain is truncated at its N-terminus. In some embodiments, a truncated TCR α-chain constant domain can have truncations of 1, 2, 3, 4, or more amino acids at its N-terminus corresponding to the amino acid sequence of SEQ ID NO:33.

In certain embodiments, a TCR Cβ domain is a truncated TCR Cβ domain. In a particular embodiment, the truncated TCR β-chain constant domain is truncated at its C-terminus. In some embodiments, a truncated TCR α-chain constant domain can have truncations of 1, 2, 3, 4, or more amino acids at its C-terminus corresponding to the amino acid sequence of SEQ ID NO:34 or 84. In a particular embodiment, the truncated TCR β-chain constant domain is truncated at its N-terminus. In some embodiments, a truncated TCR β-chain constant domain can have truncations of 1, 2, 3, 4, or more amino acids at its N-terminus corresponding to the amino acid sequence of SEQ ID NO:34 or 84.

In some embodiments, a binding protein of the present disclosure is a TCR comprising: (a) an α chain comprising at least about 75%, 80%, 85%, 90%, 91%, 92%, 93%, 94%, 95%, 96%, 97%, 98%, 99%, or 100% identity to the α chain amino acid sequence contained in any one of SEQ ID NOS:36, 38, 40, 42, 44, 86, 49, 51, 53, 57, 59, 63, 65, 67, 81, 83, 162, 165, 170, 172, 174, 176, 178, 180, and 186; (b) a β chain comprising at least about 75%, 80%, 85%, 90%, 91%, 92%, 93%, 94%, 95%, 96%, 97%, 98%, 99%, or 100% identity to the β chain amino acid sequence contained in any one of SEQ ID NOS:36, 38, 40, 42, 46, 86, 49, 51, 55, 57, 61, 63, 67, 81, 83, 162, 165, 170, 172, 174, 176, 178, 180, and 186; or (c) an α chain of (a) and a β chain of (b), wherein the binding protein is capable of specifically binding to human CCNA1 peptide FLDRFLSCM (SEQ ID NO:1): HLA complex.

Exemplary TCRs include a TCR comprising: (a) the TCR α chain comprising the α chain amino acid sequence contained in SEQ ID NO:36 and the TCR β chain comprising the β chain amino acid sequence of SEQ ID NO:36; (b) the TCR α chain comprising the α chain amino acid sequence contained in SEQ ID NO:38 and the TCR β chain comprising the β chain amino acid sequence contained in SEQ ID NO:38; (c) the TCR α chain comprising the α chain amino acid sequence contained in SEQ ID NO:40 and the TCR β chain comprising the β chain amino acid sequence contained in SEQ ID NO:40; (d) the TCR α chain comprising the α chain amino acid sequence contained in SEQ ID NO:42 and the TCR β chain comprising the β chain amino acid sequence contained in SEQ ID NO:42; (e) the TCR α chain comprising the amino acid sequence of SEQ ID NO:44 and the TCR β chain comprising the amino acid sequence of SEQ ID NO:46; (f) the TCR α chain comprising the α chain amino acid sequence contained in SEQ ID NO:86 and the TCR β chain comprising the β chain amino acid sequence contained in SEQ ID NO:86; (g) the TCR α chain comprising the α chain amino acid sequence contained in SEQ ID NO:49 and the TCR β chain comprising the β chain amino acid sequence contained in SEQ ID NO:49; (h) the TCR α chain comprising the α chain amino acid sequence contained in SEQ ID NO:51 and the TCR β chain comprising the β chain amino acid sequence contained in SEQ ID NO:51; (i) the TCR α chain comprising the amino acid sequence of SEQ ID NO:53 and the TCR β chain comprising the amino acid sequence of SEQ ID NO:55; (j) the TCR α chain comprising the α chain amino acid sequence contained in SEQ ID NO:57 and the TCR β chain comprising the β chain amino acid sequence contained in SEQ ID NO:57; (k) the TCR α chain comprising the amino acid sequence of SEQ ID NO:59 and the TCR β chain comprising the amino acid sequence of SEQ ID NO:61; (1) the TCR α chain comprising the α chain amino acid sequence contained in SEQ ID NO:63 and the TCR β chain comprising the β chain amino acid sequence contained in SEQ ID NO:63; (m) the TCR α chain comprising the amino acid sequence of SEQ ID NO:65 and the TCR β chain comprising the β chain amino acid sequence contained in SEQ ID NO:67; (n) the TCR α chain comprising the α chain amino acid sequence contained in SEQ ID NO:67 and the TCR β chain comprising the β chain amino acid sequence contained in SEQ ID NO:67; (o) the TCR α chain comprising the α chain amino acid sequence contained in SEQ ID NO:81 and the TCR β chain comprising the β chain amino acid sequence contained in SEQ ID NO:81; (p) the TCR α chain comprising the α chain amino acid sequence contained in SEQ ID NO:83 and the TCR β chain comprising the β chain amino acid sequence contained in SEQ ID NO:83; (q) the TCR α chain comprising the α chain amino acid sequence contained in SEQ ID NO:162 and the TCR β chain comprising the β chain amino acid sequence contained in SEQ ID NO:162; (r) the TCR α chain comprising the α chain amino acid sequence contained in SEQ ID NO:165 and the TCR β chain comprising the β chain amino acid sequence contained in SEQ ID NO:165; (s) the TCR α chain comprising the α chain amino acid sequence contained in SEQ ID NO:170 and the TCR β chain comprising the β chain amino acid sequence contained in SEQ ID NO:170; (t) the TCR α chain comprising the α chain amino acid sequence contained in SEQ ID NO:172 and the TCR β chain comprising the β chain amino acid sequence contained in SEQ ID NO:172; (u) the TCR α chain comprising the α chain amino acid sequence contained in SEQ ID NO:174 and the TCR β chain comprising the β chain amino acid sequence contained in SEQ ID NO:174; (v) the TCR α chain comprising the α chain amino acid sequence contained in SEQ ID NO:176 and the TCR β chain comprising the β chain amino acid sequence contained in SEQ ID NO:176; (w) the TCR α chain comprising the α chain amino acid sequence contained in SEQ ID NO:178 and the TCR β chain comprising the β chain amino acid sequence contained in SEQ ID NO:178; (x) the TCR α chain comprising the α chain amino acid sequence contained in SEQ ID NO:180 and the TCR β chain comprising the β chain amino acid sequence contained in SEQ ID NO:180; or (y) the TCR α chain comprising the α chain amino acid sequence contained in SEQ ID NO:186 and the TCR β chain comprising the β chain amino acid sequence contained in SEQ ID NO:186.

In further embodiments, a binding protein of the present disclosure is a TCR comprising: (a) an α chain comprising at least about 75%, 80%, 85%, 90%, 91%, 92%, 93%, 94%, 95%, 96%, 97%, 98%, 99%, or 100% identity to the amino acid sequence of SEQ ID NO:69 or the α chain amino acid sequence contained in SEQ ID NO:73 or 182; (b) a β chain comprising at least about 75%, 80%, 85%, 90%, 91%, 92%, 93%, 94%, 95%, 96%, 97%, 98%, 99%, or 100% identity to the amino acid sequence of SEQ ID NO:71 or the β chain amino acid sequence contained in SEQ ID NO:73 or 182; or (c) an α chain of (a) and a β chain of (b), wherein the binding protein is capable of specifically binding to human CCNA1 peptide SLIAAAAFCLA (SEQ ID NO:2):HLA complex.

An exemplary TCR comprises: (a) the TCR α chain comprising the amino acid sequence of SEQ ID NO:69 and the TCR β chain comprising the amino acid sequence of SEQ ID NO:71; (b) the TCR α chain comprising the amino acid sequence contained in SEQ ID NO:73 and the TCR β chain comprising the amino acid sequence contained in SEQ ID NO:73; or (c) the TCR α chain comprising the amino acid sequence contained in SEQ ID NO:182 and the TCR β chain comprising the amino acid sequence contained in SEQ ID NO: 182.

In yet further embodiments, a binding protein of the present disclosure is a TCR comprising: (a) an α chain comprising at least about 75%, 80%, 85%, 90%, 91%, 92%, 93%, 94%, 95%, 96%, 97%, 98%, 99%, or 100% identity to the amino acid sequence of SEQ ID NO:75 or the α chain amino acid sequence contained in SEQ ID NO:79 or 184; (b) a β chain comprising at least about 75%, 80%, 85%, 90%, 91%, 92%, 93%, 94%, 95%, 96%, 97%, 98%, 99%, or 100% identity to the amino acid sequence of SEQ ID NO:77 or a β chain amino acid sequence contained in SEQ ID NO:79 or 184; or (c) an α chain of (a) and a β chain of (b), wherein the binding protein is capable of specifically binding to human CCNA1 peptide YSLSEIVPCL (SEQ ID NO:3):HLA complex.

An exemplary TCR comprises: (a) the TCR α chain comprising the amino acid sequence of SEQ ID NO:75 and the TCR β chain comprising the amino acid sequence of SEQ ID NO:77; (b) the TCR α chain comprising the amino acid sequence contained in SEQ ID NO:79 and the TCR β chain comprising the amino acid sequence contained in SEQ ID NO:79; or (c) the TCR α chain comprising the amino acid sequence contained in SEQ ID NO:184 and the TCR β chain comprising the amino acid sequence contained in SEQ ID NO: 184.

Polynucleotides, Vectors, and Host Cells

In certain aspects, nucleic acid molecules are provided that encode any one or more binding proteins described herein.

In another aspect, the present disclosure provides a polynucleotide encoding a binding protein that comprises a T cell receptor (TCR) α chain variable (Vα) domain and a TCR β chain variable (Vβ) domain, wherein the encoded binding protein is capable of specifically binding to a human cyclin A1 (CCNA1) peptide YSLSEIVPCL (SEQ ID NO:3), wherein the heterologous polynucleotide is codon optimized for expression in a host cell.

In certain embodiments, a polynucleotide encoding a TCR α-chain or portion thereof and a polynucleotide encoding a TCR β-chain or a portion thereof are contained in a single open reading frame comprised in the engineered host cell (e.g., immune cell), wherein the single open reading frame further comprises a polynucleotide encoding a self-cleaving peptide disposed between the α-chain-encoding polynucleotide and the β-chain-encoding polynucleotide. In certain embodiments, a self-cleaving peptide is selected from internal ribosome entry sites (IRES), furin cleavage sites, viral 2A peptides, or any combination thereof. Exemplary viral self-cleaving polypeptides include a viral 2A peptide from porcine teschovirus-1 (P2A), Thosea asigna virus (T2A), equine rhinitis A virus (E2A), foot-and-mouth disease virus (F2A), or variants thereof. In certain embodiments, an exemplary T2A peptide sequence comprises an amino acid sequence of SEQ ID NO:16. Further exemplary nucleic acid and amino acid sequences for 2A peptides are set forth in, for example, Kim et al. (*PLOS One* 6:e18556, 2011, which 2A nucleic acid and amino acid sequences are incorporated herein by reference in their entirety). An exemplary P2A peptide comprises an amino acid sequence of SEQ ID NO:29. An exemplary T2A peptide comprises an amino acid sequence of SEQ ID NO:30. An exemplary E2A peptide comprises an amino acid sequence of SEQ ID NO:31. An exemplary F2A peptide comprises an amino acid sequence of SEQ ID NO:32.

A polynucleotide encoding a desired binding protein can be accomplished by using any suitable molecular biology engineering techniques known in the art, including the use of restriction endonuclease digestion, ligation, transformation, plasmid purification, and DNA sequencing as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). Alternatively, a sequence of interest can be produced synthetically.

A nucleic acid of this disclosure may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

In certain embodiments, a heterologous polynucleotide encoding a TCR α-chain and a heterologous polynucleotide encoding a TCR β-chain are contained in a single open reading frame comprised in the engineered immune cell, wherein the single open reading frame further comprises a polynucleotide encoding a self-cleaving peptide disposed between the α-chain-encoding polynucleotide and the β-chain-encoding polynucleotide.

In any of the embodiments described herein, a polynucleotide of the present disclosure may be codon optimized for efficient expression in a host cell, such as an immune cell, containing the polynucleotide (see, e.g, Scholten et al., *Clin. Immunol.* 119:135-145 (2006)). As used herein, a "codon optimized" polynucleotide comprises a heterologous polynucleotide having codons modified with silent mutations corresponding to the abundances of tRNA levels in a host cell of interest.

A single polynucleotide molecule may encode one, two, or more binding proteins according to any of the embodiments disclosed herein. A polynucleotide encoding more than one transcript may comprise a sequence (e.g., a viral 2A peptide) disposed between each transcript for multicistronic expression.

In certain embodiments, the binding proteins of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

Certain embodiments include a polynucleotide of the present disclosure contained in a vector. One of skill in the art can readily ascertain suitable vectors for use with certain embodiments disclosed herein. An exemplary vector may comprise a nucleic acid molecule capable of transporting another nucleic acid molecule to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell or promote integration of the polynucleotide insert upon introduction into the host cell and thereby replicate along with the host genome (e.g., lentiviral vector)). Additionally, some vectors are capable of directing the expression of genes to which they are operatively linked (these vectors may be referred to as "expression vectors"). According to related embodiments, it is further understood that, if one or more agents (e.g., polynucleotides encoding binding proteins as described herein) is co-administered to a subject, that each agent may reside in separate or the same vectors, and multiple vectors (each containing a different agent or the same agent) may be introduced to a cell or cell population or administered to a subject.

A vector may be, for example, a plasmid, cosmid, virus, a RNA vector, or a linear or circular DNA or RNA molecule that may include chromosomal, non-chromosomal, semi-synthetic or synthetic nucleic acid molecules. Exemplary vectors are those capable of autonomous replication (episomal vector) or expression of nucleic acid molecules to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

The viral vector can, in certain embodiments, be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing transgenes are known in the art and have been previously described, for example, in: U.S. Pat. No. 8,119, 772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5:1517, 1998).

Other vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

Construction of an expression vector that is used for genetically engineering and producing a binding protein of interest can be accomplished by using any suitable molecular biology engineering techniques known in the art. To obtain efficient transcription and translation, a polynucleotide in each recombinant expression construct includes at least one appropriate expression control sequence (also called a regulatory sequence), such as a leader sequence and particularly a promoter operably (i.e., operatively) linked to the nucleotide sequence encoding the binding protein.

Markers are sometimes used to identify or monitor expression of a heterologous polynucleotide by a host cell transduced with the same, or to detect cells expressing a binding protein of interest. In certain embodiments, a polynucleotide further comprises a polynucleotide that encodes a marker. A marker may be a selection marker, which confers drug resistance, or a detectable marker, such as a fluorescent marker or cell surface protein that can be detected by methods such as flow cytometry. In certain embodiments, the polynucleotide encoding the marker is located 3' of the polynucleotide encoding the binding protein. In other embodiments, the polynucleotide encoding the marker is located 5' of the polynucleotide encoding binding protein. Exemplary markers include green fluorescent protein (GFP), an extracellular domain of human CD2, a truncated human EGFR (huEGFRt; see Wang et al., *Blood* 118:1255 (2011)), a truncated human CD19 (huCD19t), a truncated human CD34 (huCD34t), or a truncated human NGFR (huNGFRt). In certain embodiments, the encoded marker comprises EGFRt, CD19t, CD34t, or NGFRt. An exemplary truncated human EGFR sequence comprises an amino acid sequence of SEQ ID NO:85.

In certain embodiments, the vector may further comprise a suicide gene, where expression of the suicide gene results in the death of the host cell comprising the vector. For example, in some instances, prolonged expression of the binding protein of the invention is not desirable. Inclusion of a suicide gene in the vector allows for finer control of binding protein expression in a subject. In certain embodiments, expression of the suicide gene is inducible, for example with the use of an inducible promoter regulating suicide gene expression. In a specific embodiment, a suicide gene is an inducible caspase-9 gene (see U.S. Patent Publication No. 2013/0071414, incorporated by reference in its entirety).

When a viral vector genome comprises a plurality of polynucleotides within a single transgene to be expressed in a host cell as separate proteins, the viral vector may also comprise additional sequences between the two (or more) polynucleotides allowing for bicistronic or multicistronic expression. Examples of such sequences used in viral vectors include internal ribosome entry sites (IRES), furin cleavage sites, viral 2A peptides, or any combination thereof.

In any of the embodiments described herein, a polynucleotide can further comprise a polynucleotide that encodes a self-cleaving polypeptide, wherein the polynucleotide encoding the self-cleaving polypeptide is located between the polynucleotide encoding the binding protein and the polynucleotide encoding the marker.

In certain embodiments, a self-cleaving polypeptide comprises a viral 2A peptide from porcine teschovirus-1 (P2A), Thosea asigna virus (T2A), equine rhinitis A virus (E2A), foot-and-mouth disease virus (F2A), or variant thereof. In certain embodiments, an exemplary T2A peptide sequence comprises an amino acid sequence of SEQ ID NO:16. Further exemplary nucleic acid and amino acid sequences the 2A peptides are set forth in, for example, Kim et al. (*PLOS One* 6:e18556, 2011, which 2A nucleic acid and amino acid sequences are incorporated herein by reference in their entirety). An exemplary P2A peptide comprises an amino acid sequence of SEQ ID NO:29. An exemplary T2A peptide comprises an amino acid sequence of SEQ ID NO:30. An exemplary E2A peptide comprises an amino acid sequence of SEQ ID NO:31. An exemplary F2A peptide comprises an amino acid sequence of SEQ ID NO:32.

Binding proteins of the present disclosure can, in certain aspects, be expressed on the surface of a host cell or be secreted by or isolated from a host cell. A host cell may include any individual cell or cell culture which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

In addition to vectors, certain embodiments relate to host cells modified (i.e., genetically engineered) to contain a heterologous polynucleotide encoding a binding protein (e.g., TCR) or a vector comprising a heterologous polynucleotide encoding a binding protein (e.g., TCR) that are presently disclosed. A modified or genetically engineered host cell comprising a heterologous polynucleotide encoding at least one binding protein expresses on its cell surface at least one binding protein of the instant disclosure. A modified host cell may express a single type of binding protein or two or more different types of binding proteins of the present disclosure. Host cells can be modified ex vivo or in vivo. A host cell may include any individual cell or cell culture that may receive a vector or the incorporation of a nucleic acid or protein, as well as any progeny cells. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989). In any of the aforementioned embodiments, a host cell containing a polynucleotide encoding a binding protein of this disclosure are comprised of cells that are autologous, allogeneic or syngeneic to the subject receiving the modified host cells, such as in an adoptive immunotherapy procedure.

In certain embodiments, the host cell transduced to express a binding protein of the present disclosure is a hematopoietic progenitor cell or a human immune system cell. As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a $CD24^{Lo}$ $Lin^-$ $CD117^+$ phenotype or those found in the thymus (referred to as progenitor thymocytes).

In certain embodiments, the host cell is an immune system cell, including a B cell, a $CD4^+$ T cell, a $CD8^+$ T cell, a $CD4^-$ $CD8^-$ double negative T cell, a γδ T cell, a regulatory T cell, a natural killer cell (e.g., a NK cell or a NK-T cell), and a dendritic cell.

In certain embodiments, the host cell is a T cell. A T cell may be a naïve T cell, a memory T cell ($T_M$), a helper T cell ($T_H$), an effector T cell ($T_E$), a γδ T cell, a regulatory T cell (Treg), natural killer T cell (NKT), or any combination thereof. $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells (TEM, decreased expression of CD62L, CCR7, CD28, CD45RA, and increased expression of CD127 as compared to naïve T cells or $T_{CM}$).

T cells can be collected using known techniques, and the various subpopulations or combinations thereof can be enriched or depleted by known techniques, such as by affinity binding to antibodies, flow cytometry, or immunomagnetic selection.

Methods for transfecting/transducing T cells with desired nucleic acids have been described (e.g., U.S. Patent Application Pub. No. US 2004/0087025; U.S. Pat. No. 6,410,319; PCT Publication No. WO 2014/031687; Brentjens et al., 2007, *Clin. Cancer Res.* 13:5426) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007; Kalos et al., *Sci Transl. Med.* 3:95ra73, 2011; Porter et al., 2011, *N. Engl. J. Med.* 365:725-33, 2011), such that adaptation of these methodologies to the presently disclosed embodiments is contemplated, based on the teachings herein, including those directed to binding proteins of the present disclosure.

Eukaryotic host cells contemplated as an aspect of this disclosure when harboring a polynucleotide, vector, or protein according to this disclosure include, in addition to a human immune cells (e.g., a human patient's own immune cells), VERO cells, HeLa cells, Chinese hamster ovary (CHO) cell lines (including modified CHO cells capable of modifying the glycosylation pattern of expressed multivalent binding molecules, see US Patent Application Publication No. 2003/0115614), COS cells (such as COS-7), W138, BHK, HepG2, 3T3, RIN, MDCK, A549, PC12, K562, HEK293 cells, HepG2 cells, N cells, 3T3 cells, *Spodoptera frugiperda* cells (e.g., Sf9 cells), *Saccharomyces cerevisiae* cells, and any other eukaryotic cell known in the art to be useful in expressing, and optionally isolating, a protein or peptide according to this disclosure. Also contemplated are prokaryotic cells, including *Escherichia coli, Bacillus subtilis, Salmonella typhimurium*, a Streptomycete, or any prokaryotic cell known in the art to be suitable for expressing, and optionally isolating, a protein or peptide according to this disclosure. In isolating protein or peptide from prokaryotic cells, in particular, it is contemplated that techniques known in the art for extracting protein from inclusion bodies may be used. Host cells that glycosylate the binding proteins of this disclosure are contemplated.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the heterologous polynucleotide by, for example, drug selection or deficiency in an essential nutrient which is complemented by the selectable marker carried on the expression vector or co-transfected into the host cell.

In certain embodiments, a binding protein of the present disclosure is expressed on the surface of a host cell such that binding to a target antigen elicits an activity or response from the host cell. Such expressed proteins may be functionally characterized according to any of a large number of art-accepted methodologies for assaying host cell (e.g., T cell) activity, including determination of T cell binding, activation or induction and also including determination of T cell responses that are antigen-specific. Examples include determination of T cell proliferation, T cell cytokine release, antigen-specific T cell stimulation, MHC restricted T cell stimulation, CTL activity (e.g., by detecting $^{51}$Cr or Europium release from pre-loaded target cells), changes in T cell phenotypic marker expression, and other measures of T cell functions. Procedures for performing these and similar assays are may be found, for example, in Lefkovits (*Immunology Methods Manual: The Comprehensive Sourcebook of Techniques*, 1998). See, also, *Current Protocols in Immunology; Weir, Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, Science 281:1309 (1998) and references cited therein.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-β, and Type 2 cytokines, such as IL-4, IL-5, IL-9, IL-10, and IL-13.

In other aspects, kits are provided comprising (a) a vector or an expression construct as described herein and optional reagents for transducing the vector or the expression construct into a host cell, and (b) (i) a binding protein, isolated polynucleotide, or expression vector as disclosed herein, and (ii) optional reagents for transducing the polynucleotide or expression vector into a host cell, and (c) a host cell of this disclosure.

Methods of Use

In certain aspects, the compositions provided in the present disclosure may be used in methods for treating a hyper-proliferative disorder or condition characterized by overex-pression of CCNA-1 comprising administering to a subject in need thereof a binding protein, a vector comprising a polynucleotide encoding a binding protein, a modified host cell expressing a binding protein, or a pharmaceutical composition thereof. In certain embodiments, the disease is a cancer.

As used, herein the term "cancer" includes solid tumors and hematological malignancies (e.g., leukemias). Exemplary cancers that may be treated include biliary cancer, bladder cancer, bone and soft tissue carcinoma, brain tumor, breast cancer, cervical cancer, colon cancer, colorectal adenocarcinoma, colorectal cancer, desmoid tumor, embryo-nal cancer, endometrial cancer, esophageal cancer, gastric cancer, gastric adenocarcinoma, glioblastoma multiforme, gynecological tumor, head and neck squamous cell carci-noma, hepatic cancer, lung cancer, mesothelioma, malignant melanoma, osteosarcoma, ovarian cancer, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, testicular germ-cell tumor, urothelial cancer, uter-ine sarcoma, and uterine cancer.

Exemplary hematological malignances include acute lymphoblastic leukemia (ALL), acute myeloid leukemia (AML), chronic myelogenous leukemia (CML), chronic eosinophilic leukemia (CEL), myelodysplastic syndrome (MD), Hodgkin's lymphoma, non-Hodgkin's lymphoma (NHL) (e.g., follicular lymphoma, diffuse large B-cell lym-phoma, or chronic lymphocytic leukemia), myeloma, and multiple myeloma (MM).

In certain embodiments, the subject is a human or non-human animal, such as a non-human primate, cow, horse, sheep, pig, cat, dog, goat, mouse, rat, rabbit, or guinea pig. In one embodiment, the subject is a human, such as a human adult, adolescent, child, or infant.

In certain embodiments, the modified host cells adminis-tered to the subject are autologous, allogeneic, or syngeneic.

The level of a CTL immune response may be determined by any one of numerous immunological methods described herein and routinely practice in the art. The level of a CTL immune response may be determined prior to and following administration of any one of the herein described CCNA1-specific binding proteins expressed by, for example, a T cell. Cytotoxicity assays for determining CTL activity may be performed using any one of several techniques and methods routinely practice in the art (see, e.g., Henkart et al., "Cyto-toxic T-Lymphocytes" in *Fundamental Immunology*, Paul (ed.) (2003 Lippincott, Williams & Wilkins, Philadelphia, PA), pages 1127-50, and references cited therein).

Antigen-specific T cell can be determined by comparison of observed T cell responses according to any of the herein described T cell functional parameters (e.g., proliferation, cytokine release, CTL activity, altered cell surface marker phenotype, etc.) that may be made between T cells that are exposed to a cognate antigen in an appropriate context (e.g., the antigen used to prime or activate the T cells, when presented by immunocompatible antigen-presenting cells) and T cells from the same source population that are exposed instead to a structurally distinct or irrelevant control antigen. A response to the cognate antigen that is greater, with statistical significance, than the response to the control antigen signifies antigen-specificity.

A biological sample may be obtained from a subject for determining the presence and level of an immune response to a disease antigen peptide. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a bio-logical source. Biological samples may also be obtained from the subject prior to receiving any immunogenic com-position, which biological sample is useful as a control for establishing baseline (i.e., pre-immunotherapy) data.

Binding proteins, polynucleotides, vectors, or modified host cells as described herein may be administered to a subject in a pharmaceutically or physiologically acceptable or suitable excipient or carrier. Pharmaceutically acceptable excipients are biologically compatible vehicles, e.g., physi-ological saline, which are described in greater detail herein, that are suitable for administration to a human or other non-human mammalian subject. A therapeutically effective dose, in the context of adoptive cell therapy, is an amount of host cells (expressing a binding protein according to the present disclosure) used in adoptive transfer that is capable of producing a clinically desirable result (e.g., a cytotoxic T cell response) in a statistically significant manner) in a treated human or non-human mammal. As is well known in the medical arts, the dosage for any one patient depends upon many factors, including the patient's size, weight, body surface area, age, the particular therapy to be admin-istered, sex, time and route of administration, general health, and other drugs being administered concurrently. Doses will vary, but a preferred dose for administration of a host cell comprising a recombinant expression vector as described herein is about $10^7$ cells/m$^2$, about $5\times10^7$ cells/m$^2$, about $10^8$ cells/m$^2$, about $5\times10^8$ cells/m$^2$, about $10^9$ cells/m$^2$, about $5\times10^9$ cells/m$^2$, about $10^{10}$ cells/m$^2$, about $5\times10^{10}$ cells/m$^2$, or about $10^{11}$ cells/m$^2$.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's disease, the particular form of the active ingredient, and the method of adminis-tration. In general, an appropriate dose and treatment regi-men provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunotherapeutic compositions administered according to the methods described herein can be determined by performing pre-clinical (including in vitro and in vivo animal studies) and clinical studies and analyz-ing data obtained therefrom by appropriate statistical, bio-logical, and clinical methods and techniques, all of which can readily be practiced by a person skilled in the art.

The pharmaceutical compositions described herein may be presented in unit-dose or multi-dose containers, such as sealed ampoules or vials. Such containers may be frozen to preserve the stability of the formulation until use. In certain embodiments, a unit dose comprises a recombinant host cell as described herein at a dose of about $10^7$ cells/m$^2$ to about $10^{11}$ cells/m$^2$. The development of suitable dosing and treatment regimens for using the particular compositions described herein in a variety of treatment regimens, including e.g., parenteral or intravenous administration or formulation, can be determined by a person skilled in the art.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polythethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

In general, an appropriate dosage and treatment regimen provide the active molecules or cells in an amount sufficient to provide therapeutic or prophylactic benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which may be performed using samples obtained from a subject before and after treatment.

In certain embodiments, methods of treating a disease comprise administering modified immune cells in combination with one or more additional agents.

In certain embodiments, a modified immune cell of the present disclosure is administered to a subject with an inhibitor of an immune suppression component.

As used herein, the term "immune suppression component" or "immunosuppression component" refers to one or more cells, proteins, molecules, compounds or complexes providing inhibitory signals to assist in controlling or suppressing an immune response. For example, immune suppression components include those molecules that partially or totally block immune stimulation; decrease, prevent or delay immune activation; or increase, activate, or up regulate immune suppression. Exemplary immunosuppression component targets are described in further detail herein and include immune checkpoint molecules, such as PD-1, PD-L1, PD-L2, CD80, CD86, B7-H3, B7-H4, HVEM, adenosine, GAL9, VISTA, CEACAM-1, PVRL2, CTLA-4, BTLA, KIR, LAG3, TIM3, A2aR, CD244/2B4, CD160, TIGIT, LAIR-1, PVRIG/CD112R; metabolic enzymes, such as arginase, indoleamine 2,3-dioxygenase (IDO); immunosuppressive cytokines, such as IL-10, IL-4, IL-1RA, IL-35; $T_{reg}$ cells, or any combination thereof.

An inhibitor of an immune suppression component may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments disclosed herein, a method may comprise administering a modified immune cell with one or more inhibitor of any one of the following immune suppression components, singly or in any combination.

In certain embodiments, a modified immune cell is used in combination with a PD-1 inhibitor, for example a PD-1-specific antibody or binding fragment thereof, such as pidilizumab, nivolumab (Opdivo®, formerly MDX-1106), pembrolizumab (Keytruda®, formerly MK-3475), MEDI0680 (formerly AMP-514), AMP-224, BMS-936558 or any combination thereof.

In certain embodiments, a modified immune cell is used in combination with a PD-L1 specific antibody or binding fragment thereof, such as BMS-936559, durvalumab (MEDI4736), atezolizumab (RG7446), avelumab (MSB0010718C), MPDL3280A, or any combination thereof.

In certain embodiments, a modified immune cell is used in combination with a LAG3 inhibitor, such as LAG525, IMP321, IMP701, 9H12, BMS-986016, or any combination thereof.

In certain embodiments, a modified immune cell is used in combination with an inhibitor of CTLA4. In particular embodiments, a modified immune cell is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a modified immune cell is used in combination with a B7-H3 specific antibody or binding fragment thereof, such as enoblituzumab (MGA271), 376.96, or both.

In certain embodiments, a modified immune cell is used in combination with a B7-H4 specific antibody or binding fragment thereof, such as a scFv or fusion protein thereof, as described in, for example, Dangaj et al., *Cancer Res.* 73:4820, 2013, as well as those described in U.S. Pat. No. 9,574,000 and PCT Patent Publication Nos. WO 2016/40724 and WO 2013/025779.

In some embodiments, a modified immune cell is used in combination with an inhibitor of CD244.

In certain embodiments, a modified immune cell is used in combination with an inhibitor of BLTA, HVEM, CD160, or any combination thereof. Anti CD-160 antibodies are described in, for example, PCT Publication No. WO 2010/084158.

In more embodiments, a modified immune cell is used in combination with an inhibitor of TIM3.

In still more embodiments, a modified immune cell is used in combination with an inhibitor of Ga19.

In certain embodiments, a modified immune cell is used in combination with an inhibitor of adenosine signaling, such as a decoy adenosine receptor.

In certain embodiments, a modified immune cell is used in combination with an inhibitor of A2aR.

In certain embodiments, a modified immune cell is used in combination with an inhibitor of KIR, such as lirilumab (BMS-986015).

In certain embodiments, a modified immune cell is used in combination with an inhibitor of an inhibitory cytokine (typically, a cytokine other than TGFβ) or Treg development or activity.

In certain embodiments, a modified immune cell is used in combination with an IDO inhibitor, such as levo-1-methyl tryptophan, epacadostat (INCB024360; Liu et al., *Blood* 115:3520-30, 2010), ebselen (Terentis et al., *Biochem.* 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a modified immune cell is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-borono-ethyl)-L-cysteine (BEC), or any combination thereof.

In certain embodiments, a modified immune cell is used in combination with an inhibitor of VISTA, such as CA-170 (Curis, Lexington, MA).

In certain embodiments, a modified immune cell is used in combination with a LAIR1 inhibitor.

In certain embodiments, a modified immune cell is used in combination with an inhibitor of CEACAM-1, CEACAM-3, CEACAM-5, or any combination thereof.

In certain embodiments, a modified immune cell is used in combination with an agent that increases the activity (i.e., is an agonist) of a stimulatory immune checkpoint molecule. For example, a modified immune cell can be used in combination with a CD137 (4-1BB) agonist (such as, for example, urelumab), a CD134 (OX-40) agonist (such as, for example, MEDI6469, MEDI6383, or MEDI0562), lenalido-mide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2), an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, or Icos 314-8), or any combination thereof. In any of the embodiments disclosed herein, a method may comprise adminis-tering a modified immune cell with one or more agonists of a stimulatory immune checkpoint molecule, including any of the foregoing, singly or in any combination.

In other embodiments, a method of this disclosure further comprises administering a secondary therapy comprising one or more of: an antibody or antigen binding fragment specific for a cancer antigen expressed by the cancer cell being targeted; a chemotherapeutic agent; surgery; radiation therapy treatment; a cytokine; an RNA interference therapy, or any combination thereof.

Exemplary monoclonal antibodies useful in cancer thera-pies include, for example, monoclonal antibodies described in Galluzzi et al., *Oncotarget* 5(24):12472-12508, 2014, which antibodies are incorporated by reference in their entirety.

In certain embodiments, a combination therapy method comprises administering a modified immune cell and further administering a radiation treatment or a surgery to a subject. Radiation therapy includes X-ray therapies, such as gamma-irradiation, and radiopharmaceutical therapies. Surgeries and surgical techniques appropriate to treating a given cancer or non-inflamed solid tumor may be used in a subject in combination with a modified immune cell of this disclo-sure.

In certain embodiments, a combination therapy method comprises administering a modified immune cell and a chemotherapeutic agent to a subject. A chemotherapeutic agent includes, but is not limited to, an inhibitor of chro-matin function, a topoisomerase inhibitor, a microtubule inhibiting drug, a DNA damaging agent, an antimetabolite (such as folate antagonists, pyrimidine analogs, purine ana-logs, and sugar-modified analogs), a DNA synthesis inhibi-tor, a DNA interactive agent (such as an intercalating agent), and a DNA repair inhibitor. Illustrative chemotherapeutic agents include, without limitation, the following groups: anti-metabolites/anti-cancer agents, such as pyrimidine ana-logs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including vinca alkaloids (vinblastine, vincristine, and vinorelbine), microtubule disruptors such as taxane (paclitaxel, docetaxel), vincristin, vinblastin, nocoda-zole, epothilones and navelbine, epidipodophyllotoxins (etoposide, teniposide), DNA damaging agents (actinomy-cin, amsacrine, anthracyclines, bleomycin, busulfan, camp-tothecin, carboplatin, chlorambucil, cisplatin, cyclophosph-amide, Cytoxan®, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, Taxol®, Taxotere®, temozolamide, teniposide, triethyl-enethiophosphoramide and etoposide (VP 16)); antibiotics such as dactinomycin (actinomycin D), daunorubicin, doxo-rubicin (Adriamycin®), idarubicin, anthracyclines, mitox-antrone, bleomycins, plicamycin (mithramycin) and mito-mycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclo-phosphamide and analogs, melphalan, chlorambucil), ethyl-enimines and methylmelamines (hexamethylmelamine and thiotepa), alkyl sulfonates-busulfan, nitrosoureas (carmus-tine (BCNU) and analogs, streptozocin), trazenes—dacar-bazinine (DTIC); antiproliferative/antimitotic antimetabo-lites such as folic acid analogs (methotrexate); platinum coordination complexes (cisplatin, carboplatin), procarba-zine, hydroxyurea, mitotane, aminoglutethimide; hormones, hormone analogs (estrogen, tamoxifen, goserelin, bicaluta-mide, nilutamide) and aromatase inhibitors (letrozole, anas-trozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dac-tinomycin, eniposide, epirubicin, etoposide, idarubicin, iri-notecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin,

*Pseudomonas* exotoxin, *Bordetella pertussis* adenylate cyclase toxin, or diphtheria toxin, and caspase activators; and chromatin disruptors.

Cytokines can be used to manipulate host immune response towards anticancer activity. See, e.g., Floros and Tarhini, *Semin. Oncol.* 42:539, 2015. Cytokines useful for promoting anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination.

Another cancer therapy approach involves reducing expression of oncogenes and other genes needed for growth, maintenance, proliferation, and immune evasion by cancer cells. RNA interference, and in particular the use of microR-NAs (miRNAs) small inhibitory RNAs (siRNAs) provides an approach for knocking down expression of cancer genes. See, e.g., Larsson et al., *Cancer Treat. Rev.* 16:128, 2017.

In any of the embodiments disclosed herein, any of the therapeutic agents (e.g., a modified immune cell, an inhibitor of an immune suppression component, an agonist of a stimulatory immune checkpoint molecule, a chemotherapeutic agent, a radiation therapy, a surgery, a cytokine, or an inhibitory RNA) may be administered once or more than once to the subject over the course of a treatment, and, in combinations, may be administered to the subject in any order (e.g., simultaneously, concurrently, or in any sequence) or any combination. An appropriate dose, suitable duration, and frequency of administration of the compositions will be determined by such factors as a condition of the patient; size, type, spread, growth, and severity of the tumor or cancer; particular form of the active ingredient; and the method of administration.

In certain embodiments, a plurality of doses of a modified immune cell as described herein is administered to the subject, which may be administered at intervals between administrations of about two to about four weeks. In further embodiments, a cytokine (e.g., IL-2, IL-15, IL-21) is administered sequentially, provided that the subject was administered the recombinant host cell at least three or four times before cytokine administration. In certain embodiments, a cytokine is administered concurrently with the host cell. In certain embodiments, a cytokine is administered subcutaneously.

In still further embodiments, a subject being treated is further receiving immunosuppressive therapy, such as calcineurin inhibitors, corticosteroids, microtubule inhibitors, low dose of a mycophenolic acid prodrug, or any combination thereof. In yet further embodiments, a subject being treated has received a non-myeloablative or a myeloablative hematopoietic cell transplant, wherein the treatment may be administered at least two to at least three months after the non-myeloablative hematopoietic cell transplant.

An effective amount of a therapeutic or pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

EXAMPLES

Example 1

CYCLIN A1 TCRS

Human cyclin A1 isoform 3 protein sequence (SEQ ID NO.4), which is the most conserved of cyclin A1 isoforms, was selected to maximize the chance that a targeted epitope is expressed by cancers. Cyclin A1-specific TCRs were discovered by stimulating donor CD8+ T cells with a library of over-lapping peptides spanning the entire CCNA1 protein sequence and designed to cover all possible MHC-I epitopes. When reactive T cells were observed against the full peptide library after ~3 rounds of peptide stimulation, the minimal peptide epitope and presenting HLA allele were determined by screening with individual peptides and cell lines expressing single HLA alleles of interest (see, FIG. 1).

Figure 2:
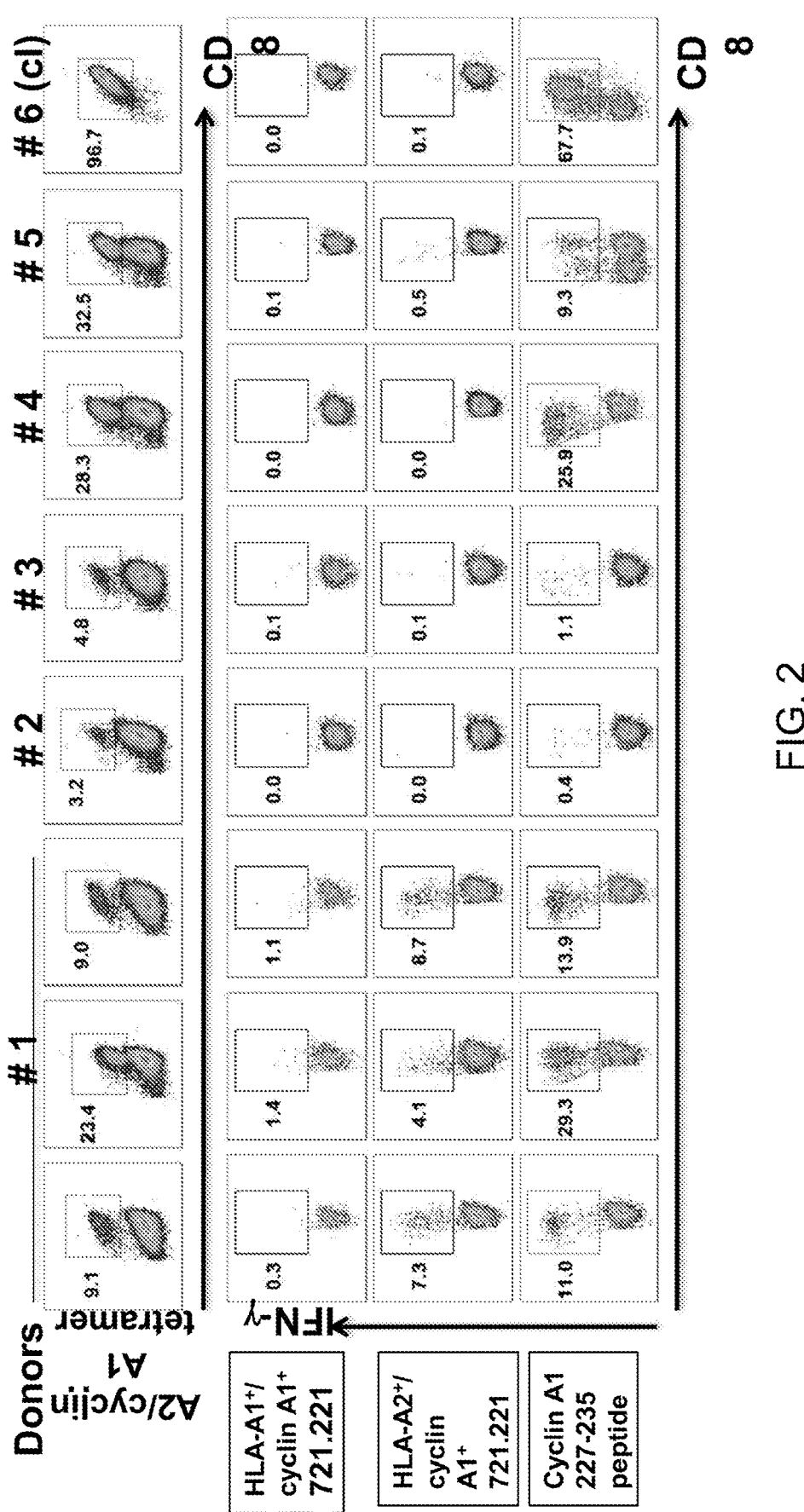
FIG. 2 shows that stimulating CD8+ T cells with a cyclin A1 overlapping peptide library resulted in the generation of antigen-specific lines.

Cyclin A1 (227-235)-specific T cell responses were detected after 3 rounds of stimulation of several different HLA-A2+donor cells. Antigen-specific responses were detected by labelling with an HLA-A2/cyclin A1(227-235) fluorescently labelled multimer (first row of FIG. 2). HLA-restriction and effector function were confirmed by incubating T cells together with 721.221 leukemia cell line transduced to express cyclin A1 as well as HLA-A1 as a negative control ($2^{nd}$ row of FIG. 2) or HLA-A2 ($3^{rd}$ row of FIG. 2). Free peptide was added to the T cells as a positive control (row 4 of FIG. 2). After a 4 hour co-incubation in the presence of golgi inhibitors, T cells were fixed and permeabilized before labelling with anti-IFNγ antibodies and analysis by flow cytometry. Several of the T cell lines demonstrated not only antigen-specificity (by tetramer binding) but effector function in response to both free peptide and naturally processed peptide presented by a cell line expressing the correct combination of tumor antigen and HLA allele.

Figure 3A:
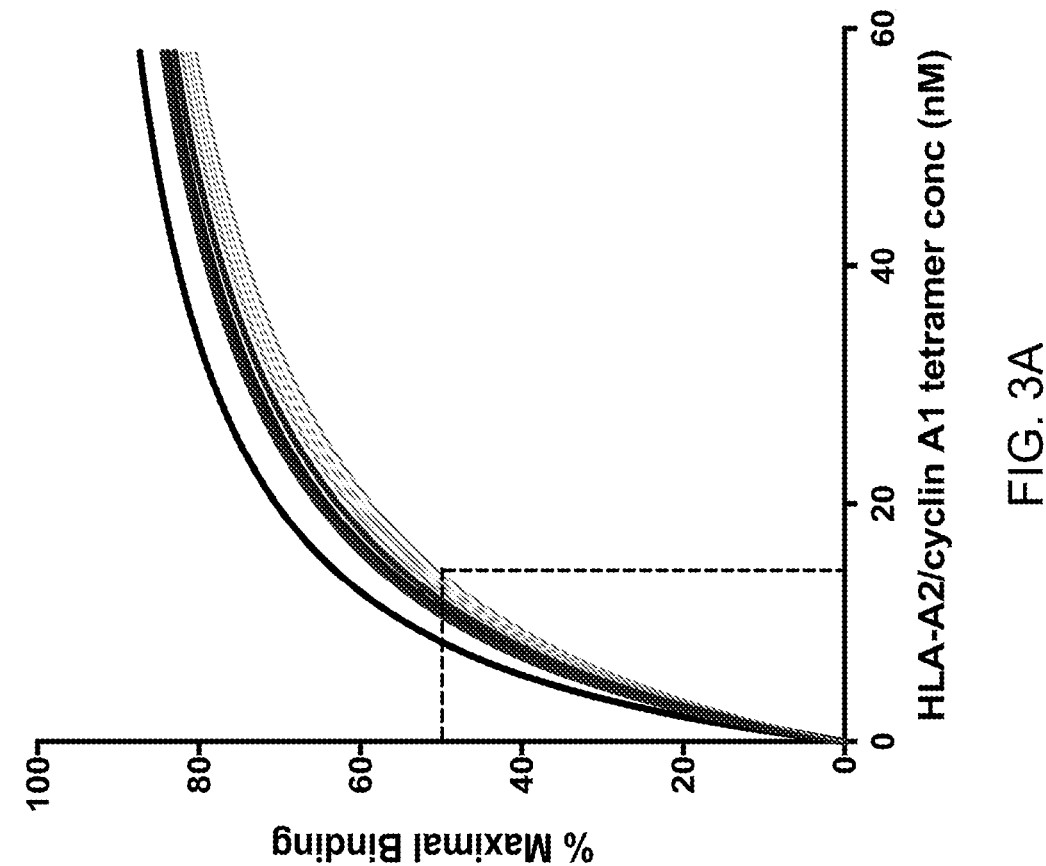
FIGS. 3A-3B show that high affinity HLA-A2:01/cyclin A1 TCRs were identified by calculating tetramer dissociation constants (Kd) for individual T cell clones.
Figure 3B:
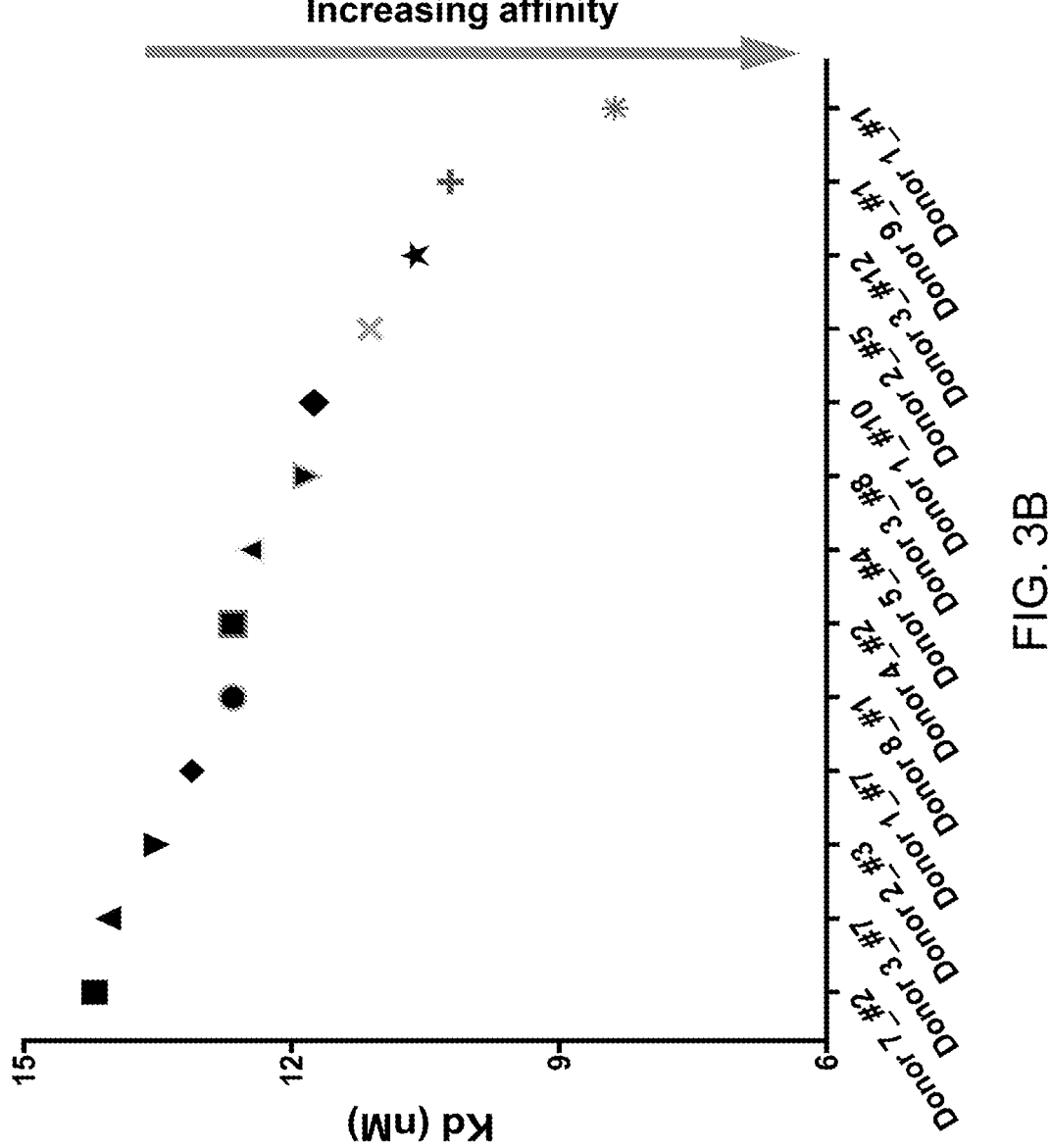

HLA-A2/cyclin A1 (227-235)-specific T cell lines were ranked by their tetramer binding affinity in order to select the highest affinity TCRs for further analysis. About 150 different T cell lines or clones were generated from 12 different donors in a series of separate experiments. A subset of these is shown in FIGS. 3A-3B. T cells were carefully counted and equal numbers of T cells from each T cell line were labelled with decreasing concentrations of a HLA-A2/cyclin A1(227-235) fluorescently labelled multimer. The mean fluorescence intensity of multimer staining for each line was plotted against tetramer concentration (FIG. 3A). From this graph a linear regression analysis was performed to determine the maximum binding coefficient, which was applied to the raw data to generate relative dissociation constants (Kd) for each line-the tetramer concentration that provides 50% maximal binding. These values were inversely related to TCR affinity, with the lowest Kd corresponding to the highest predicted affinity (FIG. 3B). There were a range of different affinities for the MHC-peptide multimer among the different donors and T cell lines tested. The 10 best candidates were selected for RACE PCR, TCR sequencing and generation of lentiviral TCR gene-transfer vectors.

Figure 5A:
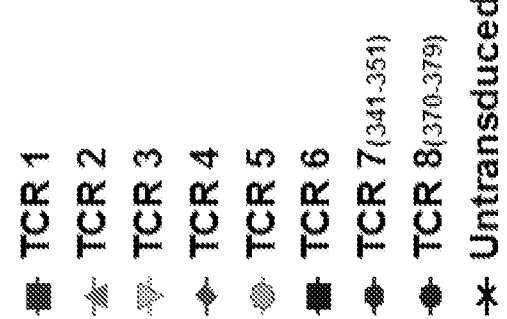
Figure 5A:
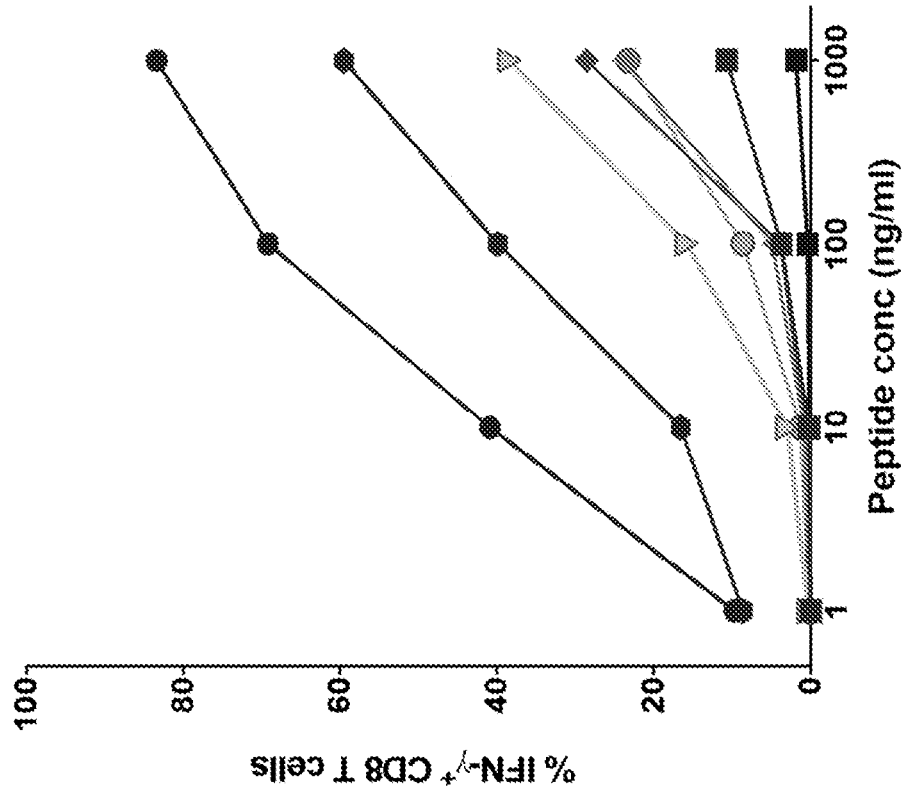
Figure 5B:
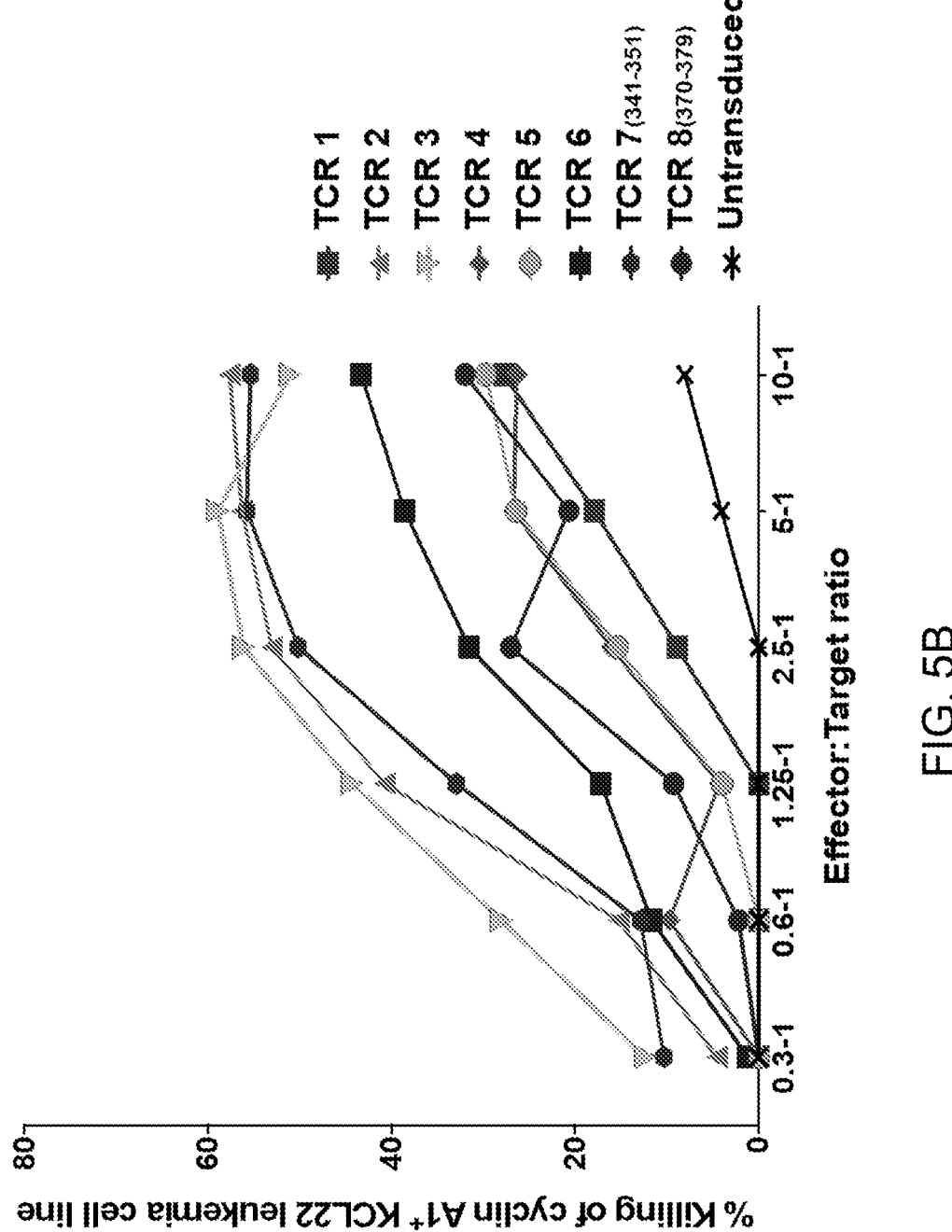
Figure 5D:
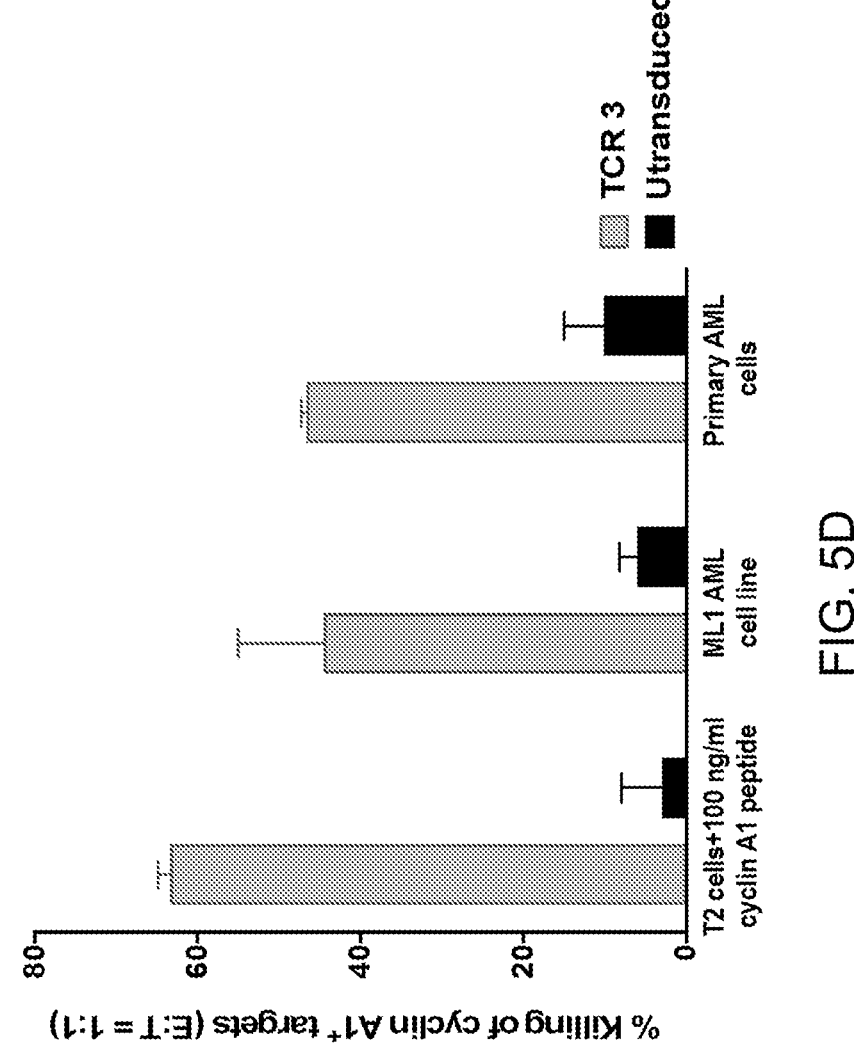

FIG. 4 shows a schematic of how TCRs from high avidity antigen-specific T cell lines, predicted to have high affinity TCRs, were isolated, identified and expressed in donor CD8+ T cells, where they were functionally compared. Of the 10 HLA-A2/cyclin A1(227-235)-specific TCRs tested, 5 were successfully cloned into lentiviral vectors, expressed in CD8+ T cells and bind to the MHC-CCNA1 peptide multimer. A previously generated HLA-A2/cyclin A1(227-235)-specific TCR #4 was included for comparison and two other TCRs specific for HLA-A2/cyclin A1(341-351), TCR #7, and HLA-A2/cyclin A1(370-379), TCR #8, were also cloned, expressed, and tested. Successfully transduced CD8+ T cells were sorted with the relevant MHC-peptide multimer and expanded before performing functional assays. CDR3 sequences, and T cell receptor α and β gene usage are provided in Table 1.

ability of the most promising cyclin A1(227-235)-specific TCR (#3) to kill peptide-loaded T2 target cells, an HLA-A2+cyclin A1+AML cell line (ML1) and an HLA-A2+cyclin A1+primary AML sample (FIG. 5D). Untransduced T cells were incubated with the same targets in separate wells to control for specificity of killing.

TABLE 1

| Cyclin A1 Specific TCRs | | | | |
|---|---|---|---|---|
| TCR Name | TCRα (TRA) gene | Vα CDR3 | TCRβ (TRB) gene | Vβ CDR3 |
| 5 | TRAV30*01 J20*01 | CGTEEANDYKLSF (SEQ ID NO: 5) | TRBV9*01 J2-7*01 | CASSVGQGSSYEQYF (SEQ ID NO: 6) |
| 9 | TRAV10*01 J34*01 | CVVWGGDTDKLIF (SEQ ID NO: 7) | TRBV2*01 J1-6*01 | CAILDGEGSPLHF (SEQ ID NO: 8) |
| 6 | TRAV24*01 J20*01 | CALGPYNDYKLSF (SEQ ID NO: 9) | TRBV6-6*01 J2-2*01 | CASSDRSNTGELFF (SEQ ID NO: 10) |
| 1 | TRAV21*01 J12*01 | CAVEGDSSYKLIF (SEQ ID NO: 11) | TRBV5-6*01 J2-5*01 | CASSFFSQETQYF (SEQ ID NO: 12) |
| 2 | TRAV21*02 J26*01 | CAVIGEQNFVF (SEQ ID NO: 13) | TRBV7-3*01 J2-6*01 | CASSLSGLGSGANVLTF (SEQ ID NO: 14) |
| 3 | TRAV12-2*02 J13*02 | CAVDSGGYQKVTF (SEQ ID NO: 15) | TRBV7-3*01 J1-1*01 | CASSLNMNTEAFF (SEQ ID NO: 16) |
| 10 | TRAV17*01 J53*01 | CATDESSNYKLTF (SEQ ID NO: 17) | TRBV7-3*01 J1-1*01 | CASSLNMNTEAFF (SEQ ID NO: 18) |
| 4 | TRAV17*01 J48*01 | CATDAWESNFGNEKLTF (SEQ ID NO: 19) | TRBV7-2*01 J2-7*01 | CASSLVVGSYEQYF (SEQ ID NO: 20) |
| 7 | TRAV24*01 J49*01 | CAYLGAGNQFYF (SEQ ID NO: 21) | TRBV19*01 J1-2*01 | CASSLNRGRYGYTF (SEQ ID NO: 22) |
| 8 | TRAV19*01 J6*01 | CALSELASGGSYIPTF (SEQ ID NO: 23) | TRBV5-6*01 J2-3*01 | CAS SFRLAGGPSTDTQYF (SEQ ID NO: 24) |
| 11 | TRAV10*01 J34*01 | CVVWGGDTDKLIF (SEQ ID NO: 7) | TRBV10-2*01 J2-7*01 | CASSDGGGQYF (SEQ ID NO: 189) |

TCRs #5, 9, 6, 1, 2, 3, 10, 11, and 4 are specific for cyclin A1 (227-235) FLDRFLSCM peptide (SEQ ID NO:1) complexed with HLA*02:01. TCR #7 is specific for cyclin A1 (341-351) SLIAAAAFCLA (SEQ ID NO:2) complexed with HLA*02:01. TCR #8 is specific for cyclin A1 (370-379) complexed with HLA*02:01.

First T cells were incubated for 4 hr with different concentrations of their specific peptide ligand in the presence of golgi inhibitors before T cells were fixed and permeabilised and labelled with anti-IFNγ antibodies for analysis by flow cytometry (FIG. 5A). The cytotoxic function of the TCR-transduced T cells was then tested by co-incubating the T cells at different ratios with HLA-A2+cyclin A1+KCL22 leukemia cell targets. Targets were labelled with a fluorescent dye and mixed at an equal ratio with antigen-negative control cells (FIG. 5B). At the end of a 6 hr incubation the frequency of remaining labelled targets (relative to control cells) was determined by flow cytometry and from this data the % of antigen-specific killing was calculated. The binding strength of the different peptide epitopes to HLA-A2 and the likelihood that these epitopes would be result from proteosomal processing of the full length protein were predicted using several open-access online algorithms (FIG. 5C). A second cytotoxicity assay was performed as in FIG. 5B, but this time comparing the FIG. 5A shows that TCRs recognizing peptides 341 and 370 are superior to the 227-specific TCRs when stimulated with low doses of free peptide. In FIG. 5B, the killing assay using target cells that endogenously express the cyclin A1 protein, which is proteosomally processed, loaded onto an MHC molecule and transported to the cell surface in order to be recognized by T cells shows superior killing by at least one of the 227-specific TCRs. This indicates that the 227 peptide may be processed more efficiently by the tumor cell line than the other epitopes, while the 341 and 370 may be more stable in solution or bind more strongly to MHC when introduced as free ligands, resulting in superior T cell function. FIG. 5C shows that there is some bioinformatics data to suggest that peptide 370 indeed binds to HLA-A2 more strongly than peptide 227, but that 227 is the only one of the three CCNA1 peptides that is predicted to be cut by the general proteosomal processing machinery of the cell. This information is supportive of peptide 227 being a good target for cancer therapy. FIG. 5D shows that the best performing 227 TCR candidate is able to kill peptide-loaded target cells, a cyclin A1 expressing AML cell line and a primary AML sample almost equally well, despite the fact that the peptide concentration on the surface of the tumor cells is likely to be much lower than in the case of peptide-loading.

Figure 6:
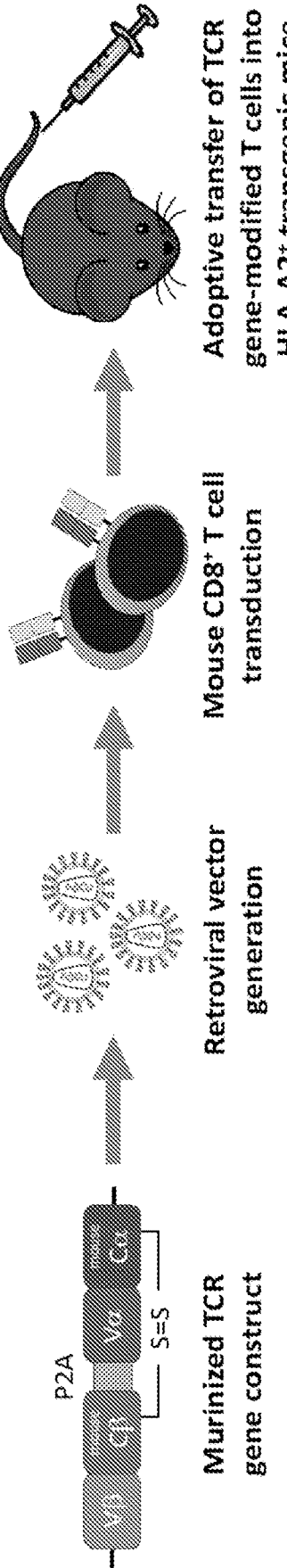
FIG. 6 shows a schematic for murinization of top HLA-A2:01/cyclin A1 TCR candidates for in vivo safety testing.

As the cyclin A1 protein sequence is highly conserved in humans and mice and both mice and humans exhibit low levels of CCNA1 mRNA expression in the lungs and brain (by qPCR), the mouse is a good model to test the safety of cyclin A1-specific TCRs in vivo. In order for the human HLA*A02:01-restricted TCRs to recognize their cognate antigen in the mice, transgenic mice that have been genetically engineered to express the HLA*A0:012 molecule are used for in vivo testing. The human TCR variable domains thus maintain their ability to recognize both the peptide and presenting MHC molecule. For effective expression of the human TCR on the surface of mouse T cells, the murine TCR constant domains have been engineered in place of the human TCR constant domains of the human TCR, thus allowing normal function in the mouse cells (see, FIG. 6).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/629,648 filed Feb. 12, 2018, U.S. Provisional Patent Application No. 62/630,198 filed Feb. 13, 2018, and U.S. Provisional Patent Application No. 62/667,207 filed May 4, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed is:

1. An isolated T cell receptor (TCR) comprising a TCR α chain and a TCR β chain, wherein the TCR α chain comprises a TCR α chain variable (Vα) domain and a TCR α chain constant (Cα) domain and the TCR β chain comprises a TCR β chain variable (Vβ) domain and a TCR β chain constant (Cβ) domain, wherein:

the Vα domain comprises the amino acid sequence of SEQ ID NO:128 and the Vβ domain comprises the amino acid sequence of SEQ ID NO:130;

the Cα domain comprises a cysteine substitution, the Cβ domain comprises a cysteine substitution, and the cysteine substitution in the Cα domain and the cysteine substitution in the Cβ domain create a disulfide bond between the Cα domain and the Cβ domain which is not present in a TCR comprising the native Cα domain and the native Cβ domain; and the TCR is capable of specifically binding to a human cyclin A1 (CCNA1) peptide FLDRFLSCM (SEQ ID NO:1):human leukocyte antigen-A*02:01 (HLA-A*02:01) complex.

2. The isolated TCR of claim 1, wherein:

(i) the Cα domain comprises at least 90% sequence identity to the amino acid sequence of SEQ ID NO:33; and (ii) the Cβ domain comprises at least 90% sequence identity to the amino acid sequence of SEQ ID NO:34 or SEQ ID NO:84.

3. The isolated TCR of claim 1, wherein:

(a) the Cα domain comprises a variant of the amino acid sequence of SEQ ID NO:33 comprising a single amino acid substitution, wherein the single amino acid substitution is a cysteine substitution at position 49 of SEQ ID NO:33; and (b) the Cβ domain comprises a variant of the amino acid sequence of SEO TD NO:34 comprising a single amino acid substitution, wherein the single amino acid substitution is a cysteine substitution at position 57 of SEO ID NO:34.

4. The isolated TCR of claim 1, wherein:

(a) the Cα domain comprises a variant of the amino acid sequence of SEQ ID NO:33 comprising a single amino acid substitution, wherein the single amino acid substitution is a cysteine substitution at position 49 of SEQ ID NO:33; and (b) the Cβ domain comprises a variant of the amino acid sequence of SEQ ID NO:34 comprising a single amino acid substitution, wherein the single amino acid substitution is a cysteine substitution at position 57 of SEQ ID NO:34, or the Cβ domain comprises a variant of the amino acid sequence of SEQ ID NO:84 comprising a single amino acid substitution, wherein the single amino acid substitution is a cysteine substitution at position 56 of SEQ ID NO:84.

5. An isolated polynucleotide encoding the TCR of claim 1.

6. An isolated vector comprising the polynucleotide of claim 5.

7. An isolated host cell comprising the polynucleotide of claim 5, wherein the host cell expresses on its cell surface the TCR encoded by the polynucleotide, wherein the host cell is a CD3+ T cell.

8. The isolated host cell of claim 7, wherein the host cell is a human CD3+ T cell.

9. The isolated host cell of claim 8, wherein the host cell is a human CD3+ CD8+ T cell.

10. A composition comprising the isolated host cell of claim 9, and a pharmaceutically acceptable carrier, diluent, or excipient.

11. A method of treating a cancer that overexpresses CCNA1, comprising administering to an HLA-A*02:01+ human subject having the cancer an effective amount of the composition of claim 10.

12. The method of claim 11, wherein the cancer is acute myeloid leukemia, testicular cancer, endometrial cancer, or ovarian cancer.

13. An isolated CD3+ T cell comprising a heterologous polynucleotide encoding a T cell receptor (TCR) comprising a TCR α chain and a TCR β chain, wherein the TCR α chain comprises a TCR α chain variable (Vα) domain and a TCR α chain constant (Cα) domain and the TCR β chain comprises a TCR β chain variable (Vβ) domain and a TCR β chain constant (Cβ) domain, wherein:

the Vα domain comprises the amino acid sequence of SEQ ID NO:128 and the Vβ domain comprises the amino acid sequence of SEQ ID NO:130; and the TCR is capable of specifically binding to a human cyclin A1 (CCNA1) peptide FLDRFLSCM (SEQ ID NO:1):human leukocyte antigen-A*02:01 (HLA-A*02:01) complex.

14. An isolated polynucleotide encoding a T cell receptor (TCR) comprising a TCR α chain and a TCR β chain, wherein the TCR α chain comprises a TCR α chain variable (Vα) domain and a TCR α chain constant (Cα) domain and the TCR β chain comprises a TCR β chain variable (Vβ) domain and a TCR β chain constant (Cβ) domain, wherein:

the Vα domain comprises the amino acid sequence of SEQ ID NO:130 the domain comprises the amino acid sequence of SEO ID NO:130;

the TCR is capable of specifically binding to a human cyclin A1 (CCNA1) peptide FLDRFLSCM (SEQ ID NO:1):human leukocyte antigen-A*02:01 (LAA*02: 01) complex;

the polynucleotide comprises a heterologous expression control sequence disposed upstream of a sequence encoding the TCR β chain and a sequence encoding the TCR α chain, and/or the polynucleotide comprises a sequence encoding a self-cleaving peptide, wherein the sequence encoding a self-cleaving peptide is disposed between the TCR β chain-encoding sequence and the TCR α chain-encoding sequence.

15. The isolated CD3+ T cell of claim 13, wherein the CD3+ T cell is a CD4+ T cell or a CD8+ T cell.

16. The isolated CD3+ T cell of claim 15, wherein the CD3+ T cell is a human CD3+ T cell.

17. A composition comprising a plurality of CD3+ T cells of claim 13, wherein the plurality comprises CD8+ T cells and CD4+ T cells.

18. An isolated polynucleotide encoding the amino acid sequence set forth in SEQ ID NO:178.

19. The isolated polynucleotide of claim 18, comprising the nucleic acid sequence set forth in SEQ ID NO:177.

20. An isolated viral vector encoding a T cell receptor (TCR), wherein the TCR comprises a TCR α chain and a TCR β chain, wherein the TCR α chain comprises a TCR α chain variable (Vα) domain and a TCR α chain constant (Cα) domain and the TCR β chain comprises a TCR β chain variable (Vβ) domain and a TCR β chain constant (Cβ) domain, wherein:

the Vα domain comprises the amino acid sequence of SEQ ID NO:128 and the Vβ domain comprises the amino acid sequence of SEQ ID NO:130; and the TCR is capable of specifically binding to a human cyclin A1 (CCNA1) peptide FLDRFLSCM (SEQ ID NO:1):human leukocyte antigen-A*02:01 (HLA-A*02:01) complex.

21. The isolated viral vector of claim 20, which is selected from a lentiviral vector, a retroviral vector, and an adenoviral vector.

* * * * *

SEQUENCE LISTING

```
<160> NUMBER OF SEQ ID NOS: 190

<210> SEQ ID NO 1
<211> LENGTH: 9
<212> TYPE: PRT
<213> ORGANISM: Homo sapiens
<220> FEATURE:
<221> NAME/KEY: MISC_FEATURE
<222> LOCATION: (1)..(9)
<223> OTHER INFORMATION: CCNA1 227-235 peptide

<400> SEQUENCE: 1

Phe Leu Asp Arg Phe Leu Ser Cys Met
1               5

<210> SEQ ID NO 2
<211> LENGTH: 11
<212> TYPE: PRT
<213> ORGANISM: Homo sapiens
<220> FEATURE:
<221> NAME/KEY: MISC_FEATURE
<222> LOCATION: (1)..(11)
<223> OTHER INFORMATION: CCNA1 341-351 peptide

<400> SEQUENCE: 2

Ser Leu Ile Ala Ala Ala Ala Phe Cys Leu Ala
1               5                   10

<210> SEQ ID NO 3
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: CCNA1 370-379 peptide

<400> SEQUENCE: 3

Tyr Ser Leu Ser Glu Ile Val Pro Cys Leu
1               5                   10

<210> SEQ ID NO 4
<211> LENGTH: 421
<212> TYPE: PRT
<213> ORGANISM: Homo sapiens
<220> FEATURE:
<221> NAME/KEY: MISC_FEATURE
<222> LOCATION: (1)..(421)
```

-continued

<223> OTHER INFORMATION: CCNA1 protein isoform 3

<400> SEQUENCE: 4

```
Met His Cys Ser Asn Pro Lys Ser Gly Val Val Leu Ala Thr Val Ala
1                5                   10                  15

Arg Gly Pro Asp Ala Cys Gln Ile Leu Thr Arg Ala Pro Leu Gly Gln
            20                  25                  30

Asp Pro Pro Gln Arg Thr Val Leu Gly Leu Leu Thr Ala Asn Gly Gln
        35                  40                  45

Tyr Arg Arg Thr Cys Gly Gln Gly Ile Thr Arg Ile Arg Cys Tyr Ser
    50                  55                  60

Gly Ser Glu Asn Ala Phe Pro Pro Ala Gly Lys Lys Ala Leu Pro Asp
65                  70                  75                  80

Cys Gly Val Gln Glu Pro Pro Lys Gln Gly Phe Asp Ile Tyr Met Asp
                85                  90                  95

Glu Leu Glu Gln Gly Asp Arg Asp Ser Cys Ser Val Arg Glu Gly Met
            100                 105                 110

Ala Phe Glu Asp Val Tyr Glu Val Asp Thr Gly Thr Leu Lys Ser Asp
            115                 120                 125

Leu His Phe Leu Leu Asp Phe Asn Thr Val Ser Pro Met Leu Val Asp
        130                 135                 140

Ser Ser Leu Leu Ser Gln Ser Glu Asp Ile Ser Ser Leu Gly Thr Asp
145                 150                 155                 160

Val Ile Asn Val Thr Glu Tyr Ala Glu Glu Ile Tyr Gln Tyr Leu Arg
                165                 170                 175

Glu Ala Glu Ile Arg His Arg Pro Lys Ala His Tyr Met Lys Lys Gln
            180                 185                 190

Pro Asp Ile Thr Glu Gly Met Arg Thr Ile Leu Val Asp Trp Leu Val
            195                 200                 205

Glu Val Gly Glu Glu Tyr Lys Leu Arg Ala Glu Thr Leu Tyr Leu Ala
        210                 215                 220

Val Asn Phe Leu Asp Arg Phe Leu Ser Cys Met Ser Val Leu Arg Gly
225                 230                 235                 240

Lys Leu Gln Leu Val Gly Thr Ala Ala Met Leu Leu Ala Ser Lys Tyr
                245                 250                 255

Glu Glu Ile Tyr Pro Pro Glu Val Asp Glu Phe Val Tyr Ile Thr Asp
            260                 265                 270

Asp Thr Tyr Thr Lys Arg Gln Leu Leu Lys Met Glu His Leu Leu Leu
            275                 280                 285

Lys Val Leu Ala Phe Asp Leu Thr Val Pro Thr Thr Asn Gln Phe Leu
        290                 295                 300

Leu Gln Tyr Leu Arg Arg Gln Gly Val Cys Val Arg Thr Glu Asn Leu
305                 310                 315                 320

Ala Lys Tyr Val Ala Glu Leu Ser Leu Leu Glu Ala Asp Pro Phe Leu
                325                 330                 335

Lys Tyr Leu Pro Ser Leu Ile Ala Ala Ala Ala Phe Cys Leu Ala Asn
            340                 345                 350

Tyr Thr Val Asn Lys His Phe Trp Pro Glu Thr Leu Ala Ala Phe Thr
            355                 360                 365

Gly Tyr Ser Leu Ser Glu Ile Val Pro Cys Leu Ser Glu Leu His Lys
        370                 375                 380

Ala Tyr Leu Asp Ile Pro His Arg Pro Gln Gln Ala Ile Arg Glu Lys
385                 390                 395                 400
```

```
Tyr Lys Ala Ser Lys Tyr Leu Cys Val Ser Leu Met Glu Pro Pro Ala
                405                 410                 415

Val Leu Leu Leu Gln
            420

<210> SEQ ID NO 5
<211> LENGTH: 13
<212> TYPE: PRT
<213> ORGANISM: Artificial Sequence
<220> FEATURE:
<223> OTHER INFORMATION: TCR number5 Valpha CDR3

<400> SEQUENCE: 5

Cys Gly Thr Glu Glu Ala Asn Asp Tyr Lys Leu Ser Phe
1               5                   10

<210> SEQ ID NO 6
<211> LENGTH: 15
<212> TYPE: PRT
<213> ORGANISM: Artificial Sequence
<220> FEATURE:
<223> OTHER INFORMATION: TCR number5 Vbeta CDR3

<400> SEQUENCE: 6

Cys Ala Ser Ser Val Gly Gln Gly Ser Ser Tyr Glu Gln Tyr Phe
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: TCR number 9 and TCR number 11 Valpha CDR3

<400> SEQUENCE: 7

Cys Val Val Trp Gly Gly Asp Thr Asp Lys Leu Ile Phe
1               5                   10

<210> SEQ ID NO 8
<211> LENGTH: 13
<212> TYPE: PRT
<213> ORGANISM: Artificial Sequence
<220> FEATURE:
<223> OTHER INFORMATION: TCR number 9 Vbeta CDR3

<400> SEQUENCE: 8

Cys Ala Ile Leu Asp Gly Glu Gly Ser Pro Leu His Phe
1               5                   10

<210> SEQ ID NO 9
<211> LENGTH: 13
<212> TYPE: PRT
<213> ORGANISM: Artificial Sequence
<220> FEATURE:
<223> OTHER INFORMATION: TCR number 6 Valpha CDR3

<400> SEQUENCE: 9

Cys Ala Leu Gly Pro Tyr Asn Asp Tyr Lys Leu Ser Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: TCR number 6 Vbeta CDR3
```

```
<400> SEQUENCE: 10

Cys Ala Ser Ser Asp Arg Ser Asn Thr Gly Glu Leu Phe Phe
1               5                   10

<210> SEQ ID NO 11
<211> LENGTH: 13
<212> TYPE: PRT
<213> ORGANISM: Artificial Sequence
<220> FEATURE:
<223> OTHER INFORMATION: TCR number 1 Valpha CDR3

<400> SEQUENCE: 11

Cys Ala Val Glu Gly Asp Ser Ser Tyr Lys Leu Ile Phe
1               5                   10

<210> SEQ ID NO 12
<211> LENGTH: 13
<212> TYPE: PRT
<213> ORGANISM: Artificial Sequence
<220> FEATURE:
<223> OTHER INFORMATION: TCR number 1 Vbeta CDR3

<400> SEQUENCE: 12

Cys Ala Ser Ser Phe Phe Ser Gln Glu Thr Gln Tyr Phe
1               5                   10

<210> SEQ ID NO 13
<211> LENGTH: 11
<212> TYPE: PRT
<213> ORGANISM: Artificial Sequence
<220> FEATURE:
<223> OTHER INFORMATION: TCR number 2 Valpha CDR3

<400> SEQUENCE: 13

Cys Ala Val Ile Gly Glu Gln Asn Phe Val Phe
1               5                   10

<210> SEQ ID NO 14
<211> LENGTH: 17
<212> TYPE: PRT
<213> ORGANISM: Artificial Sequence
<220> FEATURE:
<223> OTHER INFORMATION: TCR number 2 Vbeta CDR3

<400> SEQUENCE: 14

Cys Ala Ser Ser Leu Ser Gly Leu Gly Ser Gly Ala Asn Val Leu Thr
1               5                   10                  15

Phe

<210> SEQ ID NO 15
<211> LENGTH: 13
<212> TYPE: PRT
<213> ORGANISM: Artificial Sequence
<220> FEATURE:
<223> OTHER INFORMATION: TCR number 3 Valpha CDR3

<400> SEQUENCE: 15

Cys Ala Val Asp Ser Gly Gly Tyr Gln Lys Val Thr Phe
1               5                   10

<210> SEQ ID NO 16
<211> LENGTH: 13
<212> TYPE: PRT
<213> ORGANISM: Artificial Sequence
<220> FEATURE:
<223> OTHER INFORMATION: TCR number 3 Vbeta CDR3
```

-continued

```
<400> SEQUENCE: 16

Cys Ala Ser Ser Leu Asn Met Asn Thr Glu Ala Phe Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: TCR number 10 Valpha CDR3

<400> SEQUENCE: 17

Cys Ala Thr Asp Glu Ser Ser Asn Tyr Lys Leu Thr Phe
1               5                   10

<210> SEQ ID NO 18
<211> LENGTH: 13
<212> TYPE: PRT
<213> ORGANISM: Artificial Sequence
<220> FEATURE:
<223> OTHER INFORMATION: TCR number 10 Vbeta CDR3

<400> SEQUENCE: 18

Cys Ala Ser Ser Leu Asn Met Asn Thr Glu Ala Phe Phe
1               5                   10

<210> SEQ ID NO 19
<211> LENGTH: 17
<212> TYPE: PRT
<213> ORGANISM: Artificial Sequence
<220> FEATURE:
<223> OTHER INFORMATION: TCR number 4 Valpha CDR3

<400> SEQUENCE: 19

Cys Ala Thr Asp Ala Trp Glu Ser Asn Phe Gly Asn Glu Lys Leu Thr
1               5                   10                  15

Phe

<210> SEQ ID NO 20
<211> LENGTH: 14
<212> TYPE: PRT
<213> ORGANISM: Artificial Sequence
<220> FEATURE:
<223> OTHER INFORMATION: TCR number 4 Vbeta CDR3

<400> SEQUENCE: 20

Cys Ala Ser Ser Leu Val Val Gly Ser Tyr Glu Gln Tyr Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: TCR number 7 Valpha CDR3

<400> SEQUENCE: 21

Cys Ala Tyr Leu Gly Ala Gly Asn Gln Phe Tyr Phe
1               5                   10

<210> SEQ ID NO 22
<211> LENGTH: 14
<212> TYPE: PRT
<213> ORGANISM: Artificial Sequence
<220> FEATURE:
```

-continued

```
<223> OTHER INFORMATION: TCR number 7 Vbeta CDR3

<400> SEQUENCE: 22

Cys Ala Ser Ser Leu Asn Arg Gly Arg Tyr Gly Tyr Thr Phe
1               5                   10

<210> SEQ ID NO 23
<211> LENGTH: 16
<212> TYPE: PRT
<213> ORGANISM: Artificial Sequence
<220> FEATURE:
<223> OTHER INFORMATION: TCR number 8 Valpha CDR3

<400> SEQUENCE: 23

Cys Ala Leu Ser Glu Leu Ala Ser Gly Gly Ser Tyr Ile Pro Thr Phe
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: TCR number 8 Vbeta CDR3

<400> SEQUENCE: 24

Cys Ala Ser Ser Phe Arg Leu Ala Gly Gly Pro Ser Thr Asp Thr Gln
1               5                   10                  15

Tyr Phe

<210> SEQ ID NO 25
<211> LENGTH: 66
<212> TYPE: DNA
<213> ORGANISM: Artificial Sequence
<220> FEATURE:
<223> OTHER INFORMATION: P2A peptide encoding nucleic acid

<400> SEQUENCE: 25
ggttccggag ccacgaactt ctctctgtta aagcaagcag gagacgtgga agaaaacccc      60
ggtccc                                                                66

<210> SEQ ID NO 26
<211> LENGTH: 63
<212> TYPE: DNA
<213> ORGANISM: Artificial Sequence
<220> FEATURE:
<223> OTHER INFORMATION: T2A peptide encoding nucleic acid

<400> SEQUENCE: 26
ggaagcggag agggcagagg aagtctgcta acatgcggtg acgtcgagga gaatcctgga      60
cct                                                                   63

<210> SEQ ID NO 27
<211> LENGTH: 69
<212> TYPE: DNA
<213> ORGANISM: Artificial Sequence
<220> FEATURE:
<223> OTHER INFORMATION: E2A peptide encoding nucleic acid

<400> SEQUENCE: 27
ggaagcggac agtgtactaa ttatgctctc ttgaaattgg ctggagatgt tgagagcaac      60
cctggacct                                                             69

<210> SEQ ID NO 28
```

```
<211> LENGTH: 75
<212> TYPE: DNA
<213> ORGANISM: Artificial Sequence
<220> FEATURE:
<223> OTHER INFORMATION: F2A peptide encoding nucleic acid

<400> SEQUENCE: 28
ggaagcggag tgaaacagac tttgaatttt gaccttctca agttggcggg agacgtggag      60
tccaaccctg gacct                                                       75

<210> SEQ ID NO 29
<211> LENGTH: 22
<212> TYPE: PRT
<213> ORGANISM: Artificial Sequence
<220> FEATURE:
<223> OTHER INFORMATION: P2A peptide

<400> SEQUENCE: 29

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 30
<211> LENGTH: 21
<212> TYPE: PRT
<213> ORGANISM: Artificial Sequence
<220> FEATURE:
<223> OTHER INFORMATION: T2A peptide

<400> SEQUENCE: 30

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 31
<211> LENGTH: 23
<212> TYPE: PRT
<213> ORGANISM: Artificial Sequence
<220> FEATURE:
<223> OTHER INFORMATION: E2A peptide

<400> SEQUENCE: 31

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 32
<211> LENGTH: 25
<212> TYPE: PRT
<213> ORGANISM: Artificial Sequence
<220> FEATURE:
<223> OTHER INFORMATION: F2A peptide

<400> SEQUENCE: 32

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 33
<211> LENGTH: 142
```

<212> TYPE: PRT
<213> ORGANISM: Artificial Sequence
<220> FEATURE:
<223> OTHER INFORMATION: TCRalpha constant domain polypeptide

<400> SEQUENCE: 33

```
Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
            115                 120                 125

Ala Gly Phe Asn Leu Leu Met Thr Leu Arg Leu Trp Ser Ser
    130                 135                 140
```

<210> SEQ ID NO 34
<211> LENGTH: 177
<212> TYPE: PRT
<213> ORGANISM: Artificial Sequence
<220> FEATURE:
<223> OTHER INFORMATION: TCRbeta1 constant domain polypeptide

<400> SEQUENCE: 34

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

-continued

```
<210> SEQ ID NO 35
<211> LENGTH: 1821
<212> TYPE: DNA
<213> ORGANISM: Artificial Sequence
<220> FEATURE:
<223> OTHER INFORMATION: TCR number 5 construct; beta chain-P2A-alpha
      chain

<400> SEQUENCE: 35
atgggcttca ggctcctctg ctgtgtggcc ttttgtctcc tgggagcagg cccagtggat       60
tctggagtca cacaaacccc aaagcacctg atcacagcaa ctggacagcg agtgacgctg      120
agatgctccc ctaggtctgg agacctctct gtgtactggt accaacagag cctggaccag      180
ggcctccagt tcctcattca gtattataat ggagaagaga gagcaaaagg aaacattctt      240
gaacgattct ccgcacaaca gttccctgac ttgcactctg aactaaacct gagctctctg      300
gagctggggg actcagcttt gtatttctgt gccagcagcg tagggcaggg gtcctcctac      360
gagcagtact cgggccgggg caccaggctc acggtcacag aggacctgaa aaacgtgttc      420
ccacccgagg tcgctgtgtt tgagccatca gaagcagaga tctcccacac ccaaaaggcc      480
acactggtgt gcctggccac aggcttctac cccgaccacg tggagctgag ctggtgggtg      540
aatgggaagg aggtgcacag tggggtcagc acagacccgc agcccctcaa ggagcagccc      600
gccctcaatg actccagata ctgcctgagc agccgcctga gggtctcggc caccttctgg      660 cagaacccccc gcaaccactt ccgctgtcaa gtccagttct acgggctctc ggagaatgac      720
gagtggaccc aggatagggc caaacctgtc acccagatcg tcagcgccga ggcctggggt      780
agagcagact gtggcttcac ctccgagtct taccagcaag gggtcctgtc tgccaccatc      840
ctctatgaga tcttgctagg gaaggccacc ttgtatgccg tgctggtcag tgccctcgtg      900
ctgatggcca tggtcaagag aaaggattcc agaggcggtt ccggagccac gaacttctct      960
ctgttaaagc aagcaggaga cgtggaagaa aaccccggtc ccatggagac tctcctgaaa     1020
gtgctttcag gcaccttgtt gtggcagttg acctgggtga gaagccaaca accagtgcag     1080
agtcctcaag ccgtgatcct ccgagaaggg gaagatgctg tcatcaactg cagttcctcc     1140
aaggctttat attctgtaca ctggtacagg cagaagcatg tgaagcacc cgtcttcctg     1200 atgatattac tgaagggtgg agaacagaag ggtcatgaaa aaatatctgc ttcatttaat     1260
gaaaaaaagc agcaaagctc cctgtacctt acggcctccc agctcagtta ctcaggaacc     1320
tacttctgcg gcacagagga agctaacgac tacaagctca gctttggagc cggaaccaca     1380
gtaactgtaa gagcaaatat ccagaaccct gaccctgccg tgtaccagct gagagactct     1440
aaatccagtg acaagtctgt ctgcctattc accgattttg attctcaaac aaatgtgtca     1500
caaagtaagg attctgatgt gtatatcaca gacaaaactg tgctagacat gaggtctatg     1560
gacttcaaga gcaacagtgc tgtggcctgg agcaacaaat ctgactttgc atgtgcaaac     1620
gccttcaaca acagcattat tccagaagac accttcttcc ccagcccaga aagttcctgt     1680
gatgtcaagc tggtcgagaa aagctttgaa acagatacga acctaaactt tcaaaacctg     1740
tcagtgattg ggttccgaat cctcctcctg aaagtggccg ggtttaatct gctcatgacg     1800
ctgcggctgt ggtccagctg a                                                1821
```

```
<210> SEQ ID NO 36
<211> LENGTH: 606
<212> TYPE: PRT
<213> ORGANISM: Artificial Sequence
<220> FEATURE:
```

-continued

<223> OTHER INFORMATION: TCR number 5 construct; beta chain-P2A-alpha
      chain

<400> SEQUENCE: 36

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
        50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Gly Gln Gly Ser Ser Tyr Glu Gln Tyr Phe Gly Pro Gly Thr
        115                 120                 125

Arg Leu Thr Val Thr Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
        210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
        290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Glu
            325                 330                 335

Thr Leu Leu Lys Val Leu Ser Gly Thr Leu Leu Trp Gln Leu Thr Trp
            340                 345                 350

Val Arg Ser Gln Gln Pro Val Gln Ser Pro Gln Ala Val Ile Leu Arg
        355                 360                 365

Glu Gly Glu Asp Ala Val Ile Asn Cys Ser Ser Ser Lys Ala Leu Tyr
        370                 375                 380

Ser Val His Trp Tyr Arg Gln Lys His Gly Glu Ala Pro Val Phe Leu
385                 390                 395                 400

```
Met Ile Leu Leu Lys Gly Gly Glu Gln Lys Gly His Glu Lys Ile Ser
            405             410             415

Ala Ser Phe Asn Glu Lys Lys Gln Gln Ser Ser Leu Tyr Leu Thr Ala
            420             425             430

Ser Gln Leu Ser Tyr Ser Gly Thr Tyr Phe Cys Gly Thr Glu Glu Ala
        435             440             445

Asn Asp Tyr Lys Leu Ser Phe Gly Ala Gly Thr Thr Val Thr Val Arg
    450             455             460

Ala Asn Ile Gln Asn Pro Asp Pro Ala Val Tyr Gln Leu Arg Asp Ser
465             470             475             480

Lys Ser Ser Asp Lys Ser Val Cys Leu Phe Thr Asp Phe Asp Ser Gln
            485             490             495

Thr Asn Val Ser Gln Ser Lys Asp Ser Asp Val Tyr Ile Thr Asp Lys
            500             505             510

Thr Val Leu Asp Met Arg Ser Met Asp Phe Lys Ser Asn Ser Ala Val
            515             520             525

Ala Trp Ser Asn Lys Ser Asp Phe Ala Cys Ala Asn Ala Phe Asn Asn
            530             535             540

Ser Ile Ile Pro Glu Asp Thr Phe Phe Pro Ser Pro Glu Ser Ser Cys
545             550             555             560

Asp Val Lys Leu Val Glu Lys Ser Phe Glu Thr Asp Thr Asn Leu Asn
            565             570             575

Phe Gln Asn Leu Ser Val Ile Gly Phe Arg Ile Leu Leu Leu Lys Val
            580             585             590

Ala Gly Phe Asn Leu Leu Met Thr Leu Arg Leu Trp Ser Ser
            595             600             605
```

```
<210> SEQ ID NO 37
<211> LENGTH: 1493
<212> TYPE: DNA
<213> ORGANISM: Artificial Sequence
<220> FEATURE:
<223> OTHER INFORMATION: codon optimized TCR number 5 construct; beta
      chain-P2A-alpha chain with cysteine substitutions in beta and
      alpha chain constant domains (partial sequence)

<400> SEQUENCE: 37
ctcaataaaa gagcccacaa cccctcactc ggcgcgccac catgggcttc agactgttgt      60
gttgcgtggc cttttgcctt cttggagctg gacctgtgga ttctggagtt acacagaccc     120
ctaagcacct gattacagcc acaggacaga gagtgaccct gagatgtagc cctagaagcg     180
gagatctgag cgtgtattgg taccagcaga gcctggatca aggactccag tttctgatcc     240
agtactacaa cggcgaggag agagccaagg gcaatattct ggagaggttt tctgcccagc     300
agttccctga tctgcactct gaactgaacc tgtctagcct ggaactggga gattctgccc     360 tgtactttg tgcctctagc gttggacagg gcagctctta tgagcagtac tttgacctg      420 gcaccagact gacagtgaca gaagacctga agaacgtgtt cccccagag gtggccgtgt      480 tcgagcctag cgaggccgag atcagccaca cccagaaagc caccctcgtg tgcctggcca     540
ccggctttta ccccgaccac gtggaactgt cttggtgggt caacggcaaa gaggtgcaca     600
gcggcgtctg caccgacccc cagcccctga aagagcagcc cgccctgaac gacagccggt     660
actgtctgag cagcagactg agagtgtccg ccaccttctg gcagaacccc cggaaccact     720
tcagatgcca ggtgcagttc tacggcctga gcgagaacga cgagtggacc caggaccggg     780
ccaagcccgt gacccagatc gtgtctgctg aggcctgggg cagagccgat tgcggcttca     840
```

-continued

```
ccagcgagag ctaccagcag ggcgtgctga gcgccaccat cctgtacgag atcctgctgg    900
gcaaggccac cctgtacgcc gtgctggtgt ccgccctggt gctgatggcc atggtcaagc    960
ggaaggacag ccggggcggt tccggagcca cgaacttctc tctgttaaag caagcaggag   1020
acgtggaaga aaaccccggt cccatggaaa ccctgctgaa agtgctgagc ggaacactgt   1080
tatggcagct tacatgggtg aggtctcagc aacctgtgca atctccacag gccgttatcc   1140 tgagagaag agaagatgcc gtgatcaact gctctagctc taaagccctg tacagcgtgc   1200
actggtacag acagaaacac ggagaagctc ccgtgttcct gatgattctg ctgaaaggag   1260
gcgagcagaa gggacacgag aagatttctg ccagcttcaa cgagaagaag cagcagtcta   1320
gcctgtacct gacagcttct cagctgagct atagcggcac ctactttgt ggcacagagg    1380 aagccaacga ctacaaactg agctttggag ccggcacaac agtgacagtt agagccaata   1440
tccagaaccc cgatcctgct gtgtaccagc tgcgggacag caagagcagc gac          1493
```

```
<210> SEQ ID NO 38
<211> LENGTH: 495
<212> TYPE: PRT
<213> ORGANISM: Artificial Sequence
<220> FEATURE:
<223> OTHER INFORMATION: codon optimized TCR number 5 construct; beta
      chain-P2A-alpha chain with cysteine substitutions in beta and
      alpha chain constant domains (partial sequence)

<400> SEQUENCE: 38

Lys Ser Pro Gln Pro Leu Thr Arg Arg Ala Thr Met Gly Phe Arg Leu
1               5                   10                  15

Leu Cys Cys Val Ala Phe Cys Leu Leu Gly Ala Gly Pro Val Asp Ser
            20                  25                  30

Gly Val Thr Gln Thr Pro Lys His Leu Ile Thr Ala Thr Gly Gln Arg
        35                  40                  45

Val Thr Leu Arg Cys Ser Pro Arg Ser Gly Asp Leu Ser Val Tyr Trp
    50                  55                  60

Tyr Gln Gln Ser Leu Asp Gln Gly Leu Gln Phe Leu Ile Gln Tyr Tyr
65                  70                  75                  80

Asn Gly Glu Glu Arg Ala Lys Gly Asn Ile Leu Glu Arg Phe Ser Ala
                85                  90                  95

Gln Gln Phe Pro Asp Leu His Ser Glu Leu Asn Leu Ser Ser Leu Glu
            100                 105                 110

Leu Gly Asp Ser Ala Leu Tyr Phe Cys Ala Ser Ser Val Gly Gln Gly
        115                 120                 125

Ser Ser Tyr Glu Gln Tyr Phe Gly Pro Gly Thr Arg Leu Thr Val Thr
    130                 135                 140

Glu Asp Leu Lys Asn Val Phe Pro Pro Glu Val Ala Val Phe Glu Pro
145                 150                 155                 160

Ser Glu Ala Glu Ile Ser His Thr Gln Lys Ala Thr Leu Val Cys Leu
                165                 170                 175

Ala Thr Gly Phe Tyr Pro Asp His Val Glu Leu Ser Trp Trp Val Asn
            180                 185                 190

Gly Lys Glu Val His Ser Gly Val Cys Thr Asp Pro Gln Pro Leu Lys
        195                 200                 205

Glu Gln Pro Ala Leu Asn Asp Ser Arg Tyr Cys Leu Ser Ser Arg Leu
    210                 215                 220

Arg Val Ser Ala Thr Phe Trp Gln Asn Pro Arg Asn His Phe Arg Cys
225                 230                 235                 240
```

-continued

```
Gln Val Gln Phe Tyr Gly Leu Ser Glu Asn Asp Glu Trp Thr Gln Asp
              245               250               255

Arg Ala Lys Pro Val Thr Gln Ile Val Ser Ala Glu Ala Trp Gly Arg
              260               265               270

Ala Asp Cys Gly Phe Thr Ser Glu Ser Tyr Gln Gln Gly Val Leu Ser
              275               280               285

Ala Thr Ile Leu Tyr Glu Ile Leu Leu Gly Lys Ala Thr Leu Tyr Ala
         290               295               300

Val Leu Val Ser Ala Leu Val Leu Met Ala Met Val Lys Arg Lys Asp
    305               310               315               320

Ser Arg Gly Gly Ser Gly Ala Thr Asn Phe Ser Leu Leu Lys Gln Ala
                  325               330               335

Gly Asp Val Glu Glu Asn Pro Gly Pro Met Glu Thr Leu Leu Lys Val
              340               345               350

Leu Ser Gly Thr Leu Leu Trp Gln Leu Thr Trp Val Arg Ser Gln Gln
         355               360               365

Pro Val Gln Ser Pro Gln Ala Val Ile Leu Arg Glu Gly Glu Asp Ala
         370               375               380

Val Ile Asn Cys Ser Ser Ser Lys Ala Leu Tyr Ser Val His Trp Tyr
    385               390               395               400

Arg Gln Lys His Gly Glu Ala Pro Val Phe Leu Met Ile Leu Leu Lys
                  405               410               415

Gly Gly Glu Gln Lys Gly His Glu Lys Ile Ser Ala Ser Phe Asn Glu
                  420               425               430

Lys Lys Gln Gln Ser Ser Leu Tyr Leu Thr Ala Ser Gln Leu Ser Tyr
              435               440               445

Ser Gly Thr Tyr Phe Cys Gly Thr Glu Glu Ala Asn Asp Tyr Lys Leu
         450               455               460

Ser Phe Gly Ala Gly Thr Thr Val Thr Val Arg Ala Asn Ile Gln Asn
    465               470               475               480

Pro Asp Pro Ala Val Tyr Gln Leu Arg Asp Ser Lys Ser Ser Asp
              485               490               495
```

```
<210> SEQ ID NO 39
<211> LENGTH: 1813
<212> TYPE: DNA
<213> ORGANISM: Artificial Sequence
<220> FEATURE:
<223> OTHER INFORMATION: TCR number 11 construct; beta chain-P2A-alpha
      chain

<400> SEQUENCE: 39
atgggcacca ggctcttctt ctatgtggcc ctttgtctgc tgtgggcagg acacagggat      60
gctggaatca cccagagccc aagatacaag atcacagaga caggaaggca ggtgaccttg     120
atgtgtcacc agacttggag ccacagctat atgttctggt atcgacaaga cctgggacat     180
gggctgaggc tgatctatta ctcagcagct gctgatatta cagataaagg agaagtcccc     240
gatggctatg ttgtctccag atccaagaca gagaatttcc ccctcactct ggagtcagct     300
acccgctccc agacatctgt gtatttctgc gccagcagtg acgggggcgg gcagtacttc     360
gggccgggca ccaggctcac ggtcacagag acctgaaaa acgtgttccc acccgaggtc     420
gctgtgtttg agccatcaga agcagagatc tcccacaccc aaaaggccac actggtgtgc     480
ctggccacag gcttctaccc cgaccacgtg agctgagct ggtgggtgaa tgggaaggag     540
gtgcacagtg gggtcagcac agacccgcag cccctcaagg agcagcccgc cctcaatgac     600
```

```
tccagatact gcctgagcag ccgcctgagg gtctcggcca ccttctggca gaaccccgc    660 aaccacttcc gctgtcaagt ccagttctac gggctctcgg agaatgacga gtggacccag    720
gatagggcca aacctgtcac ccagatcgtc agcgccgagg cctgggggtag agcagactgt    780 ggcttcacct ccgagtctta ccagcaaggg gtcctgtctg ccaccatcct ctatgagatc    840
ttgctaggga aggccacctt gtatgccgtg ctggtcagtg ccctcgtgct gatggccatg    900
gtcaagagaa aggattccag aggcggttcc ggagccacga acttctctct gttaaagcaa    960
gcaggagacg tggaagaaaa ccccggtccc atgaaaaagc atctgacgac cttcttggtg    1020
attttgtggc tttattttta tagggggaat ggcaaaaacc aagtggagca gagtcctcag    1080
tccctgatca tcctggaggg aaagaactgc actcttcaat gcaattatac agtgagcccc    1140
ttcagcaact taaggtggta taagcaagat actgggagag tcctgtttc cctgacaatc    1200 atgactttca gtgagaacac aaagtcgaac ggaagatata cagcaactct ggatgcagac    1260
acaaagcaaa gctctctgca catcacagcc tcccagctca gcgattcagc ctcctacatc    1320
tgtgtggtgt ggggggggga caccgacaag ctcatctttg ggactgggac cagattacaa    1380
gtctttccaa atatccagaa ccctgaccct gccgtgtacc agctgagaga ctctaaatcc    1440
agtgacaagt ctgtctgcct attcaccgat tttgattctc aaacaaatgt gtcacaaagt    1500
aaggattctg atgtgtatat cacagacaaa actgctagac atgaggtcta tggacttcaa    1560
gagcaacagt gctgtggcct ggagcaacaa atctgacttt gcatgtgcaa acgccttcaa    1620
caacagcatt attccagaag acaccttctt ccccagccca gaaagttcct gtgatgtcaa    1680
gctggtcgag aaaagctttg aaacagatac gaacctaaac tttcaaaacc tgtcagtgat    1740
tgggttccga atcctcctcc tgaaagtggc cgggtttaat ctgctcatga cgctgcggct    1800
gtggtccagc tga                                                       1813
```

```
<210> SEQ ID NO 40
<211> LENGTH: 531
<212> TYPE: PRT
<213> ORGANISM: Artificial Sequence
<220> FEATURE:
<223> OTHER INFORMATION: TCR number 11 construct; beta chain-P2A-alpha
      chain

<400> SEQUENCE: 40

Met Gly Thr Arg Leu Phe Phe Tyr Val Ala Leu Cys Leu Leu Trp Ala
1               5                   10                  15

Gly His Arg Asp Ala Gly Ile Thr Gln Ser Pro Arg Tyr Lys Ile Thr
            20                  25                  30

Glu Thr Gly Arg Gln Val Thr Leu Met Cys His Gln Thr Trp Ser His
        35                  40                  45

Ser Tyr Met Phe Trp Tyr Arg Gln Asp Leu Gly His Gly Leu Arg Leu
    50                  55                  60

Ile Tyr Tyr Ser Ala Ala Ala Asp Ile Thr Asp Lys Gly Glu Val Pro
65                  70                  75                  80

Asp Gly Tyr Val Val Ser Arg Ser Lys Thr Glu Asn Phe Pro Leu Thr
                85                  90                  95

Leu Glu Ser Ala Thr Arg Ser Gln Thr Ser Val Tyr Phe Cys Ala Ser
            100                 105                 110

Ser Asp Gly Gly Gly Gln Tyr Phe Gly Pro Gly Thr Arg Leu Thr Val
        115                 120                 125

Thr Glu Asp Leu Lys Asn Val Phe Pro Pro Glu Val Ala Val Phe Glu
```

-continued

```
         130              135              140

Pro Ser Glu Ala Glu Ile Ser His Thr Gln Lys Ala Thr Leu Val Cys
145              150              155              160

Leu Ala Thr Gly Phe Tyr Pro Asp His Val Glu Leu Ser Trp Trp Val
             165              170              175

Asn Gly Lys Glu Val His Ser Gly Val Ser Thr Asp Pro Gln Pro Leu
             180              185              190

Lys Glu Gln Pro Ala Leu Asn Asp Ser Arg Tyr Cys Leu Ser Ser Arg
         195              200              205

Leu Arg Val Ser Ala Thr Phe Trp Gln Asn Pro Arg Asn His Phe Arg
         210              215              220

Cys Gln Val Gln Phe Tyr Gly Leu Ser Glu Asn Asp Glu Trp Thr Gln
225              230              235              240

Asp Arg Ala Lys Pro Val Thr Gln Ile Val Ser Ala Glu Ala Trp Gly
             245              250              255

Arg Ala Asp Cys Gly Phe Thr Ser Glu Ser Tyr Gln Gln Gly Val Leu
             260              265              270

Ser Ala Thr Ile Leu Tyr Glu Ile Leu Leu Gly Lys Ala Thr Leu Tyr
             275              280              285

Ala Val Leu Val Ser Ala Leu Val Leu Met Ala Met Val Lys Arg Lys
         290              295              300

Asp Ser Arg Gly Gly Ser Gly Ala Thr Asn Phe Ser Leu Leu Lys Gln
305              310              315              320

Ala Gly Asp Val Glu Glu Asn Pro Gly Pro Met Lys Lys His Leu Thr
             325              330              335

Thr Phe Leu Val Ile Leu Trp Leu Tyr Phe Tyr Arg Gly Asn Gly Lys
             340              345              350

Asn Gln Val Glu Gln Ser Pro Gln Ser Leu Ile Ile Leu Glu Gly Lys
             355              360              365

Asn Cys Thr Leu Gln Cys Asn Tyr Thr Val Ser Pro Phe Ser Asn Leu
         370              375              380

Arg Trp Tyr Lys Gln Asp Thr Gly Arg Gly Pro Val Ser Leu Thr Ile
385              390              395              400

Met Thr Phe Ser Glu Asn Thr Lys Ser Asn Gly Arg Tyr Thr Ala Thr
             405              410              415

Leu Asp Ala Asp Thr Lys Gln Ser Ser Leu His Ile Thr Ala Ser Gln
             420              425              430

Leu Ser Asp Ser Ala Ser Tyr Ile Cys Val Val Trp Gly Gly Asp Thr
             435              440              445

Asp Lys Leu Ile Phe Gly Thr Gly Thr Arg Leu Gln Val Phe Pro Asn
         450              455              460

Ile Gln Asn Pro Asp Pro Ala Val Tyr Gln Leu Arg Asp Ser Lys Ser
465              470              475              480

Ser Asp Lys Ser Val Cys Leu Phe Thr Asp Phe Asp Ser Gln Thr Asn
             485              490              495

Val Ser Gln Ser Lys Asp Ser Asp Val Tyr Ile Thr Asp Lys Thr Ala
             500              505              510

Arg His Glu Val Tyr Gly Leu Gln Glu Gln Gln Cys Cys Gly Leu Glu
         515              520              525

Gln Gln Ile
         530
```

<210> SEQ ID NO 41

<211> LENGTH: 1484
<212> TYPE: DNA
<213> ORGANISM: Artificial Sequence
<220> FEATURE:
<223> OTHER INFORMATION: codon optimized TCR number 11 construct; beta
      chain-P2A-alpha chain with cysteine substitutions in beta and
      alpha chain constant domains (partial sequence)

<400> SEQUENCE: 41
ctcaataaaa gagcccacaa cccctcactc ggcgcgccac catgggcaca cggctttttct     60 tctacgttgc cctttgcctg ctgtgggctg acatagaga tgctggaatc acacagagcc    120
ccaggtacaa gatcacagag acaggaagac aggtgaccct gatgtgtcac caaacatgga    180
gccacagcta catgttctgg tacagacagg atctgggaca cggactgaga ctgatctact    240
attctgctgc cgccgacatc accgataaag gagaagttcc tgacggctac gtggtgtcta    300
gaagcaaaac cgagaacttc cccctgacac tggaatctgc cacaagatct cagaccagcg    360
tgtacttttg cgcctcttct gatggaggag gccagtattt ccaggcaca agactgacag    420 tgaccgagga cctgaagaac gtgttccccc cagaggtggc cgtgttcgag cctagcgagg    480
ccgagatcag ccacacccag aaagccaccc tcgtgtgcct ggccaccggc ttttaccccg    540
accacgtgga actgtcttgg tgggtcaacg gcaaagaggt gcacagcggc gtctgcaccg    600 accccagcc cctgaaagag cagcccgccc tgaacgacag ccggtactgt ctgagcagca    660
gactgagagt gtccgccacc ttctggcaga accccggaa ccacttcaga tgccaggtgc    720
agttctacgg cctgagcgag aacgacgagt ggacccagga ccgggccaag cccgtgaccc    780
agatcgtgtc tgctgaggcc tggggcagag ccgattgcgg cttcaccagc gagagctacc    840
agcagggcgt gctgagcgcc accatcctgt acgagatcct gctgggcaag gccaccctgt    900
acgccgtgct ggtgtccgcc ctggtgctga tggccatggt caagcggaag acagccgggg    960
gcggttccgg agccacgaac ttctctctgt aaagcaagc aggagacgtg aagaaaacc   1020 ccggtcccat gaagaagcac ctgaccacgt tcctggtgat tctttggctg tacttctacc   1080
ggggcaacgg caaaaatcag gtggaacaaa gcccccagag cctgattatt ctggagggca   1140
agaactgcac cctccagtgt aattacaccg tgagcccttt cagcaacctg agatggtaca   1200
agcaggatac cggaagagga cctgtgtctc tgaccatcat gacctttagc gagaacacca   1260
agagcaacgg caggtataca gccacactgg atgccgatac caagcagtct tctctgcaca   1320
ttaccgcctc tcagctgtct gattctgcca gctacatctg tgtggtgtgg ggaggagata   1380
ccgataagct gatctttggc acaggcacca gactgcaagt gttccctaac atccagaacc   1440
ctgatcctgc cgtgtaccag ctgcgggaca gcaagagcag cgac              1484

<210> SEQ ID NO 42
<211> LENGTH: 492
<212> TYPE: PRT
<213> ORGANISM: Artificial Sequence
<220> FEATURE:
<223> OTHER INFORMATION: codon optimized TCR number 11 construct; beta
      chain-P2A-alpha chain with cysteine substitutions in beta and
      alpha chain constant domains (partial sequence)

<400> SEQUENCE: 42

Lys Ser Pro Gln Pro Leu Thr Arg Arg Ala Thr Met Gly Thr Arg Leu
1               5                   10                  15

Phe Phe Tyr Val Ala Leu Cys Leu Leu Trp Ala Gly His Arg Asp Ala
            20                  25                  30

Gly Ile Thr Gln Ser Pro Arg Tyr Lys Ile Thr Glu Thr Gly Arg Gln

-continued

```
                 35                    40                    45
Val Thr Leu Met Cys His Gln Thr Trp Ser His Ser Tyr Met Phe Trp
    50                    55                    60

Tyr Arg Gln Asp Leu Gly His Gly Leu Arg Leu Ile Tyr Tyr Ser Ala
65                    70                    75                    80

Ala Ala Asp Ile Thr Asp Lys Gly Glu Val Pro Asp Gly Tyr Val Val
                 85                    90                    95

Ser Arg Ser Lys Thr Glu Asn Phe Pro Leu Thr Leu Glu Ser Ala Thr
                 100                   105                   110

Arg Ser Gln Thr Ser Val Tyr Phe Cys Ala Ser Ser Asp Gly Gly Gly
                 115                   120                   125

Gln Tyr Phe Pro Gly Thr Arg Leu Thr Val Thr Glu Asp Leu Lys Asn
    130                   135                   140

Val Phe Pro Pro Glu Val Ala Val Phe Glu Pro Ser Glu Ala Glu Ile
145                   150                   155                   160

Ser His Thr Gln Lys Ala Thr Leu Val Cys Leu Ala Thr Gly Phe Tyr
                 165                   170                   175

Pro Asp His Val Glu Leu Ser Trp Trp Val Asn Gly Lys Glu Val His
                 180                   185                   190

Ser Gly Val Cys Thr Asp Pro Gln Pro Leu Lys Glu Gln Pro Ala Leu
                 195                   200                   205

Asn Asp Ser Arg Tyr Cys Leu Ser Ser Arg Leu Arg Val Ser Ala Thr
    210                   215                   220

Phe Trp Gln Asn Pro Arg Asn His Phe Arg Cys Gln Val Gln Phe Tyr
225                   230                   235                   240

Gly Leu Ser Glu Asn Asp Glu Trp Thr Gln Asp Arg Ala Lys Pro Val
                 245                   250                   255

Thr Gln Ile Val Ser Ala Glu Ala Trp Gly Arg Ala Asp Cys Gly Phe
                 260                   265                   270

Thr Ser Glu Ser Tyr Gln Gln Gly Val Leu Ser Ala Thr Ile Leu Tyr
                 275                   280                   285

Glu Ile Leu Leu Gly Lys Ala Thr Leu Tyr Ala Val Leu Val Ser Ala
    290                   295                   300

Leu Val Leu Met Ala Met Val Lys Arg Lys Asp Ser Arg Gly Gly Ser
305                   310                   315                   320

Gly Ala Thr Asn Phe Ser Leu Leu Lys Gln Ala Gly Asp Val Glu Glu
                 325                   330                   335

Asn Pro Gly Pro Met Lys Lys His Leu Thr Thr Phe Leu Val Ile Leu
                 340                   345                   350

Trp Leu Tyr Phe Tyr Arg Gly Asn Gly Lys Asn Gln Val Glu Gln Ser
                 355                   360                   365

Pro Gln Ser Leu Ile Ile Leu Glu Gly Lys Asn Cys Thr Leu Gln Cys
    370                   375                   380

Asn Tyr Thr Val Ser Pro Phe Ser Asn Leu Arg Trp Tyr Lys Gln Asp
385                   390                   395                   400

Thr Gly Arg Gly Pro Val Ser Leu Thr Ile Met Thr Phe Ser Glu Asn
                 405                   410                   415

Thr Lys Ser Asn Gly Arg Tyr Thr Ala Thr Leu Asp Ala Asp Thr Lys
                 420                   425                   430

Gln Ser Ser Leu His Ile Thr Ala Ser Gln Leu Ser Asp Ser Ala Ser
                 435                   440                   445

Tyr Ile Cys Val Val Trp Gly Gly Asp Thr Asp Lys Leu Ile Phe Gly
    450                   455                   460
```

```
Thr Gly Thr Arg Leu Gln Val Phe Pro Asn Ile Gln Asn Pro Asp Pro
465              470              475              480

Ala Val Tyr Gln Leu Arg Asp Ser Lys Ser Ser Asp
                485              490
```

```
<210> SEQ ID NO 43
<211> LENGTH: 828
<212> TYPE: DNA
<213> ORGANISM: Artificial Sequence
<220> FEATURE:
<223> OTHER INFORMATION: TCR number 6 alpha chain

<400> SEQUENCE: 43
atggagaaga atcctttggc agcccccatta ctaatcctct ggtttcatct tgactgcgtg        60
agcagcatac tgaacgtgga acaaagtcct cagtcactgc atgttcagga gggagacagc       120
accaatttca cctgcagctt cccttccagc aattttttatg ccttacactg gtacagatgg       180
gaaactgcaa aaagcccga ggccttgttt gtaatgactt aaatgggga tgaaaagaag         240 aaaggacgaa taagtgccac tcttaatacc aaggagggtt acagctattt gtacatcaaa       300
ggatcccagc ctgaagactc agccacatac ctctgtgcct tagggcctta taacgactac       360
aagctcagct ttggagccgg aaccacagta actgtaagag caaatatcca gaaccctgac       420
cctgccgtgt accagctgag agactctaaa tccagtgaca gtctgtctg cctattcacc       480 gattttgatt ctcaaacaaa tgtgtcacaa gtaaggatt ctgatgtgta tatcacagac        540
aaaactgtgc tagacatgag gtctatggac ttcaagagca cagtgctgt ggcctggagc        600 aacaaatctg actttgcatg tgcaaacgcc ttcaacaaca gcattattcc agaagacacc       660
ttcttcccca gcccagaaag ttcctgtgat gtcaagctgg tcgagaaaag ctttgaaaca       720
gatacgaacc taaacttca aaacctgtca gtgattgggg tccgaatcct cctcctgaaa        780
gtggccgggt ttaatctgct catgacgctg cggctgtggt ccagctga                    828
```

```
<210> SEQ ID NO 44
<211> LENGTH: 275
<212> TYPE: PRT
<213> ORGANISM: Artificial Sequence
<220> FEATURE:
<223> OTHER INFORMATION: TCR number 6 alpha chain

<400> SEQUENCE: 44

Met Glu Lys Asn Pro Leu Ala Ala Pro Leu Leu Ile Leu Trp Phe His
1               5               10              15

Leu Asp Cys Val Ser Ser Ile Leu Asn Val Glu Gln Ser Pro Gln Ser
            20              25              30

Leu His Val Gln Glu Gly Asp Ser Thr Asn Phe Thr Cys Ser Phe Pro
        35              40              45

Ser Ser Asn Phe Tyr Ala Leu His Trp Tyr Arg Trp Glu Thr Ala Lys
    50              55              60

Ser Pro Glu Ala Leu Phe Val Met Thr Leu Asn Gly Asp Glu Lys Lys
65              70              75              80

Lys Gly Arg Ile Ser Ala Thr Leu Asn Thr Lys Glu Gly Tyr Ser Tyr
                85              90              95

Leu Tyr Ile Lys Gly Ser Gln Pro Glu Asp Ser Ala Thr Tyr Leu Cys
            100             105             110

Ala Leu Gly Pro Tyr Asn Asp Tyr Lys Leu Ser Phe Gly Ala Gly Thr
        115             120             125
```

-continued

```
Thr Val Thr Val Arg Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
                180                 185                 190

Ser Asn Ser Ala Val Ala Trp Ser Asn Lys Ser Asp Phe Ala Cys Ala
            195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275
```

<210> SEQ ID NO 45
<211> LENGTH: 936
<212> TYPE: DNA
<213> ORGANISM: Artificial Sequence
<220> FEATURE:
<223> OTHER INFORMATION: TCR number 6 beta chain

<400> SEQUENCE: 45

```
atgagcatca gcctcctgtg ctgtgcagcc tttcctctcc tgtgggcagg tccagtgaat      60
gctggtgtca ctcagacccc aaaattccgc atcctgaaga taggacagag catgacactg     120
cagtgtaccc aggatatgaa ccataactac atgtactggt atcgacaaga cccaggcatg     180
gggctgaagc tgatttatta ttcagttggt gctggtatca ctgataaagg agaagtcccg     240
aatggctaca acgtctccag atcaaccaca gaggatttcc cgctcaggct ggagttggct     300
gctccctccc agacatctgt gtacttctgt gccagcagtg acaggtctaa caccgggggag     360 ctgttttttg gagaaggctc taggctgacc gtactggagg acctgaaaaa cgtgttccca     420
cccgaggtcg ctgtgtttga gccatcagaa gcagagatct cccacaccca aaaggccaca     480
ctggtgtgcc tggccacagg cttctacccc gaccacgtgg agctgagctg gtgggtgaat     540
gggaaggagg tgcacagtgg ggtcagcaca gacccgcagc ccctcaagga gcagcccgcc     600
ctcaatgact ccagatactg cctgagcagc cgcctgaggg tctcggccac cttctggcag     660
aacccccgca accacttccg ctgtcaagtc cagttctacg ggctctcgga gaatgacgag     720
tggacccagg atagggccaa acctgtcacc cagatcgtca gcgccgaggc ctgggggtaga     780 gcagactgtg gcttcacctc cgagtcttac cagcaagggg tcctgtctgc caccatcctc     840
tatgagatct tgctagggaa ggccaccttg tatgccgtgc tggtcagtgc cctcgtgctg     900
atggccatgg tcaagagaaa ggattccaga ggctag                               936
```

<210> SEQ ID NO 46
<211> LENGTH: 311
<212> TYPE: PRT
<213> ORGANISM: Artificial Sequence
<220> FEATURE:
<223> OTHER INFORMATION: TCR number 6 beta chain -continued

<400> SEQUENCE: 46

```
Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
                20                  25                  30

Lys Ile Gly Gln Ser Met Thr Leu Gln Cys Thr Gln Asp Met Asn His
            35                  40                  45

Asn Tyr Met Tyr Trp Tyr Arg Gln Asp Pro Gly Met Gly Leu Lys Leu
        50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
            100                 105                 110

Ser Asp Arg Ser Asn Thr Gly Glu Leu Phe Phe Gly Glu Gly Ser Arg
            115                 120                 125

Leu Thr Val Leu Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Ser Arg Gly
305                 310
```

<210> SEQ ID NO 47
<211> LENGTH: 1499
<212> TYPE: DNA
<213> ORGANISM: Artificial Sequence
<220> FEATURE:
<223> OTHER INFORMATION: codon optimized TCR number 6 construct; beta
      chain-P2A-alpha chain with cysteine substitutions in beta and
      alpha chain constant domains (partial sequence)

<400> SEQUENCE: 47

```
ctcaataaaa gagcccacaa cccctcactc ggcgcgccac catgagcatc agcctcctgt        60
gctgtgcagc ctttcctctc ctgtgggcag gtccagtgaa tgctggtgtc actcagaccc       120
```

-continued

```
caaaattccg catcctgaag ataggacaga gcatgacact gcagtgtacc caggatatga    180
accataacta catgtactgg tatcgacaag acccaggcat ggggctgaag ctgatttatt    240
attcagttgg tgctggtatc actgataaag gagaagtccc gaatggctac aacgtctcca    300
gatcaaccac agaggatttc ccgctcaggc tggagttggc tgctccctcc cagacatctg    360
tgtacttctg tgccagcagt gacaggtcta acaccgggga gctgttttt ggagaaggct    420 ctaggctgac cgtactggag gacctgaaaa acgtgttccc acccgaggtc gctgtgtttg    480
agccatcaga agcagagatc tcccacaccc aaaaggccac actggtgtgc ctggccacag    540
gcttctaccc cgaccacgtg gagctgagct ggtgggtgaa tgggaaggag gtgcacagtg    600
gggtcagcac agacccgcag cccctcaagg agcagcccgc cctcaatgac tccagatact    660
gcctgagcag ccgcctgagg gtctcggcca ccttctggca gaaccccgc aaccacttcc    720 gctgtcaagt ccagttctac gggctctcgg agaatgacga gtggacccag gatagggcca    780
aacctgtcac ccagatcgtc agcgccgagg cctggggtag agcagactgt ggcttcacct    840
ccgagtctta ccagcaaggg gtcctgtctg ccaccatcct ctatgagatc ttgctaggga    900
aggccacctt gtatgccgtg ctggtcagtg ccctcgtgct gatggccatg gtcaagagaa    960
aggattccag aggcggttcc ggagccacga acttctctct gttaaagcaa gcaggagacg    1020
tggaagaaaa ccccggtccc atggagaaga tcctttggc agccccatta ctaatcctct    1080
ggtttcatct tgactgcgtg agcagcatac tgaacgtgga acaaagtcct cagtcactgc    1140
atgttcagga gggagacagc accaatttca cctgcagctt cccttccagc aatttttatg    1200
ccttacactg gtacagatgg gaaactgcaa aaagccccga ggccttgttt gtaatgactt    1260
taaatgggga tgaaaagaag aaaggacgaa taagtgccac tcttaatacc aaggagggtt    1320
acagctattt gtacatcaaa ggatcccagc ctgaagactc agccacatac ctctgtgcct    1380
tagggcctta taacgactac aagctcagct ttggagccgg aaccacagta actgtaagag    1440
caaatatcca gaaccctgac cctgccgtgt accagctgcg ggacagcaag agcagcgac     1499
```

```
<210> SEQ ID NO 48
<211> LENGTH: 1815
<212> TYPE: DNA
<213> ORGANISM: Artificial Sequence
<220> FEATURE:
<223> OTHER INFORMATION: TCR number 1 construct; beta chain-P2A-alpha
      chain

<400> SEQUENCE: 48
atgggccccg ggctcctctg ctgggcactg ctttgtctcc tgggagcagg cttagtggac     60
gctggagtca cccaaagtcc cacacacctg atcaaaacga gaggacagca agtgactctg    120
agatgctctc ctaagtctgg gcatgacact gtgtcctggt accaacaggc cctgggtcag    180
gggccccagt ttatctttca gtattatgag gaggaagaga acagagagg caacttccct    240 gatcgattct caggtcacca gttccctaac tatagctctg agctgaatgt gaacgccttg    300
ttgctggggg actcggccct ctatctctgt gccagcagct tcttcagcca agagacccag    360
tacttcgggc caggcacgcg gctcctggtc tcgaggacc tgaaaaacgt gttcccaccc    420
gaggtcgctg tgtttgagcc atcagaagca gagatctccc acacccaaaa ggccacactg    480
gtgtgcctgg ccacaggctt ctaccccgac cacgtggagc tgagctggtg ggtgaatggg    540
aaggaggtgc acagtgggt cagcacagac ccgcagcccc tcaaggagca gcccgccctc    600
aatgactcca gatactgcct gagcagccgc ctgagggtct cggccacctt ctggcagaac    660
```

```
cccgcaacc acttccgctg tcaagtccag ttctacgggc tctcggagaa tgacgagtgg      720
acccaggata gggccaaacc tgtcacccag atcgtcagcg ccgaggcctg gggtagagca      780
gactgtggct tcacctccga gtcttaccag caaggggtcc tgtctgccac catcctctat      840
gagatcttgc tagggaaggc caccttgtat gccgtgctgg tcagtgccct cgtgctgatg      900
gccatggtca agagaaagga ttccagaggc ggttccggag ccacgaactt ctctctgtta      960
aagcaagcag agacgtgga agaaaacccc ggtcccatgg agaccctctt gggcctgctt     1020
atcctttggc tgcagctgca atgggtgagc agcaaacagg aggtgacaca gattcctgca     1080
gctctgagtg tcccagaagg agaaaacttg gttctcaact gcagtttcac tgatagcgct     1140
atttacaacc tccagtggtt taggcaggac cctgggaaag tctcacatc tctgttgctt     1200 attcagtcaa gtcagagaga gcaaacaagt ggaagactta atgcctcgct ggataaatca     1260
tcaggacgta gtactttata cattgcagct tctcagcctg tgactcagc cacctacctc     1320 tgtgccgtgg aggggggatag cagctataaa ttgatcttcg ggagtgggac cagactgctg     1380
gtcaggcctg atatccagaa ccctgaccct gccgtgtacc agctgagaga ctctaaatcc     1440
agtgacaagt ctgtctgcct attcaccgat tttgattctc aaacaaatgt gtcacaaagt     1500
aaggattctg atgtgtatat cacagacaaa actgtgctag acatgaggtc tatggacttc     1560
aagagcaaca gtgctgtggc ctggagcaac aaatctgact ttgcatgtgc aaacgccttc     1620
aacaacagca ttattccaga agacaccttc ttccccagcc cagaaagttc ctgtgatgtc     1680
aagctggtcg agaaaagctt tgaaacagat acgaacctaa actttcaaaa cctgtcagtg     1740
attgggttcc gaatcctcct cctgaaagtg gccgggttta atctgctcat gacgctgcgg     1800
ctgtggtcca gctga                                                       1815
```

<210> SEQ ID NO 49
<211> LENGTH: 604
<212> TYPE: PRT
<213> ORGANISM: Artificial Sequence
<220> FEATURE:
<223> OTHER INFORMATION: TCR number 1 construct; beta chain-P2A-alpha
      chain

<400> SEQUENCE: 49

```
Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Phe Ser Gln Glu Thr Gln Tyr Phe Gly Pro Gly Thr Arg Leu
        115                 120                 125

Leu Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
```

-continued

```
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
                275                 280                 285

Leu Tyr Ala Val Leu Val Ser Ala Leu Val Leu Met Ala Met Val Lys
            290                 295                 300

Arg Lys Asp Ser Arg Gly Gly Ser Gly Ala Thr Asn Phe Ser Leu Leu
305                 310                 315                 320

Lys Gln Ala Gly Asp Val Glu Glu Asn Pro Gly Pro Met Glu Thr Leu
                325                 330                 335

Leu Gly Leu Leu Ile Leu Trp Leu Gln Leu Gln Trp Val Ser Ser Lys
                340                 345                 350

Gln Glu Val Thr Gln Ile Pro Ala Ala Leu Ser Val Pro Glu Gly Glu
                355                 360                 365

Asn Leu Val Leu Asn Cys Ser Phe Thr Asp Ser Ala Ile Tyr Asn Leu
            370                 375                 380

Gln Trp Phe Arg Gln Asp Pro Gly Lys Gly Leu Thr Ser Leu Leu Leu
385                 390                 395                 400

Ile Gln Ser Ser Gln Arg Glu Gln Thr Ser Gly Arg Leu Asn Ala Ser
                405                 410                 415

Leu Asp Lys Ser Ser Gly Arg Ser Thr Leu Tyr Ile Ala Ala Ser Gln
                420                 425                 430

Pro Gly Asp Ser Ala Thr Tyr Leu Cys Ala Val Glu Gly Asp Ser Ser
            435                 440                 445

Tyr Lys Leu Ile Phe Gly Ser Gly Thr Arg Leu Leu Val Arg Pro Asp
            450                 455                 460

Ile Gln Asn Pro Asp Pro Ala Val Tyr Gln Leu Arg Asp Ser Lys Ser
465                 470                 475                 480

Ser Asp Lys Ser Val Cys Leu Phe Thr Asp Phe Asp Ser Gln Thr Asn
                485                 490                 495

Val Ser Gln Ser Lys Asp Ser Asp Val Tyr Ile Thr Asp Lys Thr Val
                500                 505                 510

Leu Asp Met Arg Ser Met Asp Phe Lys Ser Asn Ser Ala Val Ala Trp
                515                 520                 525

Ser Asn Lys Ser Asp Phe Ala Cys Ala Asn Ala Phe Asn Asn Ser Ile
            530                 535                 540

Ile Pro Glu Asp Thr Phe Phe Pro Ser Pro Glu Ser Ser Cys Asp Val
545                 550                 555                 560

Lys Leu Val Glu Lys Ser Phe Glu Thr Asp Thr Asn Leu Asn Phe Gln
                565                 570                 575
```

-continued

Asn Leu Ser Val Ile Gly Phe Arg Ile Leu Leu Leu Lys Val Ala Gly
            580                     585                 590

Phe Asn Leu Leu Met Thr Leu Arg Leu Trp Ser Ser
        595                 600

<210> SEQ ID NO 50
<211> LENGTH: 1487
<212> TYPE: DNA
<213> ORGANISM: Artificial Sequence
<220> FEATURE:
<223> OTHER INFORMATION: codon optimized TCR number 1 construct; beta
      chain-P2A-alpha chain with cysteine substitutions in beta and
      alpha chain constant domains (partial sequence)

<400> SEQUENCE: 50
ctcaataaaa gagcccacaa cccctcactc ggcgcgccac catgggacct ggactgcttt      60
gttgggctct tctgtgtctg cttggagctg gactggttga tgctggagtt acacagagcc     120
ctacacacct gatcaagaca agaggacagc aggtgaccct gagatgtagc cctaaatctg     180
gccacgatac cgtgagctgg tatcaacagg ctctgggaca aggacctcag ttcatcttcc     240
agtactacga ggaggaggag agacagagag gcaatttccc tgacaggttt agcggacacc     300
agttccccaa ttacagctct gagctgaacg tgaatgccct tcttctggga gattctgccc     360
tgtatctgtg tgccagcagc ttctttagcc aggaaaccca gtacttcggc ccaggaacaa     420
gactgctggt tcttgaagac ctgaagaacg tgttcccccc agaggtggcc gtgttcgagc     480
ctagcgaggc cgagatcagc cacacccaga aagccaccct cgtgtgcctg gccaccggct     540
tttaccccga ccacgtggaa ctgtcttggt gggtcaacgg caaagaggtg cacagcggcg     600
tctgcaccga cccccagccc ctgaaagagc agcccgccct gaacgacagc cggtactgtc     660
tgagcagcag actgagagtg tccgccacct tctggcagaa ccccggaaac cacttcagat     720
gccaggtgca gttctacggc ctgagcgaga cgacgagtg gacccaggac cgggccaagc     780
ccgtgaccca gatcgtgtct gctgaggcct ggggcagagc cgattgcggc ttcaccagcg     840
agagctacca gcagggcgtg ctgagcgcca ccatcctgta cgagatcctg ctgggcaagg     900
ccaccctgta cgccgtgctg gtgtccgccc tggtgctgat ggccatggtc aagcggaagg     960
acagccgggg cggttccgga gccacgaact tctctctgtt aaagcaagca ggagacgtgg    1020 aagaaaccc cggtcccatg gaaaccctgt taggcctgct cattctgtgg ttacagctcc    1080
aatgggtgag cagcaaacag gaagtgaccc agattcctgc tgccttatct gtgcctgaag    1140
gcgaaaatct ggtgctgaat tgcagcttca ccgattctgc catctacaac ctccagtggt    1200
tcagacagga tccaggaaaa ggcctgacat ctcttctgct gatccagtct agccagagag    1260
agcagacaag cggaagactg aatgcctctc tggacaagag cagcggaaga tctaccctgt    1320
atattgccgc ctctcagcct ggagattctg ccacatatct gtgtgccgtg gagggagata    1380
gcagctataa gctgatcttc ggcagcggca agattact ggtgagacct gacatccaga    1440
accctgatcc tgctgtgtac cagctgcggg acagcaagag cagcgac         1487

<210> SEQ ID NO 51
<211> LENGTH: 493
<212> TYPE: PRT
<213> ORGANISM: Artificial Sequence
<220> FEATURE:
<223> OTHER INFORMATION: codon optimized TCR number 1 construct; beta
      chain-P2A-alpha chain with cysteine substitutions in beta and
      alpha chain constant domains (partial sequence)

-continued

```
<400> SEQUENCE: 51

Lys Ser Pro Gln Pro Leu Thr Arg Arg Ala Thr Met Gly Pro Gly Leu
1               5                   10                  15

Leu Cys Trp Ala Leu Leu Cys Leu Leu Gly Ala Gly Leu Val Asp Ala
            20                  25                  30

Gly Val Thr Gln Ser Pro Thr His Leu Ile Lys Thr Arg Gly Gln Gln
            35                  40                  45

Val Thr Leu Arg Cys Ser Pro Lys Ser Gly His Asp Thr Val Ser Trp
        50                  55                  60

Tyr Gln Gln Ala Leu Gly Gln Gly Pro Gln Phe Ile Phe Gln Tyr Tyr
65                  70                  75                  80

Glu Glu Glu Glu Arg Gln Arg Gly Asn Phe Pro Asp Arg Phe Ser Gly
                85                  90                  95

His Gln Phe Pro Asn Tyr Ser Ser Glu Leu Asn Val Asn Ala Leu Leu
            100                 105                 110

Leu Gly Asp Ser Ala Leu Tyr Leu Cys Ala Ser Ser Phe Phe Ser Gln
            115                 120                 125

Glu Thr Gln Tyr Phe Gly Pro Gly Thr Arg Leu Leu Val Leu Glu Asp
        130                 135                 140

Leu Lys Asn Val Phe Pro Pro Glu Val Ala Val Phe Glu Pro Ser Glu
145                 150                 155                 160

Ala Glu Ile Ser His Thr Gln Lys Ala Thr Leu Val Cys Leu Ala Thr
                165                 170                 175

Gly Phe Tyr Pro Asp His Val Glu Leu Ser Trp Trp Val Asn Gly Lys
            180                 185                 190

Glu Val His Ser Gly Val Cys Thr Asp Pro Gln Pro Leu Lys Glu Gln
            195                 200                 205

Pro Ala Leu Asn Asp Ser Arg Tyr Cys Leu Ser Ser Arg Leu Arg Val
    210                 215                 220

Ser Ala Thr Phe Trp Gln Asn Pro Arg Asn His Phe Arg Cys Gln Val
225                 230                 235                 240

Gln Phe Tyr Gly Leu Ser Glu Asn Asp Glu Trp Thr Gln Asp Arg Ala
                245                 250                 255

Lys Pro Val Thr Gln Ile Val Ser Ala Glu Ala Trp Gly Arg Ala Asp
            260                 265                 270

Cys Gly Phe Thr Ser Glu Ser Tyr Gln Gln Gly Val Leu Ser Ala Thr
            275                 280                 285

Ile Leu Tyr Glu Ile Leu Leu Gly Lys Ala Thr Leu Tyr Ala Val Leu
    290                 295                 300

Val Ser Ala Leu Val Leu Met Ala Met Val Lys Arg Lys Asp Ser Arg
305                 310                 315                 320

Gly Gly Ser Gly Ala Thr Asn Phe Ser Leu Leu Lys Gln Ala Gly Asp
                325                 330                 335

Val Glu Glu Asn Pro Gly Pro Met Glu Thr Leu Leu Gly Leu Leu Ile
            340                 345                 350

Leu Trp Leu Gln Leu Gln Trp Val Ser Ser Lys Gln Glu Val Thr Gln
            355                 360                 365

Ile Pro Ala Ala Leu Ser Val Pro Glu Gly Glu Asn Leu Val Leu Asn
    370                 375                 380

Cys Ser Phe Thr Asp Ser Ala Ile Tyr Asn Leu Gln Trp Phe Arg Gln
385                 390                 395                 400

Asp Pro Gly Lys Gly Leu Thr Ser Leu Leu Leu Ile Gln Ser Ser Gln
                405                 410                 415
```

-continued

```
Arg Glu Gln Thr Ser Gly Arg Leu Asn Ala Ser Leu Asp Lys Ser Ser
            420                     425                 430

Gly Arg Ser Thr Leu Tyr Ile Ala Ala Ser Gln Pro Gly Asp Ser Ala
            435                     440                 445

Thr Tyr Leu Cys Ala Val Glu Gly Asp Ser Ser Tyr Lys Leu Ile Phe
            450                     455                 460

Gly Ser Gly Thr Arg Leu Leu Val Arg Pro Asp Ile Gln Asn Pro Asp
465                     470                     475                 480

Pro Ala Val Tyr Gln Leu Arg Asp Ser Lys Ser Ser Asp
                485                     490
```

```
<210> SEQ ID NO 52
<211> LENGTH: 813
<212> TYPE: DNA
<213> ORGANISM: Artificial Sequence
<220> FEATURE:
<223> OTHER INFORMATION: TCR number 2 alpha chain

<400> SEQUENCE: 52
atggagaccc tcttgggcct gcttatcctt tggctgcagc tgcaatgggt gagcagcaaa        60
caggaggtga cgcagattcc tgcagctctg agtgtcccag aaggagaaaa cttggttctc       120
aactgcagtt tcactgatag cgctatttac aacctccagt ggtttaggca ggaccctggg       180
aaaggtctca catctctgtt gcttattcag tcaagtcaga gagagcaaac aagtggaaga       240
cttaatgcct cgctggataa tcatcagga cgtagtactt tatacattgc agcttctcag        300
cctggtgact cagccaccta cctctgtgct gtgatcggcg aacagaattt tgtctttggt       360
cccggaacca gattgtccgt gctgccctat atccagaacc ctgaccctgc cgtgtaccag       420
ctgagagact ctaaatccag tgacaagtct gtctgcctat tcaccgattt tgattctcaa       480
acaaatgtgt cacaaagtaa ggattctgat gtgtatatca cagacaaaac tgtgctagac       540
atgaggtcta tggacttcaa gagcaacagt gctgtggcct ggagcaacaa atctgacttt       600
gcatgtgcaa acgccttcaa caacagcatt attccagaag acaccttctt ccccagccca       660
gaaagttcct gtgatgtcaa gctggtcgag aaaagctttg aaacagatac gaacctaaac       720
tttcaaaacc tgtcagtgat tgggttccga atcctcctcc tgaaagtggc cgggtttaat       780
ctgctcatga cgctgcggct gtggtccagc tga                                    813
```

```
<210> SEQ ID NO 53
<211> LENGTH: 270
<212> TYPE: PRT
<213> ORGANISM: Artificial Sequence
<220> FEATURE:
<223> OTHER INFORMATION: TCR number 2 alpha chain

<400> SEQUENCE: 53

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80
```

-continued

```
Leu Asn Ala Ser Leu Asp Lys Ser Ser Gly Arg Ser Thr Leu Tyr Ile
                85              90              95

Ala Ala Ser Gln Pro Gly Asp Ser Ala Thr Tyr Leu Cys Ala Val Ile
            100             105             110

Gly Glu Gln Asn Phe Val Phe Gly Pro Gly Thr Arg Leu Ser Val Leu
        115             120             125

Pro Tyr Ile Gln Asn Pro Asp Pro Ala Val Tyr Gln Leu Arg Asp Ser
    130             135             140

Lys Ser Ser Asp Lys Ser Val Cys Leu Phe Thr Asp Phe Asp Ser Gln
145             150             155             160

Thr Asn Val Ser Gln Ser Lys Asp Ser Asp Val Tyr Ile Thr Asp Lys
            165             170             175

Thr Val Leu Asp Met Arg Ser Met Asp Phe Lys Ser Asn Ser Ala Val
            180             185             190

Ala Trp Ser Asn Lys Ser Asp Phe Ala Cys Ala Asn Ala Phe Asn Asn
        195             200             205

Ser Ile Ile Pro Glu Asp Thr Phe Phe Pro Ser Pro Glu Ser Ser Cys
    210             215             220

Asp Val Lys Leu Val Glu Lys Ser Phe Glu Thr Asp Thr Asn Leu Asn
225             230             235             240

Phe Gln Asn Leu Ser Val Ile Gly Phe Arg Ile Leu Leu Leu Lys Val
            245             250             255

Ala Gly Phe Asn Leu Leu Met Thr Leu Arg Leu Trp Ser Ser
            260             265             270
```

```
<210> SEQ ID NO 54
<211> LENGTH: 948
<212> TYPE: DNA
<213> ORGANISM: Artificial Sequence
<220> FEATURE:
<223> OTHER INFORMATION: TCR number 2 beta chain

<400> SEQUENCE: 54
atgggcacca ggctcctctg ctgggcagcc ctgtgcctcc tgggggcaga tcacacaggt      60
gctggagtct cccagacccc cagtaacaag gtcacagaga agggaaaata tgtagagctc     120
aggtgtgatc caatttcagg tcatactgcc ctttactggt accgacaaag cctggggcag     180
ggcccagagt ttctaatttta cttccaaggc acgggtgcgg cagatgactc agggctgccc     240
aacgatcggt tctttgcagt caggcctgag ggatccgtct ctactctgaa gatccagcgc     300
acagagcggg gggactcagc cgtgtatctc tgtgccagca gcttaagtgg gttaggctct     360
ggggccaacg tcctgacttt cgggggcggc agcaggctga ccgtgctgga ggacctgaaa     420
aacgtgttcc cacccgaggt cgctgtgttt gagccatcag aagcagagat ctcccacacc     480
caaaaggcca cactggtgtg cctggccaca ggcttctacc ccgaccacgt ggagctgagc     540
tggtgggtga atgggaagga ggtgcacagt ggggtcagca cagacccgca gcccctcaag     600
gagcagcccg ccctcaatga ctccagatac tgcctgagca gccgcctgag ggtctcggcc     660
accttctggc agaacccccg caaccacttc cgctgtcaag tccagttcta cgggctctcg     720
gagaatgacg agtggaccca ggataggggc aaacctgtca cccagatcgt cagcgccgag     780
gcctggggta gagcagactg tggcttcacc tccgagtctt accagcaagg ggtcctgtct     840
gccaccatcc tctatgagat cttgctaggg aaggccacct tgtatgccgt gctggtcagt     900
gccctcgtgc tgatggccat ggtcaagaga aaggattcca gaggctag     948
```

<210> SEQ ID NO 55
<211> LENGTH: 315
<212> TYPE: PRT
<213> ORGANISM: Artificial Sequence
<220> FEATURE:
<223> OTHER INFORMATION: TCR number 2 beta chain

<400> SEQUENCE: 55

```
Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Leu Ser Gly Leu Gly Ser Gly Ala Asn Val Leu Thr Phe Gly
            115                 120                 125

Ala Gly Ser Arg Leu Thr Val Leu Glu Asp Leu Lys Asn Val Phe Pro
    130                 135                 140

Pro Glu Val Ala Val Phe Glu Pro Ser Glu Ala Glu Ile Ser His Thr
145                 150                 155                 160

Gln Lys Ala Thr Leu Val Cys Leu Ala Thr Gly Phe Tyr Pro Asp His
                165                 170                 175

Val Glu Leu Ser Trp Trp Val Asn Gly Lys Glu Val His Ser Gly Val
            180                 185                 190

Ser Thr Asp Pro Gln Pro Leu Lys Glu Gln Pro Ala Leu Asn Asp Ser
            195                 200                 205

Arg Tyr Cys Leu Ser Ser Arg Leu Arg Val Ser Ala Thr Phe Trp Gln
    210                 215                 220

Asn Pro Arg Asn His Phe Arg Cys Gln Val Gln Phe Tyr Gly Leu Ser
225                 230                 235                 240

Glu Asn Asp Glu Trp Thr Gln Asp Arg Ala Lys Pro Val Thr Gln Ile
                245                 250                 255

Val Ser Ala Glu Ala Trp Gly Arg Ala Asp Cys Gly Phe Thr Ser Glu
            260                 265                 270

Ser Tyr Gln Gln Gly Val Leu Ser Ala Thr Ile Leu Tyr Glu Ile Leu
            275                 280                 285

Leu Gly Lys Ala Thr Leu Tyr Ala Val Leu Val Ser Ala Leu Val Leu
    290                 295                 300

Met Ala Met Val Lys Arg Lys Asp Ser Arg Gly
305                 310                 315
```

<210> SEQ ID NO 56
<211> LENGTH: 1496
<212> TYPE: DNA
<213> ORGANISM: Artificial Sequence
<220> FEATURE:
<223> OTHER INFORMATION: codon optimized TCR number 2 construct; beta
      chain-P2A-alpha chain with cysteine substitutions in beta and
      alpha chain constant domains (partial sequence)

```
<400> SEQUENCE: 56
ctcaataaaa gagcccacaa cccctcactc ggcgcgccac catgggcacc agactgctgt      60
gttgggctgc tctgtgtctg ctgggagccg atcatacagg tgccggtgtc agccagacac     120
ctagcaacaa agtgaccgag aagggcaaat acgtggaact gagatgcgac cccatcagcg     180
gacacacagc cctgtactgg tacagacagt ctctcggcca gggacctgag ttcctgatct     240
acttccaagg caccggcgct gccgatgata gcggcctgcc taacgataga ttcttcgccg     300
tcagacccga gggcagcgtg tccacactga agatccagag aaccgagagg ggcgacagcg     360
ccgtgtatct gtgtgcctct tctctgtctg gcctcggctc tggcgctaac gtgctgacat     420
ttggcgccgg aagcagactg accgtgctgg aagatctgaa gaacgtgttc ccacctgagg     480
tggccgtgtt cgagccttct gaggccgaga tcagccacac acagaaagcc acactcgtgt     540
gtctggccac cggcttctat cccgaccatg tggaactgtc ttggtgggtc aacggcaaag     600
aggtgcacag cggcgtctgt acagatcccc agcctctgaa agaacagccc gctctgaacg     660
acagccggta ctgtctgtcc tccagactga gagtgtccgc caccttctgg cagaacccca     720
gaaaccactt cagatgccag gtgcagttct acggcctgag cgagaacgat gagtggaccc     780
aggatagagc caagcctgtg acacagatcg tgtctgccga agcctggggc agagccgatt     840
gtggctttac cagcgagagc taccagcagg gcgtgctgtc tgccacaatc ctgtacgaga     900
tcctgctggg caaagccact ctgtacgccg tgctggtgtc tgccctggtg ctgatggcca     960
tggtcaagcg gaaggacagc agaggcggtt ccggagccac gaacttctct ctgttaaagc    1020
aagcaggaga cgtggaagaa aaccccggtc ccatggaaac actgctgggc ctgctgatcc    1080
tgtggctgca actgcaatgg gtgtccagca agcaagaagt gacacagatc cctgccgctc    1140
tgtctgtgcc tgagggcgaa aacctggtgc tgaactgcag cttcaccgac agcgccatct    1200
acaacctgca gtggttcaga caggaccccg gcaagggact gacaagcctg ctgctgattc    1260
agagcagcca gagagagcag accagcggca gactgaatgc cagcctggat aagtcctccg    1320
gcagaagcac cctgtatatc gccgcttctc agcctggcga tagcgccaca tatctgtgtg    1380
ccgtgatcgg cgagcagaac ttcgtgtttg gccctggcac aagactgagc gtgctgcct     1440 acattcagaa ccccgatcct gccgtgtacc agctgcggga cagcaagagc agcgac        1496

<210> SEQ ID NO 57
<211> LENGTH: 496
<212> TYPE: PRT
<213> ORGANISM: Artificial Sequence
<220> FEATURE:
<223> OTHER INFORMATION: codon optimized TCR number 2 construct; beta
      chain-P2A-alpha chain with cysteine substitutions in beta and
      alpha chain constant domains (partial sequence)

<400> SEQUENCE: 57

Lys Ser Pro Gln Pro Leu Thr Arg Arg Ala Thr Met Gly Thr Arg Leu
1               5                   10                  15

Leu Cys Trp Ala Ala Leu Cys Leu Leu Gly Ala Asp His Thr Gly Ala
            20                  25                  30

Gly Val Ser Gln Thr Pro Ser Asn Lys Val Thr Glu Lys Gly Lys Tyr
        35                  40                  45

Val Glu Leu Arg Cys Asp Pro Ile Ser Gly His Thr Ala Leu Tyr Trp
    50                  55                  60

Tyr Arg Gln Ser Leu Gly Gln Gly Pro Glu Phe Leu Ile Tyr Phe Gln
65                  70                  75                  80
```

-continued

Gly Thr Gly Ala Ala Asp Asp Ser Gly Leu Pro Asn Asp Arg Phe Phe
                85                  90                  95

Ala Val Arg Pro Glu Gly Ser Val Ser Thr Leu Lys Ile Gln Arg Thr
            100                 105                 110

Glu Arg Gly Asp Ser Ala Val Tyr Leu Cys Ala Ser Ser Leu Ser Gly
        115                 120                 125

Leu Gly Ser Gly Ala Asn Val Leu Thr Phe Gly Ala Gly Ser Arg Leu
    130                 135                 140

Thr Val Leu Glu Asp Leu Lys Asn Val Phe Pro Pro Glu Val Ala Val
145                 150                 155                 160

Phe Glu Pro Ser Glu Ala Glu Ile Ser His Thr Gln Lys Ala Thr Leu
                165                 170                 175

Val Cys Leu Ala Thr Gly Phe Tyr Pro Asp His Val Glu Leu Ser Trp
            180                 185                 190

Trp Val Asn Gly Lys Glu Val His Ser Gly Val Cys Thr Asp Pro Gln
            195                 200                 205

Pro Leu Lys Glu Gln Pro Ala Leu Asn Asp Ser Arg Tyr Cys Leu Ser
    210                 215                 220

Ser Arg Leu Arg Val Ser Ala Thr Phe Trp Gln Asn Pro Arg Asn His
225                 230                 235                 240

Phe Arg Cys Gln Val Gln Phe Tyr Gly Leu Ser Glu Asn Asp Glu Trp
            245                 250                 255

Thr Gln Asp Arg Ala Lys Pro Val Thr Gln Ile Val Ser Ala Glu Ala
            260                 265                 270

Trp Gly Arg Ala Asp Cys Gly Phe Thr Ser Glu Ser Tyr Gln Gln Gly
            275                 280                 285

Val Leu Ser Ala Thr Ile Leu Tyr Glu Ile Leu Leu Gly Lys Ala Thr
    290                 295                 300

Leu Tyr Ala Val Leu Val Ser Ala Leu Val Leu Met Ala Met Val Lys
305                 310                 315                 320

Arg Lys Asp Ser Arg Gly Gly Ser Gly Ala Thr Asn Phe Ser Leu Leu
                325                 330                 335

Lys Gln Ala Gly Asp Val Glu Glu Asn Pro Gly Pro Met Glu Thr Leu
            340                 345                 350

Leu Gly Leu Leu Ile Leu Trp Leu Gln Leu Gln Trp Val Ser Ser Lys
            355                 360                 365

Gln Glu Val Thr Gln Ile Pro Ala Ala Leu Ser Val Pro Glu Gly Glu
    370                 375                 380

Asn Leu Val Leu Asn Cys Ser Phe Thr Asp Ser Ala Ile Tyr Asn Leu
385                 390                 395                 400

Gln Trp Phe Arg Gln Asp Pro Gly Lys Gly Leu Thr Ser Leu Leu Leu
            405                 410                 415

Ile Gln Ser Ser Gln Arg Glu Gln Thr Ser Gly Arg Leu Asn Ala Ser
            420                 425                 430

Leu Asp Lys Ser Ser Gly Arg Ser Thr Leu Tyr Ile Ala Ala Ser Gln
        435                 440                 445

Pro Gly Asp Ser Ala Thr Tyr Leu Cys Ala Val Ile Gly Glu Gln Asn
    450                 455                 460

Phe Val Phe Gly Pro Gly Thr Arg Leu Ser Val Leu Pro Tyr Ile Gln
465                 470                 475                 480

Asn Pro Asp Pro Ala Val Tyr Gln Leu Arg Asp Ser Lys Ser Ser Asp
            485                 490                 495

-continued

<210> SEQ ID NO 58
<211> LENGTH: 825
<212> TYPE: DNA
<213> ORGANISM: Artificial Sequence
<220> FEATURE:
<223> OTHER INFORMATION: TCR number 3 alpha chain

<400> SEQUENCE: 58
atgatgaaat ccttgagagt tttactagtg atcctgtggc ttcagttgag ctgggtttgg        60
agccaacaga aggaggtgga gcagaattct ggacccctca gtgttccaga gggagccatt       120
gcctctctca actgcactta cagtgaccga ggttcccagt ccttcttctg gtacagacaa       180
tattctggga aaagccctga gttgataatg tccatatact ccaatggtga caaagaagat       240
ggaaggttta cagcacagct caataaagcc agccagtatg tttctctgct catcagagac       300
tcccagccca gtgattcagc cacctacctc tgtgccgtcg attctggggg ttaccagaaa       360
gttacctttg gaactggaac aaagctccaa gtcatcccaa atatccagaa ccctgaccct       420
gccgtgtacc agctgagaga ctctaaatcc agtgacaagt ctgtctgcct attcaccgat       480
tttgattctc aaacaaatgt gtcacaaagt aaggattctg atgtgtatat cacagacaaa       540
actgtgctag acatgaggtc tatggacttc aagagcaaca gtgctgtggc ctggagcaac       600
aaatctgact ttgcatgtgc aaacgccttc aacaacagca ttattccaga agacaccttc       660
ttccccagcc cagaaagttc ctgtgatgtc aagctggtcg agaaaagctt tgaaacagat       720
acgaacctaa actttcaaaa cctgtcagtg attgggttcc gaatcctcct cctgaaagtg       780
gccgggttta atctgctcat gacgctgcgg ctgtggtcca gctga                      825

<210> SEQ ID NO 59
<211> LENGTH: 274
<212> TYPE: PRT
<213> ORGANISM: Artificial Sequence
<220> FEATURE:
<223> OTHER INFORMATION: TCR number 3 alpha chain

<400> SEQUENCE: 59

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asn Ser Gly Pro
                20                  25                  30

Leu Ser Val Pro Glu Gly Ala Ile Ala Ser Leu Asn Cys Thr Tyr Ser
            35                  40                  45

Asp Arg Gly Ser Gln Ser Phe Phe Trp Tyr Arg Gln Tyr Ser Gly Lys
        50                  55                  60

Ser Pro Glu Leu Ile Met Ser Ile Tyr Ser Asn Gly Asp Lys Glu Asp
65                  70                  75                  80

Gly Arg Phe Thr Ala Gln Leu Asn Lys Ala Ser Gln Tyr Val Ser Leu
                85                  90                  95

Leu Ile Arg Asp Ser Gln Pro Ser Asp Ser Ala Thr Tyr Leu Cys Ala
            100                 105                 110

Val Asp Ser Gly Gly Tyr Gln Lys Val Thr Phe Gly Thr Gly Thr Lys
            115                 120                 125

Leu Gln Val Ile Pro Asn Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

-continued

```
Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
            195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

```
<210> SEQ ID NO 60
<211> LENGTH: 930
<212> TYPE: DNA
<213> ORGANISM: Artificial Sequence
<220> FEATURE:
<223> OTHER INFORMATION: TCR number 3 and TCR number 10 beta chain

<400> SEQUENCE: 60
atgggcacca ggctcctctg ctgggcagcc ctgtgcctcc tggggggcaga tcacacaggt      60 gctggagtct cccagacccc cagtaacaag gtcacagaga agggaaaata tgtagagctc     120
aggtgtgatc caatttcagg tcatactgcc ctttactggt accgacaaag cctggggcag     180
ggcccagagt ttctaatttta cttccaaggc acgggtgcgg cagatgactc agggctgccc     240
aacgatcggt tctttgcagt caggcctgag ggatccgtct ctactctgaa gatccagcgc     300
acagagcggg gggactcagc cgtgtatctc tgtgccagca gcttaaatat gaacactgaa     360
gctttctttg acaaggcac cagactcaca gttgtagagg acctgaacaa ggtgttccca     420
cccgaggtcg ctgtgtttga gccatcagaa gcagagatct cccacaccca aaaggccaca     480
ctggtgtgcc tggccacagg cttcttcccc gaccacgtgg agctgagctg gtgggtgaat     540
gggaaggagg tgcacagtgg ggtcagcacg gacccgcagc ccctcaagga gcagcccgcc     600
ctcaatgact ccagatactg cctgagcagc cgcctgaggg tctcggccac cttctggcag     660 aaccccgca accacttccg ctgtcaagtc cagttctacg ggctctcgga gaatgacgag     720
tggacccagg atagggccaa acccgtcacc cagatcgtca gcgccgaggc ctggggtaga     780
gcagactgtg gctttacctc ggtgtcctac cagcaagggg tcctgtctgc caccatcctc     840
tatgagatcc tgctagggaa ggccaccctg tatgctgtgc tggtcagcgc ccttgtgttg     900
atggccatgg tcaagagaaa ggatttctga                                       930
```

```
<210> SEQ ID NO 61
<211> LENGTH: 309
<212> TYPE: PRT
<213> ORGANISM: Artificial Sequence
<220> FEATURE:
<223> OTHER INFORMATION: TCR number 3 and TCR number 10 beta chain

<400> SEQUENCE: 61

Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30
```

```
Glu Lys Gly Lys Tyr Val Glu Leu Arg Cys Asp Pro Ile Ser Gly His
    35              40              45

Thr Ala Leu Tyr Trp Tyr Arg Gln Ser Leu Gly Gln Gly Pro Glu Phe
    50              55              60

Leu Ile Tyr Phe Gln Gly Thr Gly Ala Ala Asp Asp Ser Gly Leu Pro
65              70              75              80

Asn Asp Arg Phe Phe Ala Val Arg Pro Glu Gly Ser Val Ser Thr Leu
                85              90              95

Lys Ile Gln Arg Thr Glu Arg Gly Asp Ser Ala Val Tyr Leu Cys Ala
            100             105             110

Ser Ser Leu Asn Met Asn Thr Glu Ala Phe Phe Gly Gln Gly Thr Arg
            115             120             125

Leu Thr Val Val Glu Asp Leu Asn Lys Val Phe Pro Pro Glu Val Ala
    130             135             140

Val Phe Glu Pro Ser Glu Ala Glu Ile Ser His Thr Gln Lys Ala Thr
145             150             155             160

Leu Val Cys Leu Ala Thr Gly Phe Phe Pro Asp His Val Glu Leu Ser
            165             170             175

Trp Trp Val Asn Gly Lys Glu Val His Ser Gly Val Ser Thr Asp Pro
            180             185             190

Gln Pro Leu Lys Glu Gln Pro Ala Leu Asn Asp Ser Arg Tyr Cys Leu
            195             200             205

Ser Ser Arg Leu Arg Val Ser Ala Thr Phe Trp Gln Asn Pro Arg Asn
    210             215             220

His Phe Arg Cys Gln Val Gln Phe Tyr Gly Leu Ser Glu Asn Asp Glu
225             230             235             240

Trp Thr Gln Asp Arg Ala Lys Pro Val Thr Gln Ile Val Ser Ala Glu
            245             250             255

Ala Trp Gly Arg Ala Asp Cys Gly Phe Thr Ser Val Ser Tyr Gln Gln
            260             265             270

Gly Val Leu Ser Ala Thr Ile Leu Tyr Glu Ile Leu Leu Gly Lys Ala
            275             280             285

Thr Leu Tyr Ala Val Leu Val Ser Ala Leu Val Leu Met Ala Met Val
    290             295             300

Lys Arg Lys Asp Phe
305
```

```
<210> SEQ ID NO 62
<211> LENGTH: 1490
<212> TYPE: DNA
<213> ORGANISM: Artificial Sequence
<220> FEATURE:
<223> OTHER INFORMATION: codon optimized TCR number 3 construct; beta
      chain-P2A-alpha chain with cysteine substitutions in beta and
      alpha chain constant domains (partial sequence)

<400> SEQUENCE: 62
ctcaataaaa gagcccacaa cccctcactc ggcgcgccac catgggcacc agactgctgt      60
gttgggccgc tctgtgtctg ctgggcgccg atcatacagg cgctggcgtg tcccagaccc     120
ccagcaacaa agtgaccgag aagggcaaat acgtggaact gagatgcgac cccatcagcg     180
gccacaccgc cctgtactgg tacagacagt ctctgggcca gggccccgag ttcctgatat     240
attttcaggg caccggcgct gccgacgaca gcggcctgcc taacgataga ttcttcgccg     300
tgcggcccga gggcagcgtg tccacactga agatccagag aaccgagcgg ggcgacagcg     360
ccgtgtatct gtgtgccagc agcctgaata tgaacaccga ggcattcttt gggcagggca     420
```

```
cccggctgac cgtggtggaa gatctgaaca aggtgttccc cccagaggtg gccgtgttcg      480
agccttctga ggccgagatc agccacaccc agaaagccac cctcgtgtgc ctggccaccg      540
gctttttccc cgaccatgtg gaactgtctt ggtgggtcaa cggcaaagag gtgcacagcg      600
gagtgtccac cgaccctcag cccctgaaag aacagcccgc cctgaacgac agccggtact      660
gcctgagcag cagactgaga gtgtccgcca ccttctggca gaaccccccgg aaccacttca      720 gatgccaggt gcagttctac ggcctgagcg agaacgacga gtggacccag gacagagcca      780
agcccgtgac ccagatcgtg tctgccgaag cctggggcag agccgattgc ggctttacct      840
ccgtgtccta tcagcagggc gtgctgagcg ccaccatcct gtacgagatc ctgctgggca      900
aggccaccct gtacgccgtg ctggtgtctg ccctggtgct gatggccatg gtcaagcgga      960
aggacttcgg ttccggagcc acgaacttct ctctgttaaa gcaagcagga gacgtggaag     1020
aaaaccccgg tcccatgatg aagtccctgc gggtgctgct cgtgatcctg tggctgcagc     1080
tgtcttgggt gtggtcccag cagaaagagg tggaacagaa cagcggccct ctgagcgtgc     1140
cagagggcgc cattgctagc ctgaattgca cctacagcga ccgggcagc cagagcttct     1200 tctggtatcg gcagtacagc ggcaagagcc ccgagctgat catgagcatc tacagcaacg     1260
gcgacaaaga ggacggccgg ttcaccgccc agctgaacaa agccagccag tacgtgtcac     1320
tgctgatccg ggacagccag cccagcgata gcgccacata cctgtgcgcc gtggatagcg     1380
gcggctacca gaaagtgacc ttcggcaccg gcaccaagct gcaagtgatc cccaacatcc     1440 agaacccccga ccccgctgtg taccagctgc gggacagcaa gagcagcgac              1490
```

<210> SEQ ID NO 63
<211> LENGTH: 494
<212> TYPE: PRT
<213> ORGANISM: Artificial Sequence
<220> FEATURE:
<223> OTHER INFORMATION: codon optimized TCR number 3 construct; beta
      chain-P2A-alpha chain with cysteine substitutions in beta and
      alpha chain constant domains (partial sequence)

<400> SEQUENCE: 63

```
Lys Ser Pro Gln Pro Leu Thr Arg Arg Ala Thr Met Gly Thr Arg Leu
1               5                   10                  15

Leu Cys Trp Ala Ala Leu Cys Leu Leu Gly Ala Asp His Thr Gly Ala
            20                  25                  30

Gly Val Ser Gln Thr Pro Ser Asn Lys Val Thr Glu Lys Gly Lys Tyr
        35                  40                  45

Val Glu Leu Arg Cys Asp Pro Ile Ser Gly His Thr Ala Leu Tyr Trp
    50                  55                  60

Tyr Arg Gln Ser Leu Gly Gln Gly Pro Glu Phe Leu Ile Tyr Phe Gln
65                  70                  75                  80

Gly Thr Gly Ala Ala Asp Asp Ser Gly Leu Pro Asn Asp Arg Phe Phe
                85                  90                  95

Ala Val Arg Pro Glu Gly Ser Val Ser Thr Leu Lys Ile Gln Arg Thr
            100                 105                 110

Glu Arg Gly Asp Ser Ala Val Tyr Leu Cys Ala Ser Ser Leu Asn Met
        115                 120                 125

Asn Thr Glu Ala Phe Phe Gly Gln Gly Thr Arg Leu Thr Val Val Glu
    130                 135                 140

Asp Leu Asn Lys Val Phe Pro Pro Glu Val Ala Val Phe Glu Pro Ser
145                 150                 155                 160
```

-continued

```
Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Ser Thr Asp Pro Gln Pro Leu Lys Glu
        195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
            275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Phe
305                 310                 315                 320

Gly Ser Gly Ala Thr Asn Phe Ser Leu Leu Lys Gln Ala Gly Asp Val
            325                 330                 335

Glu Glu Asn Pro Gly Pro Met Met Lys Ser Leu Arg Val Leu Leu Val
            340                 345                 350

Ile Leu Trp Leu Gln Leu Ser Trp Val Trp Ser Gln Gln Lys Glu Val
            355                 360                 365

Glu Gln Asn Ser Gly Pro Leu Ser Val Pro Glu Gly Ala Ile Ala Ser
    370                 375                 380

Leu Asn Cys Thr Tyr Ser Asp Arg Gly Ser Gln Ser Phe Phe Trp Tyr
385                 390                 395                 400

Arg Gln Tyr Ser Gly Lys Ser Pro Glu Leu Ile Met Ser Ile Tyr Ser
            405                 410                 415

Asn Gly Asp Lys Glu Asp Gly Arg Phe Thr Ala Gln Leu Asn Lys Ala
            420                 425                 430

Ser Gln Tyr Val Ser Leu Leu Ile Arg Asp Ser Gln Pro Ser Asp Ser
        435                 440                 445

Ala Thr Tyr Leu Cys Ala Val Asp Ser Gly Gly Tyr Gln Lys Val Thr
    450                 455                 460

Phe Gly Thr Gly Thr Lys Leu Gln Val Ile Pro Asn Ile Gln Asn Pro
465                 470                 475                 480

Asp Pro Ala Val Tyr Gln Leu Arg Asp Ser Lys Ser Ser Asp
                485                 490
```

```
<210> SEQ ID NO 64
<211> LENGTH: 819
<212> TYPE: DNA
<213> ORGANISM: Artificial Sequence
<220> FEATURE:
<223> OTHER INFORMATION: TCR number 10 alpha chain

<400> SEQUENCE: 64
atggaaactc tcctgggagt gtctttggtg attctatggc ttcaactggc tagggtgaac        60
agtcaacagg gagaagagga tcctcaggcc ttgagcatcc aggagggtga aaatgccacc       120
atgaactgca gttacaaaac tagtataaac aatttacagt ggtatagaca aaattcaggt       180
```

-continued

```
agaggccttg tccacctaat tttaatacgt tcaaatgaaa gagagaaaca cagtggaaga      240
ttaagagtca cgcttgacac ttccaagaaa agcagttcct tgttgatcac ggcttcccgg      300
gcagcagaca ctgcttctta cttctgtgct acggacgaga gtagcaacta taaactgaca      360
tttggaaaag gaactctctt aaccgtgaat ccaaatatcc agaaccctga ccctgccgtg      420
taccagctga gagactctaa atccagtgac aagtctgtct gcctattcac cgattttgat      480
tctcaaacaa atgtgtcaca aagtaaggat tctgatgtgt atatcacaga caaaactgtg      540
ctagacatga ggtctatgga cttcaagagc aacagtgctg tggcctggag caacaaatct      600
gactttgcat gtgcaaacgc cttcaacaac agcattattc cagaagacac cttcttcccc      660
agcccagaaa gttcctgtga tgtcaagctg gtcgagaaaa gctttgaaac agatacgaac      720
ctaaactttc aaaacctgtc agtgattggg ttccgaatcc tcctcctgaa agtggccggg      780
tttaatctgc tcatgacgct gcggctgtgg tccagctga                             819
```

<210> SEQ ID NO 65
<211> LENGTH: 272
<212> TYPE: PRT
<213> ORGANISM: Artificial Sequence
<220> FEATURE:
<223> OTHER INFORMATION: TCR number 10 alpha chain

<400> SEQUENCE: 65

```
Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
            85                  90                  95

Thr Ala Ser Arg Ala Ala Asp Thr Ala Ser Tyr Phe Cys Ala Thr Asp
            100                 105                 110

Glu Ser Ser Asn Tyr Lys Leu Thr Phe Gly Lys Gly Thr Leu Leu Thr
            115                 120                 125

Val Asn Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
            245                 250                 255
```

-continued

```
Lys Val Ala Gly Phe Asn Leu Leu Met Thr Leu Arg Leu Trp Ser Ser
            260                 265                 270
```

```
<210> SEQ ID NO 66
<211> LENGTH: 1484
<212> TYPE: DNA
<213> ORGANISM: Artificial Sequence
<220> FEATURE:
<223> OTHER INFORMATION: codon optimized TCR number 10 construct; beta
      chain-P2A-alpha chain with cysteine substitutions in beta and
      alpha chain constant domains (partial sequence)

<400> SEQUENCE: 66
ctcaataaaa gagcccacaa cccctcactc ggcgcgccac catgggcacc agactgctgt      60
gttgggccgc tctgtgtctg ctgggcgccg atcatacagg cgctggcgtg tcccagaccc     120
ccagcaacaa agtgaccgag aagggcaaat acgtggaact gagatgcgac cccatcagcg     180
gccacaccgc cctgtactgg tacagacagt ctctgggcca gggccccgag ttcctgatat     240
attttcaggg caccggcgct gccgacgaca gcggcctgcc taacgataga ttcttcgccg     300
tgcggcccga gggcagcgtg tccacactga agatccagag aaccgagcgg ggcgacagcg     360
ccgtgtatct gtgtgccagc agcctgaata tgaacaccgg ggcattcttt gggcagggca     420
cccggctgac cgtggtggaa gatctgaaca aggtgttccc cccagaggtg gccgtgttcg     480
agccttctga ggccgagatc agccacaccc agaaagccac cctcgtgtgc ctggccaccg     540
gctttttccc cgaccatgtg gaactgtctt ggtgggtcaa cggcaaagag gtgcacagcg     600
gagtgtccac cgaccctcag cccctgaaag aacagcccgc cctgaacgac agccggtact     660
gcctgagcag cagactgaga gtgtccgcca ccttctggca gaacccccgg aaccacttca     720
gatgccaggt gcagttctac ggcctgagcg agaacgacga gtggacccag gacagagcca     780
agcccgtgac ccagatcgtg tctgccgaag cctggggcag agccgattgc ggctttacct     840
ccgtgtccta tcagcagggc gtgctgagcg ccaccatcct gtacgagatc ctgctgggca     900
aggccaccct gtacgccgtg ctggtgtctg ccctggtgct gatggccatg gtcaagcgga     960
aggacttcgg ttccggagcc acgaacttct ctctgttaaa gcaagcagga gacgtggaag    1020
aaaaccccgg tcccatggaa accctgctgg gagtgtccct cgtgatcctg tggctgcagc    1080
tggccagagt gaacagccag caggggaag aggatcccca ggccctgagc attcaggaag     1140
gcgagaacgc caccatgaac tgcagctaca gaccagcat caacaacctg cagtggtaca    1200
ggcagaacag cggcagaggc ctggtgcacc tgatcctgat cagaagcaac gagagagaga    1260
agcactccgg acggctgaga gtgaccctgg acacctccaa gaagtcctcc agcctgctga    1320
tcaccgccag cagagccgcc gataccgcca gctacttctg cgccacagac gagagcagca    1380
actacaagct gaccttcggc aagggcacac tgctgacagt gaaccccaac atccagaacc    1440
ccgaccccgc tgtgtaccag ctgcgggaca gcaagagcag cgac                     1484
```

```
<210> SEQ ID NO 67
<211> LENGTH: 492
<212> TYPE: PRT
<213> ORGANISM: Artificial Sequence
<220> FEATURE:
<223> OTHER INFORMATION: codon optimized TCR number 10 construct
      polypeptide; beta chain-P2A-alpha chain with cysteine
      substitutions in beta and alpha chain constant domains (partial
      sequence)

<400> SEQUENCE: 67
```

-continued

```
Lys Ser Pro Gln Pro Leu Thr Arg Arg Ala Thr Met Gly Thr Arg Leu
1               5                   10                  15

Leu Cys Trp Ala Ala Leu Cys Leu Leu Gly Ala Asp His Thr Gly Ala
            20                  25                  30

Gly Val Ser Gln Thr Pro Ser Asn Lys Val Thr Glu Lys Gly Lys Tyr
            35                  40                  45

Val Glu Leu Arg Cys Asp Pro Ile Ser Gly His Thr Ala Leu Tyr Trp
    50                  55                  60

Tyr Arg Gln Ser Leu Gly Gln Gly Pro Glu Phe Leu Ile Tyr Phe Gln
65                  70                  75                  80

Gly Thr Gly Ala Ala Asp Asp Ser Gly Leu Pro Asn Asp Arg Phe Phe
                85                  90                  95

Ala Val Arg Pro Glu Gly Ser Val Ser Thr Leu Lys Ile Gln Arg Thr
            100                 105                 110

Glu Arg Gly Asp Ser Ala Val Tyr Leu Cys Ala Ser Ser Leu Asn Met
            115                 120                 125

Asn Thr Glu Ala Phe Phe Gly Gln Gly Thr Arg Leu Thr Val Val Glu
    130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Ser Thr Asp Pro Gln Pro Leu Lys Glu
            195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
            275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Phe
305                 310                 315                 320

Gly Ser Gly Ala Thr Asn Phe Ser Leu Leu Lys Gln Ala Gly Asp Val
                325                 330                 335

Glu Glu Asn Pro Gly Pro Met Glu Thr Leu Leu Gly Val Ser Leu Val
            340                 345                 350

Ile Leu Trp Leu Gln Leu Ala Arg Val Asn Ser Gln Gln Gly Glu Glu
            355                 360                 365

Asp Pro Gln Ala Leu Ser Ile Gln Glu Gly Glu Asn Ala Thr Met Asn
    370                 375                 380

Cys Ser Tyr Lys Thr Ser Ile Asn Asn Leu Gln Trp Tyr Arg Gln Asn
385                 390                 395                 400

Ser Gly Arg Gly Leu Val His Leu Ile Leu Ile Arg Ser Asn Glu Arg
                405                 410                 415

Glu Lys His Ser Gly Arg Leu Arg Val Thr Leu Asp Thr Ser Lys Lys
```

-continued

```
        420              425              430
Ser Ser Ser Leu Leu Ile Thr Ala Ser Arg Ala Ala Asp Thr Ala Ser
        435              440              445

Tyr Phe Cys Ala Thr Asp Glu Ser Ser Asn Tyr Lys Leu Thr Phe Gly
    450              455              460

Lys Gly Thr Leu Leu Thr Val Asn Pro Asn Ile Gln Asn Pro Asp Pro
465              470              475              480

Ala Val Tyr Gln Leu Arg Asp Ser Lys Ser Ser Asp
            485              490
```

```
<210> SEQ ID NO 68
<211> LENGTH: 825
<212> TYPE: DNA
<213> ORGANISM: Artificial Sequence
<220> FEATURE:
<223> OTHER INFORMATION: TCR number 7 alpha chain

<400> SEQUENCE: 68
atggagaaga atcctttggc agccccatta ctaatcctct ggtttcatct tgactgcgtg      60
agcagcatac tgaacgtgga acaaagtcct cagtcactgc atgttcagga gggagacagc     120
accaatttca cctgcagctt cccttccagc aattttatg ccttacactg gtacagatgg      180
gaaactgcaa aaagccccga ggccttgttt gtaatgactt aaatgggga tgaaaagaag      240 aaaggacgaa taagtgccac tcttaatacc aaggagggtt acagctattt gtacatcaaa     300
ggatcccagc ctgaagactc agccacatac tctctgtgcct atttagggggc cggtaaccag    360 ttctattttg ggacagggac aagtttgacg gtcattccaa atatccagaa ccctgaccct     420
gccgtgtacc agctgagaga ctctaaatcc agtgacaagt ctgtctgcct attcaccgat     480
tttgattctc aaacaaatgt gtcacaaagt aaggattctg atgtgtatat cacagacaaa     540
actgtgctag acatgaggtc tatggacttc aagagcaaca gtgctgtggc ctggagcaac     600
aaatctgact ttgcatgtgc aaacgccttc aacaacagct tattccaga agacaccttc      660 ttccccagcc agaaagttc ctgtgatgtc aagctggtcg agaaaagctt tgaaacagat      720
acgaacctaa actttcaaaa cctgtcagtg attgggttcc gaatcctcct cctgaaagtg     780
gccgggttta atctgctcat gacgctgcgg ctgtggtcca gctga                     825
```

```
<210> SEQ ID NO 69
<211> LENGTH: 274
<212> TYPE: PRT
<213> ORGANISM: Artificial Sequence
<220> FEATURE:
<223> OTHER INFORMATION: TCR number 7 alpha chain

<400> SEQUENCE: 69

Met Glu Lys Asn Pro Leu Ala Ala Pro Leu Leu Ile Leu Trp Phe His
1               5              10               15

Leu Asp Cys Val Ser Ser Ile Leu Asn Val Glu Gln Ser Pro Gln Ser
        20              25              30

Leu His Val Gln Glu Gly Asp Ser Thr Asn Phe Thr Cys Ser Phe Pro
        35              40              45

Ser Ser Asn Phe Tyr Ala Leu His Trp Tyr Arg Trp Glu Thr Ala Lys
    50              55              60

Ser Pro Glu Ala Leu Phe Val Met Thr Leu Asn Gly Asp Glu Lys Lys
65              70              75              80

Lys Gly Arg Ile Ser Ala Thr Leu Asn Thr Lys Glu Gly Tyr Ser Tyr
            85              90              95
```

```
Leu Tyr Ile Lys Gly Ser Gln Pro Glu Asp Ser Ala Thr Tyr Leu Cys
        100                 105                 110

Ala Tyr Leu Gly Ala Gly Asn Gln Phe Tyr Phe Gly Thr Gly Thr Ser
        115                 120                 125

Leu Thr Val Ile Pro Asn Ile Gln Asn Pro Asp Pro Ala Val Tyr Gln
        130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
        180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
        210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
        260                 265                 270

Ser Ser
```

```
<210> SEQ ID NO 70
<211> LENGTH: 930
<212> TYPE: DNA
<213> ORGANISM: Artificial Sequence
<220> FEATURE:
<223> OTHER INFORMATION: TCR number 7 beta chain

<400> SEQUENCE: 70
atgagcaacc aggtgctctg ctgtgtggtc ctttgtttcc tgggagcaaa caccgtggat        60
ggtggaatca ctcagtcccc aaagtacctg ttcagaaagg aaggacagaa tgtgaccctg       120
agttgtgaac agaatttgaa ccacgatgcc atgtactggt accgacagga cccagggcaa       180
gggctgagat tgatctacta ctcacagata gtaaatgact ttcagaaagg agatatagct       240
gaagggtaca gcgtctctcg ggagaagaag gaatcctttc tctctcactgt gacatcggcc       300 caaaagaacc cgacagcttt ctatctctgt gccagtagcc tcaacagggg ccgctatggc       360
tacaccttcg gttcggggac caggttaacc gttgtagagg acctgaacaa ggtgttccca       420
cccgaggtcg ctgtgtttga gccatcagaa gcagagatct cccacaccca aaaggccaca       480
ctggtgtgcc tggccacagg cttcttcccc gaccacgtgg agctgagctg gtgggtgaat       540
gggaaggagg tgcacagtgg ggtcagcacg gaccgcagc ccctcaagga gcagcccgcc       600
ctcaatgact ccagatactg cctgagcagc cgcctgaggg tctcggccac cttctggcag       660
aacccccgca accacttccg ctgtcaagtc cagttctacg gctctcgga gaatgacgag       720 tggacccagg ataggccaa acccgtcacc cagatcgtca gcgccgaggc ctggggtaga       780
gcagactgtg gctttacctc ggtgtcctac cagcaagggg tcctgtctgc caccatcctc       840
tatgagatcc tgctagggaa ggccaccctg tatgctgtgc tggtcagcgc ccttgtgttg       900
atggccatgg tcaagagaaa ggatttctga                                        930
```

```
<210> SEQ ID NO 71
<211> LENGTH: 309
<212> TYPE: PRT
<213> ORGANISM: Artificial Sequence
<220> FEATURE:
<223> OTHER INFORMATION: TCR number 7 beta chain

<400> SEQUENCE: 71

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Leu Asn Arg Gly Arg Tyr Gly Tyr Thr Phe Gly Ser Gly Thr Arg
            115                 120                 125

Leu Thr Val Val Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe
305

<210> SEQ ID NO 72
<211> LENGTH: 1490
<212> TYPE: DNA
<213> ORGANISM: Artificial Sequence
<220> FEATURE:
<223> OTHER INFORMATION: codon optimized TCR number 7 construct; beta
      chain-P2A-alpha chain with cysteine substitutions in beta and
      alpha chain constant domains (partial sequence)
```

<400> SEQUENCE: 72

```
ctcaataaaa gagcccacaa cccctcactc ggcgcgccac catgagcaac caggtcttgt      60
gctgtgtggt gctgtgcttt cttggcgcca atacagtgga tggcggcatt acacagagcc     120
ctaagtacct gttccggaaa gaaggccaga acgtgacact gtcttgcgag caaaacctga     180
accacgatgc catgtactgg tacagacagg atcctggaca gggacttagg ctgatctact     240
atagccagat cgtgaacgac ttccagaagg cgatattgc cgagggctat tctgtgtctc     300
gggagaaaaa ggagagcttc cctctgacag tgacatctgc ccagaagaat cctaccgcct     360
tctacctttg tgccagctct ctgaatcggg gcagatacgg atacaccttt ggatctggca     420
ccagactgac agtggtggaa gatctgaaca aggtgttccc cccagaggtg gccgtgttcg     480
agccttctga ggccgagatc tcccacaccc agaaagccac cctcgtgtgc ctggccaccg     540 gcttttccc cgaccacgtg gaactgtctt ggtgggtcaa cggcaaagag gtgcactccg     600
gcgtgtgcac cgatccccag cctctgaaag aacagcccgc cctgaacgac agccggtact     660
gcctgagcag cagactgaga gtgtccgcca ccttctggca gaaccccgg aaccacttca      720 gatgccaggt gcagttctac ggcctgagcg agaacgacga gtggaccag gacagagcca      780 agcccgtgac acagatcgtg tctgccgaag cctggggcag agccgattgc ggctttacct     840
ccgtgtccta tcagcaggc gtgctgagcg ccacaatcct gtacgagatc ctgctgggca      900
aggccaccct gtacgccgtg ctggtgtctg ccctggtgct gatggccatg gtcaagcgga     960
aggacttcgg ttccggagcc acgaacttct ctctgttaaa gcaagcagga gacgtggaag    1020 aaaacccgg tccatggag aagaacccccc ttgcagcacc tctgcttatt ctgtggttcc     1080
acctggattg cgtgagctct atcctgaatg tggagcagtc tcctcagtct ctgcatgttc    1140
aggaaggcga tagcaccaac ttcacctgta gctttcccag cagcaacttc tatgccctgc    1200
actggtacag atgggaaaca gccaaaagcc ctgaagccct gttcgtgatg accccttaatg   1260 gcgatgagaa gaagaagggc cggatttctg ccaccctgaa tacaaaagag ggctacagct    1320
acctgtacat caagggatct cagcctgagg atagcgccac atatctgtgt gcctatctgg    1380
gagccggcaa tcagttctat ttcggaacag gcaccagcct gaccgtgatt cctaatatcc    1440
agaaccccga tcctgccgtg taccagctgc gggacagcaa gagcagcgac              1490
```

<210> SEQ ID NO 73
<211> LENGTH: 494
<212> TYPE: PRT
<213> ORGANISM: Artificial Sequence
<220> FEATURE:
<223> OTHER INFORMATION: codon optimized TCR number 7 construct; beta
    chain-P2A-alpha chain with cysteine substitutions in beta and
    alpha chain constant domains (partial sequence)

<400> SEQUENCE: 73

```
Lys Ser Pro Gln Pro Leu Thr Arg Arg Ala Thr Met Ser Asn Gln Val
1               5                   10                  15

Leu Cys Cys Val Val Leu Cys Phe Leu Gly Ala Asn Thr Val Asp Gly
            20                  25                  30

Gly Ile Thr Gln Ser Pro Lys Tyr Leu Phe Arg Lys Glu Gly Gln Asn
        35                  40                  45

Val Thr Leu Ser Cys Glu Gln Asn Leu Asn His Asp Ala Met Tyr Trp
    50                  55                  60

Tyr Arg Gln Asp Pro Gly Gln Gly Leu Arg Leu Ile Tyr Tyr Ser Gln
65                  70                  75                  80
```

-continued

```
Ile Val Asn Asp Phe Gln Lys Gly Asp Ile Ala Glu Gly Tyr Ser Val
                85                  90                  95

Ser Arg Glu Lys Lys Glu Ser Phe Pro Leu Thr Val Thr Ser Ala Gln
            100                 105                 110

Lys Asn Pro Thr Ala Phe Tyr Leu Cys Ala Ser Ser Leu Asn Arg Gly
            115                 120                 125

Arg Tyr Gly Tyr Thr Phe Gly Ser Gly Thr Arg Leu Thr Val Val Glu
        130                 135                 140

Asp Leu Asn Lys Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                165                 170                 175

Thr Gly Phe Phe Pro Asp His Val Glu Leu Ser Trp Trp Val Asn Gly
            180                 185                 190

Lys Glu Val His Ser Gly Val Cys Thr Asp Pro Gln Pro Leu Lys Glu
            195                 200                 205

Gln Pro Ala Leu Asn Asp Ser Arg Tyr Cys Leu Ser Ser Arg Leu Arg
        210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                245                 250                 255

Ala Lys Pro Val Thr Gln Ile Val Ser Ala Glu Ala Trp Gly Arg Ala
            260                 265                 270

Asp Cys Gly Phe Thr Ser Val Ser Tyr Gln Gln Gly Val Leu Ser Ala
            275                 280                 285

Thr Ile Leu Tyr Glu Ile Leu Leu Gly Lys Ala Thr Leu Tyr Ala Val
        290                 295                 300

Leu Val Ser Ala Leu Val Leu Met Ala Met Val Lys Arg Lys Asp Phe
305                 310                 315                 320

Gly Ser Gly Ala Thr Asn Phe Ser Leu Leu Lys Gln Ala Gly Asp Val
                325                 330                 335

Glu Glu Asn Pro Gly Pro Met Glu Lys Asn Pro Leu Ala Ala Pro Leu
            340                 345                 350

Leu Ile Leu Trp Phe His Leu Asp Cys Val Ser Ser Ile Leu Asn Val
            355                 360                 365

Glu Gln Ser Pro Gln Ser Leu His Val Gln Glu Gly Asp Ser Thr Asn
        370                 375                 380

Phe Thr Cys Ser Phe Pro Ser Ser Asn Phe Tyr Ala Leu His Trp Tyr
385                 390                 395                 400

Arg Trp Glu Thr Ala Lys Ser Pro Glu Ala Leu Phe Val Met Thr Leu
                405                 410                 415

Asn Gly Asp Glu Lys Lys Lys Gly Arg Ile Ser Ala Thr Leu Asn Thr
                420                 425                 430

Lys Glu Gly Tyr Ser Tyr Leu Tyr Ile Lys Gly Ser Gln Pro Glu Asp
            435                 440                 445

Ser Ala Thr Tyr Leu Cys Ala Tyr Leu Gly Ala Gly Asn Gln Phe Tyr
        450                 455                 460

Phe Gly Thr Gly Thr Ser Leu Thr Val Ile Pro Asn Ile Gln Asn Pro
465                 470                 475                 480

Asp Pro Ala Val Tyr Gln Leu Arg Asp Ser Lys Ser Ser Asp
                485                 490
```

-continued

```
<210> SEQ ID NO 74
<211> LENGTH: 837
<212> TYPE: DNA
<213> ORGANISM: Artificial Sequence
<220> FEATURE:
<223> OTHER INFORMATION: TCR number 8 alpha chain

<400> SEQUENCE: 74
atgctgactg ccagcctgtt gagggcagtc atagcctcca tctgtgttgt atccagcatg       60
gctcagaagg taactcaagc gcagactgaa atttctgtgg tggagaagga ggatgtgacc      120
ttggactgtg tgtatgaaac ccgtgatact acttattact tattctggta caagcaacca      180
ccaagtggag aattggtttt ccttattcgt cggaactctt ttgatgagca aaatgaaata      240
agtggtcggt attcttggaa cttccagaaa tccaccagtt ccttcaactt caccatcaca      300
gcctcacaag tcgtggactc agcagtatac ttctgtgctc tgagtgagct agcatcagga      360
ggaagctaca tacctacatt tggaagagga accagcctta ttgttcatcc gtatatccag      420
aaccctgacc ctgccgtgta ccagctgaga gactctaaat ccagtgacaa gtctgtctgc      480
ctattcaccg attttgattc tcaaacaaat gtgtcacaaa gtaaggattc tgatgtgtat      540
atcacagaca aaactgtgct agacatgagg tctatggact tcaagagcaa cagtgctgtg      600
gcctggagca caaatctgca ctttgcatgt gcaaacgcct caacaacag cattattcca       660 gaagacacct tcttccccag cccagaaagt tcctgtgatg tcaagctggt cgagaaaagc      720
tttgaaacag atacgaacct aaactttcaa aacctgtcag tgattgggtt ccgaatcctc      780
ctcctgaaag tggccgggtt taatctgctc atgacgctgc ggctgtggtc cagctga       837
```

```
<210> SEQ ID NO 75
<211> LENGTH: 278
<212> TYPE: PRT
<213> ORGANISM: Artificial Sequence
<220> FEATURE:
<223> OTHER INFORMATION: TCR number 8 alpha chain

<400> SEQUENCE: 75

Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
                100                 105                 110

Ala Leu Ser Glu Leu Ala Ser Gly Gly Ser Tyr Ile Pro Thr Phe Gly
            115                 120                 125

Arg Gly Thr Ser Leu Ile Val His Pro Tyr Ile Gln Asn Pro Asp Pro
        130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
                165                 170                 175
```

-continued

```
Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
            210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
            245                 250                 255

Phe Arg Ile Leu Leu Leu Lys Val Ala Gly Phe Asn Leu Leu Met Thr
            260                 265                 270

Leu Arg Leu Trp Ser Ser
            275
```

```
<210> SEQ ID NO 76
<211> LENGTH: 948
<212> TYPE: DNA
<213> ORGANISM: Artificial Sequence
<220> FEATURE:
<223> OTHER INFORMATION: TCR number 8 beta chain

<400> SEQUENCE: 76
atgggccccg ggctcctctg ctgggcactg ctttgtctcc tgggagcagg cttagtggac      60
gctggagtca cccaaagtcc cacacacctg atcaaaacga gaggacagca agtgactctg     120
agatgctctc ctaagtctgg gcatgacact gtgtcctggt accaacaggc cctgggtcag     180
gggccccagt ttatctttca gtattatgag gaggaagaga gacagagagg caacttccct     240
gatcgattct caggtcacca gttccctaac tatagctctg agctgaatgt gaacgccttg     300
ttgctggggg actcggccct ctatctctgt gccagcagct ttaggctagc ggggggcct     360 agcacagata cgcagtattt tggcccaggc accggctga cagtgctcga ggacctgaaa     420
aacgtgttcc cacccgaggt cgctgtgttt gagccatcag aagcagagat ctcccacacc     480
caaaaggcca cactggtgtg cctggccaca ggcttctacc ccgaccacgt ggagctgagc     540
tggtgggtga atgggaagga ggtgcacagt ggggtcagca cagacccgca gcccctcaag     600
gagcagcccg ccctcaatga ctccagatac tgcctgagca gccgcctgag ggtctcggcc     660
accttctggc agaaccccg caaccacttc cgctgtcaag tccagttcta cgggctctcg     720
gagaatgacg agtggaccca ggatagggcc aaacctgtca cccagatcgt cagcgccgag     780
gcctggggta gagcagactg tggcttcacc tccgagtctt accagcaagg ggtcctgtct     840
gccaccatcc tctatgagat cttgctaggg aaggccacct tgtatgccgt gctggtcagt     900
gccctcgtgc tgatggccat ggtcaagaga aaggattcca gaggctag              948
```

```
<210> SEQ ID NO 77
<211> LENGTH: 315
<212> TYPE: PRT
<213> ORGANISM: Artificial Sequence
<220> FEATURE:
<223> OTHER INFORMATION: TCR number 8 beta chain

<400> SEQUENCE: 77

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30
```

```
Thr Arg Gly Gln Gln Val Thr Leu Arg Cys Ser Pro Lys Ser Gly His
        35              40              45

Asp Thr Val Ser Trp Tyr Gln Gln Ala Leu Gly Gln Gly Pro Gln Phe
    50              55              60

Ile Phe Gln Tyr Tyr Glu Glu Glu Glu Arg Gln Arg Gly Asn Phe Pro
65              70              75              80

Asp Arg Phe Ser Gly His Gln Phe Pro Asn Tyr Ser Ser Glu Leu Asn
            85              90              95

Val Asn Ala Leu Leu Leu Gly Asp Ser Ala Leu Tyr Leu Cys Ala Ser
            100             105             110

Ser Phe Arg Leu Ala Gly Gly Pro Ser Thr Asp Thr Gln Tyr Phe Gly
        115             120             125

Pro Gly Thr Arg Leu Thr Val Leu Glu Asp Leu Lys Asn Val Phe Pro
    130             135             140

Pro Glu Val Ala Val Phe Glu Pro Ser Glu Ala Glu Ile Ser His Thr
145             150             155             160

Gln Lys Ala Thr Leu Val Cys Leu Ala Thr Gly Phe Tyr Pro Asp His
            165             170             175

Val Glu Leu Ser Trp Trp Val Asn Gly Lys Glu Val His Ser Gly Val
            180             185             190

Ser Thr Asp Pro Gln Pro Leu Lys Glu Gln Pro Ala Leu Asn Asp Ser
            195             200             205

Arg Tyr Cys Leu Ser Ser Arg Leu Arg Val Ser Ala Thr Phe Trp Gln
    210             215             220

Asn Pro Arg Asn His Phe Arg Cys Gln Val Gln Phe Tyr Gly Leu Ser
225             230             235             240

Glu Asn Asp Glu Trp Thr Gln Asp Arg Ala Lys Pro Val Thr Gln Ile
            245             250             255

Val Ser Ala Glu Ala Trp Gly Arg Ala Asp Cys Gly Phe Thr Ser Glu
            260             265             270

Ser Tyr Gln Gln Gly Val Leu Ser Ala Thr Ile Leu Tyr Glu Ile Leu
    275             280             285

Leu Gly Lys Ala Thr Leu Tyr Ala Val Leu Val Ser Ala Leu Val Leu
    290             295             300

Met Ala Met Val Lys Arg Lys Asp Ser Arg Gly
305             310             315
```

<210> SEQ ID NO 78
<211> LENGTH: 1520
<212> TYPE: DNA
<213> ORGANISM: Artificial Sequence
<220> FEATURE:
<223> OTHER INFORMATION: codon optimized TCR number 8 construct; beta
      chain-P2A-alpha chain with cysteine substitutions in beta and
      alpha chain constant domains (partial sequence)

<400> SEQUENCE: 78

```
ctcaataaaa gagcccacaa cccctcactc ggcgcgccac catgggacct ggactgcttt      60
gttgggctct tctgtgtctg cttggagctg gactggttga tgctggagtt acacagagcc     120
ctacacacct gatcaagaca agaggacagc aggtgaccct gagatgtagc cctaaatctg     180
gccacgatac cgtgagctgg tatcaacagg ctctgggaca aggacctcag ttcatcttcc     240
agtactacga ggaggaggag agacagagag gcaatttccc tgacaggttt agcggacacc     300
agttccccaa ttacagctct gagctgaacg tgaatgccct tcttctggga gattctgccc     360
```

```
tgtatctgtg tgccagcagc tttagactgg ctggaggacc tagcaccgat acacagtatt      420
ttggacctgg caccaggctg acagtgttag aagacctgaa gaacgtgttc cccccagagg      480
tggccgtgtt cgagcctagc gaggccgaga tcagccacac ccagaaagcc accctcgtgt      540
gcctggccac cggcttttac cccgaccacg tggaactgtc ttggtgggtc aacggcaaag      600
aggtgcacag cggcgtctgc accgaccccc agccctgaa agagcagccc gccctgaacg       660
acagccggta ctgtctgagc agcagactga gagtgtccgc caccttctgg cagaacccc       720 ggaaccactt cagatgccag gtgcagttct acggcctgag cgagaacgac gagtggaccc      780
aggaccgggc caagcccgtg acccagatcg tgtctgctga ggcctggggc agagccgatt      840
gcggcttcac cagcgagagc taccagcagg gcgtgctgag cgccaccatc ctgtacgaga      900
tcctgctggg caaggccacc ctgtacgccg tgctggtgtc cgccctggtg ctgatggcca      960
tggtcaagcg gaaggacagc cggggcggtt ccggagccac gaacttctct ctgttaaagc     1020
aagcaggaga cgtggaagaa aaccccggtc ccatgttgac cgcttctctc ttacgtgccg     1080
tgattgccag catctgtgtg gttagctcta tggcccagaa ggtgacacaa gctcagacag     1140
agatcagcgt ggtggagaaa gaggatgtga ccctggattg cgtgtacgag accagagata     1200
ccacctacta cctgttctgg tacaagcagc tccttctgg agaactggtg ttcctgatca      1260
gacggaacag cttcgatgag cagaacgaga ttagcggcag gtatagctgg aacttccaga     1320
agagcaccag cagcttcaac ttcaccatca gcctctca ggtggtggat tctgccgtgt       1380 actttgtgc cctgtctgaa ctggcctctg gaggaagcta tatccctaca ttcggcagag      1440
gcacaagcct gattgtgcac ccttacatcc agaaccctga tcctgctgtg taccagctgc     1500
gggacagcaa gagcagcgac                                                  1520
```

```
<210> SEQ ID NO 79
<211> LENGTH: 504
<212> TYPE: PRT
<213> ORGANISM: Artificial Sequence
<220> FEATURE:
<223> OTHER INFORMATION: codon optimized TCR number 8 construct
      polypeptide; beta chain-P2A-alpha chain with cysteine
      substitutions in beta and alpha chain constant domains (partial
      sequence)

<400> SEQUENCE: 79

Lys Ser Pro Gln Pro Leu Thr Arg Arg Ala Thr Met Gly Pro Gly Leu
1               5                   10                  15

Leu Cys Trp Ala Leu Leu Cys Leu Leu Gly Ala Gly Leu Val Asp Ala
            20                  25                  30

Gly Val Thr Gln Ser Pro Thr His Leu Ile Lys Thr Arg Gly Gln Gln
        35                  40                  45

Val Thr Leu Arg Cys Ser Pro Lys Ser Gly His Asp Thr Val Ser Trp
    50                  55                  60

Tyr Gln Gln Ala Leu Gly Gln Gly Pro Gln Phe Ile Phe Gln Tyr Tyr
65                  70                  75                  80

Glu Glu Glu Glu Arg Gln Arg Gly Asn Phe Pro Asp Arg Phe Ser Gly
                85                  90                  95

His Gln Phe Pro Asn Tyr Ser Ser Glu Leu Asn Val Asn Ala Leu Leu
            100                 105                 110

Leu Gly Asp Ser Ala Leu Tyr Leu Cys Ala Ser Ser Phe Arg Leu Ala
        115                 120                 125

Gly Gly Pro Ser Thr Asp Thr Gln Tyr Phe Gly Pro Gly Thr Arg Leu
    130                 135                 140
```

-continued

```
Thr Val Leu Glu Asp Leu Lys Asn Val Phe Pro Pro Glu Val Ala Val
145                 150                 155                 160

Phe Glu Pro Ser Glu Ala Glu Ile Ser His Thr Gln Lys Ala Thr Leu
                165                 170                 175

Val Cys Leu Ala Thr Gly Phe Tyr Pro Asp His Val Glu Leu Ser Trp
                180                 185                 190

Trp Val Asn Gly Lys Glu Val His Ser Gly Val Cys Thr Asp Pro Gln
                195                 200                 205

Pro Leu Lys Glu Gln Pro Ala Leu Asn Asp Ser Arg Tyr Cys Leu Ser
        210                 215                 220

Ser Arg Leu Arg Val Ser Ala Thr Phe Trp Gln Asn Pro Arg Asn His
225                 230                 235                 240

Phe Arg Cys Gln Val Gln Phe Tyr Gly Leu Ser Glu Asn Asp Glu Trp
                245                 250                 255

Thr Gln Asp Arg Ala Lys Pro Val Thr Gln Ile Val Ser Ala Glu Ala
                260                 265                 270

Trp Gly Arg Ala Asp Cys Gly Phe Thr Ser Glu Ser Tyr Gln Gln Gly
                275                 280                 285

Val Leu Ser Ala Thr Ile Leu Tyr Glu Ile Leu Leu Gly Lys Ala Thr
        290                 295                 300

Leu Tyr Ala Val Leu Val Ser Ala Leu Val Leu Met Ala Met Val Lys
305                 310                 315                 320

Arg Lys Asp Ser Arg Gly Gly Ser Gly Ala Thr Asn Phe Ser Leu Leu
                325                 330                 335

Lys Gln Ala Gly Asp Val Glu Glu Asn Pro Gly Pro Met Leu Thr Ala
                340                 345                 350

Ser Leu Leu Arg Ala Val Ile Ala Ser Ile Cys Val Val Ser Ser Met
                355                 360                 365

Ala Gln Lys Val Thr Gln Ala Gln Thr Glu Ile Ser Val Val Glu Lys
        370                 375                 380

Glu Asp Val Thr Leu Asp Cys Val Tyr Glu Thr Arg Asp Thr Thr Tyr
385                 390                 395                 400

Tyr Leu Phe Trp Tyr Lys Gln Pro Pro Ser Gly Glu Leu Val Phe Leu
                405                 410                 415

Ile Arg Arg Asn Ser Phe Asp Glu Gln Asn Glu Ile Ser Gly Arg Tyr
                420                 425                 430

Ser Trp Asn Phe Gln Lys Ser Thr Ser Ser Phe Asn Phe Thr Ile Thr
                435                 440                 445

Ala Ser Gln Val Val Asp Ser Ala Val Tyr Phe Cys Ala Leu Ser Glu
        450                 455                 460

Leu Ala Ser Gly Gly Ser Tyr Ile Pro Thr Phe Gly Arg Gly Thr Ser
465                 470                 475                 480

Leu Ile Val His Pro Tyr Ile Gln Asn Pro Asp Pro Ala Val Tyr Gln
                485                 490                 495

Leu Arg Asp Ser Lys Ser Ser Asp
                500
```

<210> SEQ ID NO 80
<211> LENGTH: 1836
<212> TYPE: DNA
<213> ORGANISM: Artificial Sequence
<220> FEATURE:
<223> OTHER INFORMATION: TCR number 4 construct; beta chain-P2A-alpha
      chain

```
<400> SEQUENCE: 80
accatgggca ccaggctcct cttctgggtg gccttctgtc tcctgggggc agatcacaca    60
ggagctggag tctcccagtc ccccagtaac aaggtcacag agaagggaaa ggatgtagag   120
ctcaggtgtg atccaatttc aggtcatact gccctttact ggtaccgaca gagcctgggg   180
cagggcctgg agttttttaat ttacttccaa ggcaacagtg caccagacaa atcagggctg   240
cccagtgatc gcttctctgc agagaggact gggggatccg tctccactct gacgatccag   300
cgcacacagc aggaggactc ggccgtgtat ctctgtgcca gcagcttagt ggtcggctcc   360
tacgagcagt acttcgggcc gggcaccagg ctcacggtca cagaggacct gaaaaacgtg   420
ttcccacccg aggtcgctgt gtttgagcca tcagaagcag agatctccca cacccaaaag   480
gccacactgg tgtgcctggc cacaggcttc tacccCgacc acgtggagct gagctggtgg   540
gtgaatggga aggaggtgca cagtgggggtc agcacagacc cgcagcccct caaggagcag   600
cccgccctca atgactccag atactgcctg agcagccgcc tgagggtctc ggccaccttc   660
tggcagaacc cccgcaacca cttccgctgt caagtccagt tctacgggct ctcggagaat   720
gacgagtgga cccaggatag ggccaaacct gtcacccaga tcgtcagcgc cgaggcctgg   780
ggtagagcag actgtggctt cacctccgag tcttaccagc aaggggtcct gtctgccacc   840
atcctctatg agatcttgct agggaaggcc accttgtatg ccgtgctggt cagtgccctc   900
gtgctgatgg ccatggtcaa gagaaaggat tccagaggcg gttccggagc cacgaacttc   960
tctctgttaa agcaagcagg agacgtggaa gaaaacCCCg gtcccatgga aactctcctg  1020
ggagtgtctt tggtgattct atggcttcaa ctggctaggg tgaacagtca cagggagaa   1080 gaggatcctc aggccttgag catccaggag ggtgaaaatg ccaccatgaa ctgcagttac  1140
aaaactagta taaacaattt acagtggtat agacaaaatt caggtagagg ccttgtccac  1200
ctaattttaa tacgttcaaa tgaaagagag aaacacagtg gaagattaag agtcacgctt  1260
gacacttcca agaaaagcag ttccttgttg atcacggctt cccgggcagc agacactgct  1320
tcttacttct gtgctacgga cgcgtgggaa tctaactttg gaaatgagaa attaaccttt  1380
gggactggaa caagactcac catcataccc aatatccaga ccctgacccc tgccgtgtac  1440
cagctgagag actctaaatc cagtgacaag tctgtctgcc tattcaccga ttttgattct  1500
caaacaaatg tgtcacaaag taaggattct gatgtgtata tcacagacaa aactgtgcta  1560
gacatgaggt ctatggactt caagagcaac agtgctgtgg cctggagcaa caaatctgac  1620
tttgcatgtg caaacgcctt caacaacagc attattccag aagacacctt cttccccagc  1680
ccagaaagtt cctgtgatgt caagctggtc gagaaaagct ttgaaacaga tacgaaccta  1740
aactttcaaa acctgtcagt gattgggttc cgaatcctcc tcctgaaagt ggccgggttt  1800
aatctgctca tgacgctgcg gctgtggtcc agctga                            1836

<210> SEQ ID NO 81
<211> LENGTH: 611
<212> TYPE: PRT
<213> ORGANISM: Artificial Sequence
<220> FEATURE:
<223> OTHER INFORMATION: TCR number 4 construct; beta chain-P2A-alpha
      chain

<400> SEQUENCE: 81

Thr Met Gly Thr Arg Leu Leu Phe Trp Val Ala Phe Cys Leu Leu Gly
1               5                   10                  15

Ala Asp His Thr Gly Ala Gly Val Ser Gln Ser Pro Ser Asn Lys Val
```

-continued

```
                20               25               30

Thr Glu Lys Gly Lys Asp Val Glu Leu Arg Cys Asp Pro Ile Ser Gly
            35               40               45

His Thr Ala Leu Tyr Trp Tyr Arg Gln Ser Leu Gly Gln Gly Leu Glu
        50               55               60

Phe Leu Ile Tyr Phe Gln Gly Asn Ser Ala Pro Asp Lys Ser Gly Leu
65               70               75               80

Pro Ser Asp Arg Phe Ser Ala Glu Arg Thr Gly Gly Ser Val Ser Thr
                85               90               95

Leu Thr Ile Gln Arg Thr Gln Gln Glu Asp Ser Ala Val Tyr Leu Cys
            100              105              110

Ala Ser Ser Leu Val Val Gly Ser Tyr Glu Gln Tyr Phe Gly Pro Gly
        115              120              125

Thr Arg Leu Thr Val Thr Glu Asp Leu Lys Asn Val Phe Pro Pro Glu
        130              135              140

Val Ala Val Phe Glu Pro Ser Glu Ala Glu Ile Ser His Thr Gln Lys
145              150              155              160

Ala Thr Leu Val Cys Leu Ala Thr Gly Phe Tyr Pro Asp His Val Glu
            165              170              175

Leu Ser Trp Trp Val Asn Gly Lys Glu Val His Ser Gly Val Ser Thr
            180              185              190

Asp Pro Gln Pro Leu Lys Glu Gln Pro Ala Leu Asn Asp Ser Arg Tyr
            195              200              205

Cys Leu Ser Ser Arg Leu Arg Val Ser Ala Thr Phe Trp Gln Asn Pro
    210              215              220

Arg Asn His Phe Arg Cys Gln Val Gln Phe Tyr Gly Leu Ser Glu Asn
225              230              235              240

Asp Glu Trp Thr Gln Asp Arg Ala Lys Pro Val Thr Gln Ile Val Ser
            245              250              255

Ala Glu Ala Trp Gly Arg Ala Asp Cys Gly Phe Thr Ser Glu Ser Tyr
            260              265              270

Gln Gln Gly Val Leu Ser Ala Thr Ile Leu Tyr Glu Ile Leu Leu Gly
        275              280              285

Lys Ala Thr Leu Tyr Ala Val Leu Val Ser Ala Leu Val Leu Met Ala
    290              295              300

Met Val Lys Arg Lys Asp Ser Arg Gly Gly Ser Gly Ala Thr Asn Phe
305              310              315              320

Ser Leu Leu Lys Gln Ala Gly Asp Val Glu Glu Asn Pro Gly Pro Met
            325              330              335

Glu Thr Leu Leu Gly Val Ser Leu Val Ile Leu Trp Leu Gln Leu Ala
            340              345              350

Arg Val Asn Ser Gln Gln Gly Glu Glu Asp Pro Gln Ala Leu Ser Ile
            355              360              365

Gln Glu Gly Glu Asn Ala Thr Met Asn Cys Ser Tyr Lys Thr Ser Ile
        370              375              380

Asn Asn Leu Gln Trp Tyr Arg Gln Asn Ser Gly Arg Gly Leu Val His
385              390              395              400

Leu Ile Leu Ile Arg Ser Asn Glu Arg Glu Lys His Ser Gly Arg Leu
            405              410              415

Arg Val Thr Leu Asp Thr Ser Lys Lys Ser Ser Ser Leu Leu Ile Thr
            420              425              430

Ala Ser Arg Ala Ala Asp Thr Ala Ser Tyr Phe Cys Ala Thr Asp Ala
            435              440              445
```

-continued

```
Trp Glu Ser Asn Phe Gly Asn Glu Lys Leu Thr Phe Gly Thr Gly Thr
    450             455             460

Arg Leu Thr Ile Ile Pro Asn Ile Gln Asn Pro Asp Pro Ala Val Tyr
465             470             475             480

Gln Leu Arg Asp Ser Lys Ser Ser Asp Lys Ser Val Cys Leu Phe Thr
            485             490             495

Asp Phe Asp Ser Gln Thr Asn Val Ser Gln Ser Lys Asp Ser Asp Val
            500             505             510

Tyr Ile Thr Asp Lys Thr Val Leu Asp Met Arg Ser Met Asp Phe Lys
        515             520             525

Ser Asn Ser Ala Val Ala Trp Ser Asn Lys Ser Asp Phe Ala Cys Ala
    530             535             540

Asn Ala Phe Asn Asn Ser Ile Ile Pro Glu Asp Thr Phe Phe Pro Ser
545             550             555             560

Pro Glu Ser Ser Cys Asp Val Lys Leu Val Glu Lys Ser Phe Glu Thr
            565             570             575

Asp Thr Asn Leu Asn Phe Gln Asn Leu Ser Val Ile Gly Phe Arg Ile
            580             585             590

Leu Leu Leu Lys Val Ala Gly Phe Asn Leu Leu Met Thr Leu Arg Leu
        595             600             605

Trp Ser Ser
    610
```

<210> SEQ ID NO 82
<211> LENGTH: 1837
<212> TYPE: DNA
<213> ORGANISM: Artificial Sequence
<220> FEATURE:
<223> OTHER INFORMATION: codon optimized TCR number 4 construct; beta
      chain-P2A-alpha chain with cysteine substitutions in beta and
      alpha chain constant domains

<400> SEQUENCE: 82

```
caccatgggc accagactgc tgttctgggt ggccttctgt ctgctgggcg ccgatcatac     60
aggcgctggc gtgtcccaga gccccagcaa caaagtgacc gagaagggca aggacgtgga    120
actgagatgc gaccccatca gcggccacac cgccctgtac tggtacagac agtctctggg    180
ccagggcctg gaattcctga tatattttca gggcaacagc gcccctgaca agagcggcct    240
gccctccgat agattcagcg ccgagagaac aggcggcagc gtgtccaccc tgaccatcca    300
gagaacccag caggaagata cgccgtgta cctgtgcgcc agcagcctgg tcgtgggcag    360
ctacgagcag tactttggcc aggcacccg gctgaccgtg accgaggatc tgaagaacgt    420 gttccccca gaggtggccg tgttcgagcc ttctgaggcc gagatcagcc acacccagaa    480
agccaccctc gtgtgtctgg ccaccggctt ctaccccgac catgtggaac tgtcttggtg    540
ggtcaacggc aaagaggtgc actccggcgt gtgcaccgat ccccagcctc tgaaagaaca    600
gcccgccctg aacgacagcc ggtactgcct gagcagcaga ctgagagtgt ccgccacctt    660
ctggcagaac ccccggaacc acttcagatg ccaggtgcag ttctacggcc tgagcgagaa    720
cgacgagtgg acccaggaca gagccaagcc cgtgacccag atcgtgtctg ccgaagcctg    780
gggcagagcc gattgcggct ttaccagcga gagctaccag cagggcgtgc tgagcgccac    840
catcctgtac gagattctgc tgggaaaggc cacactgtac gccgtgctgg tgtctgccct    900
ggtgctgatg gccatggtca gcggaaggga cagcagaggc ggttccggag ccacgaactt    960
ctctctgtta aagcaagcag gagacgtgga agaaaacccc ggtcccatgg aaaccctgct   1020
```

-continued

```
gggagtgtcc ctcgtgatcc tgtggctgca gctggccaga gtgaacagcc agcagggga        1080 agaggatcca caggccctga gcattcagga aggcgagaac gccaccatga actgcagcta        1140
caagaccagc atcaacaacc tgcagtggta caggcagaac tccggcagag gcctggtgca        1200
cctgatcctg atcagaagca acgagagaga gaagcacagc ggacggctga gagtgaccct        1260
ggacacctcc aagaagtcca gctccctgct gatcaccgcc agcagagccg ccgataccgc        1320
cagctacttc tgtgccacag acgcctggga gagcaacttc ggcaacgaga agctgacctt        1380
cggcaccggc acaagactga ccatcatccc caacatccag aaccccgacc cgccgtgta        1440 tcagctgaga gacagcaaga gcagcgacaa gtccgtgtgc ctgttcaccg acttcgacag        1500
ccagaccaat gtgtcccagt ccaaggacag cgacgtgtac atcaccgata agtgcgtgct        1560
ggacatgcgc agcatggact tcaagagcaa ctccgccgtg gcctggtcca acaagagcga        1620
tttcgcctgc gccaacgcct tcaacaacag cattatcccc gaggacacat tcttcccaag        1680
ccccgagagc agctgcgacg tgaagctggt ggaaaagagc ttcgagacag acaccaacct        1740
gaacttccag aacctgagcg tgatcggctt ccggatcctg ctgctgaagg tggccggctt        1800
caacctgctg atgaccctga gactgtggtc cagctga                                 1837
```

```
<210> SEQ ID NO 83
<211> LENGTH: 611
<212> TYPE: PRT
<213> ORGANISM: Artificial Sequence
<220> FEATURE:
<223> OTHER INFORMATION: codon optimized TCR number 4 construct; beta
      chain-P2A-alpha chain with cysteine substitutions in beta and
      alpha chain constant domains

<400> SEQUENCE: 83

Thr Met Gly Thr Arg Leu Leu Phe Trp Val Ala Phe Cys Leu Leu Gly
1               5                   10                  15

Ala Asp His Thr Gly Ala Gly Val Ser Gln Ser Pro Ser Asn Lys Val
            20                  25                  30

Thr Glu Lys Gly Lys Asp Val Glu Leu Arg Cys Asp Pro Ile Ser Gly
        35                  40                  45

His Thr Ala Leu Tyr Trp Tyr Arg Gln Ser Leu Gly Gln Gly Leu Glu
    50                  55                  60

Phe Leu Ile Tyr Phe Gln Gly Asn Ser Ala Pro Asp Lys Ser Gly Leu
65                  70                  75                  80

Pro Ser Asp Arg Phe Ser Ala Glu Arg Thr Gly Gly Ser Val Ser Thr
                85                  90                  95

Leu Thr Ile Gln Arg Thr Gln Gln Glu Asp Ser Ala Val Tyr Leu Cys
            100                 105                 110

Ala Ser Ser Leu Val Val Gly Ser Tyr Glu Gln Tyr Phe Gly Pro Gly
            115                 120                 125

Thr Arg Leu Thr Val Thr Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
                165                 170                 175

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
        195                 200                 205
```

```
Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly Gly Ser Gly Ala Thr Asn Phe
305                 310                 315                 320

Ser Leu Leu Lys Gln Ala Gly Asp Val Glu Glu Asn Pro Gly Pro Met
            325                 330                 335

Glu Thr Leu Leu Gly Val Ser Leu Val Ile Leu Trp Leu Gln Leu Ala
            340                 345                 350

Arg Val Asn Ser Gln Gln Gly Glu Glu Asp Pro Gln Ala Leu Ser Ile
        355                 360                 365

Gln Glu Gly Glu Asn Ala Thr Met Asn Cys Ser Tyr Lys Thr Ser Ile
    370                 375                 380

Asn Asn Leu Gln Trp Tyr Arg Gln Asn Ser Gly Arg Gly Leu Val His
385                 390                 395                 400

Leu Ile Leu Ile Arg Ser Asn Glu Arg Glu Lys His Ser Gly Arg Leu
            405                 410                 415

Arg Val Thr Leu Asp Thr Ser Lys Lys Ser Ser Ser Leu Leu Ile Thr
            420                 425                 430

Ala Ser Arg Ala Ala Asp Thr Ala Ser Tyr Phe Cys Ala Thr Asp Ala
        435                 440                 445

Trp Glu Ser Asn Phe Gly Asn Glu Lys Leu Thr Phe Gly Thr Gly Thr
    450                 455                 460

Arg Leu Thr Ile Ile Pro Asn Ile Gln Asn Pro Asp Pro Ala Val Tyr
465                 470                 475                 480

Gln Leu Arg Asp Ser Lys Ser Ser Asp Lys Ser Val Cys Leu Phe Thr
            485                 490                 495

Asp Phe Asp Ser Gln Thr Asn Val Ser Gln Ser Lys Asp Ser Asp Val
            500                 505                 510

Tyr Ile Thr Asp Lys Cys Val Leu Asp Met Arg Ser Met Asp Phe Lys
        515                 520                 525

Ser Asn Ser Ala Val Ala Trp Ser Asn Lys Ser Asp Phe Ala Cys Ala
    530                 535                 540

Asn Ala Phe Asn Asn Ser Ile Ile Pro Glu Asp Thr Phe Phe Pro Ser
545                 550                 555                 560

Pro Glu Ser Ser Cys Asp Val Lys Leu Val Glu Lys Ser Phe Glu Thr
            565                 570                 575

Asp Thr Asn Leu Asn Phe Gln Asn Leu Ser Val Ile Gly Phe Arg Ile
            580                 585                 590

Leu Leu Leu Lys Val Ala Gly Phe Asn Leu Leu Met Thr Leu Arg Leu
        595                 600                 605

Trp Ser Ser
    610
```

-continued

```
<210> SEQ ID NO 84
<211> LENGTH: 178
<212> TYPE: PRT
<213> ORGANISM: Artificial Sequence
<220> FEATURE:
<223> OTHER INFORMATION: TCRbeta2 constant domain

<400> SEQUENCE: 84

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
            35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
            115                 120                 125

Asp Cys Gly Phe Thr Ser Glu Ser Tyr Gln Gln Gly Val Leu Ser Ala
        130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 85
<211> LENGTH: 335
<212> TYPE: PRT
<213> ORGANISM: Artificial Sequence
<220> FEATURE:
<223> OTHER INFORMATION: truncated EGFR polypeptide lacking signal
      peptide

<400> SEQUENCE: 85

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
            115                 120                 125
```

-continued

```
Ile Ile Ser Gly Asn Lys Asn Leu Cys Tyr Ala Asn Thr Ile Asn Trp
    130             135             140

Lys Lys Leu Phe Gly Thr Ser Gly Gln Lys Thr Lys Ile Ile Ser Asn
145             150             155             160

Arg Gly Glu Asn Ser Cys Lys Ala Thr Gly Gln Val Cys His Ala Leu
                165             170             175

Cys Ser Pro Glu Gly Cys Trp Gly Pro Glu Pro Arg Asp Cys Val Ser
                180             185             190

Cys Arg Asn Val Ser Arg Gly Arg Glu Cys Val Asp Lys Cys Asn Leu
                195             200             205

Leu Glu Gly Glu Pro Arg Glu Phe Val Glu Asn Ser Glu Cys Ile Gln
    210             215             220

Cys His Pro Glu Cys Leu Pro Gln Ala Met Asn Ile Thr Cys Thr Gly
225             230             235             240

Arg Gly Pro Asp Asn Cys Ile Gln Cys Ala His Tyr Ile Asp Gly Pro
                245             250             255

His Cys Val Lys Thr Cys Pro Ala Gly Val Met Gly Glu Asn Asn Thr
                260             265             270

Leu Val Trp Lys Tyr Ala Asp Ala Gly His Val Cys His Leu Cys His
    275             280             285

Pro Asn Cys Thr Tyr Gly Cys Thr Gly Pro Gly Leu Glu Gly Cys Pro
    290             295             300

Thr Asn Gly Pro Lys Ile Pro Ser Ile Ala Thr Gly Met Val Gly Ala
305             310             315             320

Leu Leu Leu Leu Leu Val Val Ala Leu Gly Ile Gly Leu Phe Met
                325             330             335
```

```
<210> SEQ ID NO 86
<211> LENGTH: 497
<212> TYPE: PRT
<213> ORGANISM: Artificial Sequence
<220> FEATURE:
<223> OTHER INFORMATION: codon optimized TCR number 6 construct; beta
      chain-P2A-alpha chain with cysteine substitutions in beta and
      alpha chain constant domains (partial sequence)

<400> SEQUENCE: 86
```

```
Lys Ser Pro Gln Pro Leu Thr Arg Arg Ala Thr Met Ser Ile Ser Leu
1               5               10              15

Leu Cys Cys Ala Ala Phe Pro Leu Leu Trp Ala Gly Pro Val Asn Ala
                20              25              30

Gly Val Thr Gln Thr Pro Lys Phe Arg Ile Leu Lys Ile Gly Gln Ser
                35              40              45

Met Thr Leu Gln Cys Thr Gln Asp Met Asn His Asn Tyr Met Tyr Trp
    50              55              60

Tyr Arg Gln Asp Pro Gly Met Gly Leu Lys Leu Ile Tyr Tyr Ser Val
65              70              75              80

Gly Ala Gly Ile Thr Asp Lys Gly Glu Val Pro Asn Gly Tyr Asn Val
                85              90              95

Ser Arg Ser Thr Thr Glu Asp Phe Pro Leu Arg Leu Glu Leu Ala Ala
                100             105             110

Pro Ser Gln Thr Ser Val Tyr Phe Cys Ala Ser Ser Asp Arg Ser Asn
    115             120             125

Thr Gly Glu Leu Phe Phe Gly Glu Gly Ser Arg Leu Thr Val Leu Glu
    130             135             140
```

```
Asp Leu Lys Asn Val Phe Pro Pro Glu Val Ala Val Phe Glu Pro Ser
145                 150                 155                 160

Glu Ala Glu Ile Ser His Thr Gln Lys Ala Thr Leu Val Cys Leu Ala
                    165                 170                 175

Thr Gly Phe Tyr Pro Asp His Val Glu Leu Ser Trp Trp Val Asn Gly
                    180                 185                 190

Lys Glu Val His Ser Gly Val Ser Thr Asp Pro Gln Pro Leu Lys Glu
                    195                 200                 205

Gln Pro Ala Leu Asn Asp Ser Arg Tyr Cys Leu Ser Ser Arg Leu Arg
    210                 215                 220

Val Ser Ala Thr Phe Trp Gln Asn Pro Arg Asn His Phe Arg Cys Gln
225                 230                 235                 240

Val Gln Phe Tyr Gly Leu Ser Glu Asn Asp Glu Trp Thr Gln Asp Arg
                    245                 250                 255

Ala Lys Pro Val Thr Gln Ile Val Ser Ala Glu Ala Trp Gly Arg Ala
                    260                 265                 270

Asp Cys Gly Phe Thr Ser Glu Ser Tyr Gln Gln Gly Val Leu Ser Ala
                    275                 280                 285

Thr Ile Leu Tyr Glu Ile Leu Leu Gly Lys Ala Thr Leu Tyr Ala Val
    290                 295                 300

Leu Val Ser Ala Leu Val Leu Met Ala Met Val Lys Arg Lys Asp Ser
305                 310                 315                 320

Arg Gly Gly Ser Gly Ala Thr Asn Phe Ser Leu Leu Lys Gln Ala Gly
                    325                 330                 335

Asp Val Glu Glu Asn Pro Gly Pro Met Glu Lys Asn Pro Leu Ala Ala
                    340                 345                 350

Pro Leu Leu Ile Leu Trp Phe His Leu Asp Cys Val Ser Ser Ile Leu
    355                 360                 365

Asn Val Glu Gln Ser Pro Gln Ser Leu His Val Gln Glu Gly Asp Ser
    370                 375                 380

Thr Asn Phe Thr Cys Ser Phe Pro Ser Ser Asn Phe Tyr Ala Leu His
385                 390                 395                 400

Trp Tyr Arg Trp Glu Thr Ala Lys Ser Pro Glu Ala Leu Phe Val Met
                    405                 410                 415

Thr Leu Asn Gly Asp Glu Lys Lys Gly Arg Ile Ser Ala Thr Leu
                    420                 425                 430

Asn Thr Lys Glu Gly Tyr Ser Tyr Leu Tyr Ile Lys Gly Ser Gln Pro
                    435                 440                 445

Glu Asp Ser Ala Thr Tyr Leu Cys Ala Leu Gly Pro Tyr Asn Asp Tyr
    450                 455                 460

Lys Leu Ser Phe Gly Ala Gly Thr Thr Val Thr Val Arg Ala Asn Ile
465                 470                 475                 480

Gln Asn Pro Asp Pro Ala Val Tyr Gln Leu Arg Asp Ser Lys Ser Ser
                    485                 490                 495

Asp

<210> SEQ ID NO 87
<211> LENGTH: 5
<212> TYPE: PRT
<213> ORGANISM: Artificial Sequence
<220> FEATURE:
<223> OTHER INFORMATION: TCR number 5 Valpha CDR1

<400> SEQUENCE: 87

Lys Ala Leu Tyr Ser
```

1                5

<210> SEQ ID NO 88
<211> LENGTH: 7
<212> TYPE: PRT
<213> ORGANISM: Artificial Sequence
<220> FEATURE:
<223> OTHER INFORMATION: TCR number 5 Valpha CDR2

<400> SEQUENCE: 88

Leu Leu Lys Gly Gly Glu Gln
1                5

<210> SEQ ID NO 89
<211> LENGTH: 11
<212> TYPE: PRT
<213> ORGANISM: Artificial Sequence
<220> FEATURE:
<223> OTHER INFORMATION: TCR number 5 Valpha CDR3 (IMGT)

<400> SEQUENCE: 89

Gly Thr Glu Glu Ala Asn Asp Tyr Lys Leu Ser
1                5                10

<210> SEQ ID NO 90
<211> LENGTH: 109
<212> TYPE: PRT
<213> ORGANISM: Artificial Sequence
<220> FEATURE:
<223> OTHER INFORMATION: TCR number 5 Valpha variable region

<400> SEQUENCE: 90

Gln Gln Pro Val Gln Ser Pro Gln Ala Val Ile Leu Arg Glu Gly Glu
1                5                10                15

Asp Ala Val Ile Asn Cys Ser Ser Ser Lys Ala Leu Tyr Ser Val His
            20                25                30

Trp Tyr Arg Gln Lys His Gly Glu Ala Pro Val Phe Leu Met Ile Leu
        35                40                45

Leu Lys Gly Gly Glu Gln Lys Gly His Glu Lys Ile Ser Ala Ser Phe
    50                55                60

Asn Glu Lys Lys Gln Gln Ser Ser Leu Tyr Leu Thr Ala Ser Gln Leu
65                70                75                80

Ser Tyr Ser Gly Thr Tyr Phe Cys Gly Thr Glu Glu Ala Asn Asp Tyr
                85                90                95

Lys Leu Ser Phe Gly Ala Gly Thr Thr Val Thr Val Arg
            100                105

<210> SEQ ID NO 91
<211> LENGTH: 5
<212> TYPE: PRT
<213> ORGANISM: Artificial Sequence
<220> FEATURE:
<223> OTHER INFORMATION: TCR number 5 Vbeta CDR1

<400> SEQUENCE: 91

Ser Gly Asp Leu Ser
1                5

<210> SEQ ID NO 92
<211> LENGTH: 6
<212> TYPE: PRT
<213> ORGANISM: Artificial Sequence
<220> FEATURE:
<223> OTHER INFORMATION: TCR number 5 Vbeta CDR2

<400> SEQUENCE: 92

Tyr Tyr Asn Gly Glu Glu
1               5

<210> SEQ ID NO 93
<211> LENGTH: 10
<212> TYPE: PRT
<213> ORGANISM: Artificial Sequence
<220> FEATURE:
<223> OTHER INFORMATION: TCR number 5 Vbeta CDR3 (IMGT)

<400> SEQUENCE: 93

Ala Ser Ser Val Gly Gln Gly Ser Ser Tyr
1               5                   10

<210> SEQ ID NO 94
<211> LENGTH: 114
<212> TYPE: PRT
<213> ORGANISM: Artificial Sequence
<220> FEATURE:
<223> OTHER INFORMATION: TCR number 5 Vbeta variable region

<400> SEQUENCE: 94

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
                20                  25                  30

Tyr Trp Tyr Gln Gln Ser Leu Asp Gln Gly Leu Gln Phe Leu Ile Gln
            35                  40                  45

Tyr Tyr Asn Gly Glu Glu Arg Ala Lys Gly Asn Ile Leu Glu Arg Phe
        50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Val Gly
                85                  90                  95

Gln Gly Ser Ser Tyr Glu Gln Tyr Phe Gly Pro Gly Thr Arg Leu Thr
            100                 105                 110

Val Thr

<210> SEQ ID NO 95
<211> LENGTH: 6
<212> TYPE: PRT
<213> ORGANISM: Artificial Sequence
<220> FEATURE:
<223> OTHER INFORMATION: TCR number 9 and TCR number 11 Valpha CDR1

<400> SEQUENCE: 95

Val Ser Pro Phe Ser Asn
1               5

<210> SEQ ID NO 96
<211> LENGTH: 6
<212> TYPE: PRT
<213> ORGANISM: Artificial Sequence
<220> FEATURE:
<223> OTHER INFORMATION: TCR number 9 and TCR number 11 Valpha CDR2

<400> SEQUENCE: 96

Thr Phe Ser Glu Asn Thr
1               5

```
<210> SEQ ID NO 97
<211> LENGTH: 11
<212> TYPE: PRT
<213> ORGANISM: Artificial Sequence
<220> FEATURE:
<223> OTHER INFORMATION: TCR number 9 and TCR number 11 Valpha CDR3
      (IMGT)

<400> SEQUENCE: 97

Val Val Trp Gly Gly Asp Thr Asp Lys Leu Ile
1               5                   10

<210> SEQ ID NO 98
<211> LENGTH: 111
<212> TYPE: PRT
<213> ORGANISM: Artificial Sequence
<220> FEATURE:
<223> OTHER INFORMATION: TCR number 9 and TCR number 11 Valpha variable
      region

<400> SEQUENCE: 98

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Trp Gly Gly Asp
                85                  90                  95

Thr Asp Lys Leu Ile Phe Gly Thr Gly Thr Arg Leu Gln Val Phe
                100                 105                 110

<210> SEQ ID NO 99
<211> LENGTH: 5
<212> TYPE: PRT
<213> ORGANISM: Artificial Sequence
<220> FEATURE:
<223> OTHER INFORMATION: TCR number 11 Vbeta CDR1

<400> SEQUENCE: 99

Trp Ser His Ser Tyr
1               5

<210> SEQ ID NO 100
<211> LENGTH: 6
<212> TYPE: PRT
<213> ORGANISM: Artificial Sequence
<220> FEATURE:
<223> OTHER INFORMATION: TCR number 11 Vbeta CDR2

<400> SEQUENCE: 100

Ser Ala Ala Ala Asp Ile
1               5

<210> SEQ ID NO 101
<211> LENGTH: 9
<212> TYPE: PRT
<213> ORGANISM: Artificial Sequence
<220> FEATURE:
<223> OTHER INFORMATION: TCR number 11 Vbeta CDR3 (IMGT)
```

```
<400> SEQUENCE: 101

Ala Ser Ser Asp Gly Gly Gly Gln Tyr
1               5

<210> SEQ ID NO 102
<211> LENGTH: 109
<212> TYPE: PRT
<213> ORGANISM: Artificial Sequence
<220> FEATURE:
<223> OTHER INFORMATION: TCR number 11 Vbeta variable region

<400> SEQUENCE: 102

Asp Ala Gly Ile Thr Gln Ser Pro Arg Tyr Lys Ile Thr Glu Thr Gly
1               5               10              15

Arg Gln Val Thr Leu Met Cys His Gln Thr Trp Ser His Ser Tyr Met
            20              25              30

Phe Trp Tyr Arg Gln Asp Leu Gly His Gly Leu Arg Leu Ile Tyr Tyr
        35              40              45

Ser Ala Ala Ala Asp Ile Thr Asp Lys Gly Glu Val Pro Asp Gly Tyr
    50              55              60

Val Val Ser Arg Ser Lys Thr Glu Asn Phe Pro Leu Thr Leu Glu Ser
65              70              75              80

Ala Thr Arg Ser Gln Thr Ser Val Tyr Phe Cys Ala Ser Ser Asp Gly
                85              90              95

Gly Gly Gln Tyr Phe Pro Gly Thr Arg Leu Thr Val Thr
            100             105

<210> SEQ ID NO 103
<211> LENGTH: 6
<212> TYPE: PRT
<213> ORGANISM: Artificial Sequence
<220> FEATURE:
<223> OTHER INFORMATION: TCR number 6 and TCR number 7  Valpha CDR1

<400> SEQUENCE: 103

Ser Ser Asn Phe Tyr Ala
1               5

<210> SEQ ID NO 104
<211> LENGTH: 7
<212> TYPE: PRT
<213> ORGANISM: Artificial Sequence
<220> FEATURE:
<223> OTHER INFORMATION: TCR number 6 Valpha CDR2

<400> SEQUENCE: 104

Met Thr Leu Asn Gly Asp Glu
1               5

<210> SEQ ID NO 105
<211> LENGTH: 13
<212> TYPE: PRT
<213> ORGANISM: Artificial Sequence
<220> FEATURE:
<223> OTHER INFORMATION: TCR number 6 Valpha CDR3

<400> SEQUENCE: 105

Cys Ala Leu Gly Pro Tyr Asn Asp Tyr Lys Leu Ser Phe
1               5                       10

<210> SEQ ID NO 106
<211> LENGTH: 112
<212> TYPE: PRT
```

-continued

```
<213> ORGANISM: Artificial Sequence
<220> FEATURE:
<223> OTHER INFORMATION: TCR number 6 Valpha variant region

<400> SEQUENCE: 106

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
            20                  25                  30

Leu His Trp Tyr Arg Trp Glu Thr Ala Lys Ser Pro Glu Ala Leu Phe
        35                  40                  45

Val Met Thr Leu Asn Gly Asp Glu Lys Lys Lys Gly Arg Ile Ser Ala
        50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Leu Gly Pro Tyr Asn
                85                  90                  95

Asp Tyr Lys Leu Ser Phe Gly Ala Gly Thr Thr Val Thr Val Arg Ala
            100                 105                 110

<210> SEQ ID NO 107
<211> LENGTH: 5
<212> TYPE: PRT
<213> ORGANISM: Artificial Sequence
<220> FEATURE:
<223> OTHER INFORMATION: TCR number 6 Vbeta CDR1

<400> SEQUENCE: 107

Met Asn His Asn Tyr
1               5

<210> SEQ ID NO 108
<211> LENGTH: 6
<212> TYPE: PRT
<213> ORGANISM: Artificial Sequence
<220> FEATURE:
<223> OTHER INFORMATION: TCR number 6 Vbeta CDR2

<400> SEQUENCE: 108

Ser Val Gly Ala Gly Ile
1               5

<210> SEQ ID NO 109
<211> LENGTH: 12
<212> TYPE: PRT
<213> ORGANISM: Artificial Sequence
<220> FEATURE:
<223> OTHER INFORMATION: TCR number 6 Vbeta CDR3 (IMGT)

<400> SEQUENCE: 109

Ala Ser Ser Asp Arg Ser Asn Thr Gly Glu Leu Phe
1               5                   10

<210> SEQ ID NO 110
<211> LENGTH: 113
<212> TYPE: PRT
<213> ORGANISM: Artificial Sequence
<220> FEATURE:
<223> OTHER INFORMATION: TCR number 6 Vbeta variable region

<400> SEQUENCE: 110

Asn Ala Gly Val Thr Gln Thr Pro Lys Phe Arg Ile Leu Lys Ile Gly
1               5                   10                  15
```

-continued

```
Gln Ser Met Thr Leu Gln Cys Thr Gln Asp Met Asn His Asn Tyr Met
            20                  25                  30

Tyr Trp Tyr Arg Gln Asp Pro Gly Met Gly Leu Lys Leu Ile Tyr Tyr
        35                  40                  45

Ser Val Gly Ala Gly Ile Thr Asp Lys Gly Glu Val Pro Asn Gly Tyr
    50                  55                  60

Asn Val Ser Arg Ser Thr Thr Glu Asp Phe Pro Leu Arg Leu Glu Leu
65                  70                  75                  80

Ala Ala Pro Ser Gln Thr Ser Val Tyr Phe Cys Ala Ser Ser Asp Arg
                85                  90                  95

Ser Asn Thr Gly Glu Leu Phe Phe Gly Glu Gly Ser Arg Leu Thr Val
            100                 105                 110

Leu
```

```
<210> SEQ ID NO 111
<211> LENGTH: 6
<212> TYPE: PRT
<213> ORGANISM: Artificial Sequence
<220> FEATURE:
<223> OTHER INFORMATION: TCR number 1 and TCR number 2 Valpha CDR1

<400> SEQUENCE: 111

Asp Ser Ala Ile Tyr Asn
1               5
```

```
<210> SEQ ID NO 112
<211> LENGTH: 7
<212> TYPE: PRT
<213> ORGANISM: Artificial Sequence
<220> FEATURE:
<223> OTHER INFORMATION: TCR number 1 and TCR number 2 Valpha CDR2

<400> SEQUENCE: 112

Ile Gln Ser Ser Gln Arg Glu
1               5
```

```
<210> SEQ ID NO 113
<211> LENGTH: 11
<212> TYPE: PRT
<213> ORGANISM: Artificial Sequence
<220> FEATURE:
<223> OTHER INFORMATION: TCR number 1 Valpha CDR3 (IMGT)

<400> SEQUENCE: 113

Ala Val Glu Gly Asp Ser Ser Tyr Lys Leu Ile
1               5                   10
```

```
<210> SEQ ID NO 114
<211> LENGTH: 112
<212> TYPE: PRT
<213> ORGANISM: Artificial Sequence
<220> FEATURE:
<223> OTHER INFORMATION: TCR number 1 Valpha variable region

<400> SEQUENCE: 114

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
```

```
          50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Glu Gly Asp Ser
                85                  90                  95

Ser Tyr Lys Leu Ile Phe Gly Ser Gly Thr Arg Leu Leu Val Arg Pro
            100                 105                 110
```

<210> SEQ ID NO 115
<211> LENGTH: 5
<212> TYPE: PRT
<213> ORGANISM: Artificial Sequence
<220> FEATURE:
<223> OTHER INFORMATION: TCR number 1 and TCR number 8 Vbeta CDR1

<400> SEQUENCE: 115

```
Ser Gly His Asp Thr
1               5
```

<210> SEQ ID NO 116
<211> LENGTH: 6
<212> TYPE: PRT
<213> ORGANISM: Artificial Sequence
<220> FEATURE:
<223> OTHER INFORMATION: TCR number 1 and TCR number 8 Vbeta CDR2

<400> SEQUENCE: 116

```
Tyr Tyr Glu Glu Glu Glu
1               5
```

<210> SEQ ID NO 117
<211> LENGTH: 11
<212> TYPE: PRT
<213> ORGANISM: Artificial Sequence
<220> FEATURE:
<223> OTHER INFORMATION: TCR number 1 Vbeta CDR3 (IMGT)

<400> SEQUENCE: 117

```
Ala Ser Ser Phe Phe Ser Gln Glu Thr Gln Tyr
1               5                   10
```

<210> SEQ ID NO 118
<211> LENGTH: 112
<212> TYPE: PRT
<213> ORGANISM: Artificial Sequence
<220> FEATURE:
<223> OTHER INFORMATION: TCR number 1 Vbeta variable region

<400> SEQUENCE: 118

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Phe
                85                  90                  95

Ser Gln Glu Thr Gln Tyr Phe Gly Pro Gly Thr Arg Leu Leu Val Leu
```

-continued

|       | 100   |       |       | 105   |       |       | 110   |

<210> SEQ ID NO 119
<211> LENGTH: 9
<212> TYPE: PRT
<213> ORGANISM: Artificial Sequence
<220> FEATURE:
<223> OTHER INFORMATION: TCR number 2 Valpha CDR3 (IMGT)

<400> SEQUENCE: 119

Ala Val Ile Gly Glu Gln Asn Phe Val
1               5

<210> SEQ ID NO 120
<211> LENGTH: 110
<212> TYPE: PRT
<213> ORGANISM: Artificial Sequence
<220> FEATURE:
<223> OTHER INFORMATION: TCR number 2 Valpha variable region

<400> SEQUENCE: 120

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Ile Gly Glu Gln
                85                  90                  95

Asn Phe Val Phe Gly Pro Gly Thr Arg Leu Ser Val Leu Pro
            100                 105                 110

<210> SEQ ID NO 121
<211> LENGTH: 5
<212> TYPE: PRT
<213> ORGANISM: Artificial Sequence
<220> FEATURE:
<223> OTHER INFORMATION: TCR number 2, TCR number 3, and TCR number 10
     Vbeta CDR1

<400> SEQUENCE: 121

Ser Gly His Thr Ala
1               5

<210> SEQ ID NO 122
<211> LENGTH: 6
<212> TYPE: PRT
<213> ORGANISM: Artificial Sequence
<220> FEATURE:
<223> OTHER INFORMATION: TCR number 2, TCR number 3, and TCR number 10
     Vbeta CDR2

<400> SEQUENCE: 122

Phe Gln Gly Thr Gly Ala
1               5

<210> SEQ ID NO 123
<211> LENGTH: 15
<212> TYPE: PRT
<213> ORGANISM: Artificial Sequence

```
<220> FEATURE:
<223> OTHER INFORMATION: TCR number 2 Vbeta CDR3 (IMGT)

<400> SEQUENCE: 123

Ala Ser Ser Leu Ser Gly Leu Gly Ser Gly Ala Asn Val Leu Thr
1               5                   10                  15

<210> SEQ ID NO 124
<211> LENGTH: 117
<212> TYPE: PRT
<213> ORGANISM: Artificial Sequence
<220> FEATURE:
<223> OTHER INFORMATION: TCR number 2 Vbeta variable region

<400> SEQUENCE: 124

Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
                20                  25                  30

Tyr Trp Tyr Arg Gln Ser Leu Gly Gln Gly Pro Glu Phe Leu Ile Tyr
            35                  40                  45

Phe Gln Gly Thr Gly Ala Ala Asp Asp Ser Gly Leu Pro Asn Asp Arg
    50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys Ala Ser Ser Leu
                85                  90                  95

Ser Gly Leu Gly Ser Gly Ala Asn Val Leu Thr Phe Gly Ala Gly Ser
            100                 105                 110

Arg Leu Thr Val Leu
        115

<210> SEQ ID NO 125
<211> LENGTH: 6
<212> TYPE: PRT
<213> ORGANISM: Artificial Sequence
<220> FEATURE:
<223> OTHER INFORMATION: TCR number 3 Valpha CDR1

<400> SEQUENCE: 125

Asp Arg Gly Ser Gln Ser
1               5

<210> SEQ ID NO 126
<211> LENGTH: 6
<212> TYPE: PRT
<213> ORGANISM: Artificial Sequence
<220> FEATURE:
<223> OTHER INFORMATION: TCR number 3 Valpha CDR2

<400> SEQUENCE: 126

Ile Tyr Ser Asn Gly Asp
1               5

<210> SEQ ID NO 127
<211> LENGTH: 11
<212> TYPE: PRT
<213> ORGANISM: Artificial Sequence
<220> FEATURE:
<223> OTHER INFORMATION: TCR number 3 Valpha CDR3 (IMGT)

<400> SEQUENCE: 127

Ala Val Asp Ser Gly Gly Tyr Gln Lys Val Thr
```

-continued

```
1               5                    10
```

```
<210> SEQ ID NO 128
<211> LENGTH: 110
<212> TYPE: PRT
<213> ORGANISM: Artificial Sequence
<220> FEATURE:
<223> OTHER INFORMATION: TCR number 3 Valpha variable region

<400> SEQUENCE: 128

Gln Lys Glu Val Glu Gln Asn Ser Gly Pro Leu Ser Val Pro Glu Gly
1               5                    10                   15

Ala Ile Ala Ser Leu Asn Cys Thr Tyr Ser Asp Arg Gly Ser Gln Ser
            20                   25                   30

Phe Phe Trp Tyr Arg Gln Tyr Ser Gly Lys Ser Pro Glu Leu Ile Met
        35                   40                   45

Ser Ile Tyr Ser Asn Gly Asp Lys Glu Asp Gly Arg Phe Thr Ala Gln
    50                   55                   60

Leu Asn Lys Ala Ser Gln Tyr Val Ser Leu Leu Ile Arg Asp Ser Gln
65                   70                   75                   80

Pro Ser Asp Ser Ala Thr Tyr Leu Cys Ala Val Asp Ser Gly Gly Tyr
                85                   90                   95

Gln Lys Val Thr Phe Gly Thr Gly Thr Lys Leu Gln Val Ile
            100                  105                  110

<210> SEQ ID NO 129
<211> LENGTH: 11
<212> TYPE: PRT
<213> ORGANISM: Artificial Sequence
<220> FEATURE:
<223> OTHER INFORMATION: TCR number 3 Vbeta CDR3 (IMGT)

<400> SEQUENCE: 129

Ala Ser Ser Leu Asn Met Asn Thr Glu Ala Phe
1               5                    10

<210> SEQ ID NO 130
<211> LENGTH: 113
<212> TYPE: PRT
<213> ORGANISM: Artificial Sequence
<220> FEATURE:
<223> OTHER INFORMATION: TCR number 3 Vbeta variable region

<400> SEQUENCE: 130

Gly Ala Gly Val Ser Gln Thr Pro Ser Asn Lys Val Thr Glu Lys Gly
1               5                    10                   15

Lys Tyr Val Glu Leu Arg Cys Asp Pro Ile Ser Gly His Thr Ala Leu
            20                   25                   30

Tyr Trp Tyr Arg Gln Ser Leu Gly Gln Gly Pro Glu Phe Leu Ile Tyr
        35                   40                   45

Phe Gln Gly Thr Gly Ala Ala Asp Asp Ser Gly Leu Pro Asn Asp Arg
    50                   55                   60

Phe Phe Ala Val Arg Pro Glu Gly Ser Val Ser Thr Leu Lys Ile Gln
65                   70                   75                   80

Arg Thr Glu Arg Gly Asp Ser Ala Val Tyr Leu Cys Ala Ser Ser Leu
                85                   90                   95

Asn Met Asn Thr Glu Ala Phe Phe Gly Gln Gly Thr Arg Leu Thr Val
            100                  105                  110

Val
```

<210> SEQ ID NO 131
<211> LENGTH: 5
<212> TYPE: PRT
<213> ORGANISM: Artificial Sequence
<220> FEATURE:
<223> OTHER INFORMATION: TCR number 10 and TCR number 4 Valpha CDR1

<400> SEQUENCE: 131

Thr Ser Ile Asn Asn
1               5

<210> SEQ ID NO 132
<211> LENGTH: 7
<212> TYPE: PRT
<213> ORGANISM: Artificial Sequence
<220> FEATURE:
<223> OTHER INFORMATION: TCR number 10 and TCR number 4 Valpha CDR2

<400> SEQUENCE: 132

Ile Arg Ser Asn Glu Arg Glu
1               5

<210> SEQ ID NO 133
<211> LENGTH: 11
<212> TYPE: PRT
<213> ORGANISM: Artificial Sequence
<220> FEATURE:
<223> OTHER INFORMATION: TCR number 10 Valpha CDR3 (IMGT)

<400> SEQUENCE: 133

Ala Thr Asp Glu Ser Ser Asn Tyr Lys Leu Thr
1               5                   10

<210> SEQ ID NO 134
<211> LENGTH: 110
<212> TYPE: PRT
<213> ORGANISM: Artificial Sequence
<220> FEATURE:
<223> OTHER INFORMATION: TCR number 10 Valpha variable region

<400> SEQUENCE: 134

Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Glu Ser Ser Asn
                85                  90                  95

Tyr Lys Leu Thr Phe Gly Lys Gly Thr Leu Leu Thr Val Asn
                100                 105                 110

<210> SEQ ID NO 135
<211> LENGTH: 178
<212> TYPE: PRT
<213> ORGANISM: Artificial Sequence
<220> FEATURE:
<223> OTHER INFORMATION: TCRbeta2 constant domain, cysteine modified

<400> SEQUENCE: 135

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Cys Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 136
<211> LENGTH: 113
<212> TYPE: PRT
<213> ORGANISM: Artificial Sequence
<220> FEATURE:
<223> OTHER INFORMATION: TCR number 10 Vbeta variable region

<400> SEQUENCE: 136

Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
            20                  25                  30

Tyr Trp Tyr Arg Gln Ser Leu Gly Gln Gly Pro Glu Phe Leu Ile Tyr
        35                  40                  45

Phe Gln Gly Thr Gly Ala Ala Asp Asp Ser Gly Leu Pro Asn Asp Arg
    50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys Ala Ser Ser Leu
                85                  90                  95

Asn Met Asn Thr Glu Ala Phe Phe Gly Gln Gly Thr Arg Leu Thr Val
            100                 105                 110

Val

<210> SEQ ID NO 137
<211> LENGTH: 15
<212> TYPE: PRT
<213> ORGANISM: Artificial Sequence
<220> FEATURE:
<223> OTHER INFORMATION: TCR number 4 Valpha CDR3 (IMGT)

<400> SEQUENCE: 137

```
Ala Thr Asp Ala Trp Glu Ser Asn Phe Gly Asn Glu Lys Leu Thr
1               5                   10                  15
```

<210> SEQ ID NO 138
<211> LENGTH: 114
<212> TYPE: PRT
<213> ORGANISM: Artificial Sequence
<220> FEATURE:
<223> OTHER INFORMATION: TCR number 4 Valpha variable region

<400> SEQUENCE: 138

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
                20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp Ala Trp Glu Ser
                85                  90                  95

Asn Phe Gly Asn Glu Lys Leu Thr Phe Gly Thr Gly Thr Arg Leu Thr
                100                 105                 110

Ile Ile
```

<210> SEQ ID NO 139
<211> LENGTH: 6
<212> TYPE: PRT
<213> ORGANISM: Artificial Sequence
<220> FEATURE:
<223> OTHER INFORMATION: TCR number 4 Vbeta CDR2

<400> SEQUENCE: 139

```
Phe Gln Gly Asn Ser Ala
1               5
```

<210> SEQ ID NO 140
<211> LENGTH: 12
<212> TYPE: PRT
<213> ORGANISM: Artificial Sequence
<220> FEATURE:
<223> OTHER INFORMATION: TCR number 4 Vbeta CDR3 (IMGT)

<400> SEQUENCE: 140

```
Ala Ser Ser Leu Val Val Gly Ser Tyr Glu Gln Tyr
1               5                   10
```

<210> SEQ ID NO 141
<211> LENGTH: 114
<212> TYPE: PRT
<213> ORGANISM: Artificial Sequence
<220> FEATURE:
<223> OTHER INFORMATION: TCR number 4 Vbeta variable region

<400> SEQUENCE: 141

```
Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
                20                  25                  30

Tyr Trp Tyr Arg Gln Ser Leu Gly Gln Gly Leu Glu Phe Leu Ile Tyr
```

-continued

```
                35                  40                  45

Phe Gln Gly Asn Ser Ala Pro Asp Lys Ser Gly Leu Pro Ser Asp Arg
    50                  55                  60

Phe Ser Ala Glu Arg Thr Gly Gly Ser Val Ser Thr Leu Thr Ile Gln
65                  70                  75                  80

Arg Thr Gln Gln Glu Asp Ser Ala Val Tyr Leu Cys Ala Ser Ser Leu
                85                  90                  95

Val Val Gly Ser Tyr Glu Gln Tyr Phe Gly Pro Gly Thr Arg Leu Thr
            100                 105                 110

Val Thr

<210> SEQ ID NO 142
<211> LENGTH: 7
<212> TYPE: PRT
<213> ORGANISM: Artificial Sequence
<220> FEATURE:
<223> OTHER INFORMATION: TCR number 7 Valpha CDR2

<400> SEQUENCE: 142

Met Thr Leu Asn Gly Asp Glu
1               5

<210> SEQ ID NO 143
<211> LENGTH: 10
<212> TYPE: PRT
<213> ORGANISM: Artificial Sequence
<220> FEATURE:
<223> OTHER INFORMATION: TCR number 7 Valpha CDR3 (IMGT)

<400> SEQUENCE: 143

Ala Tyr Leu Gly Ala Gly Asn Gln Phe Tyr
1               5                   10

<210> SEQ ID NO 144
<211> LENGTH: 110
<212> TYPE: PRT
<213> ORGANISM: Artificial Sequence
<220> FEATURE:
<223> OTHER INFORMATION: TCR number 7 Valpha variable region

<400> SEQUENCE: 144

Ile Leu Asn Val Glu Gln Ser Pro Gln Ser Leu His Val Gln Glu Gly
1               5                   10                  15

Asp Ser Thr Asn Phe Thr Cys Ser Phe Pro Ser Ser Asn Phe Tyr Ala
                20                  25                  30

Leu His Trp Tyr Arg Trp Glu Thr Ala Lys Ser Pro Glu Ala Leu Phe
            35                  40                  45

Val Met Thr Leu Asn Gly Asp Glu Lys Lys Gly Arg Ile Ser Ala
    50                  55                  60

Thr Leu Asn Thr Lys Glu Gly Tyr Ser Tyr Leu Tyr Ile Lys Gly Ser
65                  70                  75                  80

Gln Pro Glu Asp Ser Ala Thr Tyr Leu Cys Ala Tyr Leu Gly Ala Gly
                85                  90                  95

Asn Gln Phe Tyr Phe Gly Thr Gly Thr Ser Leu Thr Val Ile
            100                 105                 110

<210> SEQ ID NO 145
<211> LENGTH: 5
<212> TYPE: PRT
<213> ORGANISM: Artificial Sequence
<220> FEATURE:
```

-continued

```
<223> OTHER INFORMATION: TCR number 7 Vbeta CDR1

<400> SEQUENCE: 145

Leu Asn His Asp Ala
1               5

<210> SEQ ID NO 146
<211> LENGTH: 6
<212> TYPE: PRT
<213> ORGANISM: Artificial Sequence
<220> FEATURE:
<223> OTHER INFORMATION: TCR number 7 Vbeta CDR2

<400> SEQUENCE: 146

Ser Gln Ile Val Asn Asp
1               5

<210> SEQ ID NO 147
<211> LENGTH: 12
<212> TYPE: PRT
<213> ORGANISM: Artificial Sequence
<220> FEATURE:
<223> OTHER INFORMATION: TCR number 7 Vbeta CDR3 (IMGT)

<400> SEQUENCE: 147

Ala Ser Ser Leu Asn Arg Gly Arg Tyr Gly Tyr Thr
1               5                   10

<210> SEQ ID NO 148
<211> LENGTH: 113
<212> TYPE: PRT
<213> ORGANISM: Artificial Sequence
<220> FEATURE:
<223> OTHER INFORMATION: TCR number 7 Vbeta variable region

<400> SEQUENCE: 148

Asp Gly Gly Ile Thr Gln Ser Pro Lys Tyr Leu Phe Arg Lys Glu Gly
1               5                   10                  15

Gln Asn Val Thr Leu Ser Cys Glu Gln Asn Leu Asn His Asp Ala Met
            20                  25                  30

Tyr Trp Tyr Arg Gln Asp Pro Gly Gln Gly Leu Arg Leu Ile Tyr Tyr
        35                  40                  45

Ser Gln Ile Val Asn Asp Phe Gln Lys Gly Asp Ile Ala Glu Gly Tyr
    50                  55                  60

Ser Val Ser Arg Glu Lys Lys Glu Ser Phe Pro Leu Thr Val Thr Ser
65                  70                  75                  80

Ala Gln Lys Asn Pro Thr Ala Phe Tyr Leu Cys Ala Ser Ser Leu Asn
                85                  90                  95

Arg Gly Arg Tyr Gly Tyr Thr Phe Gly Ser Gly Thr Arg Leu Thr Val
            100                 105                 110

Val

<210> SEQ ID NO 149
<211> LENGTH: 7
<212> TYPE: PRT
<213> ORGANISM: Artificial Sequence
<220> FEATURE:
<223> OTHER INFORMATION: TCR number 8 Valpha CDR1

<400> SEQUENCE: 149

Thr Arg Asp Thr Thr Tyr Tyr
1               5
```

-continued

```
<210> SEQ ID NO 150
<211> LENGTH: 8
<212> TYPE: PRT
<213> ORGANISM: Artificial Sequence
<220> FEATURE:
<223> OTHER INFORMATION: TCR number 8 Valpha CDR2

<400> SEQUENCE: 150

Arg Asn Ser Phe Asp Glu Gln Asn
1               5

<210> SEQ ID NO 151
<211> LENGTH: 14
<212> TYPE: PRT
<213> ORGANISM: Artificial Sequence
<220> FEATURE:
<223> OTHER INFORMATION: TCR number 8 Valpha CDR3 (IMGT)

<400> SEQUENCE: 151

Ala Leu Ser Glu Leu Ala Ser Gly Gly Ser Tyr Ile Pro Thr
1               5                   10

<210> SEQ ID NO 152
<211> LENGTH: 117
<212> TYPE: PRT
<213> ORGANISM: Artificial Sequence
<220> FEATURE:
<223> OTHER INFORMATION: TCR number 8 Valpha variable region

<400> SEQUENCE: 152

Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
    50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95

Leu Ala Ser Gly Gly Ser Tyr Ile Pro Thr Phe Gly Arg Gly Thr Ser
            100                 105                 110

Leu Ile Val His Pro
        115

<210> SEQ ID NO 153
<211> LENGTH: 16
<212> TYPE: PRT
<213> ORGANISM: Artificial Sequence
<220> FEATURE:
<223> OTHER INFORMATION: TCR number 8 Vbeta CDR3 (IMGT)

<400> SEQUENCE: 153

Ala Ser Ser Phe Arg Leu Ala Gly Gly Pro Ser Thr Asp Thr Gln Tyr
1               5                   10                  15

<210> SEQ ID NO 154
<211> LENGTH: 117
<212> TYPE: PRT
<213> ORGANISM: Artificial Sequence
<220> FEATURE:
```

-continued

<223> OTHER INFORMATION: TCR number 8 Vbeta variable region

<400> SEQUENCE: 154

Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
            20                  25                  30

Ser Trp Tyr Gln Gln Ala Leu Gly Gln Gly Pro Gln Phe Ile Phe Gln
        35                  40                  45

Tyr Tyr Glu Glu Glu Glu Arg Gln Arg Gly Asn Phe Pro Asp Arg Phe
    50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Phe Arg
                85                  90                  95

Leu Ala Gly Gly Pro Ser Thr Asp Thr Gln Tyr Phe Gly Pro Gly Thr
            100                 105                 110

Arg Leu Thr Val Leu
        115

<210> SEQ ID NO 155
<211> LENGTH: 177
<212> TYPE: PRT
<213> ORGANISM: Artificial Sequence
<220> FEATURE:
<223> OTHER INFORMATION: TCRbeta1 constant domain, cysteine modified

<400> SEQUENCE: 155

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
            35                  40                  45

Gly Lys Glu Val His Ser Gly Val Cys Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 156
<211> LENGTH: 141
<212> TYPE: PRT
<213> ORGANISM: Artificial Sequence
<220> FEATURE:

-continued

<223> OTHER INFORMATION: TCRalpha constant domain

<400> SEQUENCE: 156

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
        130                 135                 140
```

<210> SEQ ID NO 157
<211> LENGTH: 140
<212> TYPE: PRT
<213> ORGANISM: Artificial Sequence
<220> FEATURE:
<223> OTHER INFORMATION: TCRalpha constant domain

<400> SEQUENCE: 157

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
                100                 105                 110

Asn Leu Ser Val Ile Gly Phe Arg Ile Leu Leu Leu Lys Val Ala Gly
            115                 120                 125

Phe Asn Leu Leu Met Thr Leu Arg Leu Trp Ser Ser
        130                 135                 140
```

<210> SEQ ID NO 158
<211> LENGTH: 142
<212> TYPE: PRT
<213> ORGANISM: Artificial Sequence
<220> FEATURE:
<223> OTHER INFORMATION: TCRalpha constant domain, cysteine modified

<400> SEQUENCE: 158

```
Pro Asn Ile Gln Asn Pro Asp Pro Ala Val Tyr Gln Leu Arg Asp Ser
```

```
1                5                    10                   15

Lys Ser Ser Asp Lys Ser Val Cys Leu Phe Thr Asp Phe Asp Ser Gln
             20                  25                  30

Thr Asn Val Ser Gln Ser Lys Asp Ser Asp Val Tyr Ile Thr Asp Lys
             35                  40                  45

Cys Val Leu Asp Met Arg Ser Met Asp Phe Lys Ser Asn Ser Ala Val
             50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                 85                  90                  95

Asp Val Lys Leu Val Glu Lys Ser Phe Glu Thr Asp Thr Asn Leu Asn
             100                 105                 110

Phe Gln Asn Leu Ser Val Ile Gly Phe Arg Ile Leu Leu Leu Lys Val
             115                 120                 125

Ala Gly Phe Asn Leu Leu Met Thr Leu Arg Leu Trp Ser Ser
             130                 135                 140
```

<210> SEQ ID NO 159
<211> LENGTH: 141
<212> TYPE: PRT
<213> ORGANISM: Artificial Sequence
<220> FEATURE:
<223> OTHER INFORMATION: TCRalpha constant domain, cysteine modified

<400> SEQUENCE: 159

```
Asn Ile Gln Asn Pro Asp Pro Ala Val Tyr Gln Leu Arg Asp Ser Lys
1                5                    10                   15

Ser Ser Asp Lys Ser Val Cys Leu Phe Thr Asp Phe Asp Ser Gln Thr
             20                  25                  30

Asn Val Ser Gln Ser Lys Asp Ser Asp Val Tyr Ile Thr Asp Lys Cys
             35                  40                  45

Val Leu Asp Met Arg Ser Met Asp Phe Lys Ser Asn Ser Ala Val Ala
             50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                 85                  90                  95

Val Lys Leu Val Glu Lys Ser Phe Glu Thr Asp Thr Asn Leu Asn Phe
             100                 105                 110

Gln Asn Leu Ser Val Ile Gly Phe Arg Ile Leu Leu Leu Lys Val Ala
             115                 120                 125

Gly Phe Asn Leu Leu Met Thr Leu Arg Leu Trp Ser Ser
             130                 135                 140
```

<210> SEQ ID NO 160
<211> LENGTH: 140
<212> TYPE: PRT
<213> ORGANISM: Artificial Sequence
<220> FEATURE:
<223> OTHER INFORMATION: TCRalpha constant domain, cysteine modified

<400> SEQUENCE: 160

```
Ile Gln Asn Pro Asp Pro Ala Val Tyr Gln Leu Arg Asp Ser Lys Ser
1                5                    10                   15

Ser Asp Lys Ser Val Cys Leu Phe Thr Asp Phe Asp Ser Gln Thr Asn
             20                  25                  30
```

-continued

```
Val Ser Gln Ser Lys Asp Ser Asp Val Tyr Ile Thr Asp Lys Cys Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 161
<211> LENGTH: 1821
<212> TYPE: DNA
<213> ORGANISM: Artificial Sequence
<220> FEATURE:
<223> OTHER INFORMATION: codon optimized TCR number 5 construct; beta
      chain-P2A-alpha chain with cysteine substitutions in beta and
      alpha chain constant domains

<400> SEQUENCE: 161

```
atgggcttca gactgttgtg ttgcgtggcc ttttgccttc ttggagctgg acctgtggat      60
tctggagtta cacagacccc taagcacctg attacagcca caggacagag agtgaccctg     120
agatgtagcc ctagaagcgg agatctgagc gtgtattggt accagcagag cctggatcaa     180
ggactccagt ttctgatcca gtactacaac ggcgaggaga gagccaaggg caatattctg     240
gagaggtttt ctgcccagca gttccctgat ctgcactctg aactgaacct gtctagcctg     300
gaactgggag attctgccct gtactttgt gcctctagcg ttggacaggg cagctcttat     360
gagcagtact ttggacctgg caccagactg acagtgacag aagacctgaa gaacgtgttc     420 ccccagagg tggccgtgtt cgagcctagc gaggccgaga tcagccacac ccagaaagcc     480
accctcgtgt gcctggccac cggcttttac cccgaccacg tggaactgtc ttggtgggtc     540
aacggcaaag aggtgcacag cggcgtctgc accgacccc agcccctgaa agagcagccc     600
gccctgaacg acagccggta ctgtctgagc agcagactga gagtgtccgc caccttctgg     660 cagaacccc ggaaccactt cagatgccag gtgcagttct acggcctgag cgagaacgac     720
gagtggaccc aggaccgggc caagcccgtg acccagatcg tgtctgctga ggcctggggc     780
agagccgatt gcggcttcac cagcgagagc taccagcagg gcgtgctgag cgccaccatc     840
ctgtacgaga tcctgctggg caaggccacc ctgtacgccg tgctggtgtc cgccctggtg     900
ctgatggcca tggtcaagcg gaaggacagc cggggcggtt ccggagccac gaacttctct     960
ctgttaaagc aagcaggaga cgtggaagaa aaccccggtc ccatggaaac cctgctgaaa    1020
gtgctgagcg gaacactgtt atggcagctt acatgggtga ggtctcagca acctgtgcaa    1080
tctccacagg ccgttatcct gagagaagga gaagatgccg tgatcaactg ctctagctct    1140
aaagccctgt acagcgtgca ctggtacaga cagaaacacg gagaagctcc cgtgttcctg    1200
atgattctgc tgaaaggagg cgagcagaag ggacacgaga agatttctgc cagcttcaac    1260
gagaagaagc agcagtctag cctgtacctg acagcttctc agctgagcta tagcggcacc    1320
tacttttgtg gcacagagga agccaacgac tacaaactga gctttggagc cggcacaaca    1380
```

-continued

```
gtgacagtta gagccaatat ccagaacccc gatcctgctg tgtaccagct gcgggacagc      1440
aagagcagcg acaagagcgt gtgcctgttc accgacttcg acagccagac caacgtgtcc      1500
cagagcaagg acagcgacgt gtacatcacc gataagtgcg tgctggacat gcggagcatg      1560
gacttcaaga gcaacagcgc cgtggcctgg tccaacaaga gcgacttcgc ctgcgccaac      1620
gccttcaaca acagcattat ccccgaggac acattcttcc aagccccga gagcagctgc       1680 gacgtgaagc tggtggaaaa gagcttcgag acagacacca acctgaactt ccagaacctc      1740
agcgtgatcg gcttccggat cctgctgctg aaggtggccg gcttcaacct gctgatgacc      1800
ctgcggctgt ggtccagctg a                                                 1821
```

<210> SEQ ID NO 162
<211> LENGTH: 606
<212> TYPE: PRT
<213> ORGANISM: Artificial Sequence
<220> FEATURE:
<223> OTHER INFORMATION: codon optimized TCR number 5 construct; beta
      chain-P2A-alpha chain with cysteine substitutions in beta and
      alpha chain constant domains

<400> SEQUENCE: 162

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Gly Gln Gly Ser Ser Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270
```

-continued

```
Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
        290                 295                 300

Val Lys Arg Lys Asp Ser Arg Gly Gly Ser Gly Ala Thr Asn Phe Ser
305                 310                 315                 320

Leu Leu Lys Gln Ala Gly Asp Val Glu Glu Asn Pro Gly Pro Met Glu
                325                 330                 335

Thr Leu Leu Lys Val Leu Ser Gly Thr Leu Leu Trp Gln Leu Thr Trp
                340                 345                 350

Val Arg Ser Gln Gln Pro Val Gln Ser Pro Gln Ala Val Ile Leu Arg
                355                 360                 365

Glu Gly Glu Asp Ala Val Ile Asn Cys Ser Ser Ser Lys Ala Leu Tyr
        370                 375                 380

Ser Val His Trp Tyr Arg Gln Lys His Gly Glu Ala Pro Val Phe Leu
385                 390                 395                 400

Met Ile Leu Leu Lys Gly Gly Glu Gln Lys Gly His Glu Lys Ile Ser
                405                 410                 415

Ala Ser Phe Asn Glu Lys Lys Gln Gln Ser Ser Leu Tyr Leu Thr Ala
                420                 425                 430

Ser Gln Leu Ser Tyr Ser Gly Thr Tyr Phe Cys Gly Thr Glu Glu Ala
                435                 440                 445

Asn Asp Tyr Lys Leu Ser Phe Gly Ala Gly Thr Thr Val Thr Val Arg
        450                 455                 460

Ala Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
                500                 505                 510

Cys Val Leu Asp Met Arg Ser Met Asp Phe Lys Ser Asn Ser Ala Val
                515                 520                 525

Ala Trp Ser Asn Lys Ser Asp Phe Ala Cys Ala Asn Ala Phe Asn Asn
        530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
                580                 585                 590

Ala Gly Phe Asn Leu Leu Met Thr Leu Arg Leu Trp Ser Ser
        595                 600                 605
```

```
<210> SEQ ID NO 163
<211> LENGTH: 1818
<212> TYPE: DNA
<213> ORGANISM: Artificial Sequence
<220> FEATURE:
<223> OTHER INFORMATION: TCR number 9 construct; beta chain-P2A-alpha
      chain

<400> SEQUENCE: 163
atggatacct ggctcgtatg ctgggcaatt tttagtctct tgaaagcagg actcacagaa      60
cctgaagtca cccagactcc cagccatcag gtcacacaga tgggacagga agtgatcttg     120
cgctgtgtcc ccatctctaa tcacttatac ttctattggt acagacaaat cttggggcag     180
```

-continued

```
aaagtcgagt ttctggtttc cttttataat aatgaaatct cagagaagtc tgaaatattc    240
gatgatcaat tctcagttga aaggcctgat ggatcaaatt tcactctgaa gatccggtcc    300
acaaagctgg aggactcagc catgtacttc tgtgccatcc tggatggaga aggttcaccc    360
ctccactttg ggaatgggac caggctcact gtgacagagg acctgaacaa ggtgttccca    420
cccgaggtcg ctgtgtttga gccatcagaa gcagagatct cccacaccca aaaggccaca    480
ctggtgtgcc tggccacagg cttcttccct gaccacgtgg agctgagctg gtgggtgaat    540
gggaaggagg tgcacagtgg ggtcagcacg gacccgcagc ccctcaagga gcagcccgcc    600
ctcaatgact ccagatactg cctgagcagc cgcctgaggg tctcggccac cttctggcag    660 aaccccgca accacttccg ctgtcaagtc cagttctacg ggctctcgga gaatgacgag    720
tggacccagg atagggccaa acccgtcacc cagatcgtca gcgccgaggc ctgggggtaga    780 gcagactgtg gctttacctc ggtgtcctac cagcaagggg tcctgtctgc caccatcctc    840
tatgagatcc tgctagggaa ggccaccctg tatgctgtgc tggtcagcgc ccttgtgttg    900
atggccatgg tcaagagaaa ggatttcggt tccggagcca cgaacttctc tctgttaaag    960
caagcaggag acgtggaaga aaaccccggt cccatgaaaa agcatctgac gaccttcttg   1020
gtgattttgt ggctttattt ttataggggg aatggcaaaa accaagtgga gcagagtcct   1080
cagtccctga tcatcctgga gggaaagaac tgcactcttc aatgcaatta tacagtgagc   1140
cccttcagca acttaaggtg gtataagcaa gatactggga gaggtcctgt ttccctgaca   1200
atcatgactt tcagtgagaa cacaaagtcg aacggaagat atacagcaac tctggatgca   1260
gacacaaagc aaagctctct gcacatcaca gcctcccagc tcagcgattc agcctcctac   1320
atctgtgtgg tgtggggggg ggacaccgac aagctcatct ttgggactgg gaccagatta   1380
caagtctttc aaatatcca gaaccctgac cctgccgtgt accagctgag agactctaaa   1440
tccagtgaca gtctgtctg cctattcacc gattttgatt ctcaaacaaa tgtgtcacaa   1500
agtaaggatt ctgatgtgta tatcacagac aaaactgtgc tagacatgag gtctatggac   1560
ttcaagagca acagtgctgt ggcctggagc aacaaatctg actttgcatg tgcaaacgcc   1620
ttcaacaaca gcattattcc agaagacacc ttcttcccca gcccagaaag ttcctgtgat   1680
gtcaagctgg tcgagaaaag ctttgaaaca gatacgaacc taaactttca aaacctgtca   1740
gtgattgggt ccgaatcct cctcctgaaa gtggccgggg ttaatctgct catgacgctg   1800
cggctgtggt ccagctga                                                 1818
```

<210> SEQ ID NO 164

<400> SEQUENCE: 164

000

<210> SEQ ID NO 165
<211> LENGTH: 605
<212> TYPE: PRT
<213> ORGANISM: Artificial Sequence
<220> FEATURE:
<223> OTHER INFORMATION: TCR number 9 construct; beta chain-P2A-alpha
      chain

<400> SEQUENCE: 165

```
Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
```

-continued

```
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
                100                 105                 110

Ile Leu Asp Gly Glu Gly Ser Pro Leu His Phe Gly Asn Gly Thr Arg
            115                 120                 125

Leu Thr Val Thr Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Lys Lys His Leu
                325                 330                 335

Thr Thr Phe Leu Val Ile Leu Trp Leu Tyr Phe Tyr Arg Gly Asn Gly
            340                 345                 350

Lys Asn Gln Val Glu Gln Ser Pro Gln Ser Leu Ile Ile Leu Glu Gly
            355                 360                 365

Lys Asn Cys Thr Leu Gln Cys Asn Tyr Thr Val Ser Pro Phe Ser Asn
    370                 375                 380

Leu Arg Trp Tyr Lys Gln Asp Thr Gly Arg Gly Pro Val Ser Leu Thr
385                 390                 395                 400

Ile Met Thr Phe Ser Glu Asn Thr Lys Ser Asn Gly Arg Tyr Thr Ala
                405                 410                 415

Thr Leu Asp Ala Asp Thr Lys Gln Ser Ser Leu His Ile Thr Ala Ser
            420                 425                 430

Gln Leu Ser Asp Ser Ala Ser Tyr Ile Cys Val Val Trp Gly Gly Asp
            435                 440                 445
```

-continued

```
Thr Asp Lys Leu Ile Phe Gly Thr Gly Thr Arg Leu Gln Val Phe Pro
    450             455             460

Asn Ile Gln Asn Pro Asp Pro Ala Val Tyr Gln Leu Arg Asp Ser Lys
465             470             475             480

Ser Ser Asp Lys Ser Val Cys Leu Phe Thr Asp Phe Asp Ser Gln Thr
            485             490             495

Asn Val Ser Gln Ser Lys Asp Ser Asp Val Tyr Ile Thr Asp Lys Thr
            500             505             510

Val Leu Asp Met Arg Ser Met Asp Phe Lys Ser Asn Ser Ala Val Ala
            515             520             525

Trp Ser Asn Lys Ser Asp Phe Ala Cys Ala Asn Ala Phe Asn Asn Ser
            530             535             540

Ile Ile Pro Glu Asp Thr Phe Phe Pro Ser Pro Glu Ser Ser Cys Asp
545             550             555             560

Val Lys Leu Val Glu Lys Ser Phe Glu Thr Asp Thr Asn Leu Asn Phe
            565             570             575

Gln Asn Leu Ser Val Ile Gly Phe Arg Ile Leu Leu Leu Lys Val Ala
            580             585             590

Gly Phe Asn Leu Leu Met Thr Leu Arg Leu Trp Ser Ser
            595             600             605
```

```
<210> SEQ ID NO 166
<211> LENGTH: 113
<212> TYPE: PRT
<213> ORGANISM: Artificial Sequence
<220> FEATURE:
<223> OTHER INFORMATION: TCR number 9 Vbeta variable region

<400> SEQUENCE: 166

Glu Pro Glu Val Thr Gln Thr Pro Ser His Gln Val Thr Gln Met Gly
1               5               10              15

Gln Glu Val Ile Leu Arg Cys Val Pro Ile Ser Asn His Leu Tyr Phe
            20              25              30

Tyr Trp Tyr Arg Gln Ile Leu Gly Gln Lys Val Glu Phe Leu Val Ser
        35              40              45

Phe Tyr Asn Asn Glu Ile Ser Glu Lys Ser Glu Ile Phe Asp Asp Gln
    50              55              60

Phe Ser Val Glu Arg Pro Asp Gly Ser Asn Phe Thr Leu Lys Ile Arg
65              70              75              80

Ser Thr Lys Leu Glu Asp Ser Ala Met Tyr Phe Cys Ala Ile Leu Asp
            85              90              95

Gly Glu Gly Ser Pro Leu His Phe Gly Asn Gly Thr Arg Leu Thr Val
            100             105             110

Thr
```

```
<210> SEQ ID NO 167
<211> LENGTH: 6
<212> TYPE: PRT
<213> ORGANISM: Artificial Sequence
<220> FEATURE:
<223> OTHER INFORMATION: TCR number 9 Vbeta CDR1

<400> SEQUENCE: 167

Ser Asn His Leu Tyr Phe
1               5
```

```
<210> SEQ ID NO 168
```

<211> LENGTH: 6
<212> TYPE: PRT
<213> ORGANISM: Artificial Sequence
<220> FEATURE:
<223> OTHER INFORMATION: TCR number 9 Vbeta CDR2

<400> SEQUENCE: 168

Phe Tyr Asn Asn Glu Ile
1               5

<210> SEQ ID NO 169
<211> LENGTH: 1818
<212> TYPE: DNA
<213> ORGANISM: Artificial Sequence
<220> FEATURE:
<223> OTHER INFORMATION: codon optimized TCR number 9 construct; beta
      chain-P2A-alpha chain with cysteine substitutions in beta and
      alpha chain constant domains

<400> SEQUENCE: 169
atggatacct ggctcgtgtg ttgggccatc ttttctctgc tgaaagccgg actgaccgaa      60
cctgaagtta cacaaacccc tagccaccag gtgacacaaa tgggacagga ggtgatcctg     120
agatgtgtgc ctatcagcaa ccacctgtac ttctactggt accggcagat tctgggccag     180
aaagtggagt ttctggtgag cttctacaac aacgagatca gcgagaagag cgagatcttc     240
gatgaccagt tcagcgtgga gagaccagat ggaagcaact ttaccctgaa gatccggagc     300
accaagctgg aagattctgc catgtacttc tgcgccatcc tggatggaga gggatctcct     360
ctgcactttg caatggcac aagactgacc gtgacagaag atctgaacaa ggtgttcccc     420
ccagaggtgg ccgtgttcga gccttctgag gccgagatct cccacaccca gaaagccacc     480
ctcgtgtgcc tggccaccgg cttttttcccc gaccacgtgg aactgtcttg gtgggtcaac     540
ggcaaagagg tgcactccgg cgtgtgcacc gatccccagc ctctgaaaga acagcccgcc     600
ctgaacgaca gccggtactg cctgagcagc agactgagag tgtccgccac cttctggcag     660 aaccccgga accacttcag atgccaggtg cagttctacg gcctgagcga gaacgacgag     720
tggacccagg acagagccaa gcccgtgaca cagatcgtgt ctgccgaagc ctgggggcaga     780 gccgattgcg gctttacctc cgtgtcctat cagcagggcg tgctgagcgc cacaatcctg     840
tacgagatcc tgctgggcaa ggccacccctg tacgccgtgc tggtgtctgc cctggtgctg     900
atggccatgg tcaagcggaa ggacttcggt tccggagcca cgaacttctc tctgttaaag     960
caagcaggag acgtggaaga aaaccccggt cccatgaaga agcacctgac cacgttcctg    1020
gtgattcttt ggctgtactt ctaccggggc aacggcaaaa tcaggtggga caaagccccc    1080
cagagcctga ttattctgga gggcaagaac tgcacccctcc agtgtaatta caccgtgagc    1140
cctttcagca acctgagatg gtacaagcag ataccggaa gaggacctgt gtctctgacc    1200
atcatgacct ttagcgagaa caccaagagc aacggcaggt atacagccac actggatgcc    1260
gataccaagc agtcttctct gcacattacc gcctctcagc tgtctgattc tgccagctac    1320
atctgtgtgg tgtggggagg agataccgat aagctgatct ttggcacagg caccagactg    1380
caagtgttcc ctaacatcca gaaccctgat cctgccgtgt accagctgcg ggacagcaag    1440
agcagcgaca gagcgtgtg cctgttcacc gacttcgaca ccagaccaa cgtgtcccag    1500 agcaaggaca gcgacgtgta catcaccgat aagtgcgtgc tggacatgcg gagcatggac    1560
ttcaagagca cagcgccgt ggcctggtcc aacaagagcg acttcgcctg cgccaacgcc    1620
ttcaacaaca gcattatccc cgaggacaca ttcttcccaa gccccgagag cagctgcgac    1680

-continued gtgaagctgg tggaaaagag cttcgagaca gacaccaacc tgaacttcca gaacctcagc    1740
gtgatcggct tccggatcct gctgctgaag gtggccggct tcaacctgct gatgaccctg    1800
cggctgtggt ccagctga                                                  1818

<210> SEQ ID NO 170
<211> LENGTH: 605
<212> TYPE: PRT
<213> ORGANISM: Artificial Sequence
<220> FEATURE:
<223> OTHER INFORMATION: codon optimized TCR number 9 construct; beta
      chain-P2A-alpha chain with cysteine substitutions in beta and
      alpha chain constant domains

<400> SEQUENCE: 170

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
        50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ile Leu Asp Gly Glu Gly Ser Pro Leu His Phe Gly Asn Gly Thr Arg
            115                 120                 125

Leu Thr Val Thr Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Lys Lys His Leu

```
                    325             330             335
Thr Thr Phe Leu Val Ile Leu Trp Leu Tyr Phe Tyr Arg Gly Asn Gly
            340             345             350
Lys Asn Gln Val Glu Gln Ser Pro Gln Ser Leu Ile Ile Leu Glu Gly
            355             360             365
Lys Asn Cys Thr Leu Gln Cys Asn Tyr Thr Val Ser Pro Phe Ser Asn
        370             375             380
Leu Arg Trp Tyr Lys Gln Asp Thr Gly Arg Gly Pro Val Ser Leu Thr
385             390             395             400
Ile Met Thr Phe Ser Glu Asn Thr Lys Ser Asn Gly Arg Tyr Thr Ala
                405             410             415
Thr Leu Asp Ala Asp Thr Lys Gln Ser Ser Leu His Ile Thr Ala Ser
            420             425             430
Gln Leu Ser Asp Ser Ala Ser Tyr Ile Cys Val Val Trp Gly Gly Asp
            435             440             445
Thr Asp Lys Leu Ile Phe Gly Thr Gly Thr Arg Leu Gln Val Phe Pro
        450             455             460
Asn Ile Gln Asn Pro Asp Pro Ala Val Tyr Gln Leu Arg Asp Ser Lys
465             470             475             480
Ser Ser Asp Lys Ser Val Cys Leu Phe Thr Asp Phe Asp Ser Gln Thr
                485             490             495
Asn Val Ser Gln Ser Lys Asp Ser Asp Val Tyr Ile Thr Asp Lys Cys
            500             505             510
Val Leu Asp Met Arg Ser Met Asp Phe Lys Ser Asn Ser Ala Val Ala
            515             520             525
Trp Ser Asn Lys Ser Asp Phe Ala Cys Ala Asn Ala Phe Asn Asn Ser
        530             535             540
Ile Ile Pro Glu Asp Thr Phe Phe Pro Ser Pro Glu Ser Ser Cys Asp
545             550             555             560
Val Lys Leu Val Glu Lys Ser Phe Glu Thr Asp Thr Asn Leu Asn Phe
                565             570             575
Gln Asn Leu Ser Val Ile Gly Phe Arg Ile Leu Leu Leu Lys Val Ala
            580             585             590
Gly Phe Asn Leu Leu Met Thr Leu Arg Leu Trp Ser Ser
            595             600             605
```

<210> SEQ ID NO 171
<211> LENGTH: 1827
<212> TYPE: DNA
<213> ORGANISM: Artificial Sequence
<220> FEATURE:
<223> OTHER INFORMATION: codon optimized TCR number 6 construct; beta
    chain-P2A-alpha chain with cysteine substitutions in beta and
    alpha chain constant domains

<400> SEQUENCE: 171

```
atgagcatca gcctcctgtg ctgtgcagcc tttcctctcc tgtgggcagg tccagtgaat      60
gctggtgtca ctcagacccc aaaattccgc atcctgaaga taggacagag catgacactg     120
cagtgtaccc aggatatgaa ccataactac atgtactggt atcgacaaga cccaggcatg     180
gggctgaagc tgatttatta ttcagttggt gctggtatca ctgataaagg agaagtcccg     240
aatggctaca cgtctccag atcaaccaca gaggatttcc cgctcaggct ggagttggct      300
gctccctccc agacatctgt gtacttctgt gccagcagtg acaggtctaa caccggggag     360 ctgtttttg gagaaggctc taggctgacc gtactggagg acctgaaaaa cgtgttccca     420
```

-continued

```
cccgaggtcg ctgtgtttga gccatcagaa gcagagatct cccacaccca aaaggccaca      480
ctggtgtgcc tggccacagg cttctacccc gaccacgtgg agctgagctg gtgggtgaat      540
gggaaggagg tgcacagtgg ggtctgcaca gacccgcagc ccctcaagga gcagcccgcc      600
ctcaatgact ccagatactg cctgagcagc cgcctgaggg tctcggccac cttctggcag      660
aacccccgca accacttccg ctgtcaagtc cagttctacg ggctctcgga gaatgacgag      720
tggacccagg atagggccaa acctgtcacc cagatcgtca gcgccgaggc ctggggtaga      780
gcagactgtg gcttcacctc cgagtcttac cagcaagggg tcctgtctgc caccatcctc      840
tatgagatct tgctagggaa ggccaccttg tatgccgtgc tggtcagtgc cctcgtgctg      900
atggccatgg tcaagagaaa ggattccaga ggcggttccg gagccacgaa cttctctctg      960
ttaaagcaag caggagacgt ggaagaaaac cccggtccca tggagaagaa tcctttggca     1020
gccccattac taatcctctg gtttcatctt gactgcgtga gcagcatact gaacgtggaa     1080
caaagtcctc agtcactgca tgttcaggag ggagacagca ccaatttcac ctgcagcttc     1140
ccttccagca attttatgc cttacactgg tacagatggg aaactgcaaa aagccccgag     1200
gccttgtttg taatgacttt aaatggggat gaaaagaaga aggacgaat aagtgccact     1260 cttaatacca aggagggtta cagctatttg tacatcaaag atcccagcc tgaagactca     1320 gccacatacc tctgtgcctt agggccttat aacgactaca agctcagctt ggagccgga     1380 accacagtaa ctgtaagagc aaatatccag aaccctgacc ctgccgtgta ccagctgcgg     1440
gacagcaaga gcagcgacaa gagcgtgtgc ctgttcaccg acttcgacag ccagaccaac     1500
gtgtcccaga gcaaggacag cgacgtgtac atcaccgata gtgcgtgct ggacatgcgg     1560 agcatggact tcaagagcaa cagcgccgtg gcctggtcca acaagagcga cttcgcctgc     1620
gccaacgcct tcaacaacag cattatcccc gaggacacat cttcccaag ccccgagagc     1680 agctgcgacg tgaagctggt ggaaaagagc ttcgagacag acaccaacct gaacttccag     1740
aacctcagcg tgatcggctt ccggatcctg ctgctgaagg tggccggctt caacctgctg     1800
atgaccctgc ggctgtggtc cagctga                                        1827
```

<210> SEQ ID NO 172
<211> LENGTH: 608
<212> TYPE: PRT
<213> ORGANISM: Artificial Sequence
<220> FEATURE:
<223> OTHER INFORMATION: codon optimized TCR number 6 construct; beta
      chain-P2A-alpha chain with cysteine substitutions in beta and
      alpha chain constant domains

<400> SEQUENCE: 172

```
Met Ser Ile Ser Leu Leu Cys Cys Ala Ala Phe Pro Leu Leu Trp Ala
1               5                   10                  15

Gly Pro Val Asn Ala Gly Val Thr Gln Thr Pro Lys Phe Arg Ile Leu
                20                  25                  30

Lys Ile Gly Gln Ser Met Thr Leu Gln Cys Thr Gln Asp Met Asn His
            35                  40                  45

Asn Tyr Met Tyr Trp Tyr Arg Gln Asp Pro Gly Met Gly Leu Lys Leu
        50                  55                  60

Ile Tyr Tyr Ser Val Gly Ala Gly Ile Thr Asp Lys Gly Glu Val Pro
65                  70                  75                  80

Asn Gly Tyr Asn Val Ser Arg Ser Thr Thr Glu Asp Phe Pro Leu Arg
                85                  90                  95

Leu Glu Leu Ala Ala Pro Ser Gln Thr Ser Val Tyr Phe Cys Ala Ser
```

-continued

```
               100                 105                 110
Ser Asp Arg Ser Asn Thr Gly Glu Leu Phe Phe Gly Glu Gly Ser Arg
               115                 120                 125
Leu Thr Val Leu Glu Asp Leu Lys Asn Val Phe Pro Pro Glu Val Ala
        130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
               165                 170                 175
Trp Trp Val Asn Gly Lys Glu Val His Ser Gly Val Cys Thr Asp Pro
               180                 185                 190
Gln Pro Leu Lys Glu Gln Pro Ala Leu Asn Asp Ser Arg Tyr Cys Leu
               195                 200                 205
Ser Ser Arg Leu Arg Val Ser Ala Thr Phe Trp Gln Asn Pro Arg Asn
        210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
               245                 250                 255
Ala Trp Gly Arg Ala Asp Cys Gly Phe Thr Ser Glu Ser Tyr Gln Gln
               260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
        290                 295                 300
Lys Arg Lys Asp Ser Arg Gly Gly Ser Gly Ala Thr Asn Phe Ser Leu
305                 310                 315                 320
Leu Lys Gln Ala Gly Asp Val Glu Glu Asn Pro Gly Pro Met Glu Lys
               325                 330                 335
Asn Pro Leu Ala Ala Pro Leu Leu Ile Leu Trp Phe His Leu Asp Cys
        340                 345                 350
Val Ser Ser Ile Leu Asn Val Glu Gln Ser Pro Gln Ser Leu His Val
        355                 360                 365
Gln Glu Gly Asp Ser Thr Asn Phe Thr Cys Ser Phe Pro Ser Ser Asn
        370                 375                 380
Phe Tyr Ala Leu His Trp Tyr Arg Trp Glu Thr Ala Lys Ser Pro Glu
385                 390                 395                 400
Ala Leu Phe Val Met Thr Leu Asn Gly Asp Glu Lys Lys Lys Gly Arg
               405                 410                 415
Ile Ser Ala Thr Leu Asn Thr Lys Glu Gly Tyr Ser Tyr Leu Tyr Ile
               420                 425                 430
Lys Gly Ser Gln Pro Glu Asp Ser Ala Thr Tyr Leu Cys Ala Leu Gly
        435                 440                 445
Pro Tyr Asn Asp Tyr Lys Leu Ser Phe Gly Ala Gly Thr Thr Val Thr
        450                 455                 460
Val Arg Ala Asn Ile Gln Asn Pro Asp Pro Ala Val Tyr Gln Leu Arg
465                 470                 475                 480
Asp Ser Lys Ser Ser Asp Lys Ser Val Cys Leu Phe Thr Asp Phe Asp
               485                 490                 495
Ser Gln Thr Asn Val Ser Gln Ser Lys Asp Ser Asp Val Tyr Ile Thr
        500                 505                 510
Asp Lys Cys Val Leu Asp Met Arg Ser Met Asp Phe Lys Ser Asn Ser
        515                 520                 525
```

```
Ala Val Ala Trp Ser Asn Lys Ser Asp Phe Ala Cys Ala Asn Ala Phe
    530             535             540

Asn Asn Ser Ile Ile Pro Glu Asp Thr Phe Phe Pro Ser Pro Glu Ser
545             550             555             560

Ser Cys Asp Val Lys Leu Val Glu Lys Ser Phe Glu Thr Asp Thr Asn
            565             570             575

Leu Asn Phe Gln Asn Leu Ser Val Ile Gly Phe Arg Ile Leu Leu Leu
            580             585             590

Lys Val Ala Gly Phe Asn Leu Leu Met Thr Leu Arg Leu Trp Ser Ser
            595             600             605
```

<210> SEQ ID NO 173
<211> LENGTH: 1815
<212> TYPE: DNA
<213> ORGANISM: Artificial Sequence
<220> FEATURE:
<223> OTHER INFORMATION: codon optimized TCR number 1 construct; beta
      chain-P2A-alpha chain with cysteine substitutions in beta and
      alpha chain constant domains

<400> SEQUENCE: 173

```
atgggacctg gactgctttg ttgggctctt ctgtgtctgc ttggagctgg actggttgat      60
gctggagtta cacagagccc tacacacctg atcaagacaa gaggacagca ggtgaccctg     120
agatgtagcc ctaaatctgg ccacgatacc gtgagctggt atcaacaggc tctgggacaa     180
ggacctcagt tcatcttcca gtactacgag gaggaggaga cagagagg caatttccct       240 gacaggttta gcggacacca gttccccaat tacagctctg agctgaacgt gaatgccctt     300
cttctgggag attctgccct gtatctgtgt gccagcagct ctttagcca ggaaacccag      360 tacttcggcc aggaacaag actgctggtt cttgaagacc tgaagaacgt gttcccccca      420
gaggtggccg tgttcgagcc tagcgaggcc gagatcagcc acacccagaa agccaccctc     480
gtgtgcctgg ccaccggctt ttaccccgac cacgtggaac tgtcttggtg ggtcaacggc     540
aaagaggtgc acagcggcgt ctgcaccgac ccccagcccc tgaaagagca gcccgccctg     600
aacgacagcc ggtactgtct gagcagcaga ctgagagtgt ccgccacctt ctggcagaac     660 cccggaacc acttcagatg ccaggtgcag ttctacggcc tgagcgagaa cgacgagtgg      720
acccaggacc gggccaagcc cgtgacccag atcgtgtctg ctgaggcctg gggcagagcc     780
gattgcggct tcaccagcga gagctaccag cagggcgtgc tgagcgccac catcctgtac     840
gagatcctgc tgggcaaggc cacccttac gccgtgctgg tgtccgccct ggtgctgatg     900
gccatggtca gcggaagga cagccggggc ggttccggag ccacgaactt ctctctgtta     960
aagcaagcag agacgtgga agaaaacccc ggtcccatgg aaaccctgtt aggcctgctc    1020
attctgtggt tacagctcca atgggtgagc agcaaacagg aagtgaccca gattcctgct   1080
gccttatctg tgcctgaagg cgaaaatctg gtgctgaatt gcagcttcac cgattctgcc   1140
atctacaacc tccagtggtt cagacaggat ccaggaaaag gcctgacatc tcttctgctg   1200
atccagtcta gccagagaga gcagacaagc ggaagactga atgcctctct ggacaagagc   1260
agcggaagat ctaccctgta tattgccgcc tctcagcctg agattctgc cacatatctg    1320 tgtgccgtgg agggagatag cagctataag ctgatcttcg gcagcggcac aagattactg   1380
gtgagacctg acatccagaa ccctgatcct gctgtgtacc agctgcggga cagcaagagc   1440
agcgacaaga gcgtgtgcct gttcaccgac ttcgacagcc agaccaacgt gtcccagagc    1500
aaggacagcg acgtgtacat caccgataag tgcgtgctgg acatgcggag catggacttc    1560
```

-continued

```
aagagcaaca gcgccgtggc ctggtccaac aagagcgact tcgcctgcgc caacgccttc    1620
aacaacagca ttatccccga ggacacattc ttcccaagcc ccgagagcag ctgcgacgtg    1680
aagctggtgg aaaagagctt cgagacagac accaacctga acttccagaa cctcagcgtg    1740
atcggcttcc ggatcctgct gctgaaggtg gccggcttca acctgctgat gaccctgcgg    1800
ctgtggtcca gctga                                                     1815
```

```
<210> SEQ ID NO 174
<211> LENGTH: 604
<212> TYPE: PRT
<213> ORGANISM: Artificial Sequence
<220> FEATURE:
<223> OTHER INFORMATION: codon optimized TCR number 1 construct; beta
      chain-P2A-alpha chain with cysteine substitutions in beta and
      alpha chain constant domains

<400> SEQUENCE: 174

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
            35                  40                  45

Asp Thr Val Ser Trp Tyr Gln Gln Ala Leu Gly Gln Gly Pro Gln Phe
            50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Phe Ser Gln Glu Thr Gln Tyr Phe Gly Pro Gly Thr Arg Leu
            115                 120                 125

Leu Val Leu Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
                180                 185                 190

Pro Leu Lys Glu Gln Pro Ala Leu Asn Asp Ser Arg Tyr Cys Leu Ser
                195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
            290                 295                 300
```

```
Arg Lys Asp Ser Arg Gly Gly Ser Gly Ala Thr Asn Phe Ser Leu Leu
305             310             315             Phe Ser     320

Lys Gln Ala Gly Asp Val Glu Glu Asn Pro Gly Pro Met Glu Thr Leu
                325             330             335

Leu Gly Leu Leu Ile Leu Trp Leu Gln Leu Gln Trp Val Ser Ser Lys
        340             345             350

Gln Glu Val Thr Gln Ile Pro Ala Ala Leu Ser Val Pro Glu Gly Glu
        355             360             365

Asn Leu Val Leu Asn Cys Ser Phe Thr Asp Ser Ala Ile Tyr Asn Leu
    370             375             380

Gln Trp Phe Arg Gln Asp Pro Gly Lys Gly Leu Thr Ser Leu Leu Leu
385             390             395             400

Ile Gln Ser Ser Gln Arg Glu Gln Thr Ser Gly Arg Leu Asn Ala Ser
            405             410             415

Leu Asp Lys Ser Ser Gly Arg Ser Thr Leu Tyr Ile Ala Ala Ser Gln
            420             425             430

Pro Gly Asp Ser Ala Thr Tyr Leu Cys Ala Val Glu Gly Asp Ser Ser
            435             440             445

Tyr Lys Leu Ile Phe Gly Ser Gly Thr Arg Leu Leu Val Arg Pro Asp
        450             455             460

Ile Gln Asn Pro Asp Pro Ala Val Tyr Gln Leu Arg Asp Ser Lys Ser
465             470             475             480

Ser Asp Lys Ser Val Cys Leu Phe Thr Asp Phe Asp Ser Gln Thr Asn
            485             490             495

Val Ser Gln Ser Lys Asp Ser Asp Val Tyr Ile Thr Asp Lys Cys Val
            500             505             510

Leu Asp Met Arg Ser Met Asp Phe Lys Ser Asn Ser Ala Val Ala Trp
            515             520             525

Ser Asn Lys Ser Asp Phe Ala Cys Ala Asn Ala Phe Asn Asn Ser Ile
        530             535             540

Ile Pro Glu Asp Thr Phe Phe Pro Ser Pro Glu Ser Ser Cys Asp Val
545             550             555             560

Lys Leu Val Glu Lys Ser Phe Glu Thr Asp Thr Asn Leu Asn Phe Gln
            565             570             575

Asn Leu Ser Val Ile Gly Phe Arg Ile Leu Leu Leu Lys Val Ala Gly
        580             585             590

Phe Asn Leu Leu Met Thr Leu Arg Leu Trp Ser Ser
        595             600
```

<210> SEQ ID NO 175
<211> LENGTH: 1824
<212> TYPE: DNA
<213> ORGANISM: Artificial Sequence
<220> FEATURE:
<223> OTHER INFORMATION: codon optimized TCR number 2 construct; beta
      chain-P2A-alpha chain with cysteine substitutions in beta and
      alpha chain constant domains <400> SEQUENCE: 175

```
atgggcacca gactgctgtg ttgggctgct ctgtgtctgc tgggagccga tcatacaggt      60
gccggtgtca gccagacacc tagcaacaaa gtgaccgaga agggcaaata cgtggaactg     120
agatgcgacc ccatcagcgg acacacagcc ctgtactggt acagacagtc tctcggccag     180
ggacctgagt tcctgatcta cttccaaggc accggcgctg ccgatgatag cggcctgcct     240
aacgatagat tcttcgccgt cagacccgag ggcagcgtgt ccacactgaa gatccagaga     300
```

-continued

```
accgagaggg gcgacagcgc cgtgtatctg tgtgcctctt ctctgtctgg cctcggctct      360
ggcgctaacg tgctgacatt tggcgccgga agcagactga ccgtgctgga agatctgaag      420
aacgtgttcc cacctgaggt ggccgtgttc gagccttctg aggccgagat cagccacaca      480
cagaaagcca cactcgtgtg tctggccacc ggcttctatc ccgaccatgt ggaactgtct      540
tggtgggtca acggcaaaga ggtgcacagc ggcgtctgta cagatcccca gcctctgaaa      600
gaacagcccg ctctgaacga cagccggtac tgtctgtcct ccagactgag agtgtccgcc      660
accttctggc agaaccccag aaaccacttc agatgccagg tgcagttcta cggcctgagc      720
gagaacgatg agtggaccca ggatagagcc aagcctgtga cacagatcgt gtctgccgaa      780
gcctggggca gagccgattg tggctttacc agcgagagct accagcaggg cgtgctgtct      840
gccacaatcc tgtacgagat cctgctgggc aaagccactc tgtacgccgt gctggtgtct      900
gccctggtgc tgatggccat ggtcaagcgg aaggacagca gaggcggttc cggagccacg      960
aacttctctc tgttaaagca agcaggagac gtggaagaaa accccggtcc catggaaaca      1020
ctgctgggcc tgctgatcct gtggctgcaa ctgcaatggg tgtccagcaa gcaagaagtg      1080
acacagatcc ctgccgctct gtctgtgcct gagggcgaaa acctggtgct gaactgcagc      1140
ttcaccgaca gcgccatcta caacctgcag tggttcagac aggaccccgg caagggactg      1200
acaagcctgc tgctgattca gagcagccag agagagcaga ccagcggcag actgaatgcc      1260
agcctggata agtcctccgg cagaagcacc ctgtatatcg ccgcttctca gcctggcgat      1320
agcgccacat atctgtgtgc cgtgatcggc gagcagaact cgtgtttggg ccctggcaca      1380
agactgagcg tgctgcccta cattcagaac cccgatcctg ccgtgtacca gctgcgggac      1440
agcaagagca gcgacaagag cgtgtgcctg ttcaccgact cgacagcca gaccaacgtg      1500 tcccagagca aggacagcga cgtgtacatc accgataagt gcgtgctgga catgcggagc      1560
atggacttca gagcaacag cgccgtggcc tggtccaaca agagcgactt cgcctgcgcc      1620
aacgccttca caacagcat tatccccgag gacacattct tcccaagccc cgagagcagc      1680
tgcgacgtga agctggtgga aaagagcttc gagacagaca ccaacctgaa cttccagaac      1740
ctcagcgtga tcggcttccg gatcctgctg ctgaaggtgg ccggcttcaa cctgctgatg      1800
accctgcggc tgtggtccag ctga                                            1824
```

<210> SEQ ID NO 176
<211> LENGTH: 607
<212> TYPE: PRT
<213> ORGANISM: Artificial Sequence
<220> FEATURE:
<223> OTHER INFORMATION: codon optimized TCR number 2 construct
      polypeptide; beta chain-P2A-alpha chain with cysteine
      substitutions in beta and alpha chain constant domains

<400> SEQUENCE: 176

```
Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
                20                  25                  30

Glu Lys Gly Lys Tyr Val Glu Leu Arg Cys Asp Pro Ile Ser Gly His
            35                  40                  45

Thr Ala Leu Tyr Trp Tyr Arg Gln Ser Leu Gly Gln Gly Pro Glu Phe
        50                  55                  60

Leu Ile Tyr Phe Gln Gly Thr Gly Ala Ala Asp Asp Ser Gly Leu Pro
65                  70                  75                  80
```

-continued

```
Asn Asp Arg Phe Phe Ala Val Arg Pro Glu Gly Ser Val Ser Thr Leu
            85              90              95

Lys Ile Gln Arg Thr Glu Arg Gly Asp Ser Ala Val Tyr Leu Cys Ala
            100             105             110

Ser Ser Leu Ser Gly Leu Gly Ser Gly Ala Asn Val Leu Thr Phe Gly
            115             120             125

Ala Gly Ser Arg Leu Thr Val Leu Glu Asp Leu Lys Asn Val Phe Pro
        130             135             140

Pro Glu Val Ala Val Phe Glu Pro Ser Glu Ala Glu Ile Ser His Thr
145             150             155             160

Gln Lys Ala Thr Leu Val Cys Leu Ala Thr Gly Phe Tyr Pro Asp His
            165             170             175

Val Glu Leu Ser Trp Trp Val Asn Gly Lys Glu Val His Ser Gly Val
            180             185             190

Cys Thr Asp Pro Gln Pro Leu Lys Glu Gln Pro Ala Leu Asn Asp Ser
            195             200             205

Arg Tyr Cys Leu Ser Ser Arg Leu Arg Val Ser Ala Thr Phe Trp Gln
        210             215             220

Asn Pro Arg Asn His Phe Arg Cys Gln Val Gln Phe Tyr Gly Leu Ser
225             230             235             240

Glu Asn Asp Glu Trp Thr Gln Asp Arg Ala Lys Pro Val Thr Gln Ile
            245             250             255

Val Ser Ala Glu Ala Trp Gly Arg Ala Asp Cys Gly Phe Thr Ser Glu
            260             265             270

Ser Tyr Gln Gln Gly Val Leu Ser Ala Thr Ile Leu Tyr Glu Ile Leu
            275             280             285

Leu Gly Lys Ala Thr Leu Tyr Ala Val Leu Val Ser Ala Leu Val Leu
        290             295             300

Met Ala Met Val Lys Arg Lys Asp Ser Arg Gly Gly Ser Gly Ala Thr
305             310             315             320

Asn Phe Ser Leu Leu Lys Gln Ala Gly Asp Val Glu Glu Asn Pro Gly
            325             330             335

Pro Met Glu Thr Leu Leu Gly Leu Leu Ile Leu Trp Leu Gln Leu Gln
            340             345             350

Trp Val Ser Ser Lys Gln Glu Val Thr Gln Ile Pro Ala Ala Leu Ser
            355             360             365

Val Pro Glu Gly Glu Asn Leu Val Leu Asn Cys Ser Phe Thr Asp Ser
        370             375             380

Ala Ile Tyr Asn Leu Gln Trp Phe Arg Gln Asp Pro Gly Lys Gly Leu
385             390             395             400

Thr Ser Leu Leu Leu Ile Gln Ser Ser Gln Arg Glu Gln Thr Ser Gly
            405             410             415

Arg Leu Asn Ala Ser Leu Asp Lys Ser Ser Gly Arg Ser Thr Leu Tyr
            420             425             430

Ile Ala Ala Ser Gln Pro Gly Asp Ser Ala Thr Tyr Leu Cys Ala Val
            435             440             445

Ile Gly Glu Gln Asn Phe Val Phe Gly Pro Gly Thr Arg Leu Ser Val
        450             455             460

Leu Pro Tyr Ile Gln Asn Pro Asp Pro Ala Val Tyr Gln Leu Arg Asp
465             470             475             480

Ser Lys Ser Ser Asp Lys Ser Val Cys Leu Phe Thr Asp Phe Asp Ser
            485             490             495
```

-continued

```
Gln Thr Asn Val Ser Gln Ser Lys Asp Ser Asp Val Tyr Ile Thr Asp
            500                 505                 510

Lys Cys Val Leu Asp Met Arg Ser Met Asp Phe Lys Ser Asn Ser Ala
            515                 520                 525

Val Ala Trp Ser Asn Lys Ser Asp Phe Ala Cys Ala Asn Ala Phe Asn
            530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
                580                 585                 590

Val Ala Gly Phe Asn Leu Leu Met Thr Leu Arg Leu Trp Ser Ser
            595                 600                 605
```

```
<210> SEQ ID NO 177
<211> LENGTH: 1818
<212> TYPE: DNA
<213> ORGANISM: Artificial Sequence
<220> FEATURE:
<223> OTHER INFORMATION: codon optimized TCR number 3 construct; beta
      chain-P2A-alpha chain with cysteine substitutions in beta and
      alpha chain constant domains

<400> SEQUENCE: 177
atgggcacca gactgctgtg ttgggccgct ctgtgtctgc tgggcgccga tcatacaggc        60
gctggcgtgt cccagacccc cagcaacaaa gtgaccgaga agggcaaata cgtggaactg       120
agatgcgacc ccatcagcgg ccacaccgcc ctgtactggt acagacagtc tctgggccag       180
ggccccgagt cctgatata ttttcagggc accggcgctg ccgacgacag cggcctgcct       240
aacgatagat tcttcgccgt gcggcccgag ggcagcgtgt ccacactgaa gatccagaga       300
accgagcggg gcgacagcgc cgtgtatctg tgtgccagca gcctgaatat gaacaccgag       360
gcattctttg gcagggcac ccggctgacc gtggtggaag atctgaacaa ggtgttcccc       420
ccagaggtgg ccgtgttcga gccttctgag gccgagatca gccacaccca gaaagccacc       480
ctcgtgtgcc tggccaccgg ctttttcccc gaccatgtgg aactgtcttg gtgggtcaac       540
ggcaaagagg tgcacagcgg agtgtgcacc gaccctcagc ccctgaaaga cagcccgcc       600 ctgaacgaca gccggtactg cctgagcagc agactgagag tgtccgccac cttctggcag       660
aacccccgga ccacttcag atgccaggtg cagttctacg gcctgagcga aacgacgag       720 tggacccagg acagagccaa gcccgtgacc cagatcgtgt ctgccgaagc ctgggggcaga       780 gccgattgcg gctttacctc cgtgtcctat cagcagggcg tgctgagcgc caccatcctg       840
tacgagatcc tgctgggcaa ggccacctg tacgccgtgc tggtgtctgc cctggtgctg       900
atggccatgg tcaagcggaa ggacttcggt tccggagcca cgaacttctc tctgttaaag       960
caagcaggag acgtggaaga aaaccccggt cccatgatga gtccctgcg ggtgctgctc      1020 gtgatcctgt ggctgcagct gtcttgggtg tggtcccagc agaaagaggt ggaacagaac      1080
agcggccctc tgagcgtgcc agagggcgcc attgctagcc tgaattgcac ctacagcgac      1140
cggggcagcc agagcttctt ctggtatcgg cagtacagcg caagagccc cgagctgatc      1200 atgagcatct acagcaacgg cgacaaagag gacggccggt tcaccgccca gctgaacaaa      1260
gccagccagt acgtgtcact gctgatccgg gacagccagc cagcgatag cgccacatac      1320 ctgtgcgccg tggatagcgg cggctaccag aaagtgacct cggcaccgg caccaagctg      1380
```

-continued

```
caagtgatcc ccaacatcca gaaccccgac cccgctgtgt accagctgcg ggacagcaag    1440
agcagcgaca agagcgtgtg cctgttcacc gacttcgaca gccagaccaa cgtgtcccag    1500
agcaaggaca gcgacgtgta catcaccgat aagtgcgtgc tggacatgcg gagcatggac    1560
ttcaagagca cacgcgccgt ggcctggtcc aacaagagcg acttcgcctg cgccaacgcc    1620
ttcaacaaca gcattatccc cgaggacaca ttcttcccaa gccccgagag cagctgcgac    1680
gtgaagctgg tggaaaagag cttcgagaca gacaccaacc tgaacttcca gaacctcagc    1740
gtgatcggct tccggatcct gctgctgaag gtggccggct tcaacctgct gatgaccctg    1800
cggctgtggt ccagctga                                                  1818
```

<210> SEQ ID NO 178
<211> LENGTH: 605
<212> TYPE: PRT
<213> ORGANISM: Artificial Sequence
<220> FEATURE:
<223> OTHER INFORMATION: codon optimized TCR number 3 construct; beta
      chain-P2A-alpha chain with cysteine substitutions in beta and
      alpha chain constant domains

<400> SEQUENCE: 178

```
Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Leu Asn Met Asn Thr Glu Ala Phe Phe Gly Gln Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
            260                 265                 270
```

-continued

```
Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
        290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Met Lys Ser Leu
                325                 330                 335

Arg Val Leu Leu Val Ile Leu Trp Leu Gln Leu Ser Trp Val Trp Ser
        340                 345                 350

Gln Gln Lys Glu Val Glu Gln Asn Ser Gly Pro Leu Ser Val Pro Glu
        355                 360                 365

Gly Ala Ile Ala Ser Leu Asn Cys Thr Tyr Ser Asp Arg Gly Ser Gln
        370                 375                 380

Ser Phe Phe Trp Tyr Arg Gln Tyr Ser Gly Lys Ser Pro Glu Leu Ile
385                 390                 395                 400

Met Ser Ile Tyr Ser Asn Gly Asp Lys Glu Asp Gly Arg Phe Thr Ala
                405                 410                 415

Gln Leu Asn Lys Ala Ser Gln Tyr Val Ser Leu Leu Ile Arg Asp Ser
        420                 425                 430

Gln Pro Ser Asp Ser Ala Thr Tyr Leu Cys Ala Val Asp Ser Gly Gly
        435                 440                 445

Tyr Gln Lys Val Thr Phe Gly Thr Gly Thr Lys Leu Gln Val Ile Pro
        450                 455                 460

Asn Ile Gln Asn Pro Asp Pro Ala Val Tyr Gln Leu Arg Asp Ser Lys
465                 470                 475                 480

Ser Ser Asp Lys Ser Val Cys Leu Phe Thr Asp Phe Asp Ser Gln Thr
                485                 490                 495

Asn Val Ser Gln Ser Lys Asp Ser Asp Val Tyr Ile Thr Asp Lys Cys
        500                 505                 510

Val Leu Asp Met Arg Ser Met Asp Phe Lys Ser Asn Ser Ala Val Ala
        515                 520                 525

Trp Ser Asn Lys Ser Asp Phe Ala Cys Ala Asn Ala Phe Asn Asn Ser
        530                 535                 540

Ile Ile Pro Glu Asp Thr Phe Phe Pro Ser Pro Glu Ser Ser Cys Asp
545                 550                 555                 560

Val Lys Leu Val Glu Lys Ser Phe Glu Thr Asp Thr Asn Leu Asn Phe
                565                 570                 575

Gln Asn Leu Ser Val Ile Gly Phe Arg Ile Leu Leu Leu Lys Val Ala
        580                 585                 590

Gly Phe Asn Leu Leu Met Thr Leu Arg Leu Trp Ser Ser
        595                 600                 605
```

<210> SEQ ID NO 179
<211> LENGTH: 1812
<212> TYPE: DNA
<213> ORGANISM: Artificial Sequence
<220> FEATURE:
<223> OTHER INFORMATION: codon optimized TCR number 10 construct; beta
      chain-P2A-alpha chain with cysteine substitutions in beta and
      alpha chain constant domains

<400> SEQUENCE: 179
atgggcacca gactgctgtg ttgggccgct ctgtgtctgc tgggcgccga tcatacaggc        60
gctggcgtgt cccagacccc cagcaacaaa gtgaccgaga agggcaaata cgtggaactg       120

-continued

```
agatgcgacc ccatcagcgg ccacaccgcc ctgtactggt acagacagtc tctgggccag      180
ggccccgagt tcctgatata ttttcagggc accggcgctg ccgacgacag cggcctgcct      240
aacgatagat tcttcgccgt gcggcccgag ggcagcgtgt ccacactgaa gatccagaga      300
accgagcggg cgacagcgc cgtgtatctg tgtgccagca gcctgaatat gaacaccgag       360
gcattctttg gcagggcac ccggctgacc gtggtggaag atctgaacaa ggtgttcccc       420
ccagaggtgg ccgtgttcga gccttctgag gccgagatca gccacaccca gaaagccacc      480
ctcgtgtgcc tggccaccgg cttttttcccc gaccatgtgg aactgtcttg gtgggtcaac     540
ggcaaagagg tgcacagcgg agtgtgcacc gaccctcagc ccctgaaaga acagcccgcc      600
ctgaacgaca gccggtactg cctgagcagc agactgagag tgtccgccac cttctggcag      660 aaccccgga accacttcag atgccaggtg cagttctacg gcctgagcga gaacgacgag        720
tggacccagg acagagccaa gcccgtgacc cagatcgtgt ctgccgaagc ctggggcaga      780
gccgattgcg gctttacctc cgtgtcctat cagcagggcg tgctgagcgc caccatcctg      840
tacgagatcc tgctgggcaa ggccaccctg tacgccgtgc tggtgtctgc cctggtgctg      900
atggccatgg tcaagcggaa ggacttcggt tccggagcca cgaacttctc tctgttaaag      960
caagcaggag acgtggaaga aaaccccggt cccatggaaa ccctgctggg agtgtccctc      1020
gtgatcctgt ggctgcagct ggccagagtg aacagccagc agggggaaga ggatccccag      1080
gccctgagca ttcaggaagg cgagaacgcc accatgaact gcagctacaa gaccagcatc      1140
aacaacctgc agtggtacag gcagaacagc ggcagaggcc tggtgcacct gatcctgatc      1200
agaagcaacg agagagagaa gcactccgga cggctgagag tgaccctgga cacctccaag      1260
aagtcctcca gcctgctgat caccgccagc agagccgccg ataccgccag ctacttctgc      1320 gccacagacag agagcagcaa ctacaagctg accttcggca agggcacact gctgacagtg     1380 aacccccaaca tccagaaccc cgaccccgct gtgtaccagc tgcgggacag caagagcagc      1440
gacaagagcg tgtgcctgtt caccgacttc gacagccaga ccaacgtgtc ccagagcaag      1500
gacagcgacg tgtacatcac cgataagtgc gtgctggaca tgcggagcat ggacttcaag      1560
agcaacagcg ccgtggcctg gtccaacaag agcgacttcg cctgcgccaa cgccttcaac      1620
aacagcatta tccccgagga cacattcttc ccaagccccg agagcagctg cgacgtgaag      1680
ctggtggaaa agagcttcga gacagacacc aacctgaact tccagaacct cagcgtgatc      1740
ggcttccgga tcctgctgct gaaggtggcc ggcttcaacc tgctgatgac cctgcggctg      1800
tggtccagct ga                                                         1812
```

<210> SEQ ID NO 180
<211> LENGTH: 603
<212> TYPE: PRT
<213> ORGANISM: Artificial Sequence
<220> FEATURE:
<223> OTHER INFORMATION: codon optimized TCR number 10 construct; beta
      chain-P2A-alpha chain with cysteine substitutions in beta and
      alpha chain constant domains

<400> SEQUENCE: 180

```
Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45
```

-continued

```
Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
                100                 105                 110

Ser Ser Leu Asn Met Asn Thr Glu Ala Phe Phe Gly Gln Gly Thr Arg
                115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Pro Leu Lys Glu Gln Pro Ala Leu Asn Asp Ser Arg Tyr Cys Leu
                195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
    290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Glu Thr Leu Leu
                325                 330                 335

Gly Val Ser Leu Val Ile Leu Trp Leu Gln Leu Ala Arg Val Asn Ser
                340                 345                 350

Gln Gln Gly Glu Glu Asp Pro Gln Ala Leu Ser Ile Gln Glu Gly Glu
                355                 360                 365

Asn Ala Thr Met Asn Cys Ser Tyr Lys Thr Ser Ile Asn Asn Leu Gln
    370                 375                 380

Trp Tyr Arg Gln Asn Ser Gly Arg Gly Leu Val His Leu Ile Leu Ile
385                 390                 395                 400

Arg Ser Asn Glu Arg Glu Lys His Ser Gly Arg Leu Arg Val Thr Leu
                405                 410                 415

Asp Thr Ser Lys Lys Ser Ser Ser Leu Leu Ile Thr Ala Ser Arg Ala
                420                 425                 430

Ala Asp Thr Ala Ser Tyr Phe Cys Ala Thr Asp Glu Ser Ser Asn Tyr
                435                 440                 445

Lys Leu Thr Phe Gly Lys Gly Thr Leu Leu Thr Val Asn Pro Asn Ile
    450                 455                 460

Gln Asn Pro Asp Pro Ala Val Tyr Gln Leu Arg Asp Ser Lys Ser Ser
```

-continued

```
      465               470               475               480

Asp Lys Ser Val Cys Leu Phe Thr Asp Phe Asp Ser Gln Thr Asn Val
                485                   490                   495

Ser Gln Ser Lys Asp Ser Asp Val Tyr Ile Thr Asp Lys Cys Val Leu
            500               505               510

Asp Met Arg Ser Met Asp Phe Lys Ser Asn Ser Ala Val Ala Trp Ser
        515               520               525

Asn Lys Ser Asp Phe Ala Cys Ala Asn Ala Phe Asn Asn Ser Ile Ile
    530               535               540

Pro Glu Asp Thr Phe Phe Pro Ser Pro Glu Ser Ser Cys Asp Val Lys
545               550               555               560

Leu Val Glu Lys Ser Phe Glu Thr Asp Thr Asn Leu Asn Phe Gln Asn
                565               570               575

Leu Ser Val Ile Gly Phe Arg Ile Leu Leu Leu Lys Val Ala Gly Phe
                580               585               590

Asn Leu Leu Met Thr Leu Arg Leu Trp Ser Ser
            595               600
```

```
<210> SEQ ID NO 181
<211> LENGTH: 1818
<212> TYPE: DNA
<213> ORGANISM: Artificial Sequence
<220> FEATURE:
<223> OTHER INFORMATION: codon optimized TCR number 7 construct; beta
      chain-P2A-alpha chain with cysteine substitutions in beta and
      alpha chain constant domains

<400> SEQUENCE: 181
atgagcaacc aggtcttgtg ctgtgtggtg ctgtgctttc ttggcgccaa tacagtggat      60
ggcggcatta cacagagccc taagtacctg ttccggaaag aaggccagaa cgtgacactg     120
tcttgcgagc aaaacctgaa ccacgatgcc atgtactggt acagacagga tcctggacag     180
ggacttaggc tgatctacta tagccagatc gtgaacgact ccagaagggg cgatattgcc     240
gagggctatt ctgtgtctcg ggagaaaaag gagagcttcc ctctgacagt gacatctgcc     300
cagaagaatc ctaccgcctt ctacctttgt gccagctctc tgaatcgggg cagatacgga     360
tacacctttg atctggcac agactgaca gtggtggaag atctgaacaa ggtgttcccc     420
ccagaggtgg ccgtgttcga gccttctgag gccgagatct cccacaccca gaaagccacc     480
ctcgtgtgcc tggccaccgg cttttttcccc gaccacgtgg aactgtcttg gtgggtcaac     540
ggcaaagagg tgcactccgg cgtgtgcacc gatccccagc tctgaaaga acagcccgcc     600 ctgaacgaca gccggtactg cctgagcagc agactgagag tgtccgccac cttctggcag     660
aacccccgga accacttcag atgccaggtg cagttctacg gcctgagcga gaacgacgag     720
tggacccagg acagagccaa gcccgtgaca cagatcgtgt ctgccgaagc ctggggcaga     780
gccgattgcg gctttacctc cgtgtcctat cagcagggcg tgctgagcgc cacaatcctg     840
tacgagatcc tgctgggcaa ggccaccctg tacgccgtgc tggtgtctgc cctggtgctg     900
atggccatgg tcaagcggaa ggacttcggt tccggagcca cgaacttctc tctgttaaag     960
caagcaggag acgtggaaga aaaccccggt cccatggaga gaaccccct tgcagcacct    1020 ctgcttattc tgtggttcca cctggattgc gtgagctcta tcctgaatgt ggagcagtct    1080
cctcagtctc tgcatgttca ggaaggcgat agcaccaact tcacctgtag ctttcccagc    1140
agcaacttct atgccctgca ctggtacaga tgggaaacag ccaaaagccc tgaagccctg    1200
ttcgtgatga cccttaatgg cgatgagaag aagaagggcc ggattctgc cacctgaat    1260
```

```
acaaaagagg gctacagcta cctgtacatc aagggatctc agcctgagga tagcgccaca    1320
tatctgtgtg cctatctggg agccggcaat cagttctatt tcggaacagg caccagcctg    1380
accgtgattc ctaatatcca gaaccccgat cctgccgtgt accagctgcg ggacagcaag    1440
agcagcgaca gagcgtgtg cctgttcacc gacttcgaca gccagaccaa cgtgtcccag     1500
agcaaggaca gcgacgtgta catcaccgat aagtgcgtgc tggacatgcg gagcatggac    1560
ttcaagagca cacgcgccgt ggcctggtcc aacaagagcg acttcgcctg cgccaacgcc    1620
ttcaacaaca gcattatccc cgaggacaca ttcttcccaa gccccgagag cagctgcgac    1680
gtgaagctgg tggaaaagag cttcgagaca gacaccaacc tgaacttcca gaacctcagc    1740
gtgatcggct ccggatcct gctgctgaag gtggccggct caacctgct gatgaccctg       1800 cggctgtggt ccagctga                                                  1818
```

<210> SEQ ID NO 182
<211> LENGTH: 605
<212> TYPE: PRT
<213> ORGANISM: Artificial Sequence
<220> FEATURE:
<223> OTHER INFORMATION: codon optimized TCR number 7 construct; beta
      chain-P2A-alpha chain with cysteine substitutions in beta and
      alpha chain constant domains

<400> SEQUENCE: 182

```
Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Leu Asn Arg Gly Arg Tyr Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
```

-continued

```
            245                250                255

Ala Trp Gly Arg Ala Asp Cys Gly Phe Thr Ser Val Ser Tyr Gln Gln
            260                265                270

Gly Val Leu Ser Ala Thr Ile Leu Tyr Glu Ile Leu Leu Gly Lys Ala
            275                280                285

Thr Leu Tyr Ala Val Leu Val Ser Ala Leu Val Leu Met Ala Met Val
    290                295                300

Lys Arg Lys Asp Phe Gly Ser Gly Ala Thr Asn Phe Ser Leu Leu Lys
305                310                315                320

Gln Ala Gly Asp Val Glu Glu Asn Pro Gly Pro Met Glu Lys Asn Pro
            325                330                335

Leu Ala Ala Pro Leu Leu Ile Leu Trp Phe His Leu Asp Cys Val Ser
            340                345                350

Ser Ile Leu Asn Val Glu Gln Ser Pro Gln Ser Leu His Val Gln Glu
            355                360                365

Gly Asp Ser Thr Asn Phe Thr Cys Ser Phe Pro Ser Ser Asn Phe Tyr
    370                375                380

Ala Leu His Trp Tyr Arg Trp Glu Thr Ala Lys Ser Pro Glu Ala Leu
385                390                395                400

Phe Val Met Thr Leu Asn Gly Asp Glu Lys Lys Lys Gly Arg Ile Ser
            405                410                415

Ala Thr Leu Asn Thr Lys Glu Gly Tyr Ser Tyr Leu Tyr Ile Lys Gly
            420                425                430

Ser Gln Pro Glu Asp Ser Ala Thr Tyr Leu Cys Ala Tyr Leu Gly Ala
            435                440                445

Gly Asn Gln Phe Tyr Phe Gly Thr Gly Thr Ser Leu Thr Val Ile Pro
    450                455                460

Asn Ile Gln Asn Pro Asp Pro Ala Val Tyr Gln Leu Arg Asp Ser Lys
465                470                475                480

Ser Ser Asp Lys Ser Val Cys Leu Phe Thr Asp Phe Asp Ser Gln Thr
            485                490                495

Asn Val Ser Gln Ser Lys Asp Ser Asp Val Tyr Ile Thr Asp Lys Cys
            500                505                510

Val Leu Asp Met Arg Ser Met Asp Phe Lys Ser Asn Ser Ala Val Ala
            515                520                525

Trp Ser Asn Lys Ser Asp Phe Ala Cys Ala Asn Ala Phe Asn Asn Ser
    530                535                540

Ile Ile Pro Glu Asp Thr Phe Phe Pro Ser Pro Glu Ser Ser Cys Asp
545                550                555                560

Val Lys Leu Val Glu Lys Ser Phe Glu Thr Asp Thr Asn Leu Asn Phe
            565                570                575

Gln Asn Leu Ser Val Ile Gly Phe Arg Ile Leu Leu Leu Lys Val Ala
            580                585                590

Gly Phe Asn Leu Leu Met Thr Leu Arg Leu Trp Ser Ser
    595                600                605
```

```
<210> SEQ ID NO 183
<211> LENGTH: 1848
<212> TYPE: DNA
<213> ORGANISM: Artificial Sequence
<220> FEATURE:
<223> OTHER INFORMATION: codon optimized TCR number 8 construct; beta
      chain-P2A-alpha chain with cysteine substitutions in beta and
      alpha chain constant domains

<400> SEQUENCE: 183
```

-continued

```
atgggacctg gactgctttg ttgggctctt ctgtgtctgc ttggagctgg actggttgat      60
gctggagtta cacagagccc tacacacctg atcaagacaa gaggacagca ggtgaccctg     120
agatgtagcc ctaaatctgg ccacgatacc gtgagctggt atcaacaggc tctgggacaa     180
ggacctcagt tcatcttcca gtactacgag gaggaggaga gacagagagg caatttccct     240
gacaggttta gcggacacca gttccccaat tacagctctg agctgaacgt gaatgccctt     300
cttctgggag attctgccct gtatctgtgt gccagcagct ttagactggc tggaggacct     360
agcaccgata cacagtattt tggacctggc accaggctga cagtgttaga agacctgaag     420
aacgtgttcc ccccagaggt ggccgtgttc gagcctagcg aggccgagat cagccacacc     480
cagaaagcca ccctcgtgtg cctggccacc ggcttttacc ccgaccacgt ggaactgtct     540
tggtgggtca acggcaaaga ggtgcacagc ggcgtctgca ccgaccccca gccctgaaa      600 gagcagcccg ccctgaacga cagccggtac tgtctgagca gcagactgag agtgtccgcc     660
accttctggc agaaccccg gaaccacttc agatgccagg tgcagttcta cggcctgagc      720
gagaacgacg agtggaccca ggaccgggcc aagcccgtga cccagatcgt gtctgctgag     780
gcctggggca gagccgattg cggcttcacc agcgagagct accagcaggg cgtgctgagc     840
gccaccatcc tgtacgagat cctgctgggc aaggccaccc tgtacgccgt gctggtgtcc     900
gccctggtgc tgatggccat ggtcaagcgg aaggacagcc ggggcggttc cggagccacg     960
aacttctctc tgttaaagca agcaggagac gtggaagaaa accccggtcc catgttgacc    1020
gcttctctct tacgtgccgt gattgccagc atctgtgtgg ttagctctat ggcccagaag    1080
gtgacacaag ctcagacaga gatcagcgtg gtggagaaag aggatgtgac cctggattgc    1140
gtgtacgaga ccagagatac cacctactac ctgttctggt acaagcagcc tccttctgga    1200
gaactggtgt cctgatcag acggaacagc ttcgatgagc agaacgagat tagcggcagg    1260
tatagctgga acttccagaa gagcaccagc agcttcaact tcaccatcac agcctctcag    1320
gtggtggatt ctgccgtgta cttttgtgcc ctgtctgaac tggcctctgg aggaagctat    1380
atccctacat cggcagagg cacaagcctg attgtgcacc cttacatcca gaaccctgat    1440
cctgctgtgt accagctgcg ggacagcaag agcagcgaca gagcgtgtg cctgttcacc    1500 gacttcgaca gccagaccaa cgtgtcccag agcaaggaca gcgacgtgta catcaccgat    1560
aagtgcgtgc tggacatgcg gagcatggac ttcaagagca cagcgccgt ggcctggtcc     1620 aacaagagcg acttcgcctg cgccaacgcc ttcaacaaca gcattatccc cgaggacaca    1680
ttcttcccaa gccccgagag cagctgcgac gtgaagctgg tggaaaagag cttcgagaca    1740
gacaccaacc tgaacttcca gaacctcagc gtgatcggct ccggatcct gctgctgaag    1800 gtggccggct caacctgct gatgaccctg cggctgtggt ccagctga                1848
```

<210> SEQ ID NO 184
<211> LENGTH: 615
<212> TYPE: PRT
<213> ORGANISM: Artificial Sequence
<220> FEATURE:
<223> OTHER INFORMATION: codon optimized TCR number 8 construct; beta
      chain-P2A-alpha chain with cysteine substitutions in beta and
      alpha chain constant domains

<400> SEQUENCE: 184

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys

-continued

```
                   20              25              30
Thr Arg Gly Gln Gln Val Thr Leu Arg Cys Ser Pro Lys Ser Gly His
            35              40              45
Asp Thr Val Ser Trp Tyr Gln Gln Ala Leu Gly Gln Gly Pro Gln Phe
        50              55              60
Ile Phe Gln Tyr Tyr Glu Glu Glu Arg Gln Arg Gly Asn Phe Pro
65              70              75              80
Asp Arg Phe Ser Gly His Gln Phe Pro Asn Tyr Ser Ser Glu Leu Asn
            85              90              95
Val Asn Ala Leu Leu Leu Gly Asp Ser Ala Leu Tyr Leu Cys Ala Ser
            100             105             110
Ser Phe Arg Leu Ala Gly Gly Pro Ser Thr Asp Thr Gln Tyr Phe Gly
        115             120             125
Pro Gly Thr Arg Leu Thr Val Leu Glu Asp Leu Lys Asn Val Phe Pro
        130             135             140
Pro Glu Val Ala Val Phe Glu Pro Ser Glu Ala Glu Ile Ser His Thr
145             150             155             160
Gln Lys Ala Thr Leu Val Cys Leu Ala Thr Gly Phe Tyr Pro Asp His
            165             170             175
Val Glu Leu Ser Trp Trp Val Asn Gly Lys Glu Val His Ser Gly Val
        180             185             190
Cys Thr Asp Pro Gln Pro Leu Lys Glu Gln Pro Ala Leu Asn Asp Ser
        195             200             205
Arg Tyr Cys Leu Ser Ser Arg Leu Arg Val Ser Ala Thr Phe Trp Gln
        210             215             220
Asn Pro Arg Asn His Phe Arg Cys Gln Val Gln Phe Tyr Gly Leu Ser
225             230             235             240
Glu Asn Asp Glu Trp Thr Gln Asp Arg Ala Lys Pro Val Thr Gln Ile
            245             250             255
Val Ser Ala Glu Ala Trp Gly Arg Ala Asp Cys Gly Phe Thr Ser Glu
        260             265             270
Ser Tyr Gln Gln Gly Val Leu Ser Ala Thr Ile Leu Tyr Glu Ile Leu
        275             280             285
Leu Gly Lys Ala Thr Leu Tyr Ala Val Leu Val Ser Ala Leu Val Leu
    290             295             300
Met Ala Met Val Lys Arg Lys Asp Ser Arg Gly Gly Ser Gly Ala Thr
305             310             315             320
Asn Phe Ser Leu Leu Lys Gln Ala Gly Asp Val Glu Glu Asn Pro Gly
        325             330             335
Pro Met Leu Thr Ala Ser Leu Leu Arg Ala Val Ile Ala Ser Ile Cys
        340             345             350
Val Val Ser Ser Met Ala Gln Lys Val Thr Gln Ala Gln Thr Glu Ile
        355             360             365
Ser Val Val Glu Lys Glu Asp Val Thr Leu Asp Cys Val Tyr Glu Thr
        370             375             380
Arg Asp Thr Thr Tyr Tyr Leu Phe Trp Tyr Lys Gln Pro Pro Ser Gly
385             390             395             400
Glu Leu Val Phe Leu Ile Arg Arg Asn Ser Phe Asp Glu Gln Asn Glu
            405             410             415
Ile Ser Gly Arg Tyr Ser Trp Asn Phe Gln Lys Ser Thr Ser Ser Phe
        420             425             430
Asn Phe Thr Ile Thr Ala Ser Gln Val Val Asp Ser Ala Val Tyr Phe
        435             440             445
```

-continued

```
Cys Ala Leu Ser Glu Leu Ala Ser Gly Gly Ser Tyr Ile Pro Thr Phe
    450             455             460

Gly Arg Gly Thr Ser Leu Ile Val His Pro Tyr Ile Gln Asn Pro Asp
465             470             475             480

Pro Ala Val Tyr Gln Leu Arg Asp Ser Lys Ser Ser Asp Lys Ser Val
            485             490             495

Cys Leu Phe Thr Asp Phe Asp Ser Gln Thr Asn Val Ser Gln Ser Lys
            500             505             510

Asp Ser Asp Val Tyr Ile Thr Asp Lys Cys Val Leu Asp Met Arg Ser
            515             520             525

Met Asp Phe Lys Ser Asn Ser Ala Val Ala Trp Ser Asn Lys Ser Asp
    530             535             540

Phe Ala Cys Ala Asn Ala Phe Asn Asn Ser Ile Ile Pro Glu Asp Thr
545             550             555             560

Phe Phe Pro Ser Pro Glu Ser Ser Cys Asp Val Lys Leu Val Glu Lys
            565             570             575

Ser Phe Glu Thr Asp Thr Asn Leu Asn Phe Gln Asn Leu Ser Val Ile
            580             585             590

Gly Phe Arg Ile Leu Leu Leu Lys Val Ala Gly Phe Asn Leu Leu Met
            595             600             605

Thr Leu Arg Leu Trp Ser Ser
    610             615
```

<210> SEQ ID NO 185
<211> LENGTH: 1815
<212> TYPE: DNA
<213> ORGANISM: Artificial Sequence
<220> FEATURE:
<223> OTHER INFORMATION: TCR number 11 construct; beta chain-P2A-alpha
      chain

<400> SEQUENCE: 185

```
atgggcacca ggctcttctt ctatgtggcc ctttgtctgc tgtgggcagg acacagggat      60
gctggaatca cccagagccc aagatacaag atcacagaga caggaaggca ggtgaccttg     120
atgtgtcacc agacttggag ccacagctat atgttctggt atcgacaaga cctgggacat     180
gggctgaggc tgatctatta ctcagcagct gctgatatta cagataaagg agaagtcccc     240
gatggctatg ttgtctccag atccaagaca gagaatttcc ccctcactct ggagtcagct     300
acccgctccc agacatctgt gtatttctgc gccagcagtg acggggggcgg gcagtacttc     360 gggccgggca ccaggctcac ggtcacagag gacctgaaaa cgtgttccc acccgaggtc      420 gctgtgtttg agccatcaga agcagagatc tcccacaccc aaaaggccac actggtgtgc     480
ctggccacag cttctacccc cgaccacgtg gagctgagct ggtgggtgaa tgggaaggag     540
gtgcacagtg gggtcagcac agacccgcag cccctcaagg agcagcccgc cctcaatgac     600
tccagatact gcctgagcag ccgcctgagg gtctcggcca ccttctggca gaaccccgc      660 aaccacttcc gctgtcaagt ccagttctac gggctctcgg agaatgacga gtggaccag      720 gatagggcca aacctgtcac ccagatcgtc agcgccgagg cctggggtag agcagactgt     780
ggcttcacct ccgagtctta ccagcaaggg gtcctgtctg ccaccatcct ctatgagatc     840
ttgctaggga aggccacctt gtatgccgtg ctggtcagtg ccctcgtgct gatggccatg     900
gtcaagagaa aggattccag aggcggttcc ggagccacga acttctctct gttaaagcaa     960
gcaggagacg tggaagaaaa ccccggtccc atgaaaaagc atctgacgac cttcttggtg    1020
```

-continued

```
attttgtggc tttattttta taggggaat ggcaaaaacc aagtggagca gagtcctcag     1080
tccctgatca tcctggaggg aaagaactgc actcttcaat gcaattatac agtgagcccc     1140
ttcagcaact taaggtggta taagcaagat actgggagag gtcctgtttc cctgacaatc     1200
atgactttca gtgagaacac aaagtcgaac ggaagatata cagcaactct ggatgcagac     1260
acaaagcaaa gctctctgca catcacagcc tcccagctca gcgattcagc ctcctacatc     1320
tgtgtggtgt ggggggggga caccgacaag ctcatctttg ggactgggac cagattacaa     1380
gtctttccaa atatccagaa ccctgaccct gccgtgtacc agctgagaga ctctaaatcc     1440
agtgacaagt ctgtctgcct attcaccgat tttgattctc aaacaaatgt gtcacaaagt     1500
aaggattctg atgtgtatat cacagacaaa acttggctag acatgaggtc tatggacttc     1560
aagagcaaca gtgctgtggc ctggagcaac aaatctgact ttgcatgtgc aaacgccttc     1620
aacaacagca ttattccaga agacaccttc ttccccagcc cagaaagttc ctgtgatgtc     1680
aagctggtcg agaaaagctt tgaaacagat acgaacctaa actttcaaaa cctgtcagtg     1740
attgggttcc gaatcctcct cctgaaagtg gccgggttta tctgctcat gacgctgcgg     1800 ctgtggtcca gctga                                                     1815
```

<210> SEQ ID NO 186
<211> LENGTH: 604
<212> TYPE: PRT
<213> ORGANISM: Artificial Sequence
<220> FEATURE:
<223> OTHER INFORMATION: TCR number 11 construct; beta chain-P2A-alpha
     chain

<400> SEQUENCE: 186

```
Met Gly Thr Arg Leu Phe Phe Tyr Val Ala Leu Cys Leu Leu Trp Ala
1               5                   10                  15

Gly His Arg Asp Ala Gly Ile Thr Gln Ser Pro Arg Tyr Lys Ile Thr
                20                  25                  30

Glu Thr Gly Arg Gln Val Thr Leu Met Cys His Gln Thr Trp Ser His
            35                  40                  45

Ser Tyr Met Phe Trp Tyr Arg Gln Asp Leu Gly His Gly Leu Arg Leu
        50                  55                  60

Ile Tyr Tyr Ser Ala Ala Ala Asp Ile Thr Asp Lys Gly Glu Val Pro
65                  70                  75                  80

Asp Gly Tyr Val Val Ser Arg Ser Lys Thr Glu Asn Phe Pro Leu Thr
                85                  90                  95

Leu Glu Ser Ala Thr Arg Ser Gln Thr Ser Val Tyr Phe Cys Ala Ser
            100                 105                 110

Ser Asp Gly Gly Gly Gln Tyr Phe Gly Pro Gly Thr Arg Leu Thr Val
        115                 120                 125

Thr Glu Asp Leu Lys Asn Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Tyr Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
```

-continued

```
         210              215              220
Cys Gln Val Gln Phe Tyr Gly Leu Ser Glu Asn Asp Glu Trp Thr Gln
225              230              235              240

Asp Arg Ala Lys Pro Val Thr Gln Ile Val Ser Ala Glu Ala Trp Gly
             245              250              255

Arg Ala Asp Cys Gly Phe Thr Ser Glu Ser Tyr Gln Gln Gly Val Leu
             260              265              270

Ser Ala Thr Ile Leu Tyr Glu Ile Leu Leu Gly Lys Ala Thr Leu Tyr
         275              280              285

Ala Val Leu Val Ser Ala Leu Val Leu Met Ala Met Val Lys Arg Lys
         290              295              300

Asp Ser Arg Gly Gly Ser Gly Ala Thr Asn Phe Ser Leu Leu Lys Gln
305              310              315              320

Ala Gly Asp Val Glu Glu Asn Pro Gly Pro Met Lys Lys His Leu Thr
             325              330              335

Thr Phe Leu Val Ile Leu Trp Leu Tyr Phe Tyr Arg Gly Asn Gly Lys
             340              345              350

Asn Gln Val Glu Gln Ser Pro Gln Ser Leu Ile Ile Leu Glu Gly Lys
         355              360              365

Asn Cys Thr Leu Gln Cys Asn Tyr Thr Val Ser Pro Phe Ser Asn Leu
         370              375              380

Arg Trp Tyr Lys Gln Asp Thr Gly Arg Gly Pro Val Ser Leu Thr Ile
385              390              395              400

Met Thr Phe Ser Glu Asn Thr Lys Ser Asn Gly Arg Tyr Thr Ala Thr
             405              410              415

Leu Asp Ala Asp Thr Lys Gln Ser Ser Leu His Ile Thr Ala Ser Gln
             420              425              430

Leu Ser Asp Ser Ala Ser Tyr Ile Cys Val Val Trp Gly Gly Asp Thr
             435              440              445

Asp Lys Leu Ile Phe Gly Thr Gly Thr Arg Leu Gln Val Phe Pro Asn
         450              455              460

Ile Gln Asn Pro Asp Pro Ala Val Tyr Gln Leu Arg Asp Ser Lys Ser
465              470              475              480

Ser Asp Lys Ser Val Cys Leu Phe Thr Asp Phe Asp Ser Gln Thr Asn
             485              490              495

Val Ser Gln Ser Lys Asp Ser Asp Val Tyr Ile Thr Asp Lys Thr Trp
             500              505              510

Leu Asp Met Arg Ser Met Asp Phe Lys Ser Asn Ser Ala Val Ala Trp
             515              520              525

Ser Asn Lys Ser Asp Phe Ala Cys Ala Asn Ala Phe Asn Asn Ser Ile
         530              535              540

Ile Pro Glu Asp Thr Phe Phe Pro Ser Pro Glu Ser Ser Cys Asp Val
545              550              555              560

Lys Leu Val Glu Lys Ser Phe Glu Thr Asp Thr Asn Leu Asn Phe Gln
             565              570              575

Asn Leu Ser Val Ile Gly Phe Arg Ile Leu Leu Leu Lys Val Ala Gly
             580              585              590

Phe Asn Leu Leu Met Thr Leu Arg Leu Trp Ser Ser
         595              600
```

```
<210> SEQ ID NO 187
<211> LENGTH: 1812
<212> TYPE: DNA
<213> ORGANISM: Artificial Sequence
```

-continued

<220> FEATURE:
<223> OTHER INFORMATION: codon optimized TCR number 11 construct; beta
      chain-P2A-alpha chain with cysteine substitutions in beta and
      alpha chain constant domains

<400> SEQUENCE: 187

```
atgggcacac ggcttttctt ctacgttgcc ctttgcctgc tgtgggctgg acatagagat      60
gctggaatca cacagagccc caggtacaag atcacagaga caggaagaca ggtgaccctg     120
atgtgtcacc aaacatggag ccacagctac atgttctggt acagacagga tctgggacac     180
ggactgagac tgatctacta ttctgctgcc gccgacatca ccgataaagg agaagttcct     240
gacggctacg tggtgtctag aagcaaaacc gagaacttcc ccctgacact ggaatctgcc     300
acaagatctc agaccagcgt gtacttttgc gcctcttctg atggaggagg ccagtatttt     360
ccaggcacaa gactgacagt gaccgaggac ctgaagaacg tgttcccccc agaggtggcc     420
gtgttcgagc ctagcgaggc cgagatcagc cacacccaga agccacccct cgtgtgcctg     480
gccaccggct tttaccccga ccacgtggaa ctgtcttggt gggtcaacgg caaagaggtg     540
cacagcggcg tctgcaccga cccccagccc ctgaaagagc agcccgccct gaacgacagc     600
cggtactgtc tgagcagcag actgagagtg tccgccacct tctggcagaa cccccggaac     660
cacttcagat gccaggtgca gttctacggc ctgagcgaga cgacgagtg acccaggac       720 cgggccaagc ccgtgaccca gatcgtgtct gctgaggcct ggggcagagc cgattgcggc     780
ttcaccagcg agagctacca gcagggcgtg ctgagcgcca ccatcctgta cgagatcctg     840
ctgggcaagg ccaccctgta cgccgtgctg gtgtccgccc tggtgctgat ggccatggtc     900
aagcggaagg acagccgggg cggttccgga gccacgaact tctctctgtt aaagcaagca     960
ggagacgtgg aagaaaaccc cggtcccatg aagaagcacc tgaccacgtt cctggtgatt    1020
ctttggctgt acttctaccg gggcaacggc aaaaatcagg tggaacaaag ccccagagc     1080 ctgattattc tggagggcaa gaactgcacc ctccagtgta attacaccgt gagccctttc    1140
agcaacctga gatggtacaa gcaggatacc ggaagaggac ctgtgtctct gaccatcatg    1200
acctttagcg agaacaccaa gagcaacggc aggtatacag ccacactgga tgccgatacc    1260
aagcagtctt ctctgcacat taccgcctct cagctgtctg attctgccag ctacatctgt    1320
gtggtgtggg gaggagatac cgataagctg atctttggca caggcaccag actgcaagtg    1380
ttccctaaca tccagaaccc tgatcctgcc gtgtaccagc tgcgggacag caagagcagc    1440
gacaagagcg tgtgcctgtt caccgacttc gacagccaga ccaacgtgtc ccagagcaag    1500
gacagcgacg tgtacatcac cgataagtgc gtgctggaca tgcggagcat ggacttcaag    1560
agcaacagcg ccgtggcctg tccaacaag agcgacttcg cctgcgccaa cgccttcaac    1620
aacagcatta tccccgagga cacattcttc ccaagccccg agagcagctg cgacgtgaag    1680
ctggtggaaa agagcttcga cagacacacc aacctgaact tccagaacct cagcgtgatc    1740
ggcttccgga tcctgctgct gaaggtggcc ggcttcaacc tgctgatgac cctgcggctg    1800
tggtccagct ga                                                        1812
```

<210> SEQ ID NO 188
<211> LENGTH: 603
<212> TYPE: PRT
<213> ORGANISM: Artificial Sequence
<220> FEATURE:
<223> OTHER INFORMATION: codon optimized TCR number 11 construct; beta
      chain-P2A-alpha chain with cysteine substitutions in beta and
      alpha chain constant domains -continued

<400> SEQUENCE: 188

```
Met Gly Thr Arg Leu Phe Phe Tyr Val Ala Leu Cys Leu Leu Trp Ala
1               5                   10                  15

Gly His Arg Asp Ala Gly Ile Thr Gln Ser Pro Arg Tyr Lys Ile Thr
            20                  25                  30

Glu Thr Gly Arg Gln Val Thr Leu Met Cys His Gln Thr Trp Ser His
        35                  40                  45

Ser Tyr Met Phe Trp Tyr Arg Gln Asp Leu Gly His Gly Leu Arg Leu
    50                  55                  60

Ile Tyr Tyr Ser Ala Ala Ala Asp Ile Thr Asp Lys Gly Glu Val Pro
65                  70                  75                  80

Asp Gly Tyr Val Val Ser Arg Ser Lys Thr Glu Asn Phe Pro Leu Thr
                85                  90                  95

Leu Glu Ser Ala Thr Arg Ser Gln Thr Ser Val Tyr Phe Cys Ala Ser
            100                 105                 110

Ser Asp Gly Gly Gly Gln Tyr Phe Pro Gly Thr Arg Leu Thr Val Thr
            115                 120                 125

Glu Asp Leu Lys Asn Val Phe Pro Pro Glu Val Ala Val Phe Glu Pro
    130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Cys Thr Asp Pro Gln Pro Leu Lys
            180                 185                 190

Glu Gln Pro Ala Leu Asn Asp Ser Arg Tyr Cys Leu Ser Ser Arg Leu
            195                 200                 205

Arg Val Ser Ala Thr Phe Trp Gln Asn Pro Arg Asn His Phe Arg Cys
    210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255

Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Ala Leu Val Leu Met Ala Met Val Lys Arg Lys Asp
    290                 295                 300

Ser Arg Gly Gly Ser Gly Ala Thr Asn Phe Ser Leu Leu Lys Gln Ala
305                 310                 315                 320

Gly Asp Val Glu Glu Asn Pro Gly Pro Met Lys Lys His Leu Thr Thr
                325                 330                 335

Phe Leu Val Ile Leu Trp Leu Tyr Phe Tyr Arg Gly Asn Gly Lys Asn
            340                 345                 350

Gln Val Glu Gln Ser Pro Gln Ser Leu Ile Ile Leu Glu Gly Lys Asn
            355                 360                 365

Cys Thr Leu Gln Cys Asn Tyr Thr Val Ser Pro Phe Ser Asn Leu Arg
    370                 375                 380

Trp Tyr Lys Gln Asp Thr Gly Arg Gly Pro Val Ser Leu Thr Ile Met
385                 390                 395                 400

Thr Phe Ser Glu Asn Thr Lys Ser Asn Gly Arg Tyr Thr Ala Thr Leu
                405                 410                 415
```

-continued

```
Asp Ala Asp Thr Lys Gln Ser Ser Leu His Ile Thr Ala Ser Gln Leu
            420             425             430

Ser Asp Ser Ala Ser Tyr Ile Cys Val Val Trp Gly Gly Asp Thr Asp
            435             440             445

Lys Leu Ile Phe Gly Thr Gly Thr Arg Leu Gln Val Phe Pro Asn Ile
    450             455             460

Gln Asn Pro Asp Pro Ala Val Tyr Gln Leu Arg Asp Ser Lys Ser Ser
465             470             475             480

Asp Lys Ser Val Cys Leu Phe Thr Asp Phe Asp Ser Gln Thr Asn Val
            485             490             495

Ser Gln Ser Lys Asp Ser Asp Val Tyr Ile Thr Asp Lys Cys Val Leu
            500             505             510

Asp Met Arg Ser Met Asp Phe Lys Ser Asn Ser Ala Val Ala Trp Ser
            515             520             525

Asn Lys Ser Asp Phe Ala Cys Ala Asn Ala Phe Asn Asn Ser Ile Ile
    530             535             540

Pro Glu Asp Thr Phe Phe Pro Ser Pro Glu Ser Ser Cys Asp Val Lys
545             550             555             560

Leu Val Glu Lys Ser Phe Glu Thr Asp Thr Asn Leu Asn Phe Gln Asn
            565             570             575

Leu Ser Val Ile Gly Phe Arg Ile Leu Leu Leu Lys Val Ala Gly Phe
            580             585             590

Asn Leu Leu Met Thr Leu Arg Leu Trp Ser Ser
    595             600

<210> SEQ ID NO 189
<211> LENGTH: 11
<212> TYPE: PRT
<213> ORGANISM: Artificial Sequence
<220> FEATURE:
<223> OTHER INFORMATION: TCR number 11 Vbeta CDR3

<400> SEQUENCE: 189

Cys Ala Ser Ser Asp Gly Gly Gly Gln Tyr Phe
1               5               10

<210> SEQ ID NO 190
<211> LENGTH: 11
<212> TYPE: PRT
<213> ORGANISM: Artificial Sequence
<220> FEATURE:
<223> OTHER INFORMATION: TCR number 9 Vbeta CDR3 (IMGT)

<400> SEQUENCE: 190

Ala Ile Leu Asp Gly Glu Gly Ser Pro Leu His
1               5               10
```